United States Patent
Kabakoff et al.

(10) Patent No.: US 12,171,805 B2
(45) Date of Patent: Dec. 24, 2024

(54) IL-22 FC COMPOSITIONS

(71) Applicant: Genentech, Inc., South San Francisco, CA (US)

(72) Inventors: Bruce Kabakoff, South San Francisco, CA (US); Cecilia Wong Man Sai, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 1128 days.

(21) Appl. No.: 16/938,777

(22) Filed: Jul. 24, 2020

(65) Prior Publication Data

US 2020/0353049 A1 Nov. 12, 2020

Related U.S. Application Data

(63) Continuation of application No. PCT/US2019/015268, filed on Jan. 25, 2019.

(60) Provisional application No. 62/697,372, filed on Jul. 12, 2018, provisional application No. 62/622,704, filed on Jan. 26, 2018.

(51) Int. Cl.
| | |
|---|---|
| C07K 16/46 | (2006.01) |
| A61K 38/20 | (2006.01) |
| A61K 47/02 | (2006.01) |
| C07K 14/54 | (2006.01) |
| A61K 39/395 | (2006.01) |
| A61K 47/68 | (2017.01) |

(52) U.S. Cl.
CPC ............ *A61K 38/20* (2013.01); *A61K 47/02* (2013.01); *A61K 39/39591* (2013.01); *A61K 47/6801* (2017.08); *C07K 2319/30* (2013.01)

(58) Field of Classification Search
None
See application file for complete search history.

(56) References Cited

U.S. PATENT DOCUMENTS

| | | | | |
|---|---|---|---|---|
| 7,033,992 B2* | 4/2006 | Warne | ...................... | A61K 9/19 |
| | | | | 424/85.2 |
| 8,877,194 B2* | 11/2014 | Hsieh | ...................... | A61P 25/00 |
| | | | | 424/145.1 |
| 10,646,569 B2* | 5/2020 | Shenoy | ................... | C07K 16/22 |
| 2014/0314711 A1* | 10/2014 | Scheer | ................... | A61P 39/02 |
| | | | | 435/328 |

FOREIGN PATENT DOCUMENTS

| | | |
|---|---|---|
| JP | 2013-514340 A | 4/2013 |
| JP | 2015-522654 A | 8/2015 |

(Continued)

OTHER PUBLICATIONS

Kang et al., Rapid formulation development for monoclonal antibodies, BioProcess Intl., Retrieved online :<URL:https//bioprocessintl.com/manufacturing/formulation/rapid-formulation-development-formonoclonal-antibodies/>, [retrieved on Nov. 4, 2019] Apr. 2016.*
Lim et al., Biophysical stability of hyFc fusion protein with regards to buffers and various excipients, Intl. J. Biol. Macromol. 86:622-629, 2016.*

(Continued)

*Primary Examiner* — Claire Kaufman
(74) *Attorney, Agent, or Firm* — Clark & Elbing LLP; Karen L. Elbing

(57) ABSTRACT

The invention relates to compositions (e.g., pharmaceutical compositions) that include, for example, IL-22 Fc fusion proteins, methods of making the same, and methods of using the same, e.g., for the treatment of diseases (e.g., IBD).

30 Claims, 12 Drawing Sheets
Specification includes a Sequence Listing.

(56) References Cited

FOREIGN PATENT DOCUMENTS

| | | | |
|---|---|---|---|
| JP | 2016-515515 A | 5/2016 | |
| JP | 2016-522795 A | 8/2016 | |
| TW | I394582 B | 5/2013 | |
| TW | 201524995 A | 7/2015 | |
| TW | 201712029 A | 4/2017 | |
| TW | 201722461 A | 7/2017 | |
| WO | WO-2006/044908 A2 | 4/2006 | |
| WO | WO-2011/076702 A1 | 6/2011 | |
| WO | WO-2011087986 A1 * | 7/2011 | ........... A61K 39/395 |
| WO | WO-2014/017845 A2 | 1/2014 | |
| WO | WO-2014/143909 A1 | 9/2014 | |
| WO | WO-2014/145016 A2 | 9/2014 | |
| WO | WO-2016/178905 A1 | 11/2016 | |
| WO | WO-2017/078385 A1 | 5/2017 | |

OTHER PUBLICATIONS

Lee et al., "Nonclinical safety assessment of a human interleukin-22FC IG fusion protein demonstrates in vitro to in vivo and cross-species translatability," Pharmacol Res Perspect. 6(6):e00434 (2018).

Stefanich et al., "Pre-clinical and translational pharmacology of a human interleukin-22 IgG fusion protein for potential treatment of infectious or inflammatory diseases," Biochem Pharmacol. 152:224-35 (2018).

International Preliminary Report on Patentability for International Patent Application No. PCT/US2019/015268, dated Jul. 28, 2020 (7 pages).

International Search Report and Written Opinion for International Patent Application No. PCT/US2019/015268, dated Apr. 8, 2019 (16 pages).

* cited by examiner

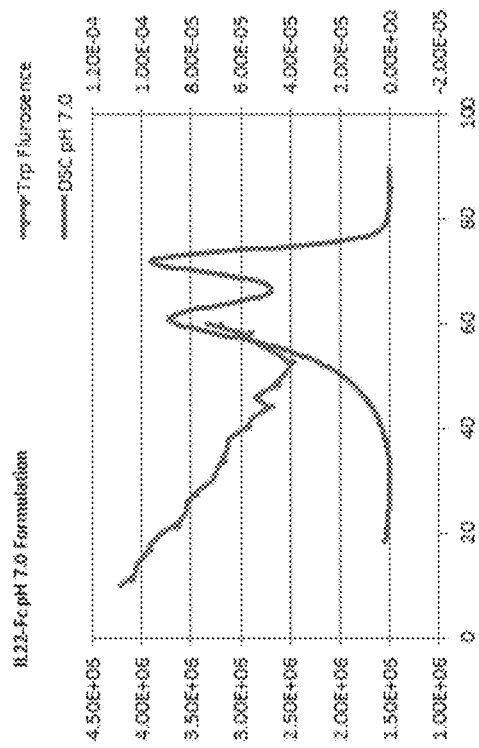
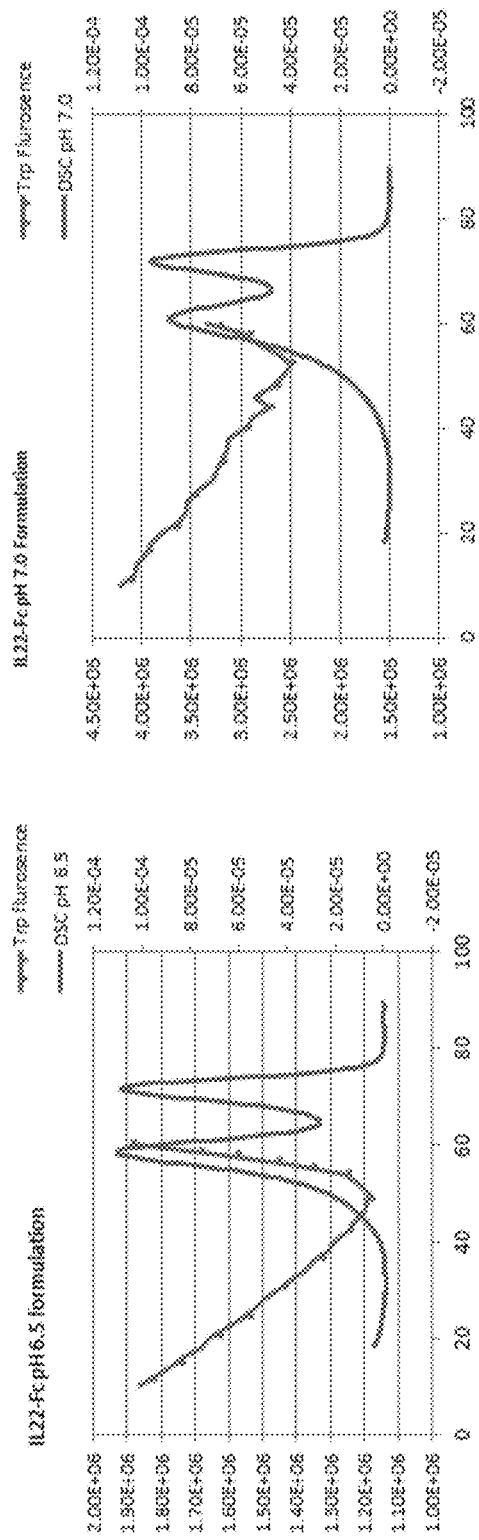

FIG. 9

IL-22 Amino Acid Sequences Alignment

```
Human (Q9GZX6)        apisshcrldksnfqqpyitnrtfmlakeasladntdvrligeklfhgvsmsercylmk    60
Chimpanzee (XP_003313806)  apisshcrldksnfqqpyitnrtfmlakeasladntdvrligeklfhgvsmsercylmk
Orangutan (KP_002823544)   apisshcrldksnfqqpyitnrtfmlakeasladntdvrligeklfhgvsmsercylmk
Mouse (Q9JJY9)            lprntrcklevsnfqqpyivnrtfmlakeasladntdvrligeklfrgvsakdgoylmk
Dog (XP_538274)           lpisshcrldksnfqqpyitnrtfmlakeasladntdvrligeklfhgvrnmgercylmi
                          *  * ********* ******************************** ** * ****

Human (Q9GZX6)            qvlnftleevlfpqsdrfqpymqevvpflarlsnrlstchiegddlhiqrnvqklkdtvk   120
Chimpanzee (XP_003313806)  qvlnftleevlfpqsdrfqpymqevvpflarlsnrlstchiegddlhiqrnvqklkdtvk
Orangutan (KP_002823544)   qvlnftleevlfpqsdrfqpymqevvpflarlsnrlstchiegddlhiqrnvqklkdtvk
Mouse (Q9JJY9)             qvlnftledrilpqsdrfqpymqevvpfltklsmqlschisqddqnsigknvrriketvk
Dog (XP_538274)            evlnftleevlfpqsdrfqpymqevvpflarlsnklsqchiemddqhiqrnvqklkdtvq
                          *** **** ******************* ** ** *  *** ** * **  *  **

Human (Q9GZX6)             klgesgeikaigeldllfmslrnaci    146    (SEQ ID NO:4)
Chimpanzee (XP_003313806)   klgengeikaigeldllfmslrnaci            (SEQ ID NO:48)
Orangutan (KP_002823544)    klgesgeikaigeldllfmslrnaci            (SEQ ID NO:49)
Mouse (Q9JJY9)              klgesgeikaigeldllfmslrnacv            (SEQ ID NO:50)
Dog (XP_538274)             klgengeikaigeldllfmslrnacv            (SEQ ID NO:51)
                           *** ********************* ******
```

IL-22 FC COMPOSITIONS

SEQUENCE LISTING

The instant application contains a Sequence Listing which has been submitted electronically in ASCII format and is hereby incorporated by reference in its entirety. Said ASCII copy, created on Jun. 5, 2024, is named 50474-177003_Sequence_Listing_6_5_24_ST25 and is 123,686 bytes in size.

FIELD OF THE INVENTION

The present invention relates to compositions (e.g., pharmaceutical compositions) comprising proteins (e.g., IL-22 Fc fusion proteins), and methods of making, purifying, and using the same.

BACKGROUND OF THE INVENTION

Interleukin (IL)-22 is a member of the IL-10 family of cytokines that is produced, e.g., by Th22 cells, NK cells, lymphoid tissue inducer (LTi) cells, dendritic cells, and Th17 cells. IL-22 binds to the IL-22R1/IL-10R2 receptor complex, which is expressed in innate cells (e.g., epithelial cells, hepatocytes, and keratinocytes) and in barrier epithelial tissues of several organs (e.g., dermis, pancreas, intestine, and the respiratory system).

IL-22 plays an important role in mucosal immunity, mediating early host defense against attaching and effacing bacterial pathogens. IL-22 promotes the production of antimicrobial peptides and pro-inflammatory cytokines from epithelial cells and stimulates proliferation and migration of colonic epithelial cells in the gut. Upon bacterial infection, IL-22 knock-out mice displayed impaired gut epithelial regeneration, high bacterial load, and increased mortality. Similarly, infection of IL-22 knock-out mice with influenza virus resulted in severe weight loss and impaired regeneration of tracheal and bronchial epithelial cells. Thus, IL-22 plays a pro-inflammatory role in suppressing microbial infection as well as an anti-inflammatory protective role in epithelial regeneration in inflammatory responses.

There remains a need for improved compositions and methods for treatment of inflammatory bowel disease (IBD), including ulcerative colitis and Crohn's disease, as well as other disorders associated with IL-22, including microbial infection, acute kidney injury, acute pancreatitis, wounds, cardiovascular conditions, metabolic syndrome, acute endotoxemia, graft-versus-host disease (GVHD), and sepsis.

SUMMARY OF THE INVENTION

The present invention provides, inter alia, compositions that include IL-22 Fc fusion proteins (e.g., pharmaceutical compositions), and methods of making and using the same.

In one aspect, the invention features a pharmaceutical composition comprising an interleukin (IL)-22 Fc fusion protein and a carrier, wherein the pharmaceutical composition has a shelf life of at least 36 months when stored at 5° C.±3° C. and protected from light, and wherein the IL-22 Fc fusion protein comprises an IL-22 polypeptide linked to an Fc region by a linker. In some embodiments, the pharmaceutical composition has a shelf life of at least 42 months when stored at 5° C.±3° C. and protected from light.

In some embodiments of the preceding aspect, the concentration of the IL-22 Fc fusion protein is about 0.5 mg/mL to about 20 mg/mL. In some embodiments, the concentration of the IL-22 Fc fusion protein is about 0.5 mg/mL to about 5 mg/mL. In some embodiments, the concentration of the IL-22 Fc fusion protein is about 1 mg/mL. In some embodiments, the concentration of the IL-22 Fc fusion protein is about 8 mg/mL to about 12 mg/mL. In some embodiments, the concentration of the IL-22 Fc fusion protein is about 10 mg/mL.

In some embodiments of the preceding aspect, the pharmaceutical composition further comprises a stabilizer. In some embodiments, the stabilizer is an amino acid, thiosorbitol, ascorbic acid, monothioglycerol, a cyclodextrin, Trolox (6-hydroxy-2,5,7,8-tetramethylchroman-2-carboxylic acid), pyridoxine, mannitol, a metal chelator, or a combination thereof. In some embodiments, the stabilizer is an amino acid. In some embodiments, the e amino acid is methionine, cysteine, tryptophan, or a combination thereof. In some embodiments, the amino acid is methionine. In some embodiments, the concentration of the stabilizer is about 1 mM to about 10 mM. In some embodiments, the concentration of the stabilizer is about 2 mM to about 8 mM. In some embodiments, the concentration of the stabilizer is about 5 mM.

In some embodiments of the preceding aspect, the oxidation of methionine at position M25 or M139 of SEQ ID NO:4 is less than 10% as assessed by an AAPH stress test. In some embodiments, the oxidation of methionine at position M25 of SEQ ID NO:4 is less than 5%, less than 3%, or less than 2%. In some embodiments, the oxidation of methionine at position M139 of SEQ ID NO:4 is less than 7%, less than 6%, or less than 5%.

In some embodiments of the preceding aspect, the pharmaceutical composition further comprises a surfactant. In some embodiments, the surfactant is a nonionic surfactant. In some embodiments, the nonionic surfactant is a polysorbate, a poloxamer, a polyoxyethelene alkyl ether, an alkyl phenyl polyoxyethylene ether, or a combination thereof. In some embodiments, the nonionic surfactant is a polysorbate. In some embodiments, the polysorbate is polysorbate 20 or polysorbate 80. In some embodiments, the polysorbate is polysorbate 20. In some embodiments, the nonionic surfactant is a poloxamer. In some embodiments, the nonionic surfactant is a poloxamer 188. In some embodiments, the concentration of the surfactant is about 0.001% (w/v) to about 0.1% (w/v). In some embodiments, the concentration of the surfactant is about 0.01% (w/v) to about 0.05% (w/v). In some embodiments, the concentration of the surfactant is about 0.01% (w/v) to about 0.07% (w/v). In some embodiments, the concentration of the surfactant is about 0.02% (w/v). In some embodiments, the concentration of polysorbate 20 is about 0.02% (w/v).

In some embodiments of the preceding aspect, the pharmaceutical composition further comprises a buffering agent. In some embodiments, the buffering agent is a phosphate, a succinate, an acetate, histidine, or a combination thereof. In some embodiments, the buffering agent is a phosphate. In some embodiments, the phosphate is sodium phosphate monobasic, sodium phosphate dibasic, sodium phosphate tribasic, potassium phosphate monobasic, potassium phosphate dibasic, potassium phosphate tribasic, or a mixture thereof. In some embodiments, the phosphate is sodium phosphate monobasic. In some embodiments, the phosphate is sodium phosphate dibasic. In some embodiments, the phosphate is a mixture of sodium phosphate monobasic and sodium phosphate dibasic. In some embodiments, the concentration of the buffering agent is about 5 mM to about 20 mM. In some embodiments, the concentration of the buffering agent is about 8 mM to about 12 mM. In some embodiments, the concentration of the buffering agent is about 10 mM.

In some embodiments of the preceding aspect, the pharmaceutical composition further comprises a tonicity agent. In some embodiments, the tonicity agent is a sugar, an amino acid, or a salt. In some embodiments, the tonicity agent is a sugar. In some embodiments, the sugar is sucrose, glucose, glycerol, or trehalose. In some embodiments, the sugar is sucrose. In some embodiments, the tonicity agent is a salt. In some embodiments, the salt is sodium chloride or potassium chloride. In some embodiments, the concentration of the tonicity agent is about 100 mM to about 500 mM. In some embodiments, the concentration of the tonicity agent is about 200 mM to about 300 mM. In some embodiments, the concentration of the tonicity agent is about 240 mM.

In some embodiments of the preceding aspect, the pharmaceutical composition has a pH of about 6.6 to about 8. In some embodiments, the pharmaceutical composition has a pH of about 6.8 to about 7.4. In some embodiments, the pharmaceutical composition has a pH of about 7.1.

In another aspect, the invention features a pharmaceutical composition comprising an IL-22 Fc fusion protein and a carrier, the IL-22 Fc fusion protein comprising an IL-22 polypeptide linked to an Fc region by a linker, wherein the pharmaceutical composition comprises about 1 mg/mL to about 10 mg/mL IL-22 Fc fusion protein, about 5 mM methionine, and about 0.02% (w/v) polysorbate 20, pH 7.1, final concentration. In some embodiments, the pharmaceutical composition further comprises about 10 mM sodium phosphate and about 240 mM sucrose. In some embodiments, the pharmaceutical composition comprises about 1 mg/mL or about 10 mg/mL IL-22 Fc fusion protein. In some embodiments, the sodium phosphate is a mixture of sodium phosphate monobasic and sodium phosphate dibasic.

In some embodiments of any of the preceding aspects, the pharmaceutical composition is in a unit dosage form. In some embodiments, the unit dosage form is a liquid formulation for infusion. In some embodiments, the liquid formulation for infusion is supplied in a container with a nominal volume of less than 100 mL. In some embodiments, the volume of the liquid formulation for infusion is between about 1 mL to about 2 mL. In some embodiments, the volume of the liquid formulation for infusion is about 1 mL.

In some embodiments of any of the preceding aspects, the number of particles ≥10 μm present in the container does not exceed 6000 particles.

In some embodiments of any of the preceding aspects, the number of particles ≥25 μm present in the container does not exceed 600 particles.

In some embodiments of any of the preceding aspects, the carrier is water.

In some embodiments of any of the preceding aspects, the pharmaceutical composition is stable through one or more freeze-thaw cycles.

In some embodiments, the pharmaceutical composition is stable through three freeze-thaw cycles.

In some embodiments of any of the preceding aspects, the pharmaceutical composition is stable for about 2 weeks or longer at about 25° C. In some embodiments, the pharmaceutical composition is stable for about 4 weeks or longer at about 25° C.

In some embodiments of any of the preceding aspects, the pharmaceutical composition is stable for about 48 months or longer at −20° C. In some embodiments, the pharmaceutical composition is stable for about 60 months or longer at −20° C.

In some embodiments of any of the preceding aspects, the pharmaceutical composition has a purity of about 85% or higher as assessed by size-exclusion high-performance liquid chromatography (SE-HPLC). In some embodiments, the pharmaceutical composition has a purity of about 90% or higher as assessed by SE-HPLC. In some embodiments, the pharmaceutical composition has a purity of about 95% or higher as assessed by SE-HPLC. In some embodiments, the pharmaceutical composition has a purity of about 95% or higher as assessed by SE-HPLC for about 36 months or longer at about 5° C. In some embodiments, the pharmaceutical composition has a purity of about 95% or higher as assessed by SE-HPLC for about 42 months or longer at about 5° C. In some embodiments, the pharmaceutical composition has a purity of about 95% or higher as assessed by SE-HPLC for about 42 months at about 5° C.

In some embodiments of any of the preceding aspects, the pharmaceutical composition has a purity of about 75% or higher as assessed by capillary electrophoresis sodium dodecyl sulfate non-gel sieving (CE-SDS-NGS) (e.g., non-reduced (NR) CE-SDS-NGS). In some embodiments, the pharmaceutical composition has a purity of about 80% or higher as assessed by CE-SDS-NGS (e.g., NR CE-SDS-NGS). In some embodiments, the pharmaceutical composition has a purity of about 85% or higher as assessed by CE-SDS-NGS (e.g., NR CE-SDS-NGS). In some embodiments, the pharmaceutical composition has a purity of about 85% or higher as assessed by CE-SDS-NGS (e.g., NR CE-SDS-NGS) for about 36 months or longer at about 5° C. In some embodiments, the pharmaceutical composition has a purity of about 85% or higher as assessed by CE-SDS-NGS (e.g., NR CE-SDS-NGS) for about 42 months or longer at about 5° C. In some embodiments, the pharmaceutical composition has a purity of about 85% or higher as assessed by CE-SDS-NGS for about 42 months at about 5° C. In any of the preceding embodiments, the CE-SDS-NGS may be NR CE-SDS-NGS.

In some embodiments of any of the preceding aspects, the pharmaceutical composition is formulated for intravenous, subcutaneous, intraperitoneal, or topical administration. In some embodiments, the pharmaceutical composition is formulated for intravenous administration. In some embodiments, the pharmaceutical composition is formulated for subcutaneous administration.

In some embodiments of any of the preceding aspects, the pharmaceutical composition does not contain a preservative. In some embodiments, the pharmaceutical composition is formulated for administration by infusion after dilution with an isotonic sodium chloride solution and/or a diluent. In some embodiments, the pharmaceutical composition is formulated for administration by infusion after dilution with an isotonic sodium chloride solution. In some embodiments, the pharmaceutical composition is formulated for administration by infusion after dilution with a diluent. In some embodiments, the pharmaceutical composition is formulated for administration by infusion after dilution with an isotonic sodium chloride solution and a diluent. In some embodiments, the isotonic sodium chloride solution comprises about 0.1% to about 2% NaCl. In some embodiments, the isotonic sodium chloride solution comprises about 0.5% to about 1.5% NaCl. In some embodiments, the isotonic sodium chloride solution comprises about 0.9% (w/v) NaCl. In some embodiments, the diluent comprises a buffering agent, a tonicity agent, and a surfactant. In some embodiments, the diluent comprises about 10 mM sodium phosphate, about 240 mM sucrose, about 0.02% (w/v) polysorbate 20, pH 7.1, final concentration.

In some embodiments of any of the preceding aspects, the IL-22 polypeptide is glycosylated. In some embodiments, the IL-22 polypeptide is N-glycosylated. In some embodiments, the Fc region is not glycosylated. In some embodiments, the amino acid residue at position 297 as in the EU index of the Fc region is glycine (Gly). In some embodiments, the amino acid residue at position 297 as in the EU index of the Fc region is alanine (Ala). In some embodiments, the amino acid residue at position 299 as in the EU index of the Fc region is Ala, Gly, or valine (Val).

In some embodiments of any of the preceding aspects, the Fc region comprises the CH2 and CH3 domain of IgG1 or IgG4. In some embodiments, the Fc region comprises the CH2 and CH3 domain of IgG4.

In some embodiments of any of the preceding aspects, the IL-22 Fc fusion protein comprises an amino acid sequence having at least 95% sequence identity to the amino acid sequence of SEQ ID NO:8. In some embodiments, the IL-22 Fc fusion protein comprises an amino acid sequence having at least 96% sequence identity to the amino acid sequence of SEQ ID NO:8. In some embodiments, the IL-22 Fc fusion protein comprises an amino acid sequence having at least 97% sequence identity to the amino acid sequence of SEQ ID NO:8. In some embodiments, the IL-22 Fc fusion protein comprises an amino acid sequence having at least 98% sequence identity to the amino acid sequence of SEQ ID NO:8. In some embodiments, the IL-22 Fc fusion protein comprises an amino acid sequence having at least 99% sequence identity to the amino acid sequence of SEQ ID NO:8. In some embodiments, the IL-22 Fc fusion protein comprises the amino acid sequence of SEQ ID NO:8, SEQ ID NO:10, or SEQ ID NO:16. In some embodiments, the IL-22 Fc fusion protein comprises the amino acid sequence of SEQ ID NO:8. In some embodiments, the IL-22 Fc fusion protein consists of the amino acid sequence of SEQ ID NO:8. In some embodiments, the IL-22 Fc fusion protein comprises the amino acid sequence of SEQ ID NO:10. In some embodiments, the IL-22 Fc fusion protein consists of the amino acid sequence of SEQ ID NO:10. In some embodiments, the IL-22 Fc fusion protein comprises the amino acid sequence of SEQ ID NO:16. In some embodiments, the IL-22 Fc fusion protein consists of the amino acid sequence of SEQ ID NO:16. In some embodiments, the Fc region is not N-glycosylated.

In some embodiments of any of the preceding aspects, the IL-22 Fc fusion protein is a dimeric IL-22 Fc fusion protein. In other embodiments of any of the preceding aspects, the IL-22 Fc fusion protein is a monomeric IL-22 Fc fusion protein.

In some embodiments of any of the preceding aspects, the IL-22 polypeptide is a human IL-22 polypeptide. In some embodiments, the IL-22 polypeptide comprises the amino acid sequence of SEQ ID NO:4.

In some embodiments of any of the preceding aspects, the linker comprises the amino acid sequence RVESKYGPP (SEQ ID NO: 44). In some embodiments, the linker consists of the amino acid sequence RVESKYGPP (SEQ ID NO: 44).

In another aspect, the invention features a pharmaceutical composition comprising an IL-22 Fc fusion protein and a carrier, the IL-22 Fc fusion protein comprising the amino acid sequence of SEQ ID NO:8, wherein the pharmaceutical composition comprises about 5 mM methionine, about 10 mM sodium phosphate, about 240 mM sucrose, and about 0.02% (w/v) polysorbate 20, pH 7.1, final concentration.

In some embodiments of any of the preceding aspects, the IL-22 Fc fusion protein binds to IL-22 receptor. In some embodiments, the IL-22 receptor is human IL-22 receptor. In some embodiments, the IL-22 Fc fusion protein binds to IL-22R1 and/or IL-10R2. In some embodiments, the IL-22 Fc fusion protein binds to IL-22R1. In some embodiments, the human IL-22 receptor comprises a heterodimer consisting of an IL-22R1 polypeptide and an IL-10R2 polypeptide. In some embodiments, the IL-22R1 polypeptide comprises the amino acid sequence of SEQ ID NO:82 and the IL-10R2 polypeptide comprises the amino acid sequence of SEQ ID NO:84.

In some embodiments of any of the preceding aspects, the pharmaceutical composition further comprises an additional therapeutic agent.

In some embodiments of any of the preceding aspects, the pharmaceutical composition further comprises a gelling agent. In some embodiments, the gelling agent is a polysaccharide. In some embodiments, the gelling agent is a cellulosic agent. In some embodiments, the gelling agent is methylcellulose, hydroxyethyl cellulose, carboxymethyl cellulose, hydroxypropyl cellulose, POE-POP block polymers, alginate, hyaluronic acid, polyacrylic acid, hydroxyethyl methylcellulose or hydroxypropyl methylcellulose. In some embodiments, the gelling agent is hydroxypropyl methylcellulose. In some embodiments, the pharmaceutical formulation is for topical administration.

In some embodiments of any of the preceding aspects, the pharmaceutical composition is for use as a medicament.

In another aspect, the invention features a method of treating inflammatory bowel disease (IBD) in a subject in need thereof, the method comprising administering to the subject any of the pharmaceutical compositions described herein. In some embodiments, the IBD is ulcerative colitis or Crohn's disease. In some embodiments, the IBD is ulcerative colitis. In some embodiments, the ulcerative colitis is moderate to severe ulcerative colitis. In some embodiments, the IBD is Crohn's disease.

In another aspect, the invention features a method of inhibiting microbial infection in the intestine, preserving goblet cells in the intestine during a microbial infection, enhancing epithelial cell integrity, epithelial cell proliferation, epithelial cell differentiation, epithelial cell migration or epithelial wound healing in the intestine, of a subject in need thereof, the method comprising administering to the subject any of the pharmaceutical compositions described herein. In some embodiments, the epithelial cell is an intestinal epithelial cell.

In another aspect, the invention features a method of treating acute kidney injury or acute pancreatitis in a subject in need thereof, the method comprising administering to the subject any of the pharmaceutical compositions described herein.

In another aspect, the invention features a method of accelerating or improving wound healing in a subject in need thereof, the method comprising administering to the subject any of the pharmaceutical compositions described herein. In some embodiments, the wound is a chronic wound or an infected wound.

In some embodiments, the subject is diabetic. In some embodiments, the diabetic subject has type II diabetes. In some embodiments, the wound is a diabetic foot ulcer. In some embodiments, the IL-22 Fc fusion protein or the pharmaceutical composition is administered until there is complete wound closure.

In another aspect, the invention features a method for preventing or treating a cardiovascular condition in a subject in need thereof, which condition includes a pathology of atherosclerotic plaque formation, the method comprising administering to the subject any of the pharmaceutical compositions described herein. In some embodiments, the cardiovascular disease is coronary artery disease, coronary microvascular disease, stroke, carotid artery disease, peripheral artery disease, or chronic kidney disease. In some embodiments, the method further comprises slowing down the progression of atherosclerotic plaque formation or preventing indicia of atherosclerosis. In some embodiments, the indicia of atherosclerosis includes plaque accumulation or vascular inflammation.

In another aspect, the invention features a method for treating metabolic syndrome in a subject in need thereof, the method comprising administering to the subject any of the pharmaceutical compositions described herein. In some embodiments, the method further comprises reducing one or more risk factors associated with metabolic syndrome, including one or more of abdominal obesity, hyperglycemia, dyslipidemia, and hypertension. In some embodiments, the method further comprises reducing the level of bacterial lipopolysaccharide in the subject.

In another aspect, the invention features a method of treating acute endotoxemia, sepsis, or both, in a subject in need thereof, the method comprising administering the subject any of the pharmaceutical compositions described herein. In some embodiments, the subject is in need of a change in HDL/LDL lipid profile.

In another aspect, the invention features a method of treating GVHD in a subject in need thereof, the method comprising administering to the subject any of the pharmaceutical compositions described herein.

In some embodiments of any of the preceding aspects, the composition comprises about 1 mg/mL to about 10 mg/mL IL-22 Fc fusion protein, about 10 mM sodium phosphate, about 240 mM sucrose, about 5 mM methionine, and about 0.02% (w/v) polysorbate 20, pH 7.1, final concentration.

In some embodiments of any of the preceding aspects, the IL-22 Fc fusion protein comprises or consists of the amino acid sequence of SEQ ID NO:8, SEQ ID NO:10, or SEQ ID NO:16. In some embodiments, the IL-22 Fc fusion protein comprises the amino acid sequence of SEQ ID NO:8. In some embodiments, the IL-22 Fc fusion protein comprises the amino acid sequence of SEQ ID NO:16.

In some embodiments of any of the preceding aspects, the pharmaceutical composition is administered intravenously, subcutaneously, intraperitoneally, or topically. In some embodiments, the pharmaceutical composition is administered intravenously. In some embodiments, the pharmaceutical composition is administered subcutaneously.

In some embodiments of any of the preceding aspects, the subject is co-administered with at least one additional therapeutic agent. In some embodiments, the subject is a human.

In another aspect, any of the pharmaceutical compositions described herein can be used in a method of treating IBD in a subject in need thereof. In some embodiments, the IBD is ulcerative colitis or Crohn's disease. In some embodiments, the IBD is ulcerative colitis. In some embodiments, the ulcerative colitis is moderate to severe ulcerative colitis. In some embodiments, the IBD is Crohn's disease.

In another aspect, any of the pharmaceutical compositions described herein can be used in a method of inhibiting microbial infection in the intestine, preserving goblet cells in the intestine during a microbial infection, enhancing epithelial cell integrity, epithelial cell proliferation, epithelial cell differentiation, epithelial cell migration or epithelial wound healing in the intestine, of a subject in need thereof. In some embodiments, the epithelial cell is an intestinal epithelial cell.

In another aspect, any of the pharmaceutical compositions described herein can be used in a method of treating acute kidney injury or acute pancreatitis in a subject in need thereof.

In another aspect, any of the pharmaceutical compositions described herein can be used in a method of accelerating or improving wound healing in a subject in need thereof. In some embodiments, the wound is a chronic wound or an infected wound. In some embodiments, the subject is diabetic. In some embodiments, the diabetic subject has type II diabetes. In some embodiments, the wound is a diabetic foot ulcer. In some embodiments, the IL-22 Fc fusion protein or the pharmaceutical composition is administered until there is complete wound closure.

In another aspect, any of the pharmaceutical compositions described herein can be used in a method for preventing or treating a cardiovascular condition in a subject in need thereof, which condition includes a pathology of atherosclerotic plaque formation. In some embodiments, the cardiovascular disease is coronary artery disease, coronary microvascular disease, stroke, carotid artery disease, peripheral artery disease, or chronic kidney disease. In some embodiments, the method comprises slowing down the progression of atherosclerotic plaque formation or preventing indicia of atherosclerosis. In some embodiments, the indicia of atherosclerosis include plaque accumulation and/or vascular inflammation.

In another aspect, any of the pharmaceutical compositions described herein can be used in a method for treating metabolic syndrome in a subject in need thereof. In some embodiments, the method further comprises reducing one or more risk factors associated with metabolic syndrome, including one or more of abdominal obesity, hyperglycemia, dyslipidemia, and hypertension. In some embodiments, the method further comprises reducing the level of bacterial lipopolysaccharide in the subject.

In another aspect, any of the pharmaceutical compositions described herein can be used in a method of treating acute endotoxemia, sepsis, or both, in a subject in need thereof.

In another aspect, any of the pharmaceutical compositions described herein can be used in a method of treating GVHD in a subject in need thereof.

In some embodiments of any of the preceding aspects, the subject is in need of a change in HDL/LDL lipid profile.

In some embodiments of any of the preceding aspects, the pharmaceutical composition comprises about an IL-22 Fc fusion protein (e.g., at a concentration of about 1 mg/mL to about 10 mg/mL), about 10 mM sodium phosphate, about 240 mM sucrose, about 5 mM methionine, and about 0.02% (w/v) polysorbate 20, pH 7.1, final concentration. In some embodiments, the IL-22 Fc fusion protein comprises the amino acid sequence of SEQ ID NO:8, SEQ ID NO:10, or SEQ ID NO:16. In some embodiments, the IL-22 Fc fusion protein comprises the amino acid sequence of SEQ ID NO:8. In some embodiments, the IL-22 Fc fusion protein comprises the amino acid sequence of SEQ ID NO:16.

In some embodiments of any of the preceding aspects, the pharmaceutical composition is administered intravenously, subcutaneously, intraperitoneally, or topically. In some embodiments, the IL-22 Fc fusion protein or the pharmaceutical composition is administered intravenously. In some embodiments, the IL-22 Fc fusion protein or the pharmaceutical composition is administered subcutaneously.

In some embodiments of any of the preceding aspects, the subject is to be co-administered with at least one additional therapeutic agent. In some embodiments of any of the preceding aspects, the subject is a human.

Each and every embodiment can be combined unless the context clearly suggests otherwise. Each and every embodiment can be applied to each and every aspect of the invention unless the context clearly suggests otherwise.

Specific embodiments of the present invention will become evident from the following more detailed description of certain preferred embodiments and the claims.

BRIEF DESCRIPTION OF THE DRAWINGS

FIG. 3C is a graph showing the DSC and Trp fluorescence profiles of IL-22 Fc fusion protein in 10 mM histidine acetate at pH 6.5.

FIG. 3D is a graph showing the DSC and Trp fluorescence profiles of IL-22 Fc fusion protein in 10 mM histidine acetate at pH 7.0.

FIG. 9 shows an amino acid sequence alignment of mature IL-22 from different mammalian species: human (GenBank Accession No. Q9GZX6, SEQ ID NO:4, chimpanzee (GenBank Accession No. XP_003313906, SEQ ID NO:48), orangutan (GenBank Accession No. XP_002823544, SEQ ID NO:49), mouse (GenBank Accession No. Q9JJY9, SEQ ID NO:50), and dog (GenBank Accession No. XP_538274, SEQ ID NO:51).

DETAILED DESCRIPTION OF EMBODIMENTS OF THE INVENTION

I. Definitions

Figure 1:
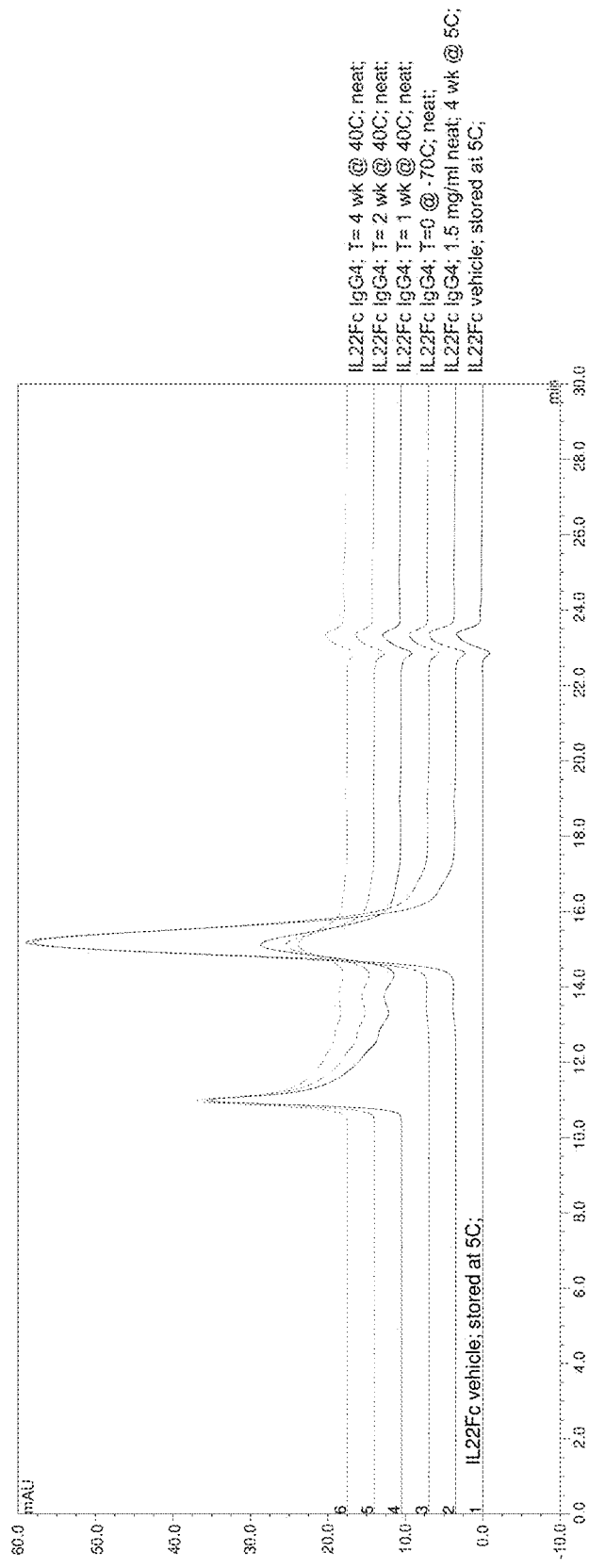
FIG. 1 is a chromatogram showing an overlay of size exclusion high-performance liquid chromatography (SE-HPLC) of an IL-22 Fc fusion protein pharmaceutical composition including 10 mg/mL in 20 mM histidine acetate, 240 mM sucrose, 0.02% polysorbate 20 (PS20) (w/v) at pH 5.5 after 4 weeks at 40° C. and 5° C.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The term "about" as used herein refers to the usual error range for the respective value readily known to the skilled person in this technical field. Reference to "about" a value or parameter herein includes (and describes) embodiments that are directed to that value or parameter per se.

As used herein, the singular forms "a," "an," and "the" include plural referents unless the context clearly dictates otherwise. For example, reference to "an isolated peptide" means one or more isolated peptides.

Throughout this specification and claims, the word "comprise," or variations such as "comprises" or "comprising" will be understood to imply the inclusion of a stated integer or group of integers but not the exclusion of any other integer or group of integers.

The term "IL-22 Fc fusion protein" or "IL-22 fusion protein" or "IL-22 Ig fusion protein" as used herein refers to a fusion protein in which IL-22 protein or polypeptide is linked, directly or indirectly, to an IgG Fc region. In some embodiments, the IL-22 protein or polypeptide is glycosylated. In certain preferred embodiments, the IL-22 Fc fusion protein comprises a human IL-22 protein or polypeptide linked to a human IgG Fc region. In certain embodiments, the human IL-22 protein comprises the amino acid sequence of SEQ ID NO:4. However, it is understood that minor sequence variations such as insertions, deletions, substitutions, especially conservative amino acid substitutions of IL-22 or Fc that do not affect the function and/or activity of IL-22 or IL-22 Fc fusion protein are also contemplated by the invention. The IL-22 Fc fusion protein of the invention can bind to IL-22 receptor, which can lead to IL-22 receptor downstream signaling. In certain embodiments, the IL-22 Fc fusion protein is capable of binding to IL-22 receptor, and/or is capable of leading to IL-22 receptor downstream signaling. The functions and/or activities of the IL-22 Fc fusion protein can be assayed by methods known in the art, including without limitation, ELISA, ligand-receptor binding assay and Stat3 luciferase assay. In certain embodiments, the invention provides an IL-22 Fc fusion protein that binds to IL-22 receptor, in which the binding can lead to IL-22 receptor downstream signaling, the IL-22 Fc fusion protein comprising an amino acid sequence having at least 95% sequence identity to the amino acid sequence selected from the group consisting of SEQ ID NO:8, SEQ ID NO:10, SEQ ID NO:12, SEQ ID NO:14, and SEQ ID NO:16, and wherein the Fc region is not glycosylated. In certain particular embodiments, the Fc region of the IL-22 fusion protein does not possess effector activities (e.g., does not bind to FcγIIIR) or exhibits substantially lower effector activity than a whole (e.g., wild-type) IgG antibody. In certain other embodiments, the Fc region of the IL-22 Fc fusion protein does not trigger cytotoxicity such as antibody-dependent cellular cytotoxicity (ADCC) or complement dependent cytotoxicity (CDC). Unless otherwise specified, "IL-22 fusion protein," "IL-22 Fc fusion," "IL-22 Ig fusion protein," "IL-22 Fc fusion protein," or "IL-22 Fc" are used interchangeably throughout this application.

The term "IL-22" or "IL-22 polypeptide" or "IL-22 protein" as used herein, broadly refers to any native IL-22 from any mammalian source, including primates (e.g. humans) and rodents (e.g., mice and rats), unless otherwise indicated. The term encompasses "full-length," unprocessed IL-22 as well as any forms of IL-22 that result from processing in the cell. For example, both full-length IL-22 containing the N-terminal leader sequence and the mature form IL-22 are encompassed by the current invention. The leader sequence (or signal peptide) can be the endogenous IL-22 leader sequence or an exogenous leader sequence of another mammalian secretary protein. In certain embodiments, the leader sequence can be from a eukaryotic or prokaryotic secretary protein. The term also encompasses naturally occurring variants of IL-22, e.g., splice variants or allelic variants. The amino acid sequence of an exemplary human IL-22 is shown in SEQ ID NO:4 (mature form, without a signal peptide). In certain embodiments, the amino acid sequence of full-length IL-22 protein with the endogenous leader sequence is provided in SEQ ID NO:71; while in other embodiments, the amino acid sequence of mature IL-22 protein with an exogenous leader sequence is provided in SEQ ID NO:2. Minor sequence variations, especially conservative amino acid substitutions of IL-22 that do not affect the IL-22's function and/or activity (e.g., binding to IL-22 receptor), are also contemplated by the invention. FIG. 9 shows an amino acid sequence alignment of mature IL-22 from several exemplary mammalian species. The asterisks indicate highly conserved amino acid residues across species that are likely important for the functions and/or activities of IL-22. Accordingly, in certain embodiments, the IL-22 Fc fusion protein comprises an IL-22 polypeptide comprising an amino acid sequence having at least 95%, at least 96%, at least 97%, at least 98%, or at least 99% sequence identity to SEQ ID NO:4. In certain other embodiments, the IL-22 protein has 95% or more sequence identity to SEQ ID NO:71, 96% or more sequence identity to SEQ ID NO:71, 97% or more sequence identity to SEQ ID NO:71; 98% or more sequence identity to SEQ ID NO:71; or 99% or more sequence identity to SEQ ID NO:71. The IL-22 polypeptides described herein can be isolated from a variety of sources, such as from human tissue or from another source, or prepared by recombinant or synthetic methods.

The term "IL-22 receptor" or "IL-22R" refers to a heterodimer consisting of IL-22R1 and IL-10R2 or naturally occurring allelic variants thereof. See, e.g., Ouyang et al., 2011, Annu. Rev. Immunol. 29:159-63. IL-10R2 is ubiquitously expressed by many cell types, and IL-22R1 is expressed only in innate cells such as epithelial cells, hepatocytes and keratinocytes. IL-22R1 is also known as IL-22Rα1 or IL-22Rα1. IL-22R1 may be paired with other polypeptides to form heterodimeric receptors for other IL-10 family members, for example IL-20 or IL-24. See, e.g., Ouyang et al., 2011, supra. The full-length amino acid sequence of an exemplary IL-22R1 polypeptide is shown in SEQ ID NO:81. This full-length sequence of IL-22R1 includes an N-terminal signal sequence (amino acids 1-15) which is cleaved in the final functional molecule (an exemplary amino acid sequence of which is shown in SEQ ID NO:82). The full-length amino acid sequence of an exemplary IL10R2 polypeptide is shown in SEQ ID NO:83. This full-length sequence of IL10R2 includes an N-terminal signal sequence (amino acids 1-19) which is cleaved in the final functional molecule (an exemplary amino acid sequence of which is shown in SEQ ID NO:84).

A "native sequence IL-22 polypeptide" or a "native sequence IL-22R polypeptide" refers to a polypeptide comprising the same amino acid sequence as a corresponding IL-22 or IL-22R polypeptide derived from nature. Such native sequence IL-22 or IL-22R polypeptides can be isolated from nature or can be produced by recombinant or synthetic means. The terms specifically encompass naturally-occurring truncated or secreted forms of the specific IL-22 or IL-22R polypeptide (e.g., an IL-22 lacking its associated signal peptide), naturally-occurring variant forms (e.g., alternatively spliced forms), and naturally-occurring allelic variants of the polypeptide. In various embodiments of the invention, the native sequence IL-22 or IL-22R polypeptides disclosed herein are mature or full-length native sequence polypeptides. An exemplary full length native human IL-22 is shown in SEQ ID NO:70 (DNA) and SEQ ID NO:71 (protein). While the IL-22 and IL-22R polypeptide sequences are shown to begin with methionine residues designated herein as amino acid position 1, it is conceivable and possible that other methionine residues located either upstream or downstream from the amino acid position 1 can be employed as the starting amino acid residue for the IL-22 or IL-22R polypeptides.

An "IL-22 variant," an "IL-22R variant," an "IL-22 variant polypeptide," or an "IL-22R variant polypeptide" means an active IL-22 or IL-22R polypeptide as defined above having at least about 80% amino acid sequence identity with a full-length native sequence IL-22 or IL-22R polypeptide sequence. Ordinarily, an IL-22 or IL-22R polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity, and alternatively at least about 99% amino acid sequence identity to a full-length or mature native sequence IL-22 or IL-22R polypeptide sequence.

The term "Fc region," "Fc domain," or "Fc" refers to a C-terminal non-antigen binding region of an immunoglobulin heavy chain that contains at least a portion of the constant region. The term includes native Fc regions and variant Fc regions. In certain embodiments, a human IgG heavy chain Fc region extends from Cys226 to the carboxyl-terminus of the heavy chain. However, the C-terminal lysine (Lys447) of the Fc region may or may not be present, without affecting the structure or stability of the Fc region. Unless otherwise specified herein, numbering of amino acid residues in the IgG or Fc region is according to the EU numbering system for antibodies, also called the EU index, as described in Kabat et al., *Sequences of Proteins of Immunological Interest*, 5th Ed. Public Health Service, National Institutes of Health, Bethesda, MD, 1991.

In certain embodiments, Fc region refers to an immunoglobulin IgG heavy chain constant region comprising a hinge region (starting at Cys226), an IgG CH2 domain, and CH3 domain. The term "hinge region" or "hinge sequence" as used herein refers to the amino acid sequence located between the linker and the CH2 domain. In certain embodiments, the hinge region comprises the amino acid sequence CPPCP (SEQ ID NO:31). In certain embodiments, the hinge region for IL-22 IgG4 Fc fusion protein comprises the CPPCP sequence (SEQ ID NO:31), a sequence found in the native IgG1 hinge region, to facilitate dimerization. In certain other embodiments, the Fc region starts at the hinge region and extends to the C-terminus of the IgG heavy chain. In certain particular embodiments, the Fc region comprises the Fc region of human IgG1, IgG2, IgG3 or IgG4. In certain particular embodiments, the Fc region comprises the CH2 and CH3 domain of IgG4. In certain other particular embodiments, the Fc region comprises the CH2 and CH3 domain of IgG1.

In certain embodiments, the IgG CH2 domain starts at Ala 231. In certain other embodiments, the CH3 domain starts at Gly 341. It is understood that the C-terminus Lys residue of human IgG can be optionally absent. It is also understood that conservative amino acid substitutions of the Fc region without affecting the desired structure and/or stability of Fc is contemplated within the scope of the invention.

In certain embodiments, the IL-22 is linked to the Fc region via a linker. In certain particular embodiments, the linker is a peptide that connects the C-terminus of IL-22 to the Fc region as described herein. In certain embodiments, native IgG sequences are present in the linker and/or hinge region to minimize and/or avoid the risk of immunogenicity. In other embodiments, minor sequence variations can be introduced to the native sequences to facilitate manufacturing. IL-22 Fc fusion constructs comprising exogenous linker or hinge sequences that exhibit high activity (as measured, e.g., by a luciferase assay) are also within the scope of the invention. In certain embodiments, the linker comprises an amino acid sequence that is 8-20 amino acids, 8-16, 8-15, 8-14, 8-13, 8-12, 8-11, 8-10, 8-9, 10-11, 10-12, 10-13, 10-14, 10-15, 10-16, 11-16, 8, 9, 10, 11, 12, 13, 14, 15, or 16 amino acids long. In certain other embodiments, the linker comprises the amino acid sequence DKTHT (SEQ ID NO:32). In certain particular embodiments, the linker does not comprise the sequence Gly-Gly-Ser (SEQ ID NO:45), Gly-Gly-Gly-Ser (SEQ ID NO:46), or Gly-Gly-Gly-Gly-Ser (SEQ ID NO:47).

In certain embodiments, the IL-22 Fc fusion protein comprises an IL-22 polypeptide linked to an Fc region by a linker. The term "linked to" or "fused to" refers to a covalent bond, e.g., a peptide bond, formed between two moieties.

The terms "glycosylation" and "glycosylated" as used herein refers to the presence of a carbohydrate (e.g., an oligosaccharide or a polysaccharide, also referred to as a "glycan") attached to biological molecule (e.g., a protein or a lipid). In particular embodiments, glycosylation refers to the presence of a glycan (e.g., an N-glycan) attached to a protein (e.g., an IL-22 Fc fusion protein) or a portion of a protein of interest (e.g., an IL-22 polypeptide moiety of an IL-22 Fc fusion protein). N-linked glycosylation refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine can also be involved in O-linked glycosylation. For a review of glycosylation, see, e.g., Varki et al., *Essentials of Glycobiology*, 3$^{rd}$ *Edition*, Cold Spring Harbor Laboratory Press, 2015-2017.

The terms "aglycosylated" and "not glycosylated," as used interchangeably herein, refer to a protein or a portion of a protein of interest (e.g., the Fc region of an IL-22 Fc fusion protein) that is not glycosylated (e.g., not N-glycosylated). It is to be understood that in some embodiments, a portion of a protein of interest (e.g., an IL-22 Fc fusion protein) is glycosylated (e.g., the IL-22 polypeptide portion of an IL-22 Fc fusion protein), while another portion of the protein of interest is not glycosylated (e.g., the Fc region of the IL-22 Fc fusion protein).

In some embodiments, provided herein are IL-22 Fc fusion proteins in which the Fc region or CH2 domain is not glycosylated. In certain embodiments, the N-glycosylation site in the CH2 domain is mutated to prevent glycosylation. For example, an IL-22 Fc fusion protein with an aglycosylated Fc region can be made by mutagenizing the amino acid residue at position 297 as in the EU index in the CH2 domain of the Fc region (e.g., N297). In certain embodiments, the glycosylation in the CH2 domain of the Fc region can be eliminated by altering the glycosylation consensus site, i.e., Asn at position 297 followed by any amino acid residue (in the case of human IgG, Ser) and Thr. The glycosylation site can be altered by amino acid insertions, deletions, and/or substitutions. For example, one or more amino acid residues can be inserted between Asn and Ser or between Ser and Thr to alter the original glycosylation site, wherein the insertions do not regenerate an N-glycosylation site. In certain particular embodiments, the amino acid residue at position 297 as in the EU index (e.g., the N-glycosylated site in Fc) within the CH2 domain of human IgG Fc is mutated to abolish the glycosylation site. In certain particular embodiments, the amino acid residue at position 297 as in the EU index (e.g., N297) is changed to Gly, Ala, Gln, Asp, or Glu. In some particular embodiments, the amino acid residue at position 297 as in the EU index (e.g., N297) is changed to Gly or Ala. In other particular embodiments, the amino acid residue at position 297 as in the EU index (e.g., N297) is changed to Gly. In certain other embodiments, the amino acid residue at position 299 as in the EU index can be substituted with another amino acid, for example, Ala, Val, or Gly. In certain particular embodiments, the mutations that result in an aglycosylated Fc do not affect the structure and/or stability of the IL-22 Fc fusion protein.

In certain embodiments, the IL-22 Fc fusion protein comprises an Fc region in which the amino acid residue at position 297 as in the EU index in the CH2 domain is mutated. In certain embodiments, the amino acid residue at position 297 as in the EU index is changed to Gly or Ala, preferably to Gly. In certain other embodiments, the amino acid residue at position 297 as in the EU index is deleted. In certain embodiments, the IL-22 Fc fusion protein comprising an Fc having an amino acid substitution at the amino acid residue at position 297 as in the EU index is aglycosylated or not glycosylated.

In other embodiments, the N-glycan attached to the wild type amino acid residue at position 297 as in the EU index (e.g., N297) can be removed enzymatically, e.g., by deglycosylation. Suitable glycolytic enzymes include without limitation, peptide-N-glycosidase (PNGase).

The term "afucosylation," "afucosylated," "defucosylation," or "defucosylated" refers to the absence or removal of core-fucose from an N-glycan, e.g., an N-glycan attached to a protein or a portion of a protein (e.g., the CH2 domain of Fc).

The term "dimeric IL-22 Fc fusion protein" refers to a dimer in which each monomer comprises an IL-22 Fc fusion protein. The term "monomeric IL-22 Fc fusion protein" refers to a dimer in which one monomer comprises an IL-22 Fc fusion protein (the IL-22 Fc arm), while the other monomer comprises an Fc region without the IL-22 polypeptide (the Fc arm). Accordingly, the dimeric IL-22 Fc fusion protein is bivalent with respect to IL-22R binding, whereas the monomeric IL-22 Fc fusion protein is monovalent with respect to IL-22R binding. The heterodimerization of the monomeric IL-22 Fc fusion protein can be facilitated by methods known in the art, including without limitation, heterodimerization by the knob-into-hole technology. The structure and assembly method of the knob-into-hole technology can be found in, e.g., U.S. Pat. Nos. 5,821,333, 7,642,228, US 2011/0287009, and PCT/US2012/059810, hereby incorporated by reference in their entireties. This technology was developed by introducing a "knob" (or a protuberance) by replacing a small amino acid residue with a large one in the CH3 domain of one Fc, and introducing a "hole" (or a cavity) in the CH3 domain of the other Fc by replacing one or more large amino acid residues with smaller ones. In certain embodiments, the IL-22 Fc fusion arm comprises a knob, and the Fc only arm comprises a hole.

The preferred residues for the formation of a knob are generally naturally occurring amino acid residues and are preferably selected from arginine (R), phenylalanine (F), tyrosine (Y), and tryptophan (W). Most preferred are tryptophan and tyrosine. In one embodiment, the original residue for the formation of the knob has a small side chain volume, such as alanine, asparagine, aspartic acid, glycine, serine, threonine or valine. Exemplary amino acid substitutions in the CH3 domain for forming the knob include without limitation the T366W, T366Y, or F405W substitution.

The preferred residues for the formation of a hole are usually naturally occurring amino acid residues and are preferably selected from alanine (A), serine (S), threonine (T), and valine (V). In one embodiment, the original residue for the formation of the hole has a large side chain volume, such as tyrosine, arginine, phenylalanine, or tryptophan. Exemplary amino acid substitutions in the CH3 domain for generating the hole include without limitation the T366S, L368A, F405A, Y407A, Y407T, and Y407V substitutions. In certain embodiments, the knob comprises T366W substitution, and the hole comprises the T366S/L368A/Y407V substitutions. In certain particular embodiments, the Fc region of the monomeric IL-22 Fc fusion protein comprises an IgG1 Fc region. In certain particular embodiments, the monomeric IL-22 IgG1 Fc fusion comprises an IL-22 Fc knob arm and an Fc hole arm. In certain embodiments, the IL-22 Fc knob arm comprises a T366W substitution (SEQ ID NO:61), and the Fc hole arm comprises T366S, L368A, and Y407V (SEQ ID NO:62). In certain other embodiments, the Fc region of both arms further comprises an N297G or N297A mutation. In certain embodiments, the monomeric IL-22 Fc fusion protein is expressed in E. coli cells. It is understood that other modifications to the Fc region known in the art that facilitate heterodimerization are also contemplated and encompassed by the instant application.

The term "wound" refers to an injury, especially one in which the skin or another external surface is torn, pierced, cut, or otherwise broken.

The term "ulcer" is a site of damage to the skin or mucous membrane that is often characterized by the formation of pus, death of tissue, and is frequently accompanied by an inflammatory reaction.

The terms "intestine" or "gut" as used interchangeably herein broadly encompasses the small intestine and large intestine.

The term "accelerating wound healing" or "acceleration of wound healing" refers to the increase in the rate of healing, e.g., a reduction in time until complete wound closure occurs or a reduction in time until a percent (%) reduction in wound area occurs.

A "diabetic wound" is a wound that associated with diabetes.

A "diabetic ulcer" is an ulcer that is associated with diabetes.

A "chronic wound" refers to a wound that does not heal. See, e.g., Lazarus et al., Definitions and guidelines for assessment of wounds and evaluation of healing, Arch. Dermatol. 130:489-93 (1994). Chronic wounds include, but are not limited to, e.g., arterial ulcers, diabetic ulcers, pressure ulcers or bed sores, venous ulcers, and the like. An acute wound can develop into a chronic wound. Acute wounds include, but are not limited to, wounds caused by, e.g., thermal injury (e.g., burn), trauma, surgery, excision of extensive skin cancer, deep fungal and bacterial infections, vasculitis, scleroderma, pemphigus, toxic epidermal necrolysis, and the like. See, e.g., Buford, Wound Healing and Pressure Sores, HealingWell.com, published on: Oct. 24, 2001. Thus, in certain embodiments, a chronic wound is an infected wound. A "normal wound" refers to a wound that undergoes normal wound healing repair.

"Affinity" refers to the strength of the sum total of non-covalent interactions between a single binding site of a molecule (e.g., a ligand or an antibody) and its binding partner (e.g., a receptor or an antigen). Unless indicated otherwise, as used herein, "binding affinity" refers to intrinsic binding affinity which reflects a 1:1 interaction between members of a binding pair (e.g., IL-22 Fc fusion protein and IL-22 receptor). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and multispecific antibodies formed from antibody fragments.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called $\alpha$, $\delta$, $\varepsilon$, $\gamma$, and $\mu$, respectively.

"Effector functions" or "effector activities" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation. In certain embodiments, the IL-22 Fc fusion protein does not exhibit any effector function or any detectable effector function. In certain other embodiments, the IL-22 Fc fusion protein exhibits substantially reduced effector function, e.g., about 50%, 60%, 70% 80%, or 90% reduced effector function.

An "effective amount" or "therapeutically effective amount" of an agent, e.g., a pharmaceutical formulation, refers to an amount effective, at dosages and for periods of time necessary, to achieve the desired therapeutic or prophylactic result.

For example, in the case of a cardiovascular disease or condition, the therapeutically effective amount of the IL-22 Fc fusion protein can reduce the degree of atherosclerotic plaque formation; reduce the size of the atherosclerotic plaque(s); inhibit (i.e., slow to some extent and preferably stop) atherosclerotic plaque; inhibit (i.e., slow to some extent and preferably stop) thrombosis or rupture of an atherosclerotic plaque; and/or relieve to some extent one or more of the symptoms associated with the disease or condition.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of atherosclerotic plaques, or the number of atherosclerotic plaque(s).

A "suboptimal amount" refers to the amount less than the optimal amount of a therapeutic agent typically used for a certain treatment. When two therapeutic agents are given to a subject, either concurrently or sequentially, each therapeutic agent can be given at a suboptimal amount as compared to the treatment when each therapeutic agent is given alone. For example, in certain embodiments, the subject in need of IBD treatment is administered with the pharmaceutical composition comprising the IL-22 Fc fusion protein of the invention and a dexamethasone at a suboptimal amount.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. The transformed cell includes transiently or stably transformed cell. Progeny may not be completely identical in nucleic acid content to a parent cell, but may contain mutations. Mutant progeny that have the same function or biological activity as screened or selected for in the originally transformed cell are included herein. In certain embodiments, the host cell is transiently transfected with the exogenous nucleic acid. In certain other embodiments, the host cell is stably transfected with the exogenous nucleic acid.

An "immunoconjugate" is an antibody or a fragment of an antibody conjugated to one or more heterologous molecule(s), including but not limited to a cytotoxic agent.

An "individual," "subject," or "patient" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual, subject or patient is a human.

An "isolated" IL-22 Fc fusion protein is one which has been separated from the environment of a host cell that recombinantly produces the fusion protein. In some embodiments, an IL-22 Fc fusion protein is purified to greater than 80%, 85%, 90%, 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC) approaches.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "isolated nucleic acid encoding an IL-22 Fc fusion protein" refers to one or more nucleic acid molecules encoding an IL-22 Fc fusion protein, including such nucleic acid molecule(s) in a single vector or separate vectors, such nucleic acid molecule(s) transiently or stably transfected into a host cell, and such nucleic acid molecule(s) present at one or more locations in a host cell.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "native sequence Fc region" comprises an amino acid sequence identical to the amino acid sequence of an Fc region found in nature. Native sequence human Fc regions include, without limitation, a native sequence human IgG1 Fc region (non-A and A allotypes); native sequence human IgG2 Fc region; native sequence human IgG3 Fc region; and native sequence human IgG4 Fc region, as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith. In certain embodiments, the variant Fc region is not glycosylated.

A "disorder," a "disease," or a "condition," as used interchangeably herein, is any condition that would benefit from treatment with a composition (e.g., a pharmaceutical composition) described herein, e.g., a composition (e.g., a pharmaceutical composition) that includes an IL-22 Fc fusion protein. This includes chronic and acute disorders or diseases including those pathological conditions which predispose the mammal to the disorder in question. In some embodiments, the disorder an IL-22 associated disorder. Exemplary disorders include, but are not limited to, IBD (e.g., UC or Crohn's disease), microbial infection, acute kidney injury, acute pancreatitis, wounds, cardiovascular conditions, metabolic syndrome, acute endotoxemia, and sepsis.

The terms "inflammatory bowel disorder," "inflammatory bowel disease," or "IBD," as used interchangeably herein, are used herein in the broadest sense and includes all diseases and pathological conditions the pathogenesis of which involves recurrent inflammation in the intestine, including small intestine and colon. IBD includes, e.g., ulcerative colitis (UC) and Crohn's disease. IBD is not limited to UC and CD. The manifestations of the disease include but not limited to inflammation and a decrease in epithelial integrity in the intestine.

The terms "cardiovascular disease" or "cardiovascular disorder" are used herein in the broadest sense and includes all diseases and pathological conditions the pathogenesis of which involves abnormalities of the blood vessels, such as, for example, atherosclerotic plaque formation (including stable or unstable/vulnerable plaques), atherosclerosis, arteriosclerosis, arteriolosclerosis, and elevated systemic lipopolysaccharide (LPS) exposure. The term additionally includes diseases and pathological conditions that benefit from the inhibition of the formation of atherosclerotic plaques. Cardiovascular diseases include, without limitation, coronary artery atherosclerosis, coronary microvascular disease, stroke, carotid artery disease, peripheral arterial disease, ischemia, coronary artery disease (CAD), acute coronary syndrome (ACS), coronary heart disease (CHD), conditions associated with CAD and CHD, cerebrovascular disease, peripheral vascular disease, aneurysm, vasculitis, venous thrombosis, diabetes mellitus, metabolic syndromechronic kidney disease, remote tissue injury after ischemia and reperfusion, and cardiopulmonary bypass. Specifically included within this group are all cardiovascular diseases associated with the occurrence, development, or progression of which can be controlled by the inhibition of the atherosclerotic plaque formation.

The term "cardiovascular condition" is used herein in the broadest sense and includes all cardiovascular conditions and diseases the pathology of which involves atherosclerotic plaque formation (including stable or unstable/vulnerable plaques), atherosclerosis, arteriosclerosis, arteriolosclerosis, and elevated systemic lipopolysaccharide (LPS) exposure. Specifically included within this group are all cardiovascular conditions and diseases associated with the atherosclerotic plaque formation, the occurrence, development, or progression of which can be controlled by the inhibition of the atherosclerotic plaque formation. The term specifically includes diseases and pathological conditions that benefit from the inhibition of the formation of atherosclerotic plaques. Cardiovascular conditions include, without limitation, coronary artery atherosclerosis, coronary microvascular disease, stroke, carotid artery disease, peripheral arterial disease, ischemia, coronary artery disease (CAD), coronary heart disease (CHD), conditions associated with CAD and CHD, cerebrovascular disease and conditions associated with cerebrovascular disease, peripheral vascular disease and conditions associated with peripheral vascular disease, aneurysm, vasculitis, venous thrombosis, diabetes mellitus, metabolic syndromechronic kidney disease, remote tissue injury after ischemia and reperfusion, and cardiopulmonary bypass. "Conditions associated with cerebrovascular disease" as used herein include, for example, transient ischemic attack (TIA) and stroke. "Conditions associated with peripheral vascular disease" as used herein include, for example, claudication. Specifically included within this group are all cardiovascular diseases and conditions associated with the occurrence, development, or progression of which can be controlled by the inhibition of the atherosclerotic plaque formation.

Atherosclerotic plaque formation can occur as a result of an innate immune response to metabolic endotoxemia, which is characterized by elevated levels of systemic lipopolysaccharides (LPS) that originate from gut microbiota and a loss of functional integrity in the gut mucosal barrier. The innate immune response to endotoxemia results in the low-grade chronic inflammation that is responsible for plaque formation.

The term "metabolic syndrome" is used herein in the broadest sense. Metabolic syndrome includes the co-occurrence in an adult subject of several metabolic risk factors, including at least three of the following five traits: abdominal obesity, which can be, for example, a waist circumference in men of greater than or equal to 90 cm and in women greater than or equal to 80 cm; elevated serum triglycerides, which can be, for example, greater than or equal to 150 mg/dL, or drug treatment for elevated triglycerides; reduced serum HDL cholesterol level, which can be, for example, below 40 mg/dL in men and below 50 mg/dL in women, or drug treatment for low HDL cholesterol; hypertension, which can be, for example, systolic blood pressure greater than 130 mmHg and diastolic blood pressure greater than 85 mmHg, or drug treatment for hypertension; and elevated fasting plasma glucose, which can be, for example, greater than or equal to 100 mg/dL, drug treatment for elevated glucose, or previously diagnosed type 2 diabetes.

For children over 16 years old, the above criteria for adults can be used. For children between 10-16 year old, metabolic syndrome includes the co-occurrence in a subject of several metabolic risk factors, including at least three of the following five traits: abdominal obesity, which can be, for example, a waist circumference greater than $90^{th}$ percentile; elevated serum triglycerides, which can be, for example, greater than or equal to 110 mg/dL, greater than $95^{th}$ percentile, or drug treatment for elevated triglycerides; reduced serum HDL cholesterol level, which can be, for example, below 40 mg/dL, less than $5^{th}$ percentile, or drug treatment for low HDL cholesterol; hypertension, which can be, for example, systolic blood pressure greater than 130 mmHg and diastolic blood pressure greater than 85 mmHg, greater than $90^{th}$ percentile, or drug treatment for hypertension; and elevated fasting plasma glucose, which can be, for example, greater than or equal to 100 mg/dL, impaired glucose tolerance, drug treatment for elevated glucose, or previously diagnosed type 2 diabetes.

Generally speaking, the risk factors that co-occur in metabolic syndrome include obesity (such as abdominal obesity), hyperglycemia, dyslipidemia, insulin resistance, and/or hypertension. All these risk factors promote the development of atherosclerotic cardiovascular disease, diabetes, or both. Metabolic syndrome can also feature chronic adipose tissue inflammation.

Metabolic syndrome can be recognized as a proinflammatory, prothrombic state, and can be associated with elevated levels of one or more of C-reactive protein, IL-6, LPS, and plasminogen activator inhibitor 1; such markers can be associated with an increased risk for subsequent development of atherosclerotic cardiovascular disease, diabetes, or both.

Metabolic syndrome can be associated with several obesity-related disorders, including one or more of fatty liver disease with steatosis, fibrosis, and cirrhosis, hepatocellular and intrahepatic cholangiocarcinoma, chronic kidney disease, polycystic ovary syndrome, sleep disordered breathing, including obstructive sleep apnea, and hyperuricemia and gout.

The term "insulin-related disorder" encompasses diseases or conditions characterized by impaired glucose tolerance. In one embodiment, the insulin-related disorder is diabetes mellitus including, without limitation, Type I (insulin-dependent diabetes mellitus or IDDM), Type II (non-insulin dependent diabetes mellitus or NIDDM) diabetes, gestational diabetes, and any other disorder that would be benefited by agents that stimulate insulin secretion. In another embodiment, the insulin-related disorder is characterized by insulin resistance.

The term "sepsis" is used in its broadest sense and can encompass a systemic inflammatory state caused by severe infection. Sepsis can caused by the immune system's response to a serious infection, most commonly bacteria, but also fungi, viruses, and parasites in the blood, urinary tract, lungs, skin, or other tissues.

The term "acute endotoxemia" is used in its broadest sense and can encompass the condition of increased plasma bacterial lipopolysaccharide (LPS). Acute endotoxemia in turn could result in sepsis. Increased LPS in systemic circulation will induce low grade chronic inflammation, activating the endogenous protective host response to elevate plasma lipids that, in the chronic condition contributes to diet induced obesity, insulin resistance and atherosclerosis, and eventual CVD events.

The term "graft-versus-host disease (GVHD)" refers to a complication of allogeneic stem cell transplantation. In GVHD, donor hematopoietic stem cells recognize the transplant recipient as foreign and attack the patient's tissues and organs, which can impair the tissue or organ's function or cause it to fail. As used herein, GVHD includes, for example, acute GVHD or chronic GVHD. Further, non-limiting examples include intestinal GVHD.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

For example, with regard to IBD, "treatment" can refer to a decrease in the likelihood of developing IBD, a decrease in the rate of developing IBD, and a decrease in the severity of the disease. As another example, with regard to atherosclerotic plaque formation, "treatment" can refer to a decrease in the likelihood of developing atherosclerotic plaque deposits, a decrease in the rate of development of deposits, a decrease in the number or size of existing deposits, or improved plaque stability. Those in need of treatment include those already with the disorder as well as those in which the disorder is to be prevented. Desirable effects of treatment include, but are not limited to, preventing occurrence or recurrence of disease, alleviating symptoms, diminishing any direct or indirect pathological consequences of the disease, preventing the disease, decreasing the rate of disease progression, ameliorating or palliating the disease state, and causing remission or improved prognosis. In some embodiments, IL-22 Fc fusion protein of the invention are used to delay development of a disease or to slow the progression of a disease.

In certain embodiments, a "subject in need thereof" in the context of preventing or treating a cardiovascular condition refers to a subject diagnosed with a cardiovascular disease or cardiovascular condition (CVD) or metabolic syndrome or exhibiting one or more conditions associated with CVD or metabolic syndrome, a subject who has been diagnosed with or exhibited one or more conditions associated with CVD or metabolic syndrome in the past, or a subject who has been deemed at risk of developing CVD or metabolic syndrome or one or more conditions associated with CVD or metabolic syndrome in the future due to hereditary or environmental factors. Therefore, in certain embodiments, a subject in need thereof can be a subject exhibiting a CVD or metabolic syndrome or a condition associated with a CVD or metabolic syndrome or a subject that has exhibited a CVD or metabolic syndrome or a condition associated with a CVD or metabolic syndrome in the past or has been deemed at risk for developing a CVD or metabolic syndrome or a condition associated with a CVD or metabolic syndrome in the future.

In treatment of a cardiovascular disease or condition, a therapeutic agent can directly alter the magnitude of response of a component of the immune response, or render the disease more susceptible to treatment by other therapeutic agents, e.g., antibiotics, antifungals, anti-inflammatory agents, chemotherapeutics, etc. In treatment of an arterial disease, treatment might, for example, prevent or slow down the progression of a disease. Thus, treatment of an arterial disease specifically includes the prevention, inhibition, or slowing down of the development of the condition, or of the progression from one stage of the condition to another, more advanced stage, or into a more severe, related condition.

The "pathology" of a disease or condition includes all phenomena that compromise the well-being of the subject. In the case of a cardiovascular disease or condition, this includes, without limitation, atherosclerotic plaque formation (including stable or unstable/vulnerable plaques), atherosclerosis, arteriosclerosis, arteriolosclerosis, and elevated systemic lipopolysaccharide (LPS) exposure.

"Alleviation," "alleviating," or equivalents thereof, refer to both therapeutic treatment and prophylactic or preventative measures, wherein the object is to ameliorate, prevent, slow down (lessen), decrease or inhibit a disease or condition, e.g., the formation of atherosclerotic plaques. Those in need of treatment include those already with the disease or condition as well as those prone to having the disease or condition or those in whom the disease or condition is to be prevented.

"Chronic" administration refers to administration of an agent(s) in a continuous mode as opposed to an acute mode, so as to maintain the initial therapeutic effect for an extended period of time.

"Intermittent" administration is treatment that is not consecutively done without interruption, but rather is cyclic in nature.

The term "package insert" is used to refer to instructions customarily included in commercial packages of therapeutic products, that contain information about the indications, usage, dosage, administration, combination therapy, contraindications, and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Below are examples of how to calculate the % amino acid sequence identity of the amino acid sequence designated "Comparison Protein" or "Reference Protein" to the amino acid sequence designated "IL-22," wherein "IL-22" represents the amino acid sequence of an IL-22 polypeptide of interest, "Comparison Protein" represents the amino acid sequence of a polypeptide against which the "IL-22" polypeptide of interest is being compared, and "X," "Y," and "Z" each represent different amino acid residues.

| IL-22 | XXXXXXXXXXXXXXX | (Length = 15 amino acids) |
| Reference Protein | XXXXXYYYYYYY | (Length = 12 amino acids) |
| IL-22 | XXXXXXXXXX | (Length = 10 amino adds) |
| Reference Protein | XXXXXYYYYYYZZYZ | (Length = 15 amino acids) |

% amino acid sequence identity = (the number of identically matching amino acid residues between the two polypeptide sequences) divided by (the total number of amino acid residues of the IL-22 polypeptide) = 5 divided by 15 = 33.3%
% amino acid sequence identity = (the number of identically matching amino acid residues between the two polypeptide sequences) divided by (the total number of amino acid residues of the IL-22 polypeptide) = 5 divided by 10 = 50%

The term "agonist" is used in the broadest sense and includes any molecule that partially or fully mimics a biological activity of an IL-22 polypeptide. Also encompassed by "agonist" are molecules that stimulate the transcription or translation of mRNA encoding the polypeptide.

Suitable agonist molecules include, e.g., agonist antibodies or antibody fragments; a native polypeptide; fragments or amino acid sequence variants of a native polypeptide; peptides; antisense oligonucleotides; small organic molecules; and nucleic acids that encode polypeptides agonists or antibodies. Reference to "an" agonist encompasses a single agonist or a combination of two or more different agonists.

The term "IL-22 agonist" is used in the broadest sense, and includes any molecule that mimics a qualitative biological activity (as hereinabove defined) of a native sequence IL-22 polypeptide. IL-22 agonists specifically include IL-22-Fc or IL-22 Ig polypeptides (immunoadhesins), but also small molecules mimicking at least one IL-22 biological activity. Preferably, the biological activity is binding of the IL-22 receptor, interacting with IL-22BP, facilitating an innate immune response pathway, or in the case of a cardiovascular disease or condition, to affect the formation of atherosclerotic plaques, in particular to inhibit formation of atherosclerotic plaque formation. Inhibition of plaque formation can be assessed by any suitable imaging method known to those of ordinary skill in the art.

IL-22R1 pairs with other proteins to form heterodimers as the receptors for certain IL-10 family members. See Ouyang et al., 2011, supra. Thus, in certain embodiments, IL-22 agonists may include an IL-22 receptor agonist, including a cytokine (or a fusion protein or agonist thereof) that binds to and triggers downstream signaling of the IL-22R1. In certain embodiments, the IL-22 agonists include an IL-22R1 agonist, including without limitation an anti-IL-22R1 agonist antibody; an IL-20 agonist, including without limitation IL-20 polypeptide or IL-20 Fc fusion protein; and an IL-24 agonist, including without limitation IL-24 polypeptide or IL-24 fusion protein. In certain other embodiments, the IL-22R1 agonists include an IL-19 agonist, including without limitation IL-19 polypeptide or IL-19 Fc fusion protein; and an IL-26 agonist, including without limitation IL-26 polypeptide or IL-26 Fc fusion protein. Exemplary sequences for IL-19 (GenBank Accession No. AAG16755.1, SEQ ID NO:77), IL-20 (GenBank Accession No. AAH69311.1, SEQ ID NO:78), IL-24 (GenBank Accession No. AAH09681.1, SEQ ID NO:79) and IL-26 (GenBank Accession No. NP_060872.1, SEQ ID NO:80) are provided herein. In certain embodiments, an IL-19 polypeptide comprises the amino acid sequence of SEQ ID NO:77 or the mature protein without the signal peptide. In certain other embodiments, an IL-20 polypeptide comprises the amino acid sequence of SEQ ID NO:78 or the mature protein without the signal peptide. In yet other embodiments, an IL-24 polypeptide comprises the amino acid sequence of SEQ ID NO:79 or the mature protein without the signal peptide. In certain other embodiments, an IL-26 polypeptide comprises the amino acid sequence of SEQ ID NO:80 or the mature protein without the signal peptide.

A "small molecule" is defined herein to have a molecular weight below about 600, preferably below about 1000 daltons.

An "agonist antibody," as used herein, is an antibody which partially or fully mimics a biological activity of an IL-22 polypeptide.

The terms "pharmaceutical formulation" or "pharmaceutical composition" are used interchangeably herein and refer to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, diluent, stabilizer, or preservative.

The term "shelf life" refers to the length of time that a product (e.g., a protein (e.g., an IL-22 Fc fusion protein) may be stored without becoming unfit for use (e.g., administration to a subject) or sale. In some embodiments, the shelf life is the length of time in which a composition (e.g., a pharmaceutical composition) is stable. For example, in some embodiments, a composition herein has a shelf life of at least 36 months when stored at 5° C.±3° C. and protected from light. In some embodiments, a composition herein has a shelf life of at least 48 months when stored at −20° C. In some embodiments, a composition herein has a shelf life of at least 60 months when stored at −20° C.

A "stable" pharmaceutical formulation is one in which the protein (e.g., an IL-22 Fc fusion protein) therein essentially retains its physical stability and/or chemical stability and/or biological activity upon storage. Preferably, the formulation essentially retains its physical and chemical stability, as well as its biological activity upon storage. The storage period is generally selected based on the intended shelf life of the formulation. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected amount of light exposure and/or temperature for a selected time period. Stability can be evaluated qualitatively and/or quantitatively in a variety of different ways, including evaluation of aggregate formation (for example, using size exclusion chromatography, by measuring turbidity, and/or by visual inspection); evaluation of ROS formation (for example, by using a light stress assay or an 2,2'-azobis(2-amidinopropane) dihydrochloride (AAPH) stress assay); oxidation of specific amino acid residues of the protein (for example, a Met residue of an IL-22 Fc fusion protein); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact polypeptides (e.g., IL-22 Fc fusion proteins); peptide map (for example, tryptic or LYS-C) analysis; evaluating biological activity or target binding function of the protein (e.g., binding of an IL-22 Fc fusion protein to an IL-22 receptor); and the like. Instability may involve any one or more of: aggregation, deamidation (e.g., Asn deamidation), oxidation (e.g., Met oxidation and/or Trp oxidation), isomerization (e.g., Asp isomerization), clipping/hydrolysis/fragmentation (e.g., hinge region fragmentation), succinimide formation, unpaired cysteine(s), N-terminal extension, C-terminal processing, glycosylation differences, and the like.

A protein (e.g., an IL-22 Fc fusion protein) "retains its physical stability" in a pharmaceutical formulation if it shows no signs or very little of aggregation, precipitation, fragmentation, and/or denaturation upon visual examination of color and/or clarity, or as measured by UV light scattering or by size exclusion chromatography.

A protein (e.g., an IL-22 Fc fusion protein) "retains its chemical stability" in a pharmaceutical formulation, if the chemical stability at a given time is such that the protein (e.g., an IL-22 Fc fusion protein) is considered to still retain its biological activity as defined below. Chemical stability can be assessed by detecting and quantifying chemically altered forms of the protein (e.g., an IL-22 Fc fusion protein). Chemical alteration may involve protein oxidation which can be evaluated using tryptic peptide mapping, reverse-phase high-performance liquid chromatography (HPLC) and liquid chromatography-mass spectrometry (LC/MS), for example. Other types of chemical alteration include charge alteration of the protein (e.g., an IL-22 Fc fusion protein) which can be evaluated by ion-exchange chromatography or icIEF, for example.

A protein (e.g., an IL-22 Fc fusion protein) "retains its biological activity" in a pharmaceutical formulation, if the biological activity of the protein (e.g., an IL-22 Fc fusion protein) at a given time is within about 20% (such as within about 10%) of the biological activity exhibited at the time the pharmaceutical formulation was prepared (within the errors of the assay), as determined, for example, in a receptor binding assay.

As used herein, "biological activity" of protein (e.g., an IL-22 Fc fusion protein) refers to the ability of the protein (e.g., an IL-22 Fc fusion protein) to bind its target, for example, the ability of an IL-22 Fc fusion protein to bind an IL-22 receptor. It can further include a biological response which can be measured in vitro or in vivo. Such activity may be antagonistic or agonistic. In particular embodiments, the activity is agonistic (e.g., receptor activation).

A protein (e.g., an IL-22 Fc fusion protein) which is "susceptible to oxidation" is one comprising one or more residue(s) that has been found to be prone to oxidation such as, but not limited to, methionine (Met), cysteine (Cys), histidine (His), tryptophan (Trp), and tyrosine (Tyr). For example, one or more methionine residues in an IL-22 polypeptide may be susceptible to oxidation.

The term "percent oxidation" refers to the percentage of proteins (e.g., IL-22 Fc fusion proteins) in a formulation (e.g., a pharmaceutical composition) that are oxidized at a particular amino acid residue, for example, a Met residue. Percent oxidation can be determined by, e.g., mass spectrometry (MS) analysis of one or more tryptic peptides, in which one or more particular oxidation-prone amino acid residues reside. Percent oxidation may be determined, for example, following an AAPH stress test, within 9 months, 12 months, 18 months, or two years from the initial production of a protein (e.g., an IL-22 Fc fusion protein) or pharmaceutical composition thereof.

The term "as assessed by an AAPH stress test," as used herein, means that the percent oxidation at a particular amino acid residue (for example, a Met residue) is determined by mass spectrometry analysis of tryptic peptides following formulating the protein (e.g., the IL-22 Fc fusion protein) with AAPH (e.g., about 0 mM AAPH, about 1 mM AAPH, about 3 mM AAPH, about 3.5 mM AAPH, or about 5 mM AAPH), for example, in a formulation of about 10 mg/mL IL-22 Fc fusion protein, about 10 mM sodium phosphate, about 240 mM sucrose, about 0.02 (w/v) polysorbate 20, pH about 7.1 for about 24 hours at about 40° C. The stressed protein (e.g., an IL-22 Fc fusion protein) is digested with trypsin and the digested peptides are subjected to LC-MS-MS to determine the percentage of oxidation.

As used herein, "buffer" refers to a buffered solution that resists changes in pH by the action of its acid-base conjugate components (also referred to herein as "buffering agents"). In some embodiments, the buffer of this invention has a pH in the range of from about 6 to about 8. In some embodiments, the buffer has a pH that is substantially neutral. The buffer preferably has a pH in the range from about 6.8 to about 7.4 (e.g., about 6.8, about 6.9, about 7.0, about 7.1, about 7.2, about 7.3, or about 7.4), e.g., about pH 7.1. Exemplary buffering agents for use in the invention include, but are not limited to, a phosphate, a succinate, an acetate, histidine, or a combination thereof. In some embodiments, the phosphate is sodium phosphate monobasic, sodium phosphate dibasic, sodium phosphate tribasic, potassium phosphate monobasic, potassium phosphate dibasic, potassium phosphate tribasic, or a mixture thereof. In some embodiments, the phosphate is sodium phosphate monobasic. In some embodiments, the phosphate is sodium phosphate dibasic. In some embodiments, the phosphate is a mixture of sodium phosphate monobasic and sodium phosphate dibasic.

The term "substantially neutral," as used herein, refers to a pH range of about 6.6 to about 8 (e.g., about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0), as measured at a temperature of from about 20° C. to about 30° C. (e.g., about 20° C., about 21° C., about 22° C., about 23° C., about 24° C., about 25° C., about 26° C., about 27° C., about 28° C., about 29° C., about 30° C.).

As used herein, a "surfactant" refers to a surface-active agent, preferably a nonionic surfactant. Examples of surfactants herein include polysorbate (for example, polysorbate 20 and polysorbate 80); poloxamer (e.g., poloxamer 188); TRITON®; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g., PLURONIC® type block copolymers, e.g., PLURONIC® F-68); and the like. In one embodiment, the surfactant herein is polysorbate 20. In yet another embodiment, the surfactant herein is poloxamer 188.

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl, and benzyl alcohol; alkyl parabens such as methyl or propyl paraben; catechol; resorcinol; cyclohexanol; 3-pentanol, and m-cresol. In one embodiment, the preservative herein is benzyl alcohol. In some embodiments, the formulation does not include a preservative.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *PCR Protocols: A Guide to Methods and Applications* (Innis, et al. 1990. Academic Press, San Diego, CA), and Harlow and Lane (1988) *Antibodies: A Laboratory Manual* ch. 14 (Cold Spring Harbor Laboratory, Cold Spring Harbor, NY).

As appropriate, procedures involving the use of commercially available kits and reagents are generally carried out in accordance with manufacturer defined protocols and/or parameters unless otherwise noted. Before the present methods and uses therefore are described, it is to be understood that this invention is not limited to the particular methodology, protocols, cell lines, animal species or genera, constructs, and reagents described as such can, of course, vary. It is also to be understood that the terminology used herein is for the purpose of describing particular embodiments only, and is not intended to limit the scope of the present invention which will be limited only by the appended claims.

II. Compositions and Methods

The invention provides compositions (e.g., pharmaceutical compositions) that include proteins (e.g., Fc fusion proteins, such as IL-22 Fc fusion proteins), and uses thereof, for example, for the treatment of IL-22 associated diseases such as IBD (e.g., ulcerative colitis (UC) and Crohn's disease), cardiovascular conditions, metabolic syndrome, GVHD, and for accelerating wound healing (e.g., diabetic wound healing). Also provided herein are methods of making the compositions.

The invention is based at least in part on the present discovery that particular formulations of the IL-22 Fc fusion proteins described herein provide advantageous properties, e.g., as described in the present Examples. In certain aspects, such advantageous properties include increased stability and/or increased shelf life of the presently described IL-22 Fc fusion proteins and compositions comprising the IL-22 Fc fusion proteins. Further, it is presently discovered that the IL-22 Fc proteins unexpectedly have higher thermal stability at higher pH values, as described in, e.g., Example 1. These and other advantageous properties of the presently discovered compositions are described in more detail, below.

A. Pharmaceutical Compositions

The Invention provides compositions (e.g., pharmaceutical compositions) that include proteins (e.g., Fc fusion proteins, such as IL-22 Fc fusion proteins) with improved shelf life and stability. Any of the IL-22 Fc fusion proteins described herein can be used in the compositions, but it is to be understood that other Fc fusion proteins (e.g., Fc fusion proteins that include other interleukins) can also be used.

For example, in one aspect, the invention provides a composition (e.g., a pharmaceutical composition) that includes an IL-22 Fc fusion protein and a carrier, wherein the composition has a shelf life of at least about 12 months (e.g., at least about 12 months, about 18 months, about 24 months, about 30 months, about 36 months, about 42 months, about 48 months, about 54 months, about 60 months, about 66 months, or about 72 months) when stored at 5° C.±3° C. and protected from light, and wherein the IL-22 Fc fusion protein includes an IL-22 polypeptide linked to an Fc region by a linker. In some embodiments, the pharmaceutical composition has a shelf life of at least 36 months when stored at 5° C.±3° C. and protected from light. In some embodiments, the composition has a shelf life of at least 42 months when stored at 5° C.±3° C. and protected from light. In some embodiments, the composition has a shelf life of at least 48 months when stored at 5° C.±3° C. and protected from light.

For example, in some embodiments, the shelf life when stored at 5° C.±3° C. and protected from light is between about 1 month and about 72 months (e.g., about 1 month, about 5 months, about 10 months, about 15 months, about 20 months, about 24 months, about 25 months, about 30 months, about 35 months, about 40 months, about 45 months, about 48 months, about 50 months, about 55 months, about 60 months, about 65 months, about 70 months, or about 72 months). In some embodiments, the shelf life when stored at 5° C.±3° C. and protected from light is between about 1 month and about 72 months, about 1 month and about 70 months, about 1 month and about 65 months, about 1 month and about 60 months, about 1 month and about 55 months, about 1 month and about 50 months, about 1 month and about 48 months, about 1 month and about 45 months, about 1 month and about 40 months, about 1 month and about 35 months, about 1 month and about 30 months, about 1 month and about 25 months, about 1 month and about 24 months, about 1 month and about 20 months, about 1 month and about 18 months, about 1 month and about 15 months, about 1 month and about 12 months, about 1 month and about 9 months, about 1 month and about 6 months, about 1 month and about 3 months, about 5 months and about 72 months, about 5 months and about 70 months, about 5 months and about 65 months, about 5 months and about 60 months, about 5 months and about 55 months, about 5 months and about 50 months, about 5 months and about 45 months, about 5 months and about 40 months, about 5 months and about 35 months, about 5 months and about 30 months, about 5 months and about 25 months, about 5 months and about 24 months, about 5 months and about 20 months, about 5 months and about 18 months, about 5 months and about 15 months, about 5 months and about 12 months, about 5 months and about 9 months, about 5 months and about 6 months, about 10 months and about 72 months, about 10 months and about 70 months, about 10 months and about 65 months, about 10 months and about 60 months, about 10 months and about 55 months, about 10 months and about 50 months, about 10 months and about 48 months, about 10 months and about 45 months, about 10 months and about 40 months, about 10 months and about 35 months, about 10 months and about 30 months, about 10 months and about 25 months, about 10 months and about 24 months, about 10 months and about 20 months, about 10 months and about 18 months, about 10 months and about 15 months, about 10 months and about 12 months, about 12 months and about 72 months, about 12 months and about 70 months, about 12 months and about 65 months, about 12 months and about 60 months, about 12 months and about 55 months, about 12 months and about 50 months, about 12 months and about 48 months, about 12 months and about 45 months, about 12 months and about 40 months, about 12 months and about 35 months, about 12 months and about 30 months, about 12 months and about 25 months, about 12 months and about 24 months, about 12 months and about 20 months, about 12 months and about 18 months, about 12 months and about 15 months, about 18 months and about 72 months, about 18 months and about 70 months, about 18 months and about 65 months, about 18 months and about 60 months, about 18 months and about 55 months, about 18 months and about 50 months, about 18 months and about 48 months, about 18 months and about 45 months, about 18 months and about 40 months, about 18 months and about 35 months, about 18 months and about 30 months, about 18 months and about 25 months, about 18 months and about 24 months, about 18 months and about 20 months, about 24 months and about 72 months, about 24 months and about 70 months, about 24 months and about 65 months, about 24 months and about 60 months, about 24 months and about 55 months, about 24 months and about 50 months, about 24 months and about 48 months, about 24 months and about 45 months, about 24 months and about 40 months, about 24 months and about 35 months, about 24 months and about 30 months, about 24 months and about 25 months, about 30 months and about 72 months, about 30 months and about 70 months, about 30 months and about 65 months, about 30 months and about 60 months, about 30 months and about 55 months, about 30 months and about 50 months, about 30 months and about 48 months, about 30 months and about 45 months, about 30 months and about 40 months, about 35 months and about 36 months, about 36 months and about 72 months, about 36 months and about 70 months, about 36 months and about 65 months, about 36 months and about 60 months, about 36 months and about 55 months, about 36 months and about 50 months, about 36 months and about 48 months, about 36 months and about 45 months, about 36 months and about 40 months, about 40 months and about 72 months, about 40 months and about 70 months, about 40 months and about 65 months, about 40 months and about 60 months, about 40 months and about 55 months, about 40 months and about 50 months, about 40 months and about 48 months, about 40 months and about 45 months, about 42 months and about 72 months, about 42 months and about 70 months, about 42 months and about 65 months, about 42 months and about 60 months, about 42 months and about 55 months, about 42 months and about 50 months, about 42 months and about 48 months, about 42 months and about 45 months, about 46 months and about 70 months, about 72 months and about 46 months and about 70 months, about 46 months and about 65 months, about 46 months and about 60 months, about 46 months and about 55 months, about 46 months and about 50 months, about 46 months and about 48 months, about 48 months and about 72 months, about 48 months and about 70 months, about 48 months and about 65 months, about 48 months and about 60 months, about 48 months and about 55 months, about 48 months and about 50 months, about 50 months and about 72 months, about 50 months and about 70 months, about 50 months and about 65 months, about 50 months and about 60 months, about 50 months and about 55 months, about 55 months and about 72 months, about 55 months and about 70 months, about 55 months and about 65 months, about 55 months and about 60 months, about 60 months and about 72 months, about 60 months and about 70 months, or about 60 months and about 65 months.

The compositions (e.g., pharmaceutical compositions) may have any suitable concentration of the IL-22 Fc fusion protein. For example, in any of the preceding compositions (e.g., pharmaceutical compositions), the concentration of the IL-22 Fc fusion protein can be about 0.01 mg/mL to about 30 mg/mL, e.g., about 0.01 mg/mL, about 0.05 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL.

For example, in some embodiments, the concentration of the IL-22 Fc fusion is about 1 mg/mL to about 30 mg/mL, about 2 mg/mL to about 30 mg/mL, about 3 mg/mL to about 30 mg/mL, about 4 mg/mL to about 30 mg/mL, about 5 mg/mL to about 30 mg/mL, about 6 mg/mL to about 30 mg/mL, about 7 mg/mL to about 30 mg/mL, about 8 mg/mL to about 30 mg/mL, about 9 mg/mL to about 30 mg/mL, about 10 mg/mL to about 30 mg/mL, about 11 mg/mL to about 30 mg/mL, about 12 mg/mL to about 30 mg/mL, about 13 mg/mL to about 30 mg/mL, about 14 mg/mL to about 30 mg/mL, about 15 mg/mL to about 30 mg/mL, about 20 mg/mL to about 30 mg/mL, about 25 mg/mL to about 30 mg/mL, about 1 mg/mL to about 20 mg/mL, about 2 mg/mL to about 20 mg/mL, about 3 mg/mL to about 20 mg/mL, about 4 mg/mL to about 20 mg/mL, about 5 mg/mL to about 20 mg/mL, about 6 mg/mL to about 20 mg/mL, about 7 mg/mL to about 20 mg/mL, about 8 mg/mL to about 20 mg/mL, about 9 mg/mL to about 20 mg/mL, about 10 mg/mL to about 20 mg/mL, about 11 mg/mL to about 20 mg/mL, about 12 mg/mL to about 20 mg/mL, about 13 mg/mL to about 20 mg/mL, about 14 mg/mL to about 20 mg/mL, about 15 mg/mL to about 20 mg/mL, about 1 mg/mL to about 15 mg/mL, about 2 mg/mL to about 15 mg/mL, about 3 mg/mL to about 15 mg/mL, about 4 mg/mL to about 15 mg/mL, about 5 mg/mL to about 15 mg/mL, about 6 mg/mL to about 15 mg/mL, about 7 mg/mL to about 15 mg/mL, about 8 mg/mL to about 15 mg/mL, about 9 mg/mL to about 15 mg/mL, about 10 mg/mL to about 15 mg/mL, about 11 mg/mL to about 15 mg/mL, about 12 mg/mL to about 15 mg/mL, about 13 mg/mL to about 15 mg/mL, about 14 mg/mL to about 15 mg/mL, about 1 mg/mL to about 10 mg/mL, about 2 mg/mL to about 10 mg/mL, about 3 mg/mL to about 10 mg/mL, about 4 mg/mL to about 10 mg/mL, about 5 mg/mL to about 10 mg/mL, about 6 mg/mL to about 10 mg/mL, about 7 mg/mL to about 10 mg/mL, about 8 mg/mL to about 10 mg/mL, about 9 mg/mL to about 10 mg/mL, about 1 mg/mL to about 5 mg/mL, about 2 mg/mL to about 5 mg/mL, about 3 mg/mL to about 5 mg/mL, or about 4 mg/mL to about 5 mg/mL.

In some embodiments, the concentration of the IL-22 Fc fusion protein is about 0.5 mg/mL to about 20 mg/mL. In some embodiments, the concentration of the IL-22 Fc fusion protein is about 0.5 mg/mL to about 5 mg/mL. In some embodiments, the concentration of the IL-22 Fc fusion protein is about 1 mg/mL. In other embodiments, the concentration of the IL-22 Fc fusion protein is about 8 mg/mL to about 12 mg/mL. In some embodiments, the concentration of the IL-22 Fc fusion protein is about 10 mg/mL.

Any of the preceding compositions (e.g., pharmaceutical compositions) can include a stabilizer. Any suitable stabilizer can be used. For example, in some embodiments, the stabilizer is an amino acid, thiosorbitol, ascorbic acid, monothioglycerol, a cyclodextrin, Trolox (6-hydroxy-2,5,7, 8-tetramethylchroman-2-carboxylic acid), pyridoxine, mannitol, a metal chelator, or a combination thereof. In some embodiments, the stabilizer is an amino acid. In some embodiments, the amino acid is methionine, cysteine, tryptophan, or a combination thereof. In some embodiments, the amino acid is methionine.

Any suitable concentration of the stabilizer may be used. For example, in some embodiments of any of the preceding compositions (e.g., pharmaceutical compositions), the concentration of the stabilizer (e.g., methionine) is about 0.01 mM to about 30 mM, e.g., about 0.01 mM, about 0.05 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, or about 30 mM. In some embodiments, the concentration of the stabilizer (e.g., methionine) is about 1 mM to about 30 mM, about 2 mM to about 30 mM, about 3 mM to about 30 mM, about 4 mM to about 30 mM, about 5 mM to about 30 mM, about 6 mM to about 30 mM, about 7 mM to about 30 mM, about 8 mM to about 30 mM, about 9 mM to about 30 mM, about 10 mM to about 30 mM, about 11 mM to about 30 mM, about 12 mM to about 30 mM, about 13 mM to about 30 mM, about 14 mM to about 30 mM, about 15 mM to about 30 mM, about 20 mM to about 30 mM, about 25 mM to about 30 mM, about 1 mM to about 20 mM, about 2 mM to about 20 mM, about 3 mM to about 20 mM, about 4 mM to about 20 mM, about 5 mM to about 20 mM, about 6 mM to about 20 mM, about 7 mM to about 20 mM, about 8 mM to about 20 mM, about 9 mM to about 20 mM, about 10 mM to about 20 mM, about 11 mM to about 20 mM, about 12 mM to about 20 mM, about 13 mM to about 20 mM, about 14 mM to about 20 mM, about 15 mM to about 20 mM, about 1 mM to about 15 mM, about 2 mM to about 15 mM, about 3 mM to about 15 mM, about 4 mM to about 15 mM, about 5 mM to about 15 mM, about 6 mM to about 15 mM, about 7 mM to about 15 mM, about 8 mM to about 15 mM, about 9 mM to about 15 mM, about 10 mM to about 15 mM, about 11 mM to about 15 mM, about 12 mM to about 15 mM, about 13 mM to about 15 mM, about 14 mM to about 15 mM, about 1 mM to about 10 mM, about 2 mM to about 10 mM, about 3 mM to about 10 mM, about 4 mM to about 10 mM, about 5 mM to about 10 mM, about 6 mM to about 10 mM, about 7 mM to about 10 mM, about 8 mM to about 10 mM, about 9 mM to about 10 mM, about 1 mM to about 5 mM, about 2 mM to about 5 mM, about 3 mM to about 5 mM, or about 4 mM to about 5 mM. In some embodiments, the concentration of the stabilizer (e.g., methionine) is about 2 mM to about 8 mM. In particular embodiments, the concentration of the stabilizer (e.g., methionine) is about 5 mM.

In any of the preceding compositions (e.g., pharmaceutical compositions), the oxidation of methionine at position M25 or M139 (for example, relative to the amino acid sequence of SEQ ID NO:4) is less than about 10% as assessed by an AAPH stress test, e.g., less than about 10%, about 9%, about 8%, about 7%, about 6%, about 5%, about 4%, about 3%, about 2%, about 1%, or less. In some embodiments, the oxidation of methionine at position M25 of SEQ ID NO:4 is less than 5%, less than 3%, or less than 2%. In some embodiments, the oxidation of methionine at position M139 of SEQ ID NO:4 is less than 7%, less than 6%, or less than 5%.

Any of the preceding compositions (e.g., pharmaceutical compositions) can further include a surfactant. Any suitable surfactant can be used. In some embodiments, the surfactant is a nonionic surfactant (e.g., a polysorbate, a poloxamer, a polyoxyethelene alkyl ether, an alkyl phenyl polyoxyethylene ether, or a combination thereof). In some embodiments, the nonionic surfactant is a polysorbate (e.g., polysorbate 20 or polysorbate 80). In particular embodiments, the polysorbate is polysorbate 20. In other embodiments, the nonionic surfactant is a poloxamer (e.g., poloxamer 188).

Any suitable concentration of the surfactant may be used. For example, in some embodiments of any of the preceding compositions (e.g., pharmaceutical compositions), the concentration of the surfactant (e.g., polysorbate 20 or poloxamer 188) is about 0.001% (w/v) to about 2% (w/v), e.g., about 0.001%, about 0.01%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, or about 2% (w/v). In some embodiments, the concentration of the surfactant (e.g., polysorbate 20 or poloxamer 188) is about 0.01% (w/v) to about 0.05% (w/v). In some embodiments, the concentration of the surfactant (e.g., polysorbate 20 or poloxamer 188) is about 0.01% (w/v) to about 0.07% (w/v). In particular embodiments, the concentration of the surfactant (e.g., polysorbate 20 or poloxamer 188) is about 0.02% (w/v).

Any of the preceding compositions (e.g., pharmaceutical compositions) can further include a buffering agent. Any suitable buffering agent can be used. In some embodiments, the buffering agent is a phosphate, a succinate, an acetate, histidine, or a combination thereof. In some embodiments, the phosphate is sodium phosphate monobasic, sodium phosphate dibasic, sodium phosphate tribasic, potassium phosphate monobasic, potassium phosphate dibasic, potassium phosphate tribasic, or a mixture thereof. In some embodiments, the phosphate is sodium phosphate monobasic. In some embodiments, the phosphate is sodium phosphate dibasic. In some embodiments, the phosphate is a mixture of sodium phosphate monobasic and sodium phosphate dibasic.

Any suitable concentration of the buffering agent can be used. For example, in some embodiments of any of the preceding compositions (e.g., pharmaceutical compositions), the concentration of the buffering agent (e.g., sodium phosphate) is about 0.01 mM to about 50 mM, e.g., about 0.01 mM, about 0.05 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, or about 50 mM. In some embodiments, the concentration of the buffering agent (e.g., sodium phosphate) is about 5 mM to about 20 mM. In some embodiments, the concentration of the buffering agent (e.g., sodium phosphate) is about 8 mM to about 12 mM. In particular embodiments, the concentration of the buffering agent (e.g., sodium phosphate) is about 10 mM.

Any of the preceding compositions (e.g., pharmaceutical compositions) can further include a tonicity agent. Any suitable tonicity agent can be used. In some embodiments, the tonicity agent is a sugar (e.g., sucrose, glucose, glycerol, or trehalose), an amino acid, or a salt (e.g., sodium chloride or potassium chloride). In particular embodiments, the tonicity agent is sucrose.

Any suitable concentration of the tonicity agent can be used. For example, in some embodiments of any of the preceding compositions (e.g., pharmaceutical compositions), the concentration of the tonicity agent (e.g., sucrose) is about 1 mM to about 1 M, e.g., about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, about 410 mM, about 420 mM, about 430 mM, about 440 mM, about 450 mM, about 460 mM, about 470 mM, about 480 mM, about 490 mM, about 500 mM, about 510 mM, about 520 mM, about 530 mM, about 540 mM, about 550 mM, about 560 mM, about 570 mM, about 580 mM, about 590 mM, about 600 mM, about 700 mM, about 800 mM, about 900 mM, or about 1 M. In some embodiments, the concentration of the tonicity agent is about 100 mM to about 500 mM. In some embodiments, the concentration of the tonicity agent is about 200 mM to about 300 mM. In some embodiments, the concentration of the tonicity agent is about 240 mM.

The compositions (e.g., pharmaceutical compositions) described herein may have any suitable pH. For example, in some embodiments, the pH of the composition is about 5 to about 9, e.g., about 5, about 5.5, about 6, about 6.5, about 6.6, about 6.7, about 6.8, about 6.9, about 7.0, about 7.1, about 7.15, about 7.2, about 7.3, about 7.4, about 7.5, about 8.0, about 8.5, or about 9. For example, in some embodiments, the pH is about 6.0 to about 8.0, about 6.0 to about 7.9, about 6.0 to about 7.8, about 6.0 to about 7.7, about 6.0 to about 7.6, about 6.0 to about 7.5, about 6.0 to about 7.4, about 6.0 to about 7.3, about 6.0 to about 7.2, about 6.0 to about 7.1, about 6.0 to about 7.0, about 6.0 to about 6.9, about 6.0 to about 6.8, about 6.0 to about 6.7, about 6.0 to about 6.6, about 6.0 to about 6.5, about 6.0 to about 6.4, about 6.0 to about 6.3, about 6.0 to about 6.2, about 6.0 to about 6.1, about 6.5 to about 8.0, about 6.5 to about 7.9, about 6.5 to about 7.8, about 6.5 to about 7.7, about 6.5 to about 7.6, about 6.5 to about 7.5, about 6.5 to about 7.4, about 6.5 to about 7.3, about 6.5 to about 7.2, about 6.5 to about 7.1, about 6.5 to about 7.0, about 6.5 to about 6.9, about 6.5 to about 6.8, about 6.5 to about 6.7, about 6.5 to about 6.6, about 6.6 to about 8.0, about 6.6 to about 7.9, about 6.6 to about 7.8, about 6.6 to about 7.7, about 6.6 to about 7.6, about 6.6 to about 7.5, about 6.6 to about 7.4, about 6.6 to about 7.3, about 6.6 to about 7.2, about 6.6 to about 7.1, about 6.6 to about 7.0, about 6.6 to about 6.9, about 6.6 to about 6.8, about 6.6 to about 6.7, about 6.7 to about 8.0, about 6.7 to about 7.9, about 6.7 to about 7.8, about 6.7 to about 7.7, about 6.7 to about 7.6, about 6.7 to about 7.5, about 6.7 to about 7.4, about 6.7 to about 7.3, about 6.7 to about 7.2, about 6.7 to about 7.1, about 6.7 to about 7.0, about 6.7 to about 6.9, about 6.7 to about 6.8, about 6.8 to about 8.0, about 6.8 to about 7.9, about 6.8 to about 7.8, about 6.8 to about 7.7, about 6.8 to about 7.6, about 6.8 to about 7.5, about 6.8 to about 7.4, about 6.8 to about 7.3, about 6.8 to about 7.2, about 6.8 to about 7.1, about 6.8 to about 7.0, about 6.8 to about 6.9, about 6.9 to about 8.0, about 6.9 to about 7.9, about 6.9 to about 7.8, about 6.9 to about 7.7, about 6.9 to about 7.6, about 6.9 to about 7.5, about 6.9 to about 7.4, about 6.9 to about 7.3, about 6.9 to about 7.2, about 6.9 to about 7.1, about 6.9 to about 7.0, about 7.0 to about 8.0, about 7.0 to about 7.9, about 7.0 to about 7.8, about 7.0 to about 7.7, about 7.0 to about 7.6, about 7.0 to about 7.5, about 7.0 to about 7.4, about 7.0 to about 7.3, about 7.0 to about 7.2, about 7.0 to about 7.1, about 7.01 to about 7.2, about 7.02 to about 7.2, about 7.03 to about 7.2, about 7.04 to about 7.2, about 7.05 to about 7.2, about 7.06 to about 7.2, about 7.07 to about 7.2, about 7.08 to about 7.2, about 7.09 to about 7.2, about 7.1 to about 7.2, about 7.01 to about 7.15, about 7.02 to about 7.15, about 7.03 to about 7.15, about 7.04 to about 7.15, about 7.05 to about 7.15, about 7.06 to about 7.15, about 7.07 to about 7.15, about 7.08 to about 7.15, about 7.09 to about 7.15, or about 7.1 to about 7.15

For example, in some embodiments, the pH is substantially neutral. For example, in some embodiments, the pH is about 6.6 to about 8 (e.g., about 6.6, about 6.7, about 6.8, about 6.9, about 7.0, about 7.1, about 7.15, about 7.2, about 7.3, about 7.4, about 7.5, about 8.0). In some embodiments, the pH is about 6.8 to about 7.4 (e.g., about 6.8, about 6.85, about 6.9, about 6.95, about 7.0, about 7.05, about 7.1, about 7.15, about 7.2, about 7.25, about 7.3, about 7.35, or about 7.4). In particular embodiments, the pH is about 7.1.

For example, provided herein is a composition (e.g., a pharmaceutical composition) that includes an IL-22 Fc fusion protein and a carrier, the IL-22 Fc fusion protein including an IL-22 polypeptide linked to an Fc region by a linker, wherein the pharmaceutical composition includes about 0.01 mg/mL to about 30 mg/mL IL-22 Fc fusion protein (e.g., about 0.01 mg/mL, about 0.05 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL IL-22 Fc fusion protein), about 5 mM methionine, and about 0.02% (w/v) polysorbate 20, pH 7.1, final concentration.

In some embodiments, the composition (e.g., the pharmaceutical composition) includes about 10 mM sodium phosphate and about 240 mM sucrose. In some embodiments, the composition (e.g., the pharmaceutical composition) includes about 1 mg/mL of the IL-22 Fc fusion protein. In some embodiments, the composition (e.g., the pharmaceutical composition) includes about 10 mg/mL of the IL-22 Fc fusion protein. In some embodiments, the sodium phosphate is a mixture of sodium phosphate monobasic and sodium phosphate dibasic.

Any of the compositions (e.g., pharmaceutical compositions) provided herein can be in a unit dosage form. In some embodiments, the unit dosage form is a liquid formulation for infusion. In some embodiments, the unit dosage form is a liquid formulation for injection. In some embodiments, the liquid formulation (e.g., for infusion or injection) is supplied in a container with a nominal volume of less than about 100 mL, e.g., less than about 100 mL, less than about 90 mL, less than about 80 mL, less than about 70 mL, less than about 60 mL, less than about 50 mL, less than about 40 mL, less than about 30 mL, less than about 20 mL, less than about 10 mL, or less than about 5 mL. In some embodiments, the volume of the liquid formulation (e.g., for infusion or injection) is between about 1 mL to about 2 mL, e.g., about 1 mL, about 1.1 mL, about 1.2 mL, about 1.3 mL, about 1.4 mL, about 1.5 mL, about 1.6 mL, about 1.7 mL, about 1.8 mL, about 1.9 mL, or about 2 mL. In some embodiments, the volume of the liquid formulation (e.g., for infusion or injection) is about 1 mL.

In embodiments of any of the compositions (e.g., pharmaceutical compositions) provided herein, the number of particles ≥10 μm present in the container does not exceed about 10,000 particles. For example, in some embodiments, the number of particles ≥10 μm present in the container does not exceed about 10,000 particles, about 9,000 particles, about 7,000 particles, about 6,000 particles, about 5,000 particles, about 4,000 particles, about 3,000 particles, about 2,000 particles, about 1,000 particles, about 900 particles, about 800 particles, about 700 particles, about 600 particles, about 500 particles, about 400 particles, about 300 particles, about 200 particles, or about 100 particles. In some embodiments, the number of particles ≥10 μm present in the container does not exceed 6000 particles.

In embodiments of any of the compositions (e.g., pharmaceutical compositions) provided herein, the number of particles ≥25 μm present in the container does not exceed about 2,000 particles, e.g., about 2,000 particles, about 1,500 particles, about 1,200 particles, about 1,000 particles, about 900 particles, about 800 particles, about 700 particles, about 600 particles, about 500 particles, about 400 particles, about 300 particles, about 200 particles, or about 100 particles. In some embodiments, the number of particles ≥25 μm present in the container does not exceed 600 particles.

Any suitable carrier can be used in any of the compositions (e.g., pharmaceutical compositions) provided herein. For example, in some embodiments, the carrier is water.

Any of the preceding compositions (e.g., pharmaceutical compositions) can be stable through one or more freeze-thaw cycles, e.g., one or more, two or more, three or more, four or more, five or more, six or more, seven or more, eight or more, nine or more, or ten or more freeze-thaw cycles. In some embodiments, the pharmaceutical composition is stable through three freeze-thaw cycles.

In some embodiments, any of the preceding compositions (e.g., pharmaceutical compositions) is stable for about 1 month or longer at about 5° C., e.g., about 1 month or longer, about 2 months or longer, about 3 months or longer, about 4 months or longer, about 5 months or longer, about 6 months or longer, about 7 months or longer, about 8 months or longer, about 9 months or longer, about 10 months or longer, about 11 months or longer, about 12 months or longer, about 14 months or longer, about 16 months or longer, about 18 months or longer, about 20 months or longer, about 22 months or longer, about 24 months or longer, about 26 months or longer, about 28 months or longer, about 30 months or longer, about 32 months or longer, about 34 months or longer, about 36 months or longer, about 38 months or longer, about 40 months or longer, about 42 months or longer, about 44 months or longer, about 46 months or longer, about 48 months or longer, about 50 months or longer, about 52 months or longer, about 54 months or longer, about 56 months or longer, about 58 months or longer, about 60 months or longer, about 62 months or longer, about 64 months or longer, about 66 months or longer, about 68 months or longer, about 70 months or longer, about 72 months or longer, about 74 months or longer, about 76 months or longer, about 78 months or longer, about 80 months or longer, about 82 months or longer, about 84 months or longer, about 86 months or longer, about 88 months or longer, about 90 months or longer, about 92 months or longer, about 94 months or longer, about 96 months or longer, about 98 months or longer, or about 100 months or longer. In some embodiments, the pharmaceutical composition is stable for about 24 months or longer at 5° C. In some embodiments, the pharmaceutical composition is stable for about 36 months or longer at 5° C. In some embodiments, the pharmaceutical composition is stable for about 42 months or longer at 5° C. In some embodiments, the pharmaceutical composition is stable for about 48 months or longer at 5° C.

In some embodiments, any of the preceding compositions (e.g., pharmaceutical compositions) is stable for about 1 week or longer at about 25° C., e.g., about 1 week or longer, about 2 weeks or longer, about 3 weeks or longer, about 4 weeks or longer, about 5 weeks or longer, about 6 weeks or longer, about 7 weeks or longer, about 8 weeks or longer, about 9 weeks or longer, about 10 weeks or longer, about 12 weeks or longer, about 14 weeks or longer, about 16 weeks or longer, about 18 weeks or longer, about 20 weeks or longer, about 22 weeks or longer, about 24 weeks or longer, about 26 weeks or longer, about 28 weeks or longer, about 30 weeks or longer, about 32 weeks or longer, about 34 weeks or longer, about 36 weeks or longer, about 38 weeks or longer, about 40 weeks or longer, about 42 weeks or longer, about 44 weeks or longer, about 46 weeks or longer, about 48 weeks or longer, about 50 weeks or longer, or about 52 weeks or longer. In some embodiments, the pharmaceutical composition is stable for about 2 weeks or longer at about 25° C. In some embodiments, the pharmaceutical composition is stable for about 4 weeks or longer at about 25° C. In some embodiments, the pharmaceutical composition is stable for about 8 weeks or longer at about 25° C.

In some embodiments, any of the preceding compositions (e.g., pharmaceutical compositions) is stable for about 12 months or longer at about −20° C., e.g., about 12 months or longer, about 14 months or longer, about 16 months or longer, about 18 months or longer, about 20 months or longer, about 22 months or longer, about 24 months or longer, about 26 months or longer, about 28 months or longer, about 30 months or longer, about 32 months or longer, about 34 months or longer, about 36 months or longer, about 38 months or longer, about 40 months or longer, about 42 months or longer, about 44 months or longer, about 46 months or longer, about 48 months or longer, about 50 months or longer, about 52 months or longer, about 54 months or longer, about 56 months or longer, about 58 months or longer, about 60 months or longer, about 62 months or longer, about 64 months or longer, about 66 months or longer, about 68 months or longer, about 70 months or longer, about 72 months or longer, about 74 months or longer, about 76 months or longer, about 78 months or longer, about 80 months or longer, about 82 months or longer, about 84 months or longer, about 86 months or longer, about 88 months or longer, about 90 months or longer, about 92 months or longer, about 94 months or longer, about 96 months or longer, about 98 months or longer, or about 100 months or longer. In some embodiments, the pharmaceutical composition is stable for about 48 months or longer at −20° C. In some embodiments, the pharmaceutical composition is stable for about 60 months or longer at −20° C. In some embodiments, the pharmaceutical composition is stable for about 72 months or longer at −20° C. In some embodiments, the pharmaceutical composition is stable for about 84 months or longer at −20° C. In some embodiments, the pharmaceutical composition is stable for about 96 months or longer at −20° C.

Any of the preceding compositions (e.g., pharmaceutical compositions) can have a purity of about 70% or higher, for example, as assessed by size-exclusion high-performance liquid chromatography (SE-HPLC). For example, the composition (e.g., the pharmaceutical composition) can have a purity of about 70% or higher, about 72% or higher, about 74% or higher, about 76% or higher, about 78% or higher, about 80% or higher, about 82% or higher, about 84% or higher, about 86% or higher, about 88% or higher, about 90% or higher, about 91% or higher, about 92% or higher, about 94% or higher, about 95% or higher, about 96% or higher, about 97% or higher, about 98% or higher, about 99% or higher, or about 100%, as assessed by SE-HPLC. In some embodiments, the pharmaceutical composition has a purity of about 85% or higher as assessed by SE-HPLC. In some embodiments, the pharmaceutical composition has a purity of about 90% or higher as assessed by SE-HPLC. In some embodiments, the pharmaceutical composition has a purity of about 95% or higher as assessed by SE-HPLC.

Any of the preceding compositions (e.g., pharmaceutical compositions) can have a purity of about 70% or higher (e.g., about 70% or higher, about 72% or higher, about 74% or higher, about 76% or higher, about 78% or higher, about 80% or higher, about 82% or higher, about 84% or higher, about 86% or higher, about 88% or higher, about 90% or higher, about 91% or higher, about 92% or higher, about 94% or higher, about 95% or higher, about 96% or higher, about 97% or higher, about 98% or higher, about 99% or higher, or about 100%) as assessed by SE-HPLC for about 6 months or longer at about 5° C., e.g., about 6 months or longer, about 7 months or longer, about 8 months or longer, about 9 months or longer, about 10 months or longer, about 11 months or longer, about 12 months or longer, about 14 months or longer, about 16 months or longer, about 18 months or longer, about 20 months or longer, about 22 months or longer, about 24 months or longer, about 26 months or longer, about 28 months or longer, about 30 months or longer, about 32 months or longer, about 34 months or longer, about 36 months or longer, about 38 months or longer, about 40 months or longer, about 42 months or longer, about 44 months or longer, about 46 months or longer, about 48 months or longer, about 50 months or longer, about 52 months or longer, about 54 months or longer, about 56 months or longer, about 58 months or longer, about 60 months or longer, about 62 months or longer, about 64 months or longer, about 66 months or longer, about 68 months or longer, about 70 months or longer, about 72 months or longer, about 74 months or longer, about 76 months or longer, about 78 months or longer, about 80 months or longer, about 82 months or longer, about 84 months or longer, about 86 months or longer, about 88 months or longer, about 90 months or longer, about 92 months or longer, about 94 months or longer, about 96 months or longer, about 98 months or longer, or about 100 months or longer. For example, in some embodiments, the composition has a purity of about 95% or higher as assessed by SE-HPLC for about 36 months or longer at about 5° C. In some embodiments, the composition has a purity of about 95% or higher as assessed by SE-HPLC for about 42 months or longer at about 5° C. In some embodiments, the composition has a purity of about 95% or higher as assessed by SE-HPLC for about 48 months or longer at about 5° C.

Any of the preceding compositions (e.g., pharmaceutical compositions) can have a purity of about 65% or higher, for example, as assessed by capillary electrophoresis sodium dodecyl sulfate non-gel sieving (CE-SDS-NGS), e.g., NR CE-SDS-NGS. For example, the composition (e.g., the pharmaceutical composition) can have a purity of about 65% or higher, about 66% or higher, about 67% or higher, about 68% or higher, about 69% or higher, about 70% or higher, about 72% or higher, about 74% or higher, about 76% or higher, about 78% or higher, about 80% or higher, about 82% or higher, about 84% or higher, about 86% or higher, about 88% or higher, about 90% or higher, about 91% or higher, about 92% or higher, about 94% or higher, about 95% or higher, about 96% or higher, about 97% or higher, about 98% or higher, about 99% or higher, or about 100%, as assessed by CE-SDS-NGS (e.g., NR CE-SDS-NGS). In some embodiments, the pharmaceutical composition has a purity of about 75% or higher as assessed by CE-SDS-NGS (e.g., NR CE-SDS-NGS). In some embodiments, the pharmaceutical composition has a purity of about 80% or higher as assessed by CE-SDS-NGS (e.g., NR CE-SDS-NGS). In some embodiments, the pharmaceutical composition has a purity of about 85% or higher as assessed by CE-SDS-NGS (e.g., NR CE-SDS-NGS). In some embodiments, the pharmaceutical composition has a purity of about 90% or higher as assessed by CE-SDS-NGS (e.g., NR CE-SDS-NGS). In some embodiments, the pharmaceutical composition has a purity of about 55% or higher as assessed by CE-SDS-NGS (e.g., NR CE-SDS-NGS).

Any of the preceding compositions (e.g., pharmaceutical compositions) can have a purity of about 65% or higher (e.g., about 65% or higher, about 66% or higher, about 67% or higher, about 68% or higher, about 69% or higher, about 70% or higher, about 72% or higher, about 74% or higher, about 76% or higher, about 78% or higher, about 80% or higher, about 82% or higher, about 84% or higher, about 86% or higher, about 88% or higher, about 90% or higher, about 91% or higher, about 92% or higher, about 94% or higher, about 95% or higher, about 96% or higher, about 97% or higher, about 98% or higher, about 99% or higher, or about 100%) as assessed by CE-SDS-NGS (e.g., NR CE-SDS-NGS) for about 6 months or longer at about 5° C., e.g., about 6 months or longer, about 7 months or longer, about 8 months or longer, about 9 months or longer, about 10 months or longer, about 11 months or longer, about 12 months or longer, about 14 months or longer, about 16 months or longer, about 18 months or longer, about 20 months or longer, about 22 months or longer, about 24 months or longer, about 26 months or longer, about 28 months or longer, about 30 months or longer, about 32 months or longer, about 34 months or longer, about 36 months or longer, about 38 months or longer, about 40 months or longer, about 42 months or longer, about 44 months or longer, about 46 months or longer, about 48 months or longer, about 50 months or longer, about 52 months or longer, about 54 months or longer, about 56 months or longer, about 58 months or longer, about 60 months or longer, about 62 months or longer, about 64 months or longer, about 66 months or longer, about 68 months or longer, about 70 months or longer, about 72 months or longer, about 74 months or longer, about 76 months or longer, about 78 months or longer, about 80 months or longer, about 82 months or longer, about 84 months or longer, about 86 months or longer, about 88 months or longer, about 90 months or longer, about 92 months or longer, about 94 months or longer, about 96 months or longer, about 98 months or longer, or about 100 months or longer. For example, in some embodiments, the composition has a purity of about 85% or higher as assessed by CE-SDS-NGS (e.g., NR CE-SDS-NGS) for about 36 months or longer at about 5° C. In some embodiments, the composition has a purity of about 85% or higher as assessed by CE-SDS-NGS (e.g., NR CE-SDS-NGS) for about 42 months or longer at about 5° C. In some embodiments, the composition has a purity of about 85% or higher as assessed by CE-SDS-NGS (e.g., NR CE-SDS-NGS) for about 48 months or longer at about 5° C.

Any of the compositions (e.g., pharmaceutical compositions) can be formulated for administration by any suitable administration route. For example, in some embodiments, the pharmaceutical composition is formulated for intravenous, subcutaneous, intraperitoneal, or topical administration. In some embodiments, the pharmaceutical composition is formulated for intravenous administration. In some embodiments, the pharmaceutical composition is formulated for subcutaneous administration.

Any of the preceding compositions (e.g., pharmaceutical compositions) can include a preservative. In other embodiments, any of the preceding compositions does not contain a preservative.

Any of the preceding compositions (e.g., pharmaceutical compositions) can be formulated for administration (e.g., by infusion or injection) after dilution with an isotonic sodium chloride solution and/or a diluent. In some embodiments, the pharmaceutical composition is formulated for administration by infusion after dilution with an isotonic sodium chloride solution. In some embodiments, the pharmaceutical composition is formulated for administration by infusion after dilution with a diluent. In some embodiments, the pharmaceutical composition is formulated for administration by infusion after dilution with an isotonic sodium chloride solution and a diluent. For example, in some embodiments, an IL-22 Fc fusion protein is administered to a subject by infusing an IL-22 Fc fusion protein that is diluted with diluent only (e.g., in a syringe pump). In other embodiments, an IL-22 Fc fusion protein is administered to a subject by infusion of IL-22 Fc fusion protein that is diluted with diluent and saline (e.g., in an IV bag). In some embodiments, an IL-22 Fc fusion protein is administered to a subject by infusing an IL-22 Fc fusion protein that is diluted directly into saline (e.g., isotonic saline). In some embodiments, the isotonic sodium chloride solution includes about 0.001% to about 5% (w/v) NaCl. In some embodiments, the isotonic sodium chloride solution includes about 0.1% to about 2% (w/v) NaCl. In some embodiments, the isotonic sodium chloride solution includes about 0.5% to about 1.5% (w/v) NaCl. In some embodiments, the isotonic sodium chloride solution includes about 0.9% (w/v) NaCl. In some embodiments, the diluent includes a buffering agent, a tonicity agent, and/or a surfactant. Any of the buffering agents, tonicity agents, and/or surfactants described herein, and at any concentration described herein, can be used in the diluent. In some embodiments, the diluent includes about 10 mM sodium phosphate, about 240 mM sucrose, about 0.02% (w/v) polysorbate 20, pH 7.1, final concentration.

In some embodiments of any of the preceding compositions (e.g., pharmaceutical compositions), the Fc region of the IL-22 Fc fusion protein is not glycosylated. In some embodiments, the amino acid residue at position 297 as in the EU index of the Fc region is Gly. In some embodiments, the amino acid residue at position 297 as in the EU index of the Fc region is Ala. In some embodiments, the amino acid residue at position 299 as in the EU index of the Fc region is Ala, Gly, or Val. In some embodiments, the Fc region comprises the CH2 and CH3 domain of IgG1 or IgG4. In some embodiments, the Fc region comprises the CH2 and CH3 domain of IgG4.

In some embodiments of any of the preceding compositions (e.g., pharmaceutical compositions), the IL-22 Fc fusion protein comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence selected from the group consisting of SEQ ID NO:8, SEQ ID NO:10, SEQ ID NO:12, SEQ ID NO:14, and SEQ ID NO:16. In some embodiments, the IL-22 Fc fusion protein comprises an amino acid sequence having at least 96% sequence identity to the amino acid sequence of SEQ ID NO:8. In some embodiments, the IL-22 Fc fusion protein comprises an amino acid sequence having at least 97% sequence identity to the amino acid sequence of SEQ ID NO:8. In some embodiments, the IL-22 Fc fusion protein comprises an amino acid sequence having at least 98% sequence identity to the amino acid sequence of SEQ ID NO:8. In some embodiments, the IL-22 Fc fusion protein comprises an amino acid sequence having at least 99% sequence identity to the amino acid sequence of SEQ ID NO:8. In some embodiments, the IL-22 Fc fusion protein comprises the amino acid sequence of SEQ ID NO:8, SEQ ID NO:10, or SEQ ID NO:16. In some embodiments, the IL-22 Fc fusion protein comprises the amino acid sequence of SEQ ID NO:8. In some embodiments, the IL-22 Fc fusion protein consists of the amino acid sequence of SEQ ID NO:8. In some embodiments, the IL-22 Fc fusion protein comprises the amino acid sequence of SEQ ID NO:10. In some embodiments, the IL-22 Fc fusion protein consists of the amino acid sequence of SEQ ID NO:10. In some embodiments, the IL-22 Fc fusion protein comprises the amino acid sequence of SEQ ID NO:16. In some embodiments, the IL-22 Fc fusion protein consists of the amino acid sequence of SEQ ID NO:16. In some embodiments, the Fc region is not N-glycosylated.

In any of the preceding compositions (e.g., pharmaceutical compositions), the IL-22 Fc fusion protein can be a dimeric IL-22 Fc fusion protein. In other embodiments, the IL-22 Fc fusion protein can be monomeric IL-22 Fc fusion protein.

In any of the preceding compositions (e.g., pharmaceutical compositions), the IL-22 Fc fusion protein can include a human IL-22 polypeptide. In some embodiments, the amino acid sequence of SEQ ID NO:4.

Any suitable linker can be used in the IL-22 Fc fusion proteins contained in the compositions (e.g., pharmaceutical compositions) described herein. In some embodiments, the linker comprises the amino acid sequence RVESKYGPP (SEQ ID NO: 44). In some embodiments, the linker consists of the amino acid sequence RVESKYGPP (SEQ ID NO: 44).

In any of the preceding compositions (e.g., pharmaceutical compositions), the IL-22 Fc fusion protein can bind to IL-22 receptor. In some embodiments, the IL-22 receptor is human IL-22 receptor. In some embodiments, the IL-22 Fc fusion protein binds to IL-22R1 and/or IL-10R2. In some embodiments, the IL-22 Fc fusion protein binds to IL-22R1. In some embodiments, the human IL-22 receptor comprises a heterodimer consisting of an IL-22R1 polypeptide and an IL-10R2 polypeptide. In some embodiments, the IL-22R1 polypeptide comprises the amino acid sequence of SEQ ID NO:82 and the IL-10R2 polypeptide comprises the amino acid sequence of SEQ ID NO:84.

As one non-limiting example, the invention provides a pharmaceutical composition including an IL-22 Fc fusion protein and a carrier (e.g., water), the IL-22 Fc fusion protein including the amino acid sequence of SEQ ID NO:8 or SEQ ID NO:16, wherein the pharmaceutical composition includes about 5 mM methionine, about 10 mM sodium phosphate, about 240 mM sucrose, and about 0.02% (w/v) polysorbate 20, pH 7.1, final concentration.

In some embodiments, the IL-22 Fc fusion proteins contained in any of the preceding compositions (e.g., pharmaceutical compositions) is produced by the method comprising the step of culturing a host cell capable of expressing the IL-22 Fc fusion protein under conditions suitable for expression of the IL-22 Fc fusion protein. In some embodiments, the method further comprises the step of obtaining the IL-22 Fc fusion protein from the cell culture or culture medium. In some embodiments, the host cell is a CHO cell.

The compositions (e.g., pharmaceutical compositions comprising IL-22 Fc fusion proteins) herein will be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. In one embodiment, the composition can be used for increasing the duration of survival of a human subject susceptible to or diagnosed with the disease or condition disease. Duration of survival is defined as the time from first administration of the drug to death. In one embodiment, the composition can be used to reduce one or more symptoms of a human subject susceptible to or diagnosed with the disease or condition disease, for example, any disorder described herein (e.g., IBD, e.g., UC or Crohn's disease).

Pharmaceutical formulations can be prepared using standard methods known in the art by mixing the active ingredient having the desired degree of purity with one or more optional pharmaceutically acceptable carriers (see, e.g., *Remington's Pharmaceutical Sciences* 16th edition, Osol, A. Ed. (1980) and *Remington's Pharmaceutical Sciences* 20$^{th}$ edition, ed. A. Gennaro, 2000, Lippincott, Williams & Wilkins, Philadelphia, Pa), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or nonionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Optionally, the formulation contains a pharmaceutically acceptable salt, preferably sodium chloride, and preferably at about physiological concentrations.

Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, benzalkonium chloride and propylparaben are preferred preservatives. Optionally, the formulations of the invention can include a pharmaceutically acceptable surfactant at a concentration of 0.005 to 0.02%.

The formulation herein can also contain more than one active compound as necessary for the particular indication being treated, preferably those with complementary activities that do not adversely affect each other. Such molecules are suitably present in combination in amounts that are effective for the purpose intended.

Exemplary lyophilized formulations are described in U.S. Pat. No. 6,267,958. Aqueous formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a steroid, TNF antagonist or other anti-inflammatory therapeutics. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the IL-22 Fc fusion protein, which matrices are in the form of shaped articles, e.g., films or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

A pharmaceutical composition for topical administration can be formulated, for example, in the form of a topical gel. See e.g., U.S. Pat. Nos. 4,717,717; 5,130,298; 5,427,778; 5,457,093; 5,705,485; 6,331,309; and WO2006/138,468. In certain embodiments, the composition can be formulated in the presence of cellulose derivatives. In certain other embodiments, the topical formulation can be reconstituted from lyophilized formulation with sufficient buffer or diluent before administration. In certain embodiments, IL-22 polypeptide or IL-22 Fc fusion protein is formulated for topical administration to a subject having a defect in epithelial wound healing. In certain particular embodiments, the epithelial wound healing occurs in the skin. In certain other particular embodiments, the subject is a human having a defect in wound healing. In certain other embodiments, the topical formulation comprising an IL-22 Fc fusion protein of the invention can be used to improve wound healing after internal or external surgical incisions.

In one embodiment of the invention, an IL-22 polypeptide or IL-22 Fc fusion protein for use in accelerating, promoting or improving wound healing is in a formulation of a topical gel, e.g., in a pre-filled syringe or container, or alternatively, the compound of the invention can be mixed with a gel matrix right before topical administration to a patient. In certain embodiments, an additional therapeutic agent is also administered topically, either concurrently or sequentially. Other routes of administration can also be optionally used, e.g., administered by any suitable means, including but not limited to, parenteral, subcutaneous, intraperitoneal, intrapulmonary, intracerobrospinal, subcutaneous, intra-articular, intrasynovial, intrathecal, oral, and intranasal administration. Parenteral infusions include intramuscular, intravenous, intraarterial, intraperitoneal, or subcutaneous administration.

Typically for wound healing, an IL-22 Fc fusion protein is formulated for site-specific delivery. When applied topically, the IL-22 Fc fusion protein is suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, sprays, or suspensions, with or without purified collagen. The compositions also may be impregnated into sterile dressings, transdermal patches, plasters, and bandages, optionally in liquid or semi-liquid form. An oxidized regenerated cellulose/collagen matrices can also be used, e.g., PROMOGRAN Matrix Wound Dressing or PROMOGRAN PRISMA MATRIX.

For obtaining a gel formulation, the IL-22 polypeptide or IL-22 Fc fusion protein formulated in a liquid composition may be mixed with an effective amount of a water-soluble polysaccharide or synthetic polymer to form a gel (e.g., a gelling agent) such as polyethylene glycol to form a formulation of the proper viscosity to be applied topically. The polysaccharide or gelling agent that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; Sodium carboxymethyl cellulose; POE-POP block polymers: poloxamer USP in various grades; Hyaluronic acid; Polyacrylic acid such as carbopol 940; starch and fractionated starch; agar; alginic acid and alginates; gum Arabic; pullullan; agarose; carrageenan; dextrans; dextrin; fructans; inulin; mannans; xylans; arabinans; chitosans; glycogens; glucans; and synthetic biopolymers; as well as gums such as xanthan gum; guar gum; locust bean gum; gum Arabic; tragacanth gum; and karaya gum; and derivatives, combinations and mixtures thereof. In one embodiment of the invention, the gelling agent herein is one that is, e.g., inert to biological systems, nontoxic, simple to prepare, and/or not too runny or viscous, and will not destabilize the IL-22 polypeptide or IL-22 Fc fusion held within it.

In certain embodiments of the invention, the polysaccharide is an etherified cellulose derivative, in another embodiment one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose (all referred to as cellulosic agents). In some embodiments, the polysaccharide is hydroxyethyl methylcellulose or hydroxypropyl methylcellulose.

The polyethylene glycol useful for gelling is typically a mixture of low and high molecular weight polyethylene glycols to obtain the proper viscosity. For example, a mixture of a polyethylene glycol of molecular weight 400-600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

In certain embodiments, methylcellulose is employed in the gel, for example, it comprises about 1-5%, or about 1%, about 2%, about 3%, about 4% or about 5%, of the gel and the IL-22 Fc fusion protein is present in an amount of about 50-2000 µg, 100-2000 µg, or 100-1000 µg per ml of gel. In certain embodiments, the effective amount of IL-22 Fc fusion protein for wound healing by topical administration can be about 25 µg to about 500 µg, about 50 µg to about 300 µg, about 100 µg to about 250 µg, about 50 µg to about 250 µg, about 50 µg to about 150 µg, about 75 µg, about 100 µg, about 125 µg, about 150 µg, about 175 µg, about 200 µg, about 225 µg, about 250 µg, about 300 µg, or about 350 µg, per cm² wound area.

The formulations to be used for in vivo administration are generally sterile. Sterility may be readily accomplished, e.g., by filtration through sterile filtration membranes.

The present invention provides dosages for the IL-22 Fc fusion protein-based therapeutics. For example, depending on the type and severity of the disease, about 1 µg/kg to 15 mg/kg (e.g., 0.1-20 mg/kg) of polypeptide is an initial candidate dosage for administration to the subject, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens can be useful. The progress of this therapy is easily monitored by conventional techniques and assays.

For the prevention or treatment of disease, the appropriate dosage of a polypeptide (e.g., an IL-22 Fc fusion protein) of the invention (when used alone or in combination with one or more other additional therapeutic agents) will depend on the type of disease to be treated, the type of polypeptide, the severity and course of the disease, whether the polypeptide is administered for preventive or therapeutic purposes, previous therapy, the subject's clinical history and response to the polypeptide, and the discretion of the attending physician. The polypeptide is suitably administered to the subject at one time or over a series of treatments. Depending on the type and severity of the disease, about 1 µg/kg to 20 mg/kg (e.g. 0.1 mg/kg-15 mg/kg) of the polypeptide can be an initial candidate dosage for administration to the subject, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the polypeptide would be in the range from about 0.05 mg/kg to about 20 mg/kg. Thus, one or more doses of about 0.5 mg/kg, 2.0 mg/kg, 4.0 mg/kg, 10 mg/kg, 12 mg/kg, 15 mg/kg, or 20 mg/kg (or any combination thereof) may be administered to the subject. In certain embodiments, about 0.5 mg/kg, 1.0 mg·kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10 mg/kg, 12 mg/kg, 15 mg/kg, or 20 mg/kg (or any combination thereof) may be administered to the subject. Such doses may be administered intermittently, e.g. every week, every two weeks, or every three weeks (e.g. such that the subject receives from about two to about twenty, or e.g. about six doses of the polypeptide). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

The compounds of the invention for prevention or treatment of a cardiovascular disease or condition, metabolic syndrome, acute endotoxemia or sepsis, GVHD, or diabetes are typically administered by intravenous injection.

Other methods of administration can also be used, which includes but is not limited to, topical, parenteral, as intravenous, subcutaneous, intraperitoneal, intrapulmonary, intranasal, ocular, intraocular, intravitreal, intralesional, intracerobrospinal, intra-articular, intrasynovial, intrathecal, oral, or inhalation administration. Parenteral infusions include intramuscular, intravenous, intraarterial, intraperitoneal, or subcutaneous administration. In addition, the compounds described herein are administered to a human subject, in accord with known methods, such as intravenous administration as a bolus or by continuous infusion over a period of time.

1. Exemplary IL-22 Fc Fusion Proteins for Use in the Compositions

Any suitable IL-22 Fc fusion protein can be used in the compositions. In general, the IL-22 Fc fusion proteins include an IL-22 polypeptide linked to an Fc region by a linker. Any of the IL-22 Fc fusion proteins described in U.S. Pat. No. 9,815,880, which is incorporated by reference herein in its entirety, may be used in the compositions described herein. In some embodiments of any of the preceding IL-22 Fc fusion proteins, the Fc region is not glycosylated. In some embodiments, the amino acid residue at position 297 as in the EU index of the Fc region is Gly. In some embodiments, the amino acid residue at position 297 as in the EU index of the Fc region is Ala. In some embodiments, the amino acid residue at position 299 as in the EU index of the Fc region is Ala, Gly, or Val. In some embodiments, the Fc region comprises the CH2 and CH3 domain of IgG1 or IgG4. In some embodiments, the Fc region comprises the CH2 and CH3 domain of IgG4.

In some embodiments of any of the preceding IL-22 Fc fusion proteins, the IL-22 Fc fusion protein comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence selected from the group consisting of SEQ ID NO:8, SEQ ID NO:10, SEQ ID NO:12, SEQ ID NO:14, and SEQ ID NO:16. In some embodiments, the IL-22 Fc fusion protein comprises an amino acid sequence having at least 96% sequence identity to the amino acid sequence of SEQ ID NO:8. In some embodiments, the IL-22 Fc fusion protein comprises an amino acid sequence having at least 97% sequence identity to the amino acid sequence of SEQ ID NO:8. In some embodiments, the IL-22 Fc fusion protein comprises an amino acid sequence having at least 98% sequence identity to the amino acid sequence of SEQ ID NO:8. In some embodiments, the IL-22 Fc fusion protein comprises an amino acid sequence having at least 99% sequence identity to the amino acid sequence of SEQ ID NO:8. In some embodiments, the IL-22 Fc fusion protein comprises the amino acid sequence of SEQ ID NO:8, SEQ ID NO:10, or SEQ ID NO:16. In some embodiments, the IL-22 Fc fusion protein comprises the amino acid sequence of SEQ ID NO:8. In some embodiments, the IL-22 Fc fusion protein consists of the amino acid sequence of SEQ ID NO:8. In some embodiments, the IL-22 Fc fusion protein comprises the amino acid sequence of SEQ ID NO:10. In some embodiments, the IL-22 Fc fusion protein consists of the amino acid sequence of SEQ ID NO:10. In some embodiments, the IL-22 Fc fusion protein comprises the amino acid sequence of SEQ ID NO:16. In some embodiments, the IL-22 Fc fusion protein consists of the amino acid sequence of SEQ ID NO:16. In some embodiments, the Fc region is not N-glycosylated.

Any of the preceding IL-22 Fc fusion proteins can be a dimeric IL-22 Fc fusion protein. In other embodiments, any of the preceding IL-22 Fc fusion proteins can be a monomeric IL-22 Fc fusion protein.

Any of the preceding IL-22 Fc fusion proteins can include a human IL-22 polypeptide. In some embodiments, the amino acid sequence of SEQ ID NO:4.

Any suitable linker can be used in the IL-22 Fc fusion proteins described herein. In some embodiments, the linker comprises the amino acid sequence RVESKYGPP (SEQ ID NO: 44). In some embodiments, the linker consists of the amino acid sequence RVESKYGPP (SEQ ID NO: 44).

In some embodiments, any of the IL-22 Fc fusion proteins described herein binds to IL-22 receptor. In some embodiments, the IL-22 receptor is human IL-22 receptor. In some embodiments, the IL-22 Fc fusion protein binds to IL-22RA1 and/or IL-10R2. In some embodiments, the IL-22 Fc fusion protein binds to IL-22RA1.

In some embodiments, any of the preceding IL-22 Fc fusion proteins is produced by the method comprising the step of culturing a host cell capable of expressing the IL-22 Fc fusion protein under conditions suitable for expression of the IL-22 Fc fusion protein. In some embodiments, the method further comprises the step of obtaining the IL-22 Fc fusion protein from the cell culture or culture medium. In some embodiments, the host cell is a CHO cell.

In certain embodiments, any of the IL-22 Fc fusion proteins described herein binds to and induces IL-22 receptor activity or signaling and/or is an agonist of IL-22 receptor activity.

In another aspect, an IL-22 Fc fusion protein provided herein comprises a polypeptide having at least 90%, 91%, 92%, 93%, 94%, 95%, 96%, 97%, 98%, 99%, or 100% sequence identity to the amino acid sequence of SEQ ID NO:4. In other embodiments, the IL-22 Fc fusion protein comprises a polypeptide having at least 90%, 91%, 92%, 93%, 94%, 95%, 96%, 97%, 98%, or 99% sequence identity contains substitutions (e.g., conservative substitutions), insertions, or deletions relative to the reference sequence, but an IL-22 Fc fusion protein comprising that sequence retains the ability to bind to IL-22 receptor. In certain embodiments, a total of 1 to 10 amino acids have been substituted, inserted, and/or deleted in SEQ ID NOs: 8, 10, 12, 14, 16, 24, or 26. In certain embodiments, substitutions, insertions, or deletions occur in regions outside the IL-22 (i.e., in the Fc). In some embodiments, the substitutions, insertions, or deletions can be in the linker, the hinge, the CH2 domain, the CH3 domain of the IL-22 Fc fusion protein In certain particular embodiments, the C-terminus Lys residue of Fc is deleted. In certain other embodiments, the C-terminus Gly and Lys residues of Fc are both deleted.

In certain embodiments, IL-22 Fc fusion proteins variants having one or more amino acid substitutions are provided. Conservative substitutions are shown in Table A under the heading of "preferred substitutions." More substantial changes are provided in Table A under the heading of "exemplary substitutions," and as further described below in reference to amino acid side chain classes. Amino acid substitutions may be introduced into the IL-22 Fc fusion protein and the products screened for a desired activity, e.g., retained/improved IL-22 receptor binding, decreased immunogenicity, or improved IL-22 receptor signaling.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
  (1) hydrophobic: Norleucine, Met, Ala, Val, Leu, lie;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class.

A useful method for identification of residues or regions of a protein that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the protein with its binding partner is affected. Further substitutions may be introduced at the amino acid locations demonstrating functional sensitivity to the initial substitutions. Alternatively, or additionally, a crystal structure of a protein complex (e.g., a cytokine-receptor complex) can be used to identify contact points between a protein and its binding partner. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues.

Provided herein are nucleic acids encoding IL-22 Fc fusion proteins. In some embodiments, the nucleic acid encodes the IL-22 Fc fusion protein comprising the amino acid sequence of SEQ ID NO:8, SEQ ID NO:10, SEQ ID NO:12, SEQ ID NO:14, SEQ ID NO:24 or SEQ ID NO:26, preferably SEQ ID NO:8, SEQ ID NO:10, or SEQ ID NO:16, more preferably SEQ ID NO:8. In certain other embodiments, the nucleic acid comprises the polynucleotide sequence of SEQ ID NO:7, SEQ ID NO:9, SEQ ID NO:11, SEQ ID NO:13, SEQ ID NO:23 or SEQ ID NO:25. In certain particular embodiments, the nucleic acid comprises the polynucleotide sequence of SEQ ID NO:7 or SEQ ID NO:11, preferably SEQ ID NO:7. In certain embodiments, the isolated nucleic acid comprises a polynucleotide sequence that is at least 80%, 85%, 86%, 87%, 88%, 89%, 90%, 91%, 92%, 93%, 94%, 95%, 96%, 97%, 98%, 99% or 100% sequence identity to the polynucleotide sequence of SEQ ID NO:7, SEQ ID NO:9, SEQ ID NO:11, SEQ ID NO:13; SEQ ID NO:23 or SEQ ID NO:25. In certain embodiments, the isolated nucleic acid comprises a polynucleotide sequence that is at least 80%, 85%, 86%, 87%, 88%, 89%, 90%, 91%, 92%, 93%, 94%, 95%, 96%, 97%, 98%, 99% or 100% sequence identity to the polynucleotide sequence of SEQ ID NO:7, SEQ ID NO:9, SEQ ID NO:11, SEQ ID NO:13; SEQ ID NO:23 or SEQ ID NO:25, wherein the isolated nucleic acid is capable of encoding an IL-22 Fc fusion protein that is capable of binding to IL-22R and/or triggering IL-22R activity and wherein the Fc region of the IL-22 Fc fusion protein is not glycosylated. In certain embodiments, the isolated nucleic acid comprises a polynucleotide sequence that is at least 80%, 85%, 86%, 87%, 88%, 89%, 90%, 91%, 92%, 93%, 94%, 95%, 96%, 97%, 98%, 99% or 100% sequence identity to the polynucleotide sequence of SEQ ID NO:7, SEQ ID NO:9, SEQ ID NO:11, SEQ ID NO:13; SEQ ID NO:23 or SEQ ID NO:25, wherein the isolated nucleic acid is capable of encoding an IL-22 Fc fusion protein comprising the amino acid sequence of SEQ ID NO:8, 10, 12, or 14. In related aspects, the invention provides vectors comprising the nucleic acid described above, and a host cell comprising the vector. In certain embodiments, the host cell is a prokaryotic cell or eukaryotic cell. In certain particular embodiments, the host cell is a prokaryotic cell, including without limitation, an *E. coli* cell. In certain other embodiments, the host cell is a eukaryotic cell, including without limitation, a CHO cell. In certain embodiments, the host cell comprises a vector comprising a nucleic acid encoding the IL-22 Fc fusion protein comprising the amino acid sequence of SEQ ID NO:8.

a) Glycosylation Variants

In certain embodiments, an IL-22 Fc fusion protein provided herein is altered to increase or decrease the extent to which the fusion protein or a portion thereof (e.g., the Fc portion of the fusion protein) is glycosylated. Addition or deletion of glycosylation sites to a protein may be conveniently accomplished by altering the amino acid sequence such that one or more glycosylation sites is created or removed.

Where the fusion protein comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody or the Fc region of an antibody may be made in order to create Fc variants with certain improved properties.

The amount of fucose attached to the CH2 domain of the Fc region can be determined by calculating the average amount of fucose within the sugar chain at Asn297, relative to the sum of all glycostructures attached to Asn 297 or N297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); U.S. Pat. Appl. No. US 2003/0157108 A1; and WO 2004/056312 A1, especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

b) Fc Region Variants

In certain embodiments, one or more amino acid modifications may be introduced into the Fc region of an Fc fusion protein provided herein, thereby generating an Fc region variant. The Fc region variant may comprise a human Fc region sequence (e.g., a human IgG1, IgG2, IgG3, or IgG4 Fc region) comprising an amino acid modification (e.g., a substitution) at one or more amino acid positions. For example, the hinge may include a Ser to Pro substitution, for example, as shown in the bolded and underlined Pro residue in the amino acid sequence of CPPCP (SEQ ID NO:31). Such a Ser to Pro substitution may increase the stability of the molecule.

In certain embodiments, the invention contemplates an Fc variant that possesses some but not all effector functions, which make it a desirable candidate for applications in which the half-life of the antibody or a fusion protein comprising an Fc region in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody or Fc lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch et al., *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom et al., *Proc. Nat'l Acad. Sci. USA* 83:7059-7063 (1986) and Hellstrom et al., *Proc. Nat'l Acad. Sci. USA* 82:1499-1502 (1985); U.S. Pat. No. 5,821,337 (see Bruggemann et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CYTOTOX 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci.* USA 95:652-656 (1998). C1q binding assays may also be carried out to confirm that the antibody or Fc is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg et al., *Blood* 101:1045-1052 (2003); and Cragg et al., *Blood* 103:2738-2743 (2004)). FcRn binding and in vivo clearance/half-life determinations can also be performed using methods known in the art (see, e.g., Petkova et al., *Int'l. Immunol.* 18(12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody or Fc variants with improved or diminished binding to FcRs are described. (See, e.g., U.S. Pat. No. 6,737,056; WO 2004/056312, and Shields et al., *J. Biol. Chem.* 9(2): 6591-6604 (2001).) In certain embodiments, an IL-22 Fc fusion protein comprises an Fc variant with one or more amino acid substitutions which reduce ADCC, e.g., substitution at position 297 of the Fc region to remove the N-glycosylation site and yet retain FcRn binding activity (EU numbering of residues).

In some embodiments, alterations are made in the Fc region that result in diminished C1 q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

c) Cysteine Engineered Variants

In certain embodiments, it may be desirable to create cysteine engineered Fc fusion protein, in which one or more residues of the Fc region of an antibody are substituted with cysteine residues. In particular embodiments, the substituted residues occur at accessible sites of the Fc. By substituting those residues with cysteine, reactive thiol groups are thereby positioned at accessible sites of the Fc and may be used to conjugate the Fc to other moieties, such as drug moieties or linker-drug moieties, to create an immunoconjugate, as described further herein. For example, S400 (EU numbering) of the heavy chain Fc region can be substituted with Cys. See, e.g., U.S. Pat. No. 7,521,541.

2. Exemplary IL-22 Polypeptides

Any suitable IL-22 polypeptide can be included in the IL-22 Fc fusion proteins described herein. For example, in any of the IL-22 Fc fusion proteins described herein, the IL-22 polypeptide can include a polypeptide comprising an amino acid sequence comprising SEQ ID NO:71 (human IL-22 with the endogenous IL-22 leader sequence), or a polypeptide comprising an amino acid sequence that has at least 80% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity) with SEQ ID NO:71. In certain embodiments, the IL-22 polypeptide comprises an amino acid sequence comprising SEQ ID NO:4 (human IL-22 without a leader sequence) or a polypeptide comprising an amino acid sequence that has at least 80% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity) with SEQ ID NO:4. In certain embodiments, the IL-22 polypeptide comprises an amino acid sequence comprising SEQ ID NO:4.

The preparation of native IL-22 molecules, along with their nucleic acid and polypeptide sequences, can be achieved through methods known to those of ordinary skill in the art. For example, IL-22 polypeptides can be produced by culturing cells transformed or transfected with a vector containing IL-22 nucleic acid. It is, of course, contemplated that alternative methods, which are well known in the art, can be employed to prepare IL-22. For instance, the IL-22 sequence, or portions thereof, can be produced by direct peptide synthesis using solid-phase techniques (see, e.g., Stewart et al., 1969, Solid-Phase Peptide Synthesis, W.H. Freeman Co., San Francisco, Calif. (1969); Merrifield, J. Am. Chem. Soc., 1963, 85:2149-2154). In vitro protein synthesis can be performed using manual techniques or by automation. Automated synthesis can be accomplished, for instance, using an Applied Biosystems Peptide Synthesizer (Foster City, Calif.) using manufacturer's instructions. Various portions of IL-22 can be chemically synthesized separately and combined using chemical or enzymatic methods to produce the full-length IL-22.

IL-22 variants can be prepared by introducing appropriate nucleotide changes into the DNA encoding a native sequence IL-22 polypeptide, or by synthesis of the desired IL-22 polypeptide. Those skilled in the art will appreciate that amino acid changes can alter post-translational processes of IL-22, such as changing the number or position of glycosylation sites or altering the membrane anchoring characteristics.

Variations in the native sequence IL-22 polypeptides described herein can be made, for example, using any of the techniques and guidelines for conservative and non-conservative mutations set forth, for instance, in U.S. Pat. No. 5,364,934. Variations can be a substitution, deletion, or insertion of one or more codons encoding a native sequence or variant IL-22 that results in a change in its amino acid sequence as compared with a corresponding native sequence or variant IL-22. Optionally the variation is by substitution of at least one amino acid with any other amino acid in one or more of the domains of a native sequence IL-22 polypeptide. Guidance in determining which amino acid residue can be inserted, substituted or deleted without adversely affecting the desired activity can be found by comparing the sequence of the IL-22 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions can optionally be in the range of 1 to 5 amino acids. The variation allowed can be determined by systematically making insertions, deletions or substitutions of amino acids in the sequence and testing the resulting variants for activity, for example, in the in vitro assay described in the Examples below.

In particular embodiments, conservative substitutions of interest are shown in Table A under the heading of preferred substitutions. If such substitutions result in a change in biological activity, then more substantial changes, denominated exemplary substitutions in Table A, or as further described below in reference to amino acid classes, are introduced and the products screened.

Another type of covalent modification of the IL-22 polypeptides included within the scope of this invention comprises altering the native glycosylation pattern of the polypeptides. "Altering the native glycosylation pattern" is intended for purposes herein to mean deleting one or more carbohydrate moieties found in native sequence IL-22, and/ or adding one or more glycosylation sites that are not present in the native sequence IL-22, and/or alteration of the ratio and/or composition of the sugar residues attached to the glycosylation site(s).

Glycosylation of polypeptides is typically either N-linked or O-linked. Addition of glycosylation sites to the IL-22 polypeptide can be accomplished by altering the amino acid sequence. The alteration can be made, for example, by the addition of, or substitution by, one or more serine or threonine residues to the native sequence IL-22 (for N-linked glycosylation sites), or the addition of a recognition sequence for O-linked glycosylation. The IL-22 amino acid sequence can optionally be altered through changes at the DNA level, particularly by mutating the DNA encoding the IL-22 polypeptide at preselected bases such that codons are generated that will translate into the desired amino acids.

Another means of increasing the number of carbohydrate moieties on the IL-22 polypeptide is by chemical or enzymatic coupling of glycosides to the polypeptide. Such methods are described in the art, e.g., in WO 87/05330 and in Aplin et al., CRC Crit. Rev. Biochem., pp. 259-306 (1981).

Removal of carbohydrate moieties present on an IL-22 polypeptide can be accomplished chemically or enzymatically or by mutational substitution of codons encoding for amino acid residues that serve as targets for glycosylation. Chemical deglycosylation techniques are known in the art and described, for instance, by Hakimuddin et al., Arch. Biochem. Biophys. 259:52 (1987) and by Edge et al., Anal. Biochem. 118:131 (1981). Enzymatic cleavage of carbohydrate moieties on polypeptides can be achieved by the use of a variety of endo- and exo-glycosidases as described by Thotakura et al., Meth. Enzymol. 138:350 (1987).

The variations can be made using methods known in the art such as oligonucleotide-mediated (site-directed) mutagenesis, alanine scanning, and PCR mutagenesis. Site-directed mutagenesis (Carter et al., 1986, Nucl. Acids Res. 13:4331; Zoller et al., 1987, Nucl. Acids Res. 10:6487), cassette mutagenesis (Wells et al., 1985, Gene 34:315), restriction selection mutagenesis (Wells et al., 1986, Philos. Trans. R. Soc. London A 317:415), or other known techniques can be performed on the cloned DNA to produce the IL-22 variant DNA.

Fragments of an IL-22 polypeptide are also provided herein. Such fragments can be truncated at the N-terminus or C-terminus, or can lack internal residues, for example, when compared with a full length native protein. Certain fragments lack amino acid residues that are not essential for a desired biological activity of an IL-22 polypeptide of the present invention. Accordingly, in certain embodiments, a fragment of an IL-22 polypeptide is biologically active. In certain embodiments, a fragment of full length IL-22 lacks the N-terminal signal peptide sequence.

Covalent modifications of native sequence and variant IL-22 polypeptides are included within the scope of this invention. One type of covalent modification includes reacting targeted amino acid residues of IL-22 with an organic derivatizing agent that is capable of reacting with selected side chains or the N- or C-terminal residues of the IL-22 polypeptide. Derivatization with bifunctional agents is useful, for instance, for crosslinking IL-22 to a water-insoluble support matrix or surface, for example, for use in the method for purifying anti-IL-22 antibodies. Commonly used crosslinking agents include, e.g., 1,1-bis(diazo-acetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane, and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, 1983, Proteins: Structure and Molecular Properties, W. H. Freeman & Co., San Francisco, pp. 79-86i), acetylation of the N-terminal amine, and amidation of any C-terminal carboxyl group.

Another type of covalent modification of IL-22 comprises linking the IL-22 polypeptide to one of a variety of non-proteinaceous polymers, e.g., polyethylene glycol, polypropylene glycol, or polyoxyalkylenes, for example in the manner set forth in U.S. Pat. Nos. 4,640,835; 4,496,689; 4,301,144; 4,670,417; 4,791,192; or 4,179,337. The native sequence and variant IL-22 can also be modified in a way to form a chimeric molecule comprising IL-22, including fragments of IL-22, fused to another, heterologous polypeptide or amino acid sequence.

In one embodiment, such a chimeric molecule comprises a fusion of IL-22 with a tag polypeptide which provides an epitope to which an anti-tag antibody can selectively bind. The epitope tag is generally placed at the amino- or carboxyl-terminus of the IL-22 polypeptide. The presence of such epitope-tagged forms of the IL-22 polypeptide can be detected using an antibody against the tag polypeptide. Also, provision of the epitope tag enables the IL-22 polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., 1988, *Mol. Cell. Biol.*, 8:2159-2165); the c-myc tag and the 8F9, 3C7, 6E10, G4, and 9E10 antibodies thereto (Evan et al., 1985, *Mol. Cell. Biol.* 5:3610-3616); and the Herpes Simplex virus glycoprotein D (gD) tag and its antibody (Paborsky et al., 1990, *Protein Engineering* 3(6): 547-553). Other tag polypeptides include the Flag-peptide (Hopp et al., 1988, *BioTechnology* 6:1204-1210); the KT3 epitope peptide (Martin et al., 1992, *Science* 255:192-194); a tubulin epitope peptide (Skinner et al., 1991, *J. Biol. Chem.* 266:15163-15166); and the T7 gene 10 protein peptide tag (Lutz-Freyermuth et al., 1990, *Proc. Natl. Acad. Sci. USA*, 87:6393-6397).

In another embodiment, the chimeric molecule can comprise a fusion of the IL-22 polypeptide or a fragment thereof with an immunoglobulin or a particular region of an immunoglobulin. For a bivalent form of the chimeric molecule, such a fusion can be to the Fc region of an IgG molecule. These fusion polypeptides are antibody-like molecules which combine the binding specificity of a heterologous protein (an "adhesin") with the effector functions of immunoglobulin constant domains, and are often referred to as immunoadhesins. Structurally, the immunoadhesins comprise a fusion of an amino acid sequence of IL-22, or a variant thereof, and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin can be obtained from any immunoglobulin, such as IgG1, IgG2, IgG3, or IgG4 subtypes, IgA (including IgA1 and IgA2), IgE, IgD, or IgM. In certain embodiments, the IL-22 Fc fusion protein exhibits modified effector activities.

The IL-22 polypeptide, or a fragment thereof, can be fused, for example, to an immunoglobulin heavy chain constant region sequence to produce an IL-22-Ig fusion protein (e.g., IL-22 Fc fusion protein). The IL-22 polypeptide can be human or murine IL-22. The immunoglobulin heavy chain constant region sequence can be human or murine immunoglobulin heavy chain constant region B. Methods of Making IL-22 Fc Fusion Proteins for Use in the Compositions The IL-22 Fc fusion proteins described herein can be prepared by any suitable method, e.g., culturing cells transformed or transfected with a vector containing a nucleic acid encoding an IL-22 Fc fusion protein, a fragment, or a variant thereof. Host cells comprising any such vector are also provided. Any suitable host cell can be used, e.g., mammalian cells (e.g., CHO cells), *E. coli*, or yeast. Processes for producing any of the herein described IL-22 Fc fusion proteins are further provided and, in general, involve culturing host cells under conditions suitable for expression of the desired IL-22 Fc fusion protein and recovering, and optionally purifying, the desired IL-22 Fc fusion protein from the cell culture. For example, any of the methods described in U.S. Provisional Patent Application No. 62/622,762, which is incorporated herein by reference in its entirety, may be used.

Host cells are transfected or transformed with expression or cloning vectors described herein for IL-22 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: A Practical Approach, M. Butler, ed. (IRL Press, 1991) and Sambrook et al., supra.

Methods of transfection are known to the ordinarily skilled artisan, for example, by CaPO$_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transformations have been described in U.S. Pat. No. 4,399,216. Transformations into yeast are typically carried out according to the method of Van Solingen et al., J. Bact, 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, can also be used. For various techniques for transforming mammalian cells, see Keown et al., Methods in Enzymology, 185:527-537 (1990) and Mansour et al., Nature, 336:348-352 (1988).

Recombinantly expressed polypeptides of the present invention can be recovered from culture medium or from host cell lysates. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of a polypeptide of the present invention. Various methods of protein purification can be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular polypeptide produced.

Alternative methods, which are well known in the art, can be employed to prepare a polypeptide of the present invention. For example, a sequence encoding a polypeptide or portion thereof, can be produced by direct peptide synthesis using solid-phase techniques (see, e.g., Stewart et al., 1969, *Solid-Phase Peptide Synthesis*, W.H. Freeman Co., San Francisco, CA; Merrifield, J. 1963, *Am. Chem. Soc.*, 85:2149-2154. In vitro protein synthesis can be performed using manual techniques or by automation. Automated synthesis can be accomplished, for instance, using an Applied Biosystems Peptide Synthesizer (Foster City, CA) using manufacturer's instructions. Various portions of a polypeptide of the present invention or portion thereof can be chemically synthesized separately and combined using chemical or enzymatic methods to produce the full-length polypeptide or portion thereof.

In other embodiments, the invention provides chimeric molecules comprising any of the herein described polypeptides fused to a heterologous polypeptide or amino acid sequence. Examples of such chimeric molecules include, but are not limited to, any of the herein described polypeptides fused to an epitope tag sequence or an Fc region of an immunoglobulin.

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for IL-22-encoding vectors. *Saccharomyces cerevisiae* is a commonly used lower eukaryotic host microorganism.

Suitable host cells for the expression of glycosylated-IL-22 are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 cells transformed by SV40 (COS-7, ATCC CRL 1651); human embryonic kidney cells (293 or 293 cells subcloned for growth in suspension culture, Graham et al., J. Gen Virol., 36:59 (1977)); Chinese hamster ovary cells/-DHFR (CHO, Urlaub and Chasin, Proc. Natl. Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor cells (MMT 060562, ATCC CCL51). The selection of the appropriate host cell is deemed to be within the skill in the art.

The nucleic acid (e.g., cDNA or genomic DNA) encoding IL-22 can be inserted into a replicable vector for cloning (amplification of the DNA) or for expression. Various vectors are publicly available. The vector can, for example, be in the form of a plasmid, cosmid, viral particle, or phage. The appropriate nucleic acid sequence can be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The IL-22 polypeptides can be produced recombinantly not only directly, but also as a fusion polypeptide with a heterologous polypeptide, which can be a signal sequence or other polypeptide having a specific cleavage site at the N-terminus of the mature protein or polypeptide, as well as an IL-22 Fc fusion protein. In general, the signal sequence can be a component of the vector, or it can be a part of the IL-22 DNA that is inserted into the vector. The signal sequence can be a prokaryotic signal sequence selected, for example, from the group of the alkaline phosphatase, penicillinase, 1 pp, or heat-stable enterotoxin II leaders. For yeast secretion the signal sequence can be, e.g., the yeast invertase leader, alpha factor leader (including *Saccharomyces* and *Kluyveromyces* alpha-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences can be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2: plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells is one that enables the identification of cells competent to take up the IL-22 nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7 (see, e.g., Stinchcomb et al., Nature, 282:39 (1979); Kingsman et al., Gene, 7:141 (1979); Tschemper et al., Gene, 10:157 (1980)). The trp1 gene provides a selection marker for a mutant strain of yeast lacking the ability to grow in tryptophan, for example, ATCC No. 44076 or PEP4-1 (Jones, Genetics, 85:12 (1977)).

Expression and cloning vectors usually contain a promoter operably linked to the IL-22 nucleic acid sequence to direct mRNA synthesis. Promoters recognized by a variety of potential host cells are well known. Promoters suitable for use with prokaryotic hosts include the quadrature-lactamase and lactose promoter systems (see, e.g., Chang et al., Nature, 275:615 (1978); Goeddel et al., Nature, 281:544 (1979)), alkaline phosphatase, a tryptophan (trp) promoter system (see, e.g., Goeddel, Nucleic Acids Res., 8:4057 (1980); EP 36,776), and hybrid promoters such as the tac promoter (see, e.g., deBoer et al., Proc. Natl. Acad. Sci. USA, 80:21-25 (1983)). Promoters for use in bacterial systems also will contain a Shine-Dalgarno (S.D.) sequence operably linked to the DNA encoding IL-22.

Examples of suitable promoter sequences for use with yeast hosts include the promoters for 3-phosphoglycerate kinase (see, e.g., Hitzeman et al., J. Biol. Chem, 255:2073 (1980)) or other glycolytic enzymes (see, e.g., Hess et al., J. Adv. Enzyme Reg., 7:149 (1968); Holland, Biochemistry, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

IL-22 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the IL-22 polypeptides by higher eukaryotes can be increased by inserting an enhancer sequence into the vector. Enhancers are cis-acting elements of DNA, usually about from 10 to 300 bp, which act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer can be spliced into the vector at a position 5' or 3' to the IL-22 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding IL-22.

Still other methods, vectors, and host cells suitable for adaptation to the synthesis of IL-22 in recombinant vertebrate cell culture are described in Gething et al., Nature, 293:620-625 (1981); Mantei et al., Nature, 281:4046 (1979); EP 117,060; and EP 117,058.

Gene amplification and/or expression can be measured in a sample directly, for example, by conventional Southern blotting, Northern blotting to quantitate the transcription of mRNA (see, e.g., Thomas, Proc. Natl. Acad. Sci. USA, 77:5201-5205 (1980)), dot blotting (DNA analysis), or in situ hybridization, using an appropriately labeled probe, based on the sequences provided herein. Alternatively, antibodies can be employed that can recognize specific duplexes, including DNA duplexes, RNA duplexes, and DNA-RNA hybrid duplexes or DNA-protein duplexes. The antibodies in turn can be labeled and the assay can be carried out where the duplex is bound to a surface, so that upon the formation of duplex on the surface, the presence of antibody bound to the duplex can be detected.

Gene expression, alternatively, can be measured by immunological methods, such as immunohistochemical staining of cells or tissue sections and assay of cell culture or body fluids, to quantitate directly the expression of gene product. Antibodies useful for immunohistochemical staining and/or assay of sample fluids can be either monoclonal or polyclonal, and can be prepared in any mammal. Conveniently, the antibodies can be prepared against a native sequence IL-22 polypeptide or against a synthetic peptide based on the DNA sequences provided herein or against exogenous sequence fused to IL-22 DNA and encoding a specific antibody epitope.

IL-22 Fc fusion proteins can be recovered from culture medium or from host cell lysates. If membrane-bound, it can be released from the membrane using a suitable detergent solution (e.g. TRITON® X-100) or by enzymatic cleavage. Cells employed in expression of IL-22 can be disrupted by various physical or chemical means, such as freeze-thaw cycling, sonication, mechanical disruption, or cell lysing agents.

It may be desired to purify IL-22Fc fusion proteins from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the IL-22 polypeptide. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular IL-22 produced. The above-described general methods can be applied to the preparation of IL-2 Fc fusion protein as well.

Similarly, IL-22 Fc fusion proteins may be produced using recombinant methods and compositions, as described in, e.g., *Molecular Cloning: A Laboratory Manual* (Sambrook, et al., 1989, Cold Spring Harbor Laboratory Press) and *PCR Protocols: A Guide to Methods and Applications* (Innis, et al. 1990. Academic Press, San Diego, CA). In one embodiment, isolated nucleic acid encoding IL-22 Fc fusion proteins described herein is provided. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with) a vector comprising a nucleic acid that encodes an amino acid sequence comprising the IL-22 Fc fusion protein. In certain embodiment, the vector is an expression vector. In one embodiment, the host cell is eukaryotic, e.g. a Chinese Hamster Ovary (CHO) cell or lymphoid cell (e.g., Y0, NS0, Sp20 cell). In one embodiment, a method of making an IL-22 Fc fusion protein is provided, wherein the method comprises culturing a host cell comprising a nucleic acid encoding the IL-22 Fc fusion protein, as provided above, under conditions suitable for expression of the Fc fusion protein, and optionally recovering the Fc fusion protein from the host cell (or host cell culture medium).

For recombinant production of an IL-22 Fc fusion protein, nucleic acid encoding an Fc fusion protein, e.g., as described herein, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the fusion protein). In certain embodiments, when preparing the IL-22 Fc fusion proteins, nucleic acid encoding the IL-22 polypeptide or a fragment thereof can be ligated to nucleic acid encoding an immunoglobulin constant domain sequence at specified location on the constant domain to result in an Fc fusion at the C-terminus of IL-22; however N-terminal fusions are also possible.

As an example of constructing an IL-22 Fc fusion protein, the DNA encoding IL-22 is cleaved by a restriction enzyme at or proximal to the 3' end of the DNA encoding IL-22 and at a point at or near the DNA encoding the N-terminal end of the mature polypeptide (where use of a different leader is contemplated) or at or proximal to the N-terminal coding region for IL-22 full-length protein (where a native signal is employed). This DNA fragment then is readily inserted into DNA encoding an immunoglobulin light or heavy chain constant region and, if necessary, tailored by deletional mutagenesis. Preferably, this is a human immunoglobulin when the fusion protein is intended for in vivo therapy for humans.

In some embodiments, the IL-22-immunoglobulin chimeras are assembled as monomers, hetero- or homo-multimer, or as dimers or tetramers. Generally, these assembled immunoglobulins will have known unit structures as represented by the following diagrams. A basic four chain structural unit is the form in which IgG, IgD, and IgE exist. A four chain unit is repeated in the higher molecular weight immunoglobulins; IgM generally exists as a pentamer of, basic four-chain units held together by disulfide bonds. IgA globulin, and occasionally IgG globulin, may also exist in a multimeric form in serum. In the case of multimers, each four chain unit may be the same or different. See also Capon et al. U.S. Pat. No. 5,116,964, incorporated herein by reference in its entirety.

DNA encoding immunoglobulin light or heavy chain constant regions is known or readily available from cDNA libraries or is synthesized. See for example, Adams et al., Biochemistry 19:2711-2719 (1980); Gough et al., Biochemistry 19:2702-2710 (1980); Dolby et al; P.N.A.S. USA, 77:6027-6031 (1980); Rice et al P.N.A.S USA 79:7862-7865 (1982); Falkner et al; Nature 298:286-288 (1982); and Morrison et al; Ann. Rev. Immunol. 2:239-256 (1984). DNA sequence encoding human IL-22 with the endogenous leader sequence is provided herein (SEQ ID NO:70). DNA sequences encoding other desired binding partners which are known or readily available from cDNA libraries are suitable in the practice of this invention.

DNA encoding an IL-22 Fc fusion protein of this invention is transfected into a host cell for expression. If multimers are desired then the host cell is transformed with DNA encoding each chain that will make up the multimer, with the host cell optimally being selected to be capable of assembling the chains of the multimers in the desired fashion. If the host cell is producing an immunoglobulin prior to transfection then one needs only transfect with the binding partner fused to light or to heavy chain to produce a heteroantibody. The aforementioned immunoglobulins having one or more arms bearing the binding partner domain and one or more arms bearing companion variable regions result in dual specificity for the binding partner ligand and for an antigen or therapeutic moiety. Multiply cotransformed cells are used with the above-described recombinant methods to produce polypeptides having multiple specificities such as the heterotetrameric immunoglobulins discussed above.

Although the presence of an immunoglobulin light chain is not required in the immunoadhesins of the present invention, an immunoglobulin light chain might be present either covalently associated to an IL-22-immunoglobulin heavy chain fusion polypeptide. In this case, DNA encoding an immunoglobulin light chain is typically co-expressed with the DNA encoding the IL-22-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567 issued Mar. 28, 1989. Suitable host cells for cloning or expression of target protein-encoding vectors include prokaryotic or eukaryotic cells described herein. For example, IL-22 Fc fusion protein may be produced in bacteria, in particular when glycosylation and Fc effector function are not needed or are detrimental. For expression of polypeptides in bacteria, see, e.g., U.S. Pat. Nos. 5,648,237, 5,789,199, and 5,840,523. See also Charlton, *Methods in Molecular Biology*, Vol. 248 (B. K. C. Lo, ed., Humana Press, Totowa, NJ, 2003), pp. 245-254, describing expression of antibody fragments in *E. coli*. After expression, the Fc fusion protein may be isolated from the bacterial cell paste in a soluble fraction and can be further purified. As exemplified in the example section, further purification methods include without limitation purification using a Protein A column.

In addition to prokaryotes, eukaryotic microbes such as filamentous fungi or yeast are suitable cloning or expression hosts, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated proteins are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177; 6,040,498; 6,420,548; 7,125,978; and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B.K.C. Lo, ed., Humana Press, Totowa, NJ), pp. 255-268 (2003).

C. Assays

The compositions (e.g., pharmaceutical compositions) provided herein, or their constituents, may be identified, screened for, or characterized for their physical/chemical properties and/or biological activities by various assays known in the art.

1. Binding Assays and Other Assays

In one aspect, an IL-22 Fc fusion protein is tested for its receptor binding activity, e.g., by known methods such as ELISA, western blotting analysis, cell surface binding by Scatchard, surface plasmon resonance. In another aspect, competition assays may be used to identify an antibody that competes with the IL-22 Fc fusion protein for binding to the IL-22 receptor. In a further aspect, an IL-22 Fc fusion protein of the invention can be used for detecting the presence or amount of IL-22 receptor or IL22-Binding Protein (soluble receptor) present in a biological sample. In a further aspect, an IL-22 Fc fusion protein of the invention can be used for detecting the presence or amount of IL-22 receptor present in a biological sample. In certain embodiments, the biological sample is first blocked with a non-specific isotype control antibody to saturate any Fc receptors in the sample. Exemplary assays are described below in the Examples (e.g., the potency assay described in Example 1).

2. Activity Assays

In one aspect, assays are provided for identifying biological activity of a composition (e.g., a pharmaceutical composition that includes an IL-22 Fc fusion protein). Biological activity of an IL-22 polypeptide or IL-22 Fc fusion protein in a composition (e.g., a pharmaceutical composition) may include, e.g., binding to IL-22 receptor, stimulating IL-22 signaling, and inducing STAT3, RegIII and/or PancrePAP expression. Further, in the case of a cardiovascular disease or condition, the biological activity may include affecting the formation of atherosclerotic plaques, in particular to inhibit formation of atherosclerotic plaque formation. Inhibition of plaque formation can be assessed by any suitable imaging method known to those of ordinary skill in the art.

3. Stability Assays

In one aspect, assays are provided for determining the stability of a composition. For example, a composition (e.g., a pharmaceutical composition) can be evaluated qualitatively and/or quantitatively in a variety of different ways, including evaluation of aggregate formation (for example, using size exclusion chromatography, by measuring turbidity, and/or by visual inspection); evaluation of ROS formation (for example, by using a light stress assay or an 2,2'-azobis(2-amidinopropane) dihydrochloride (AAPH) stress assay); oxidation of specific amino acid residues of the protein (for example, a Met residue of an IL-22 Fc fusion protein); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact polypeptides (e.g., IL-22 Fc fusion proteins); peptide map (for example, tryptic or LYS-C) analysis; evaluating biological activity or target binding function of the protein (e.g., binding of an IL-22 Fc fusion protein to an IL-22 receptor); and the like. Instability may involve any one or more of: aggregation, deamidation (e.g., Asn deamidation), oxidation (e.g., Met oxidation and/or Trp oxidation), isomerization (e.g., Asp isomerization), clipping/hydrolysis/fragmentation (e.g., hinge region fragmentation), succinimide formation, unpaired cysteine(s), N-terminal extension, C-terminal processing, glycosylation differences, and the like. Exemplary assays are described below in the Examples, for example, Example 1 and Example 3.

D. Conjugates for Use in the Compositions

The invention also provides compositions (e.g., pharmaceutical compositions) that include conjugates comprising an IL-22 Fc fusion protein described herein conjugated to one or more agents for detection, formulation, half-life extension, mitigating immunogenicity, or tissue penetration. Exemplary conjugation includes without limitation PEGylation and attaching to radioactive isotopes.

In another embodiment, a conjugate comprises an IL-22 Fc fusion protein as described herein conjugated to a radioactive atom to form a radioconjugate. A variety of radioactive isotopes are available for the production of radioconjugates. Examples include $At^{21}$, $I^{131}$, $I^{125}$, $Y^{90}$, $Re^{186}$, $Re^{188}$, $Sm^{153}$, $Bi^{212}$, $P^{32}$, $Pb^{212}$, and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese, or iron.

E. Therapeutic Methods and Uses of the Compositions

Any of compositions (e.g., pharmaceutical compositions) provided herein may be used in therapeutic methods and uses, for example, any of the therapeutic methods and uses described below.

a) Inflammatory Bowel Disease

In one aspect, a composition (e.g., a pharmaceutical composition that includes an IL-22 Fc fusion protein) for use as a medicament is provided. In further aspects, a composition (e.g., a pharmaceutical composition that includes an IL-22 Fc fusion protein) for use in treating IBD, including UC and CD, is provided. In certain embodiments, a composition (e.g., a pharmaceutical composition that includes an IL-22 Fc fusion protein) for use in a method of treatment is provided. In certain embodiments, the invention provides a composition (e.g., a pharmaceutical composition that includes an IL-22 Fc fusion protein) for use in a method of treating an individual having UC or CD comprising administering to the individual an effective amount of the IL-22 Fc fusion protein. In one such embodiment, the method further comprises administering to the individual an effective amount of at least one additional therapeutic agent, e.g., as described below. In further embodiments, the invention provides a composition (e.g., a pharmaceutical composition that includes an IL-22 Fc fusion protein) for use in enhancing epithelial proliferation, differentiation and/or migration. In certain particular embodiments, the epithelial tissue is intestinal epithelial tissue. In certain embodiments, the invention provides a composition (e.g., a pharmaceutical composition that includes an IL-22 Fc fusion protein) for use in a method of enhancing epithelial proliferation, differentiation and/or migration in an individual comprising administering to the individual an effective amount of the composition to enhance epithelial proliferation, differentiation and/or migration. In yet other embodiments, the invention provides a composition (e.g., a pharmaceutical composition that includes an IL-22 Fc fusion protein) for use in treating diabetes, especially type II diabetes, diabetic wound healing, metabolic syndromes and atherosclerosis. In certain embodiments, the invention provides a composition (e.g., a pharmaceutical composition that includes an IL-22 Fc fusion protein) for use in a method of treating diabetes, especially type II diabetes, diabetic wound healing, metabolic syndromes and atherosclerosis in an individual comprising administering to the individual an effective amount of the composition. See International Patent Application Publication No. WO 2014/145016, which is incorporated herein by reference in its entirety. An "individual" or "subject" or "patient" according to any of the above embodiments is preferably a human.

In a further aspect, the invention provides for the use of a composition (e.g., a pharmaceutical composition that includes an IL-22 Fc fusion protein) in the manufacture or preparation of a medicament. In one embodiment, the medicament is for treatment of IBD and wound healing. In a further embodiment, the medicament is for use in a method of treating IBD and wound healing comprising administering to an individual having IBD an effective amount of the medicament. In one such embodiment, the method further comprises administering to the individual an effective amount of at least one additional therapeutic agent, e.g., as described below. In a further embodiment, the medicament is for suppressing inflammatory response in the gut epithelial cells. In a further embodiment, the medicament is for use in a method of enhancing epithelial proliferation, differentiation and/or migration in an individual comprising administering to the individual an amount effective of the medicament to enhance epithelial proliferation, differentiation and/or migration. An "individual" according to any of the above embodiments may be a human.

In a further aspect, the invention provides a method for treating IBD, including UC and CD. In one embodiment, the method comprises administering to an individual having IBD an effective amount of a composition (e.g., a pharmaceutical composition that includes an IL-22 Fc fusion protein). In one such embodiment, the method further comprises administering to the individual an effective amount of at least one additional therapeutic agent, as described below. An "individual" according to any of the above embodiments may be a human.

In a further aspect, the invention provides a method for enhancing epithelial proliferation, differentiation and/or migration in an individual. In one embodiment, the method comprises administering to the individual an effective amount of a composition (e.g., a pharmaceutical composition that includes an IL-22 Fc fusion protein) to enhance epithelial proliferation, differentiation and/or migration. In one embodiment, an "individual" is a human.

b) Other Therapeutic Indications

The present invention provides compositions (e.g., pharmaceutical compositions that include an IL-22 Fc fusion protein) for cardiovascular diseases and conditions, metabolic syndrome, acute endotoxemia and sepsis, graft-versus-host disease (GVHD), and diabetes. For the prevention, treatment or reduction in the severity of a given disease or condition, the appropriate dosage of a composition of the invention will depend on the type of disease or condition to be treated, as defined above, the severity and course of the disease or condition, whether the agent is administered for preventive or therapeutic purposes, previous therapy, the subject's clinical history and response to the compound, and the discretion of the attending physician. The compound is suitably administered to the subject at one time or over a series of treatments. Preferably, it is desirable to determine the dose-response curve and the pharmaceutical composition of the invention first in vitro, and then in useful animal models prior to testing in humans.

In one aspect, the present invention provides methods of treatment for a cardiovascular disease or disorder, metabolic syndrome, acute endotoxemia and sepsis, GVHD, and an insulin-related disorder. In one embodiment, the method comprises administering to a subject in need a therapeutically effective amount of a composition (e.g., a pharmaceutical composition that includes an IL-22 Fc fusion protein). In another aspect, the invention provides a method for the delaying or slowing down of the progression of a cardiovascular disease or disorder, metabolic syndrome, GVHD, and an insulin-related disorder. In one embodiment, the method comprises administering to subject diagnosed with the disease, condition, or disorder, an effective amount of a composition (e.g., a pharmaceutical composition that includes an IL-22 Fc fusion protein). In another aspect, the invention provides a method for preventing indicia of a cardiovascular disease or disorder, GVHD, and an insulin-related disorder. In one embodiment, the method comprises administering an effective amount of a composition (e.g., a pharmaceutical composition that includes an IL-22 Fc fusion protein) to a subject at risk of the disease, condition, or disorder, wherein the composition is effective against the development of indicia of the disease, condition, or disorder. In one aspect, the present invention provides methods of treatment for GVHD. In another aspect, the invention provides a method for the delaying or slowing down of the progression of GVHD. In one embodiment, the method comprises administering to subject diagnosed with the disease, condition, or disorder, an effective amount of an IL-22 Fc fusion protein.

Cardiovascular Diseases and Conditions

In one aspect, the IL-22 Fc fusion proteins provide a therapeutic, preventative, or prophylactic effect against the development of, or the progression of, clinical and/or histological and/or biochemical and/or pathological indicia (including both symptoms and signs) of cardiovascular diseases or conditions in a subject. In one embodiment, the disease or condition is atherosclerosis. In one embodiment, the indicia include atherosclerotic plaque formation and/or vascular inflammation. In another embodiment, the subject is at risk for cardiovascular disease. In general, a subject at risk will previously have had a cardiovascular disease or condition as described herein, or will have a genetic predisposition for a cardiovascular disease or condition.

The efficacy of the treatment of cardiovascular diseases and conditions can be measured by various assessments commonly used in evaluating cardiovascular diseases. For example, cardiovascular health can be assessed. Cardiovascular health can be evaluated by, but not limited to, e.g., blood tests (e.g., total cholesterol, LDL-C, HDL-C, triglyceride, C-reactive protein, fibrinogen, homocysteine, fasting insulin, ferritin, lipoprotein, and LPS), blood pressure, auscultation, electrocardiogram, cardiac stress testing, cardiac imaging (e.g., coronary catheterization, echocardiogram, intravascular ultrasound, positron emission tomography, computed tomography angiography, and magnetic resonance imaging).

Metabolic Syndrome

In one aspect, the compositions (e.g., the pharmaceutical compositions that include an IL-22 Fc fusion protein) provide a therapeutic, preventative, or prophylactic effect against the development of, or the progression of, clinical and/or histological and/or biochemical and/or pathological indicia (including both symptoms and signs) of metabolic syndrome (or metabolic disorder or disease) in a subject. In one or more embodiment, the subject is at risk for metabolic syndrome.

The efficacy of the treatment of metabolic syndrome can be measured by various assessments commonly used in evaluating metabolic syndrome. For example, obesity can be measured. As a further example, hyperglycemia, dyslipidemia, insulin resistance, chronic adipose tissue inflammation, and/or hypertension can be measured. Reduction in in levels of one or more of C-reactive protein, IL-6, LPS, and plasminogen activator inhibitor 1 can be measured. These measurements can be performed by any methods well known in the art.

Insulin-Related Disorders

For insulin-related disorders, the term "treatment" refers to both therapeutic treatment and prophylactic or preventative measures for the disorder, wherein the object is to prevent or slow down (lessen) the targeted pathologic condition or disorder. Those in need of treatment include those already with an insulin-related disorder as well as those prone to have such a disorder or those in whom the disorder is to be prevented.

In one aspect, the compositions (e.g., the pharmaceutical compositions that include an IL-22 Fc fusion protein) provide a preventative or prophylactic effect against the development of, or the progression of, clinical and/or histological and/or biochemical and/or pathological indicia (including both symptoms and signs) of an insulin-related disorder in a subject. In one embodiment, the disorder is Type I diabetes, Type II diabetes, or gestational diabetes. In one embodiment, the pathology or pathological indicia include one or more of: little or no insulin production by the pancreas (e.g., islet cells), insulin resistance, and hyperglycemia. In another embodiment, the subject is at risk for an insulin-related disorder. In general, a subject at risk has a genetic predisposition for an insulin-related disorder, has been exposed to a virus that triggers autoimmune destruction of islet cells (e.g., Epstein-Barr virus, coxsackievirus, mumps virus or cytomegalovirus), is obese, is pre-diabetic (higher than normal blood sugar levels), or has gestational diabetes.

The efficacy of the treatment of an insulin-related disorder can be measured by various assessments commonly used in evaluating such disorders. For example, both Type I and Type II diabetes can be evaluated with one or more of the following: a glycated hemoglobin test (A1C), a regular blood sugar test, and a fasting blood sugar test. Type I can also be evaluated by testing for autoantibodies in the blood and/or ketones in the urine. Type II can also be evaluated by testing for oral glucose tolerance.

Acute Endotoxemia and Sepsis

In one aspect, the compositions (e.g., the pharmaceutical compositions that include an IL-22 Fc fusion protein) provide a therapeutic, preventative or prophylactic effect against the development of, or the progression of, clinical and/or histological and/or biochemical and/or pathological indicia (including both symptoms and signs) of acute endotoxemia, sepsis, or both, in a subject. In one or more embodiment, the subject is at risk for acute endotoxemia, sepsis, or both.

The efficacy of the treatment of acute endotoxemia, sepsis, or both can be measured by various assessments commonly used in evaluating acute endotoxemia, sepsis, or both. For example, reduction in in levels of LPS or inflammatory markers can be measured. These measurements can be performed by any methods well known in the art.

Wound Healing

There are a variety of ways to measure wound healing. Often images are taken to calculate linear dimensions, perimeter and area. The NIH has a free program, Image J, which allows measurement of wound areas from an image. The final healing prognosis can be extrapolated from initial healing rates based on the migration of the periphery towards the center. This is done using a number of mathematical equations, the most common of which is a modified Gilman's equation. In addition to visual inspection, wound healing measurement can also be aided by spectroscopic methods or MRI. See e.g., Dargaville et al., Biosensors Bioelectronics, 2013, 41:30-42, Tan et al., 2007, British J. Radiol. 80:939-48. If healing is slow/inadequate, biopsies of the wound edges may be taken to rule out or determine infection and malignancy. In certain embodiments, the acceleration or improvement of wound healing can be assessed by comparing wound closure in IL-22-treated and control wounds. In certain embodiments, the acceleration or improvement of wound healing is at least 20%, 30%, 40%, 50%, 60%, 70%, 80% or 90% faster or better than the control.

In certain aspect, the invention provides methods for promoting/accelerating/improving healing of a wound with or without active infection, microbial contamination or colonization in the wound. The compositions (e.g., the pharmaceutical compositions that include an IL-22 Fc fusion protein) can be used for treating infected wounds or promoting/accelerating/improving infected wound healing. In certain embodiments, the compositions (e.g., the pharmaceutical compositions that include an IL-22 Fc fusion protein) can be used for treating wounds, or promoting/accelerating/improving wound healing, in the presence of infection. In some embodiments, the compositions (e.g., the pharmaceutical compositions that include an IL-22 Fc fusion protein) can be used for treating wounds or promoting/accelerating/improving wound healing in the presence of microbial contamination or colonization with risk for infection. In further embodiments, the patient in need of wound healing treatment can be a diabetic patient. Accordingly, in some embodiments, the wound is a diabetic wound, for example, diabetic foot ulcer. In some further embodiments, the wound is an infected diabetic wound, for example, infected diabetic foot ulcer.

GVHD

In one aspect, the IL-22 Fc fusion proteins may provide a prophylactic effect against the development of, or a therapeutic effect against the progression of, clinical and/or histological and/or biochemical and/or pathological indicia (including both symptoms and signs) of GVHD. For example, the method provides a method for treating GVHD that includes administering to a subject in need thereof an effective amount of an IL-22 Fc fusion protein or composition thereof (including a pharmaceutical composition) as described herein. Administration of an IL-22 Fc fusion protein or composition thereof as described herein may reduce one or more symptoms of GVHD, including pain, rashes, skin thickness, yellow skin or eyes, mouth dryness or ulcers, taste abnormalities, dry eyes, infections, or weight loss. The IL-22 Fc fusion proteins or compositions thereof can be administered in combination with additional GVHD therapy, including, for example, immunosuppressive agents (e.g., cyclosporine, mycophenolate mofetil (MMF), or tacrolimus), mTOR inhibitors (e.g., sirolimus or everolimus)), chemotherapy agents (e.g., imatinib, pentostatin, methotrexate, or thalidomide), TNF antagonists (e.g., etanercept), steroids (e.g., prednisolone, methylprednisolone, topical steroids, or steroid eye drops), light treatment (e.g., extracorporeal photopheresis), hydroxychloroquine, anti-fibrotic agents (e.g., halofuginone), monoclonal antibodies (e.g., alemtuzumab, infliximab, or rituximab), or combinations thereof.

A composition (e.g., a pharmaceutical composition that includes an IL-22 Fc fusion protein) of the invention can be used either alone or in combination with other agents in a therapy. For instance, a composition (e.g., a pharmaceutical composition that includes an IL-22 Fc fusion protein) of the invention may be co-administered with at least one additional therapeutic agent. In certain embodiments, an additional therapeutic agent is an immune suppressant that reduces the inflammatory response, including, without limitation, methotrexate, a TNF inhibitor, a TNF antagonist, mesalazine, steroid, dexamethasone, azathioprine, and a combination thereof. Suitable additional therapeutic agents that reduce an inflammatory response include, without limitation, 5-aminosalicyiic acid (5-ASA), mercaptopurine (also called 6-mercaptopurine or 6-MP), or combination thereof. In certain embodiments, the composition (e.g., a pharmaceutical composition that includes an IL-22 Fc fusion protein) may be co-administered with one or more additional therapeutic agents that reduce an inflammatory response (for example, 5-ASA, 6-MP, or a TNF antagonist) for the treatment of IBD. In certain other embodiments, the composition (e.g., a pharmaceutical composition that includes an IL-22 Fc fusion protein) may be co-administered with an integrin antagonist such as etrolizumab for the treatment of IBD. In one embodiment, the composition (e.g., a pharmaceutical composition that includes an IL-22 Fc fusion protein) is used in combination with an IL-22 agonist.

For accelerating chronic wound healing, such as for the treatment of diabetic foot ulcer, the administration of a composition (e.g., a pharmaceutical composition that includes an IL-22 Fc fusion protein) can be combined with one or more additional wound healing agents. Suitable additional wound healing agents include, without limitation, growth factors (e.g., EGF, FGF, IGF, PDGF, TGF, and VEGF), nerve growth factor (NGF), angiogenesis factors (e.g., HGF, TNF-α, angiogenin, IL-8, angiopoietins 1 and 2, Tie-2, integrin α5, matrix metalloproteinases, nitric oxide, and COX-2), members of the platelet derived growth factor (PDGF) family (e.g., PDGF-A, PDGF-B, PDGF-C, and PDGF-D), members of the insulin growth factor (IGF) family (e.g., IGF-I and IGF-II), members of the transforming growth factor (TGF) family (e.g., TGF-α and TGF-β), and anabolic oxygen (vacuum therapy). In certain embodiments, the composition (e.g., a pharmaceutical composition that includes an IL-22 Fc fusion protein) can be co-administered with one or more additional wound healing agents described herein and/or one or more antibacterial agents or antibiotics suitable for use in topical administration. See, e.g., WO 2006/138468, which is incorporated herein by reference in its entirety. In such embodiments, the antibiotic can be a sulfur antibiotic, including, without limitation, silver sulfadiazine, i.e., silvadeen. The co-administered one or more additional agents can be administered concurrently, alternatively, or sequentially with the composition (e.g., a pharmaceutical composition that includes an IL-22 Fc fusion protein).

In further exemplary embodiments, if the target is prevention or treatment of cardiovascular diseases or conditions or metabolic syndrome, the administration of a composition (e.g., a pharmaceutical composition that includes an IL-22 Fc fusion protein) can be combined with or supplement the administration of the cholesterol-lowering agents such as statins (e.g., lovastatin, rosuvastatin, fluvastatin, atorvastatin, pravastatin, and simvastatin), bile acid binding resins (colestipol, cholestyramine sucrose, and colesevelam), ezetimibe, or a ezetimibe-simvastatin combination; anti-platelet agents such as cyclooxygenase inhibitors (e.g., aspirin), adenosine diphosphate (ADP) receptor inhibitors (e.g., clopidogrel, prasugrel, ticagrelor, and ticlopidine), phosphodiesterase inhibitors (e.g., cilostazol), glycoprotein IIB/IIIA inhibitors (e.g., abciximab, eptifibatide, and tirofiban), adenosine reuptake inhibitors (e.g., dipyridamole), thromboxane inhibitors (e.g., thromboxane synthase inhibitors, thromboxane receptor antagonists, and terutroban); beta blockers such as alprenolol, bucindolol, carteolol, carvedilol, labetalol, nadolol, oxprenolol, penbutolol, pindolol, propranolol, sotalol, timolol, eucommia bark, acebutolol, atenolol, betaxolol, bisoprolol, celiprolol, esmolol, metoprolol, nebivolol, butaxamine, ICI-118,551, and SR 59230A; angiotensin-converting enzyme (ACE) inhibitors such as captopril, zofenopril, dicarboxylate-containing agents (e.g., enalapril, ramipril, quinapril, perindopril, lisinopril, benazepril, imidapril, and zofenopril), phosphonate-containing agents (e.g., fosinopril), casokinins, lactokinins, lactotripeptides (e.g., Val-Pro-Pro, and Ile-Pro-Pro produced by the probiotic *Lactobacillus helveticus* or derived from casein); calcium channel blockers such as dihydropyridines (e.g., amlodipine, aranidipine, azelnidipine, barnidipine, benidipine, cilnidipine, clevidipine, isradipine, efonidipine, felodipine, lacidipine, lercanidipine, manidipine, nicardipine, nifedipine, nilvadipine, nimodipine, nisoldipine, nitrendipine, and pranidipine), phenylalkylamine (e.g., verapamil), benzothiazepines (e.g., diltiazem), mibefradil, bepridil, fluspirilene, and fendiline; diuretics such as high ceiling loop diuretics (e.g., furosemide, ethacrynic acid, torsemide and bumetanide), thiazides (e.g., hydrochlorothiazide acid), carbonic anhydrase inhibitors (e.g., acetazolamide and methazolamide), potassium-sparing diuretics (e.g., aldosterone antagonists: spironolactone, and epithelial sodium channel blockers: amiloride and triamterene), and calcium-sparing diuretics, and pharmaceutically acceptable salts, acids or derivatives of any of the above.

For insulin-related disorders or metabolic syndrome, the administration of a composition (e.g., a pharmaceutical composition that includes an IL-22 Fc fusion protein) can be combined with or supplement the administration of various therapeutic agents. In the case of Type I diabetes (insulin-dependent diabetes mellitus or IDDM), the IL-22 Fc fusion protein described herein can be combined with one or more of regular insulin replacement therapy (including rapid-acting and long-acting insulin), immunosuppression treatment, islet transplantation and stem cell therapy. In one embodiment, the regular insulin replacement therapy includes, without limitation, regular insulin (e.g., HUMULIN R®, NOVOLIN R®), insulin isophane (e.g., HUMULIN N®, NOVOLIN N®), insulin lispro (e.g., HUMALOG®), insulin aspart (e.g., NOVOLOG®), insulin glargine (e.g., LANTUS®), and insulin detemir (e.g., LEVEMIR®). In other embodiments, the insulin replacement therapy further includes pramlintide (SYMLIN®).

In the case of Type II diabetes (non-insulin dependent diabetes mellitus or NIDDM) or metabolic syndrome, the composition (e.g., a pharmaceutical composition that includes an IL-22 Fc fusion protein) described herein can be combined with one or more of insulin replacement therapy (as discussed above), an agent to lower glucose production by the liver, an agent to stimulate pancreatic production and release of insulin, an agent that blocks enzymatic break down of carbohydrates, or an agent that increases insulin sensitivity. In one embodiment, the agent to lower glucose production is metformin (e.g., GLUCOPHAGE® and GLUMETZA®). In another embodiment, the agent to stimulate pancreatic production and release of insulin is glipizide (e.g., GLUCOTROL® and GLUCOTROL XL®), glyburide (e.g., DIABETA® and GLYNASE®) or glimepiride (e.g., AMARYL®). In one other embodiment, the agent that blocks enzymatic break down of carbohydrates or increases insulin sensitivity is pioglitazone (e.g., Actos). In another embodiment, the IL-22 Fc fusion protein can be combined with one of the following replacements for metformin: sitagliptin (e.g., JANUVIA®), saxagliptin (e.g., ONGLYZA®), repaglinide (e.g., PRANDIN®) and nateglinide (e.g., STARLIX®), exenatide (e.g., BYETTA®) and liraglutide (e.g., VICTOZA®). In another embodiment, the composition (e.g., a pharmaceutical composition that includes an IL-22 Fc fusion protein) can be combined with an oral hypoglycemic agent, e.g., sulfonylureas.

In the case of gestational diabetes or metabolic syndrome, the composition (e.g., a pharmaceutical composition that includes an IL-22 Fc fusion protein) described herein can be combined with an oral blood sugar control medication. In one embodiment, the medication is glyburide.

The combination therapy can provide "synergy" and prove "synergistic," i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g. by different injections in separate syringes. In general, during alternation therapy, an effective dosage of each active ingredient is administered sequentially, i.e., serially, whereas in combination therapy, effective dosages of two or more active ingredients are administered together.

Such combination therapies noted above encompass combined administration (where two or more therapeutic agents are included in the same or separate formulations), and separate administration, in which case, administration of the composition (e.g., a pharmaceutical composition that includes an IL-22 Fc fusion protein) of the invention can occur prior to, simultaneously, and/or following, administration of the additional therapeutic agent or agents. In one embodiment, administration of the composition (e.g., a pharmaceutical composition that includes an IL-22 Fc fusion protein) and administration of an additional therapeutic agent occur within about one month, or within about one, two or three weeks, or within about one, two, three, four, five, or six days, of each other.

A composition (e.g., a pharmaceutical composition that includes an IL-22 Fc fusion protein) of the invention (and any additional therapeutic agent) can be administered by any suitable means, including parenteral, intrapulmonary, topical and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

A composition (e.g., a pharmaceutical composition that includes an IL-22 Fc fusion protein) of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The composition (e.g., a pharmaceutical composition that includes an IL-22 Fc fusion protein) need not be, but is optionally formulated with one or more agents currently used to prevent or treat the disorder in question. The effective amount of such other agents depends on the amount of the fusion protein present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a composition (e.g., a pharmaceutical composition that includes an IL-22 Fc fusion protein) of the invention (when used alone or in combination with one or more other additional therapeutic agents) will depend on the type of disease to be treated, the type of Fc region, the severity and course of the disease, whether the fusion protein is administered for preventive or therapeutic purposes, previous therapy, the patient's clinical history and response to the IL-22 Fc fusion protein, and the discretion of the attending physician. The composition (e.g., a pharmaceutical composition that includes an IL-22 Fc fusion protein) is suitably administered to the patient at one time or over a series of treatments. Depending on the type and severity of the disease, about 1 µg/kg to 15 mg/kg (e.g., 0.1 mg/kg-10 mg/kg) or about 0.1 µg/kg to 1.5 mg/kg (e.g., 0.01 mg/kg-1 mg/kg) of the IL-22 Fc fusion protein can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the IL-22 Fc fusion protein would be in the range from about 0.05 mg/kg to about 10 mg/kg. Certain other dosages include the range from about 0.01 mg/kg to about 10 mg/kg, about 0.02 mg/kg to about 10 mg/kg, and about 0.05 mg/kg to about 10 mg/kg. Thus, one or more doses of about 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 2.0 mg/kg, 3.0 mg/kg, 4.0 mg/kg, 5 mg/kg, 6 mg/kg, 7 mg/kg, 8 mg/kg, 9 mg/kg or 10 mg/kg (or any combination thereof) may be administered to the patient. For topical wound healing, one or more doses of about 0.001 mg/cm$^2$ to about 10 mg/cm$^2$ wound area, about 0.05 mg/cm$^2$ to about 5 mg/cm$^2$ wound area, about 0.01 mg/cm$^2$ to about 1 mg/cm$^2$ wound area, about 0.05 mg/cm$^2$ to about 0.5 mg/cm$^2$ wound area, about 0.01 mg/cm$^2$ to about 0.5 mg/cm$^2$ wound area, about 0.05 mg/cm$^2$ to about 0.2 mg/cm$^2$ wound area, or about 0.1 mg/cm$^2$ to about 0.5 mg/cm$^2$ wound area (or any combination thereof) may be administered to the patient. In certain embodiments, one or more doses of about 0.01 mg/cm$^2$, 0.02 mg/cm$^2$, 0.03 mg/cm$^2$, 0.04 mg/cm$^2$, 0.05 mg/cm$^2$, 0.06 mg/cm$^2$, 0.07 mg/cm$^2$, 0.08 mg/cm$^2$, 0.09 mg/cm$^2$, 0.1 mg/cm$^2$, 0.15 mg/cm$^2$, 0.2 mg/cm$^2$, 0.25 mg/cm$^2$, 0.3 mg/cm$^2$, 0.4 mg/cm$^2$, or 0.5 mg/cm$^2$ wound area may be administered to the patient. Such doses may be administered intermittently, e.g., every week or every three weeks (e.g., such that the patient receives from about two to about twenty, or e.g., about six doses of the IL-22 Fc fusion protein). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using conjugate of the invention in place of or in addition to an IL-22 Fc fusion protein.

F. Articles of Manufacture

In another aspect of the invention, an article of manufacture containing materials useful for the treatment, prevention and/or diagnosis of the disorders described above is provided. The article of manufacture may include any of the compositions (e.g., pharmaceutical compositions that include an IL-22 Fc fusion protein) provided herein. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). In some embodiments, at least one active agent in the composition is an IL-22 Fc fusion protein. The label or package insert indicates that the composition is used for treating the condition of choice. In some embodiments, the article of manufacture or the containers are protected from light. The articles of manufacture can include any of the compositions (e.g., pharmaceutical compositions) described herein.

In some embodiments, the article of manufacture includes a vial having a volume of about 1 mL or more, for example, about 1 mL, about 2 mL, about 3 mL, about 4 mL, about 5 mL, about 6 mL, about 7 mL, about 8 mL, about 9 mL, about 10 mL, or more. In some embodiments, the container is a vial having a volume of about 2 mL. In some embodiments, the vial is for single-use. In some embodiments, the vial contains about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, or more IL-22 Fc fusion protein. In some embodiments, the vial includes about 10 mg of IL-22 Fc fusion protein. In some embodiments, the vial includes IL-22 Fc fusion protein formulated in 10 mM sodium phosphate, 5 mM methionine, 240 mM sucrose, 0.02% (w/v) polysorbate 20, pH 7.1. In some embodiments, the container closure system comprises one or more, or all, of a glass vial, a stopper, and a cap.

Moreover, the article of manufacture may comprise (a) a first container with a composition of the invention contained therein, wherein the composition comprises an IL-22 Fc fusion protein; and (b) a second container with a composition contained therein, wherein the composition comprises an additional therapeutic agent. The article of manufacture in this embodiment of the invention may further comprise a package insert indicating that the compositions can be used to treat a particular condition (e.g., IBD, e.g., UC or Crohn's disease), or any other disorder described herein. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include a conjugate of the invention in place of or in addition to an IL-22 Fc fusion protein.

EXAMPLES

The following are examples of methods and compositions of the invention. It is understood that various other embodiments may be practiced, given the general description provided above, and the examples are not intended to limit the scope of the claims.

Example 1: IL-22 Fc Fusion Protein Stability Studies

The purpose of these studies was to investigate IL-22 Fc fusion protein stability and the manufacturability of a liquid formulation of 10 mM sodium phosphate, 240 mM sucrose, 5 mM methionine, 0.02% (w/v) polysorbate 20 (PS20), pH 7.1. A full pH screen at intended storage temperatures of −70, −20, and 5° C., and stressed temperatures of 25, 30, and 40° C., was performed for 10 mg/mL IL-22 Fc fusion protein at pH 5.5-7.6. The results demonstrated that formulation at pH 7.1 was suitable by color, appearance, and clarity (CAC), concentration, pH, size exclusion-high performance liquid chromatography (SE-HPLC), DSC, imaged capillary isoelectric focusing (ICIEF), and potency.

An agitation study for 10 mg/mL IL-22 Fc fusion protein with 0.0%, 0.01%, 0.02% and 0.04% (w/v) polysorbate 20 was completed to determine appropriate polysorbate 20 concentration specifications to protect IL-22 Fc fusion protein pharmaceutical composition from agitation stress.

Although 0.01% polysorbate 20 was determined to be suitable for IL-22 Fc fusion protein, the target recommendation was 0.02% to account for the specification range. In addition to the formulation screen for IL-22 Fc fusion protein pharmaceutical composition at 10 mg/mL, a freeze-thaw stability study for IL-22 Fc fusion protein at 10 mg/mL in the same aforementioned formulation was completed. There were no significant changes for IL-22 Fc fusion protein stored at −20° C. and 5° C. for 1 week and three cycles of freeze-thaw by SE-HPLC. AAPH stress stability studies were conducted in the absence of methionine or in the presence of methionine (3, 3.5, and 5 mM) to assess the oxidation potential of key receptor binding methionines and the protective value of added methionine. These studies demonstrate that the physical and chemical stability of IL-22 Fc fusion protein formulated at 10 mg/mL for a pharmaceutical composition containing 10 mM sodium phosphate, 240 mM sucrose, 5 mM methionine, 0.02% polysorbate 20, pH 7.1 is acceptable for use as a pharmaceutical composition, and that manufacturing of the IL-22 Fc fusion protein is supportable in this formulation.

Materials and Methods

Materials

Starting material of the IL-22 Fc fusion protein pharmaceutical composition at 10 mg/mL in 10 mM sodium phosphate and pH 5.5 was stored at 5° C. prior to study initiation. This material was used for Formulation Screens 1-3, as well as agitation and freeze/thaw studies. Preliminary AAPH studies were conducted with the analytical standard (no methionine) and subsequent studies were conducted with the IL-22 Fc fusion protein formulated with 0, 3, 3.5, and 5 mM methionine.

IL-22 Fc Fusion Protein Formulation Screen 1

The stability of IL-22 Fc fusion protein in the early pharmaceutical composition formulation at 10 mg/mL in 20 mM histidine acetate, 240 mM sucrose, pH 5.5, 0.02% (w/v) polysorbate 20 (PS20) was evaluated for the preliminary formulation screen. The material was sterile filtered and 1.0 mL was aseptically filled into autoclaved 2-cc Forma Vitrum vials in a laminar flow hood. Vials were stoppered with Daikyo 13-mm diameter stoppers, sealed with aluminum flip-top seals, and stored upright at −20° C., 5° C., 25° C., and 40° C. Samples were analyzed by SE-HPLC and DSC.

IL-22 Fc Fusion Protein Formulation Screen 2

Starting material at 10 mg/mL was dialyzed against 10 mM histidine acetate and 240 mM sucrose, pH 5.5, pH 6.0, pH 6.5, and pH 7.0, respectively, with a Thermo Scientific dialysis cassette. After dialysis PS20 was added to a final concentration of 0.02% (w/v). Protein concentration after dialysis and dilution step was volumetrically determined. To set up the formulation screen, the material at pH 5.5, 6.0, pH 6.5, and pH 7.0 was sterile filtered, and 1.0 mL was aseptically filled into autoclaved 2-cc Forma Vitrum vials in a laminar flow hood. Vials were stoppered with Daikyo 13-mm diameter stoppers, sealed with aluminum flip-top seals, IDC-2 and stored upright at −20° C., 5° C., 25° C., and 30° C. An overview of this screen is shown in Table 1.

TABLE 1

| Buffer | Conc. (mg/mL) | Surfactant | Tonicity agent | Temp. (° C.) | pH 5.5 | pH 6.0 | pH 6.5 | pH 7.0 |
|---|---|---|---|---|---|---|---|---|
| 10 mM Histidine Acetate Phosphate (pKa = 6.1) | 10 | 0.02% P20 | 240 mM Sucrose | −20 |   |   | x |   |
|  |  |  |  | 5 | x | x | x | x |
|  |  |  |  | 25 | x | x | x | x |
|  |  |  |  | 30 |   |   | x |   |

IL-22 Fc Fusion Protein Formulation Screen 3

Starting material at 10 mg/mL was dialyzed against 10 mM sodium phosphate, 240 mM sucrose, 0.02% (w/v) PS20, pH 6.5, pH 7.0, pH 7.3, 7.6, and 20 mM Tris pH 7.3, respectively, with a Thermo Scientific dialysis cassette. Protein concentration after dialysis and dilution step was volumetrically determined. To set up the formulation screen, the material at pH 6.5, pH 7.0, pH 7.3, pH 7.6, and tris pH 7.3 were sterile filtered and 1.0 mL was aseptically filled into autoclaved 2-cc Forma Vitrum vials in a laminar flow hood. Vials were stoppered with Daikyo 13-mm diameter stoppers, sealed with aluminum flip-top seals, and stored upright at −20° C., 5° C., 25° C., and 30° C. An overview of this screen is shown in Table 2.

TABLE 2

| Buffer | Conc. (mg/mL) | Surfactant | Tonicity agent | Temp. (° C.) | pH 6.5 | pH 7.0 | pH 7.3 | pH 7.6 |
|---|---|---|---|---|---|---|---|---|
| 20 mM Tris (pKa = 8.0) | 10 | 0.02% P20 | 240 mM Sucrose | −20 |   |   | x |   |
|  |  |  |  | 5 |   |   | x |   |
|  |  |  |  | 25 |   |   | x |   |
|  |  |  |  | 30 |   |   | x |   |
| 10 mM Sodium Phosphate (pKa = 7.2) | 10 | 0.02% P20 | 240 mM Sucrose | −20 |   |   | x |   |
|  |  |  |  | 5 | x | x | x | x |
|  |  |  |  | 25 | x | x | x | x |
|  |  |  |  | 30 |   |   | x |   |

IL-22 Fc Fusion Protein Agitation Studies

The agitation study was conducted at room temperature with varying levels of PS20. Starting material at 10 mg/mL was formulated in 10 mM sodium phosphate, 240 mM sucrose, pH 7.1 containing 0.0%, 0.01%, 0.02%, and 0.04% (w/v) PS20. Protein formulations were sterile filtered and 1.0 mL was filled into 2-cc vials as described above. Vials were placed in a horizontal orientation and subjected to continuous shaking using a Bench Top Shaker at a speed of 50 cycles per minute (motor speed of 70) at room temperature for 24 hours. Control samples (0.0% PS20) were placed next to the agitated samples at room temperature without shaking.

IL-22 Fc Fusion Protein Freeze-Thaw Stability Studies

The stability of freeze-thawed IL-22 Fc fusion protein pharmaceutical compositions in vials was assessed on formulations containing 10 mM sodium phosphate, 240 mM sucrose, 0.02% (w/v) PS20 at pH 6.5, 7.0, 7.3, and 7.6, as well as one formulation containing the same excipients, except with a buffer of 20 mM Tris at pH 7.3. Protein formulations were sterile filtered and 1.0 mL was filled into 2-cc vials as described above. Vials were placed at −20° C. for T=0 and 1 week. The vials were frozen and thawed for a total of three times to room temperature. Only the T=0 and third freeze-thaw cycles were analyzed.

AAPH Stress Stability Studies to Determine Methionine Level in the Formulation

The purpose of this study was to generate degraded samples using 2,2'-azobis-2-methyl-propanimidamide, dihydrochloride (AAPH) to support assay development and to explore oxidation of IL-22 Fc fusion protein. IL-22 Fc fusion protein pharmaceutical composition formulations at 10 mg/ml in 10 mM sodium phosphate, 240 mM sucrose, 0.02% (w/v) PS20, pH 7.1 with 0, 3, and 3.5 mM methionine were subjected to AAPH stress. The samples were incubated with 1 mM AAPH for 24 hours at 40° C. Upon completion of AAPH stress, the samples were buffer exchanged into formulation buffer, aliquoted, and frozen at −70° C. for subsequent analysis. The above samples were compared to IL-22 Fc fusion protein, 10 mM sodium phosphate, 240 mM sucrose, 0.02% PS20, pH 7.1, 5 mM methionine, previously stressed in an identical fashion.

Assays

Color, Appearance, and Clarity

The color, appearance, and clarity of the samples were visually assessed under white fluorescent light using a light inspection station with a black and white background.

pH

The solution pH was measured using a SevenMulti Mettler Toledo pH meter with a Beckman Coulter microelectrode. Prior to testing, pH meter standardization was performed. Standard solutions of pH 7.0 and pH 4.0 were used for calibration.

Volumetric Protein Concentration (Strength)

An Agilent 8453 was used to measure protein concentration or strength by absorption. Prior to measurement, the samples were diluted volumetrically to ~0.5 mg/mL with respective formulation buffers. Absorption was measured in a quartz cuvette with a path length of 1.0 cm. The instrument was blanked with respective formulation buffers. Protein concentration was calculated using absorbances at 280 nm ($A_{max}$) and 320 nm ($A_{320}$), and an extinction coefficient (E) of 0.98 $(mg/mL)^{-1} cm^{-1}$.

$$\text{Concentration (mg/mL)} = \frac{(A_{max} - A_{320}) \times \text{dilution factor (mL/mL)}}{\varepsilon \times \text{cell path length(cm)}}$$

Size Exclusion High-Performance Liquid Chromatography (SE-HPLC)

Size exclusion chromatography was performed with an Agilent 1100 HPLC. Separation was done on a TOSOH Bioscience TSKgel G3000SWXL 30-cm column at ambient temperature. The mobile phase was maintained at a flow rate of 0.5 mL/min. Samples were injected undiluted for Formulation Screen 1, but were diluted to 2 mg/mL in mobile phase of 0.20 M potassium phosphate, 0.25 M potassium chloride, pH 6.2±0.1 prior to injection for subsequent screens. An injection of 50 μg protein per sample was detected at 280 nm. Each sample run time was 30 minutes. Reagent blanks were performed with respective formulation buffers. Peak areas were integrated with respect to the baseline.

Imaged Capillary Isoelectric Focusing (ICIEF)

Charge variant distribution was assessed by an iCE280 analyzer (ProteinSimple) with PrinCE microinjector and a fluorocarbon-coated capillary cartridge of 100 μm×5 cm (ProteinSimple). To remove heavy chain C-terminal lysine residue, carboxypeptidase B (CpB) was added to each sample after the dilution step at an enzyme-to-substrate ratio of 1:1000 (w/w). In addition, sialidase A was added to remove sialic acid. After addition of CpB and sialidase A, samples were incubated at 37° C. for 10 minutes. The incubated samples were mixed with the ampholyte solution consisted of a mixture of 700 μL of 1% methyl cellulose, 1218 μL of purified water, 8 μL of pharmalyte 8-10.5, 55 μL of pharmalyte 5-8, 15 μL of μl marker 5.12, 4 μL of μl marker 7.05. The samples were focused by introducing a potential of 1500 V for 1 minute, followed by a potential of 3000 V for 5 minutes with the anolyte of 80 mM phosphoric acid, and the catholyte of 100 mM sodium hydroxide, both in 0.1% methyl cellulose. An image of the focused charge variants was obtained by passing 280 nm ultraviolet (UV) light through the capillary and into the lens of a charge-coupled device digital camera.

Thermal Stability by Differential Scanning Calorimetry (DSC) and Intrinsic Tryptophan Fluorescence DSC is a thermoanalytical technique in which the difference in the amount of heat required to increase the temperature of a sample is measured as a function of temperature linearly. Melting points $T_m$ and onset temperature of melting can determine the sensitivity of protein to thermal unfolding. The fusion molecule melts at much lower temperature than full-length monoclonal antibodies. Therefore, DSC was employed to quickly assess the effect of pH on thermal stability to further guide formulation development. The IL-22 Fc fusion protein was diluted to 1 mg/mL in different pH formulation buffers (pH 5.5-7.6). Samples were loaded into a 96-well plate, alternating with wells containing 500 μL of formulation buffers of corresponding pH. The instrument scanned each sample-buffer pair over the temperature range 15-95° C. at a rate of 1° C./min. Data analysis was performed using Origin software (Originlab, Northampton, MA).

Thermal denaturation studies using intrinsic tryptophan fluorescence emission spectra were conducted using a Horiba Jobin Yvon Fluoromax-4 Spectrometer with a Thermo Scientific NESLAB RTE 7 circulating water bath. A tryptophan emission spectrum was collected from 300 to 450 nm upon excitation at 295 nm. Measurement was repeated at 2° C. intervals from approximately 5 to 65° C. The fluorescence intensity at 350 nm ($\lambda_{max}$) was monitored to assess the change in peak fluorescence throughout the thermal ramp. Unfolding curves were generated using principal component analysis of all of the spectra obtained and $T_{onset}$ was defined as the first change in slope in the unfolding curve.

Tryptic Peptide Map (Methionine Oxidation)

Peptide map analysis by high resolution liquid chromatography tandem mass spectrometry (LC-MS-MS) was used to assess oxidation of methionine. IL-22 Fc fusion peptide samples were subjected to denaturing conditions with guanidinium hydrochloride, followed by reduction with dithiothreitol (DTT) and carboxymethylation of cysteines with iodoacetic acid (IAA). The reduced and carboxymethylated samples were then digested with trypsin enzyme for 4 hours at 37° C. to generate tryptic peptides. The resulting tryptic peptides were separated by an Agilent 1200 RP-HPLC coupled to a Thermo OrbiTrap Elite III MS-MS-capable mass spectrometer. Data analysis of the separated tryptic peptide mixture was performed using Thermo Xcalibur software. There are eight methionine-containing tryptic peptides in the IL-22 Fc fusion protein. Extracted ion chromatograms (EIC) for the masses of the native methionine-containing tryptic peptides were compared to the EIC of the masses of oxidized methionine-containing peptides (if observed). Methionine oxidation for each tryptic peptide is reported as a percentage from the ratio of oxidized tryptic peptide to that of total tryptic peptide (native+oxidized).

Potency Assay

The IL-22 Fc fusion protein potency assay measures the ability of IL-22 Fc fusion protein to bind to the IL22-R1a extracellular domain (ECD). In the assay, varying concentrations of IL-22 Fc fusion protein Reference Standard, control, and samples were added to a 96-well plate coated with IL22-R1a ECD. Bound IL-22 Fc fusion protein was detected with goat anti-human IgG-HRP antibody and a tetramethylbenzidine substrate solution. The results, expressed in optical density (OD) units, were plotted against IL-22 Fc fusion protein concentrations, and a parallel curve program was used to calculate the measured potency of IL-22 Fc fusion protein sample(s) relative to the Reference Standard.

To determine the corrected relative potency value: first, the predicted relative potency (y) for a sample was determined by entering the SA value (x) for a sample and solving the equation of the correlation line (y=178.25−10.604x). The predicted relative potency value (y) was then subtracted from 100. This value was then added to the measured relative potency to get the corrected relative potency value for the sample: Corrected relative potency=measured relative potency+(100−y).

The SA level in sample(s) was monitored and controlled using an analytical method specific for SA on the control system. The acceptance criterion on the control system for SA content is 8-12 mol/mol. The reference standard has an SA content of 8 mol/mol, which is at the low end of the acceptance criteria for SA. Therefore, solely due to the negative correlation between SA and potency, samples with SA content higher than 8 mol/mol could artificially appear to be sub-potent. Using the line of correlation to generate corrected relative potency values provides a correction that is specific for the SA content of each sample. The specificity of the correction for each sample, maintains the ability of the potency assay to detect molecular changes that could be obscured by a fixed correction value that may over compensate for the impact of SA on potency.

Results

IL-22 Fc Fusion Protein Formulation Screen 1

Figure 2A:
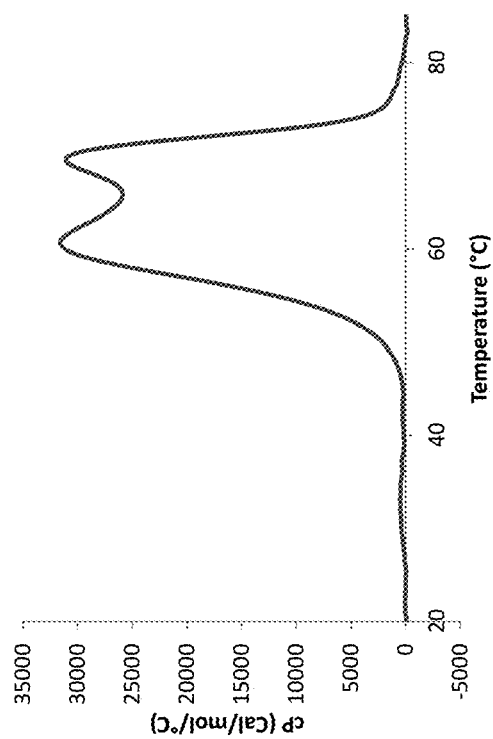
FIG. 2A is a graph showing the thermal stability of an IL-22 Fc fusion protein pharmaceutical composition by differential scanning calorimetry (DSC) at 10 mg/mL in 20 mM histidine acetate, 240 mM sucrose, 0.02% PS20 (w/v) at pH 5.5.
Figure 2B:
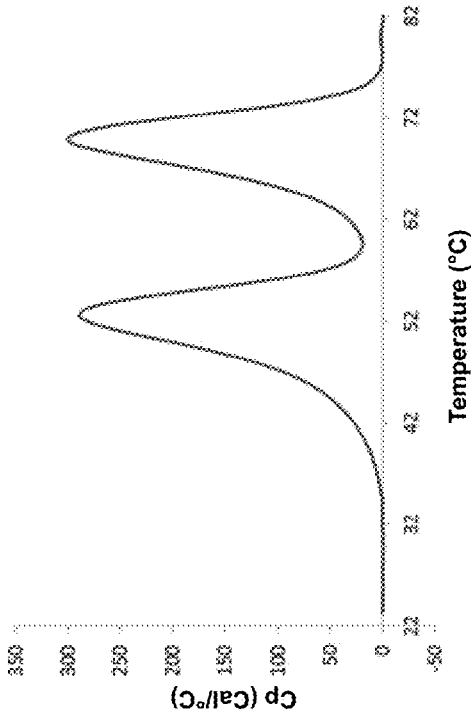
FIG. 2B is a graph showing the thermal stability of an IL-22 Fc fusion protein pharmaceutical composition by DSC at 10 mg/mL in PBS at pH 7.4. The onset melting temperature ($T_m$) for IgG4 is approximately 34° C. compared to PBS, pH 7.4 with a $T_m$ of approximately 45° C.

A pharmaceutical composition having IL-22 Fc fusion protein at 10 mg/mL in 20 mM histidine acetate, 240 mM sucrose, pH 5.5, 0.02% (w/v) PS20 was used as the initial testing. After one week at 40° C., results by SE-HPLC analysis demonstrated increases in very high molecular weight species (vHMWS), indicative of thermal denaturation (Table 3 and FIG. 1). This was confirmed by DSC measurement of the onset melting temperature ($T_m$) of IL-22 Fc fusion protein, which was approximately 34° C. (FIG. 2A). This led to concern about the physical stability of IL-22 Fc fusion protein after administration. Therefore, the $T_m$ was measured for IL-22 Fc fusion protein in phosphate buffered saline (PBS) at pH 7.4 to mimic physiologic conditions (FIG. 2B).

TABLE 3

SE-HPLC of IL-22 Fc Fusion Protein at 10 mg/mL in 20 mM histidine acetate, 240 mM sucrose, 0.02% PS20 (w/v) at pH 5.5 (Screen 1)

| Sample | SE-HPLC | | |
|---|---|---|---|
| | % HMWS | % MONOMER | % LMWS |
| 1.5 mg/ml neat; stored at 5° C. | 0.62 | 99.06 | 0.33 |
| T = 0 @ −70° C.; neat | 0.61 | 99.06 | 0.34 |
| T = 1 wk @ 40° C.; neat | 55.64 | 43.81 | 0.55 |
| T = 2 wk @ 40° C.; neat | 62.60 | 36.92 | 0.48 |
| T = 4 wk @ 40° C.; neat | 68.54 | 30.41 | 1.05 |

IL-22 Fc Fusion Protein Formulation Screen 2

Figure 3B:
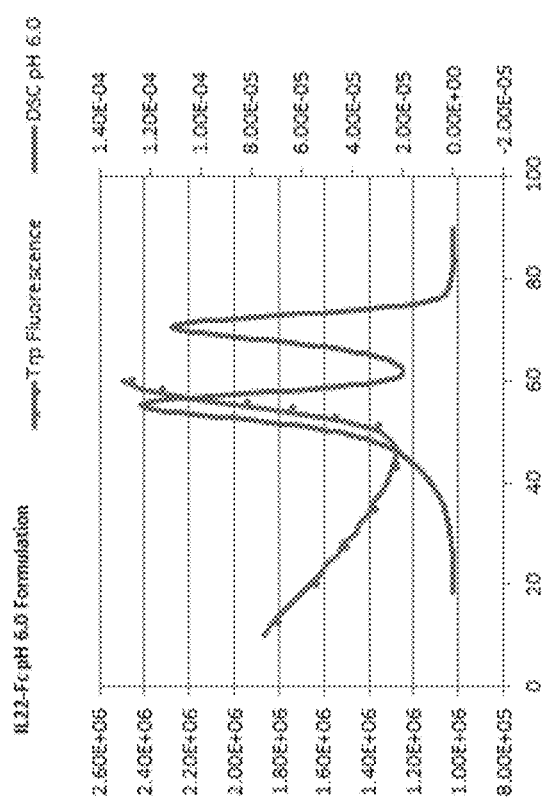
FIG. 3B is a graph showing the DSC and intrinsic tryptophan (Trp) fluorescence profiles of IL-22 Fc fusion protein in 10 mM histidine acetate at pH 6.0.
Figure 3A:
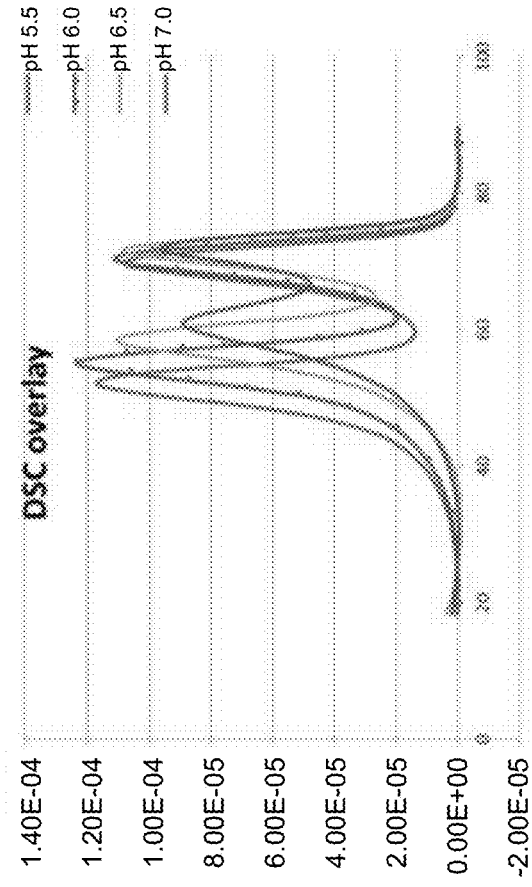
FIG. 3A is a graph comparing the DSC profiles of IL-22 Fc fusion protein in 10 mM histidine acetate at pH 5.5, 6.0, 6.5, and 7.0.
Figure 3E:
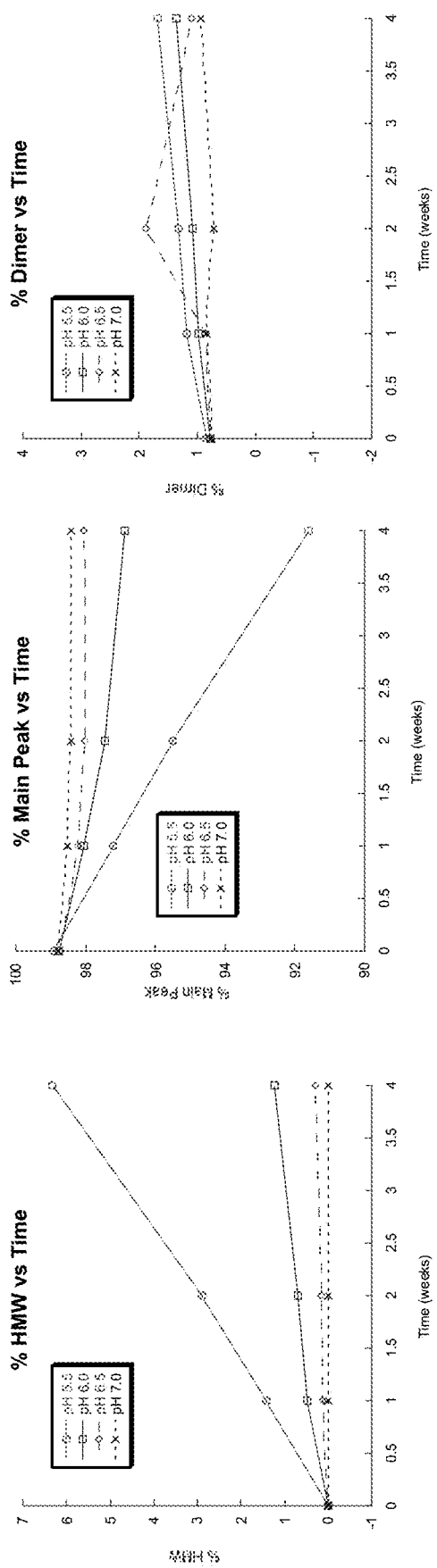
FIG. 3E is a series of graphs showing the SE-HPLC analyses, represented as percent high molecular weight (% HMW) vs time (left panel), % main peak vs time (center panel), and % dimer vs time (right panel), of thermally stressed IL-22 Fc fusion protein in 10 mM histidine acetate at pH 5.5, 6.0, 6.5, and 7.0 after 4 weeks at 30° C.

The DSC result with PBS at pH 7.4 unexpectedly suggested that IL-22 Fc fusion protein might have better thermal stability at higher pH. This led to a second round of DSC with material formulated in 10 mM histidine acetate at pH 5.5, pH 6.0, pH 6.5 and pH 7.0. The DSC results, as well as the thermal denaturation studies utilizing fluorescence monitoring (Trp Fluorescence) demonstrated that as the pH of the formulation is increased, the $T_m$ also increased up to ~12° C. higher at pH 7.0 (Table 4 and FIGS. 3A-3D). Analysis of thermally stressed IL-22 Fc fusion protein in these formulations by SE-HPLC demonstrated that IL-22 Fc fusion protein achieves physical stability at around pH 6.5 and 7.0, while increases in HMWS were observed at pH 5.5 and 6.0 (FIG. 3E). Thus, a final screen was initiated with a target of pH 7.0 in buffers of more appropriate $pK_a$ to establish the acceptable pH range for IL-22 Fc fusion protein.

TABLE 4

$T_m$ measured by DSC and Trp Fluorescence of IL-22 Fc Fusion Protein in 10 mM histidine acetate at pH 5.5, 6.0, 6.5 and 7.0 (Screen 2)

| Sample | $T_m$ by Trp Fluorescence | $T_m$ by DSC |
|---|---|---|
| pH 5.5 | 40-45° C. (~42° C.) | 30-35° C. (~32° C.) |
| pH 6.0 | 45-50° C. (~46° C.) | 35-40° C. (~36° C.) |
| pH 6.5 | 50-55° C. (~52° C.) | 40-45° C. (~42° C.) |
| pH 7.0 | 50-55° C. (~54° C.) | 40-45° C. (~44° C.) |

IL-22 Fc Fusion Protein Formulation Screen 3

Figure 4:
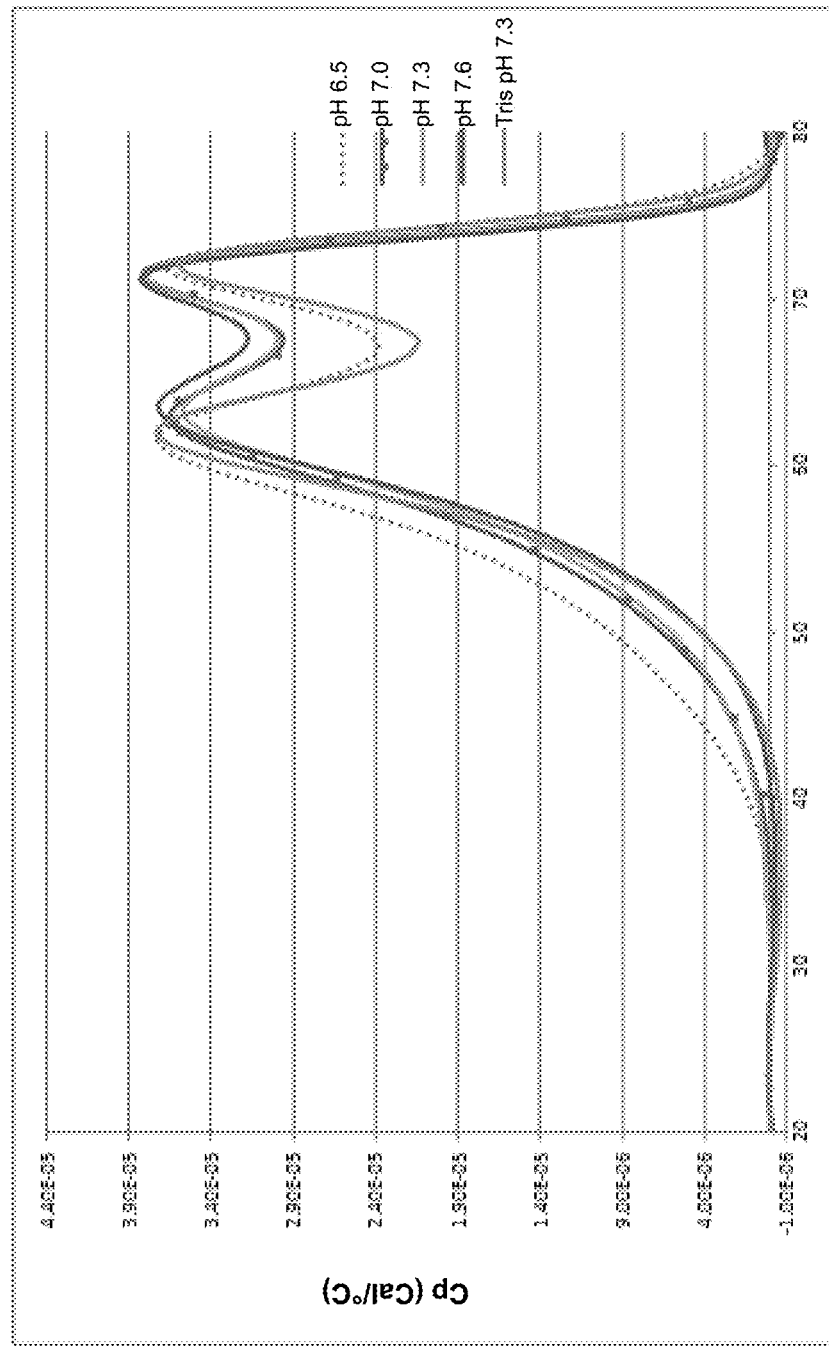
FIG. 4 is a graph showing the DSC profile of the IL-22 Fc fusion protein pharmaceutical composition at pH 6.5, 7.0, 7.3, and 7.6 in 10 mM sodium phosphate, and pH 7.3 in 20 mM tris.
Figure 5A:
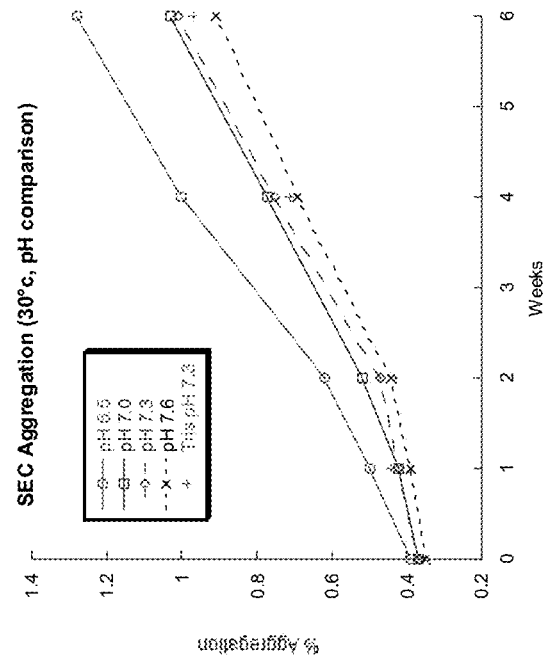
FIGS. 5A-5B are a series of graphs showing the rate of degradation of the main peak (5A) and percent aggregation over time (5B) of IL-22 Fc fusion protein by SE-HPLC in 10 mM sodium phosphate, 240 mM sucrose, 0.02% polysorbate 20, pH 7.1 after T=0 and 6 weeks of storage at 30° C.
Figure 5B:
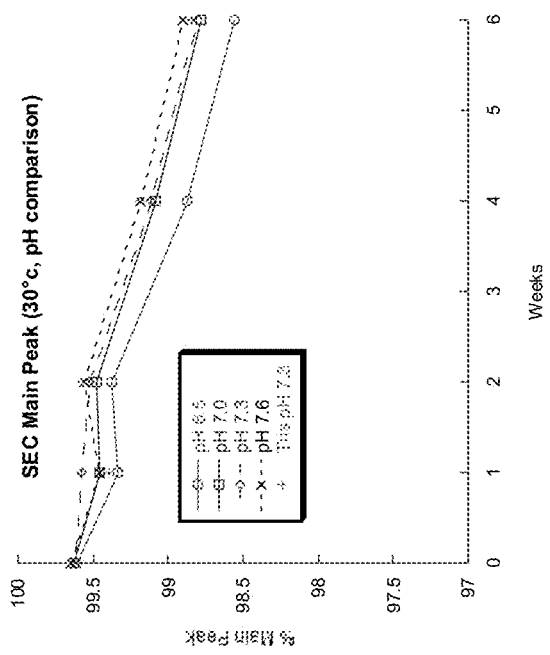
Figure 5C:
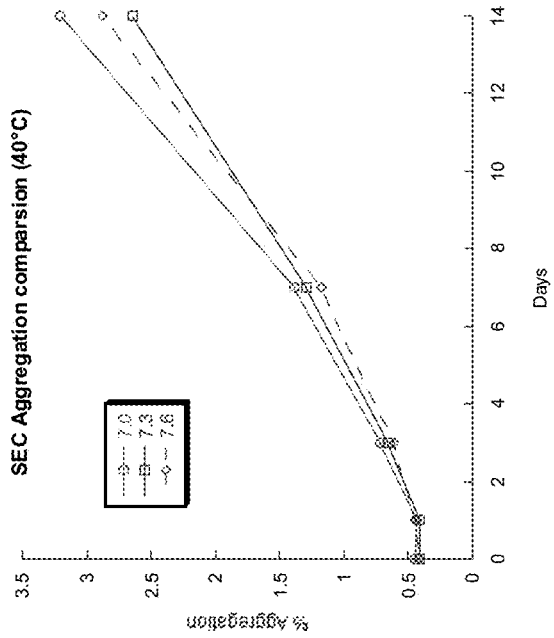
FIGS. 5C-5D are a series of graphs showing the rate of degradation of the main peak (5C) and percent aggregation over time (5D) of IL-22 Fc fusion protein by SE-HPLC in 10 mM sodium phosphate, 240 mM sucrose, 0.02% polysorbate 20, pH 7.1 after T=0 and 6 weeks of storage at 40° C.
Figure 5D:
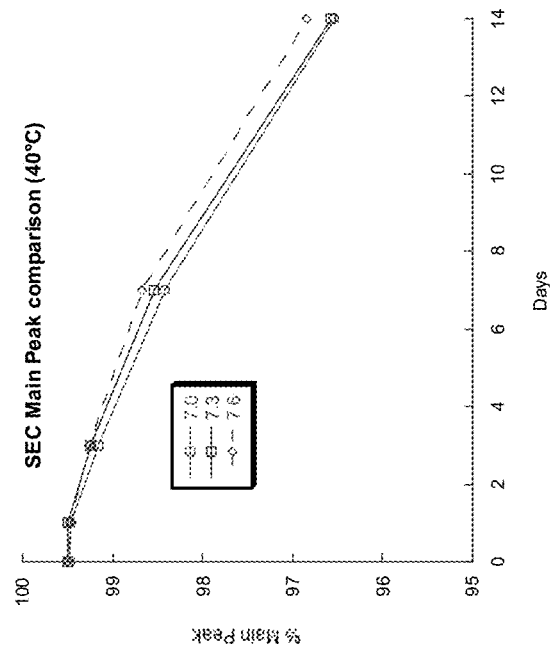
Figure 6:
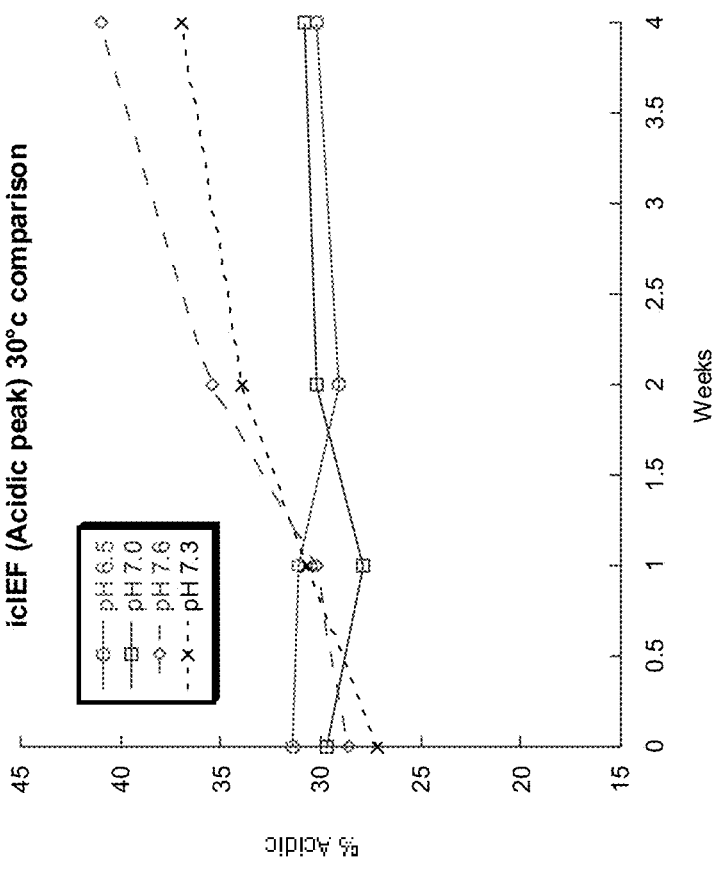
FIG. 6 is a graph showing the rate of formation of acidic peaks by imaged capillary isoelectric focusing (ICIEF) of IL-22 Fc fusion protein in 10 mM sodium phosphate, 240 mM sucrose, 0.02% polysorbate 20, pH 7.1 after T=0 and 4 weeks of storage at 30° C.
Figure 7:
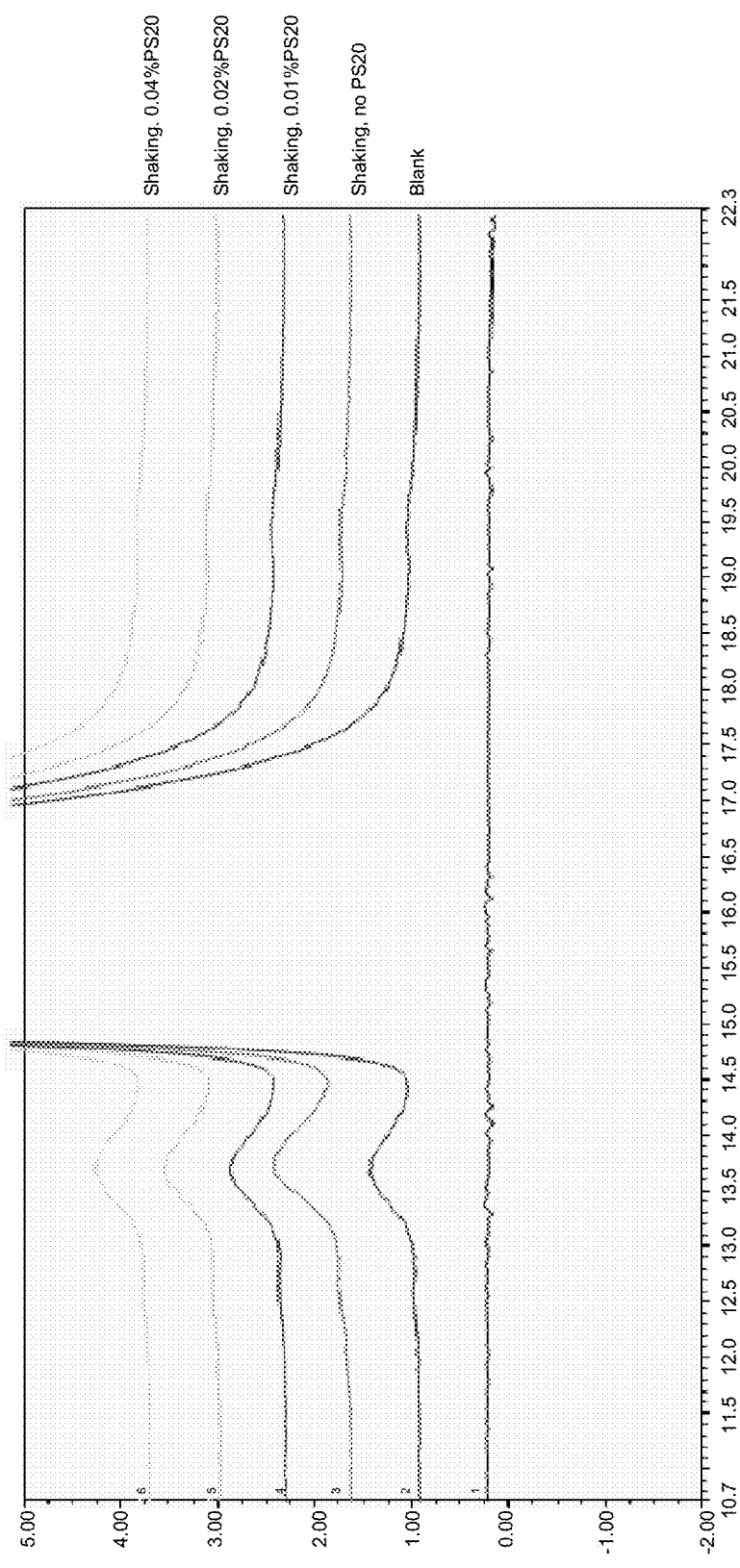
FIG. 7 is an overlay of chromatograms showing the SE-HPLC profiles of IL-22 Fc fusion protein following an agitation study.

The final formulation screen was set up at pH 6.5, 7.0, 7.3, and 7.6 in 10 mM sodium phosphate and at pH 7.3 in 20 mM Tris. These formulations were first evaluated by DSC to determine the onset $T_m$ (FIG. 4). By DSC, there appeared to be smaller gains in thermal stability beyond pH 7.3. At the recommended IL-22 Fc fusion protein pharmaceutical composition storage temperature at 5° C., no changes were observed for all formulations at pH 6.5, 7.0, 7.3, and 7.6 after 6 weeks of storage by SE-HPLC and ICIEF (Tables 5-9). There were no changes observed in visual appearance, pH, and strength for all formulations at −70° C., −20° C., 5° C., 25° C., 30° C., and 40° C. for all time points. After 6 weeks at 30° C. (FIGS. 5A-51B) and 2 weeks at 40° C. (FIGS. 5C-5D), the rates of degradation by SE-HPLC for the formulations at pH 7.0, 7.3, and 7.6 were comparable. From the 30° C. data, the rate of degradation was higher at pH 6.5 and consistent with the DSC results. Main peak loss was due predominantly to an increase of HMWF (high molecular weight form) with a smaller increase observed in LMWF (low molecular weight form). At 30° C. after 4 weeks (FIG.

6) there was a clear trend by ICIEF towards faster degradation and a faster rate of formation of acidic peaks as the pH increased from 7.0 to 7.3 to 7.6. There was little difference between pH 6.5 and 7.0 in the rates of degradation. No loss in potency assay was observed after storage at 4 weeks in 30° C. and 1 week at 40° C., pH 7.0 (Table 10).

This formulation screen suggested that a pharmaceutical composition containing 10 mg/mL IL-22 Fc fusion protein in 10 mM sodium phosphate, 240 mM sucrose, 0.02% polysorbate 20, at pH 7.1 would provide a balance in maintaining both physical and chemical stability. Therefore, a pH of 7.1 was selected for the pharmaceutical formulation.

TABLE 5

Stability of the IL-22 Fc Fusion Protein Pharmaceutical Composition in the Formulation of 10 mM sodium phosphate, 240 mM sucrose, and 0.02% polysorbate 20, pH 6.5 stored at −70, 20, 5, 25, 30, and 40° C. for up to 6 weeks (Screen 3)

| Temp. (° C.) | Time point (days/ weeks) | CAC | Strength (mg/mL) | pH | ICIEF % Acidic | ICIEF % Main | ICIEF % Basic | SE-HPLC % HMWF | SE-HPLC % Main | SE-HPLC % LMWF |
|---|---|---|---|---|---|---|---|---|---|---|
| −70 | 0 | CO/CL | 10.0 | 6.5 | 31.4 | 38.0 | 30.7 | 0.4 | 99.6 | 0.0 |
| −20 |  | CO/CL | 10.0 | 6.5 | NT | NT | NT | 0.4 | 99.4 | 0.2 |
|  |  | CO/CL | 10.0 | 6.5 | NT | NT | NT | 0.4 | 99.6 | 0.0 |
|  |  | CO/CL | 10.0 | 6.5 | NT | NT | NT | 0.4 | 99.5 | 0.1 |
| 5 | 7/1 | CO/CL | 10.0 | 6.5 | NT | NT | NT | 0.5 | 99.4 | 0.2 |
|  | 14/2 | CO/CL | 10.0 | 6.5 | NT | NT | NT | 0.4 | 99.5 | 0.1 |
|  | 28/4 | CO/CL | 10.0 | 6.5 | 31.1 | 39.5 | 29.5 | 0.4 | 99.5 | 0.1 |
| 25 | 7/1 | CO/CL | 10.0 | 6.5 | NT | NT | NT | 0.5 | 99.3 | 0.2 |
|  | 14/2 | CO/CL | 10.0 | 6.5 | NT | NT | NT | 0.6 | 99.4 | 0.0 |
|  | 28/4 | CO/CL | 10.0 | 6.5 | NT | NT | NT | 0.6 | 99.3 | 0.1 |
| 30 | 7/1 | CO/CL | 10.0 | 6.5 | 31.1 | 38.2 | 30.8 | 0.5 | 99.3 | 0.2 |
|  | 14/2 | CO/CL | 10.0 | 6.5 | 29.1 | 40.7 | 30.2 | 0.6 | 99.4 | 0.0 |
|  | 28/4 | CO/CL | 10.0 | 6.5 | 30.16 | 40.93 | 28.93 | 1.0 | 98.9 | 0.1 |
|  | 42/6 | CO/CL | 10.0 | 6.5 | NT | NT | NT | 1.3 | 98.6 | 0.2 |
| 40 | 1/NA | CO/CL | 10.0 | 6.5 | NT | NT | NT | NT | NT | NT |
|  | 3/NA | CO/CL | 10.0 | 6.5 | NT | NT | NT | NT | NT | NT |
|  | 7/1 | CO/CL | 10.0 | 6.5 | NT | NT | NT | NT | NT | NT |
|  | 14/2 | CO/CL | 10.0 | 6.5 | NT | NT | NT | NT | NT | NT |

CAC color, appearance, clarity; CO/CL: clear and colorless, NT: not tested, HMWF high molecular weight forms, LMWF: low molecular weight forms, ICIEF imaged capillary isoelectric focusing

TABLE 6

Stability of the IL-22 Fc Fusion Protein Pharmaceutical Composition in the Formulation of 10 mM sodium phosphate, 240 mM sucrose, and 0.02% polysorbate 20, pH 7.0 stored at −70, 20, 5, 25, 30, and 40° C. for up to 6 weeks (Screen 3)

| Temp. (° C.) | Time point (days/ weeks) | CAC | Strength (mg/mL) | pH | ICIEF % Acidic | ICIEF % Main | ICIEF % Basic | SE-HPLC % HMWF | SE-HPLC % Main | SE-HPLC % LMWF |
|---|---|---|---|---|---|---|---|---|---|---|
| −70 | 0 | CO/CL | 10.0 | 7.0 | 29.7 | 40.2 | 30.1 | 0.4 | 99.6 | 0.0 |
| −20 | 7/1 | CO/CL | 10.0 | 7.0 | NT | NT | NT | 0.5 | 99.3 | 0.2 |
|  | 14/2 | CO/CL | 10.0 | 7.0 | NT | NT | NT | 0.4 | 99.6 | 0.0 |
|  | 28/4 | CO/CL | 10.0 | 7.0 | NT | NT | NT | 0.4 | 99.5 | 0.1 |
| 5 | 7/1 | CO/CL | 10.0 | 7.0 | NT | NT | NT | 0.4 | 99.4 | 0.2 |
|  | 14/2 | CO/CL | 10.0 | 7.0 | NT | NT | NT | 0.5 | 99.5 | 0.0 |
|  | 28/4 | CO/CL | 10.0 | 7.0 | NT | NT | NT | 0.4 | 99.5 | 0.1 |
| 25 | 7/1 | CO/CL | 10.0 | 7.0 | NT | NT | NT | 0.4 | 99.4 | 0.1 |
|  | 14/2 | CO/CL | 10.0 | 7.0 | NT | NT | NT | 0.5 | 99.5 | 0.0 |
|  | 28/4 | CO/CL | 10.0 | 7.0 | NT | NT | NT | 0.6 | 99.4 | 0.1 |
| 30 | 7/1 | CO/CL | 10.0 | 7.0 | 27.9 | 41.6 | 30.5 | 0.4 | 99.5 | 0.1 |
|  | 14/2 | CO/CL | 10.0 | 7.0 | 30.2 | 41.5 | 28.3 | 0.5 | 99.5 | 0.0 |
|  | 28/4 | CO/CL | 10.0 | 7.0 | 30.8 | 40.8 | 28.4 | 0.8 | 99.1 | 0.2 |
|  | 42/6 | CO/CL | 10.0 | 7.0 | NT | NT | NT | 1.0 | 98.8 | 0.2 |
| 40 | 1/NA | CO/CL | 10.0 | 7.0 | 30.9 | 39.0 | 30.1 | 0.4 | 99.5 | 0.1 |
|  | 3/NA | CO/CL | 10.0 | 7.0 | 30.8 | 38.9 | 30.4 | 0.7 | 99.2 | 0.1 |
|  | 7/1 | CO/CL | 10.0 | 7.0 | 31.7 | 40.0 | 28.4 | 1.4 | 98.4 | 0.2 |
|  | 14/2 | CO/CL | 10.0 | 7.0 | NT | NT | NT | 3.2 | 96.5 | 0.3 |

CAC color, appearance, clarity; CO/CL: clear and colorless, NT: not tested, HMWF high molecular weight forms, LMWF: low molecular weight forms, ICIEF imaged capillary isoelectric focusing

TABLE 7

Stability of the IL-22 Fc Fusion Protein Pharmaceutical Composition in the Formulation of 10 mM sodium phosphate, 240 mM sucrose, and 0.02% polysorbate 20, pH 7.3 stored at −70, 20, 5, 25, 30, and 40° C. for up to 6 weeks (Screen 3)

| Temp. (° C.) | Time point (days/ weeks) | CAC | Strength (mg/mL) | pH | ICIEF | | | SE-HPLC | | |
|---|---|---|---|---|---|---|---|---|---|---|
| | | | | | % Acidic | % Main | % Basic | % HMWF | % Main | % LMWF |
| −70 | 0 | CO/CL | 10.0 | 7.3 | 27.2 | 42.1 | 30.7 | 0.4 | 99.6 | 0.0 |
| −20 | 7/1 | CO/CL | 10.0 | 7.3 | NT | NT | NT | 0.4 | 99.4 | 0.2 |
| | 14/2 | CO/CL | 10.0 | 7.3 | NT | NT | NT | 0.4 | 99.6 | 0.0 |
| | 28/4 | CO/CL | 10.0 | 7.3 | NT | NT | NT | 0.4 | 99.6 | 0.1 |
| 5 | 7/1 | CO/CL | 10.0 | 7.3 | NT | NT | NT | 0.4 | 99.5 | 0.2 |
| | 14/2 | CO/CL | 10.0 | 7.3 | NT | NT | NT | 0.5 | 99.6 | 0.0 |
| | 28/4 | CO/CL | 10.0 | 7.3 | 29.6 | 40.3 | 30.1 | 0.4 | 99.5 | 0.1 |
| 25 | 7/1 | CO/CL | 10.0 | 7.3 | NT | NT | NT | 0.4 | 99.5 | 0.1 |
| | 14/2 | CO/CL | 10.0 | 7.3 | 33.5 | 37.4 | 30.1 | 0.4 | 99.6 | 0.0 |
| | 28/4 | CO/CL | 10.0 | 7.3 | NT | NT | NT | 0.5 | 99.4 | 0.1 |
| 30 | 7/1 | CO/CL | 10.0 | 7.3 | 30.7 | 39.7 | 29.6 | 0.4 | 99.6 | 0.0 |
| | 14/2 | CO/CL | 10.0 | 7.3 | 34.0 | 37.8 | 28.3 | 0.5 | 99.5 | 0.0 |
| | 28/4 | CO/CL | 10.0 | 7.3 | 37.0 | 37.9 | 25.1 | 0.8 | 99.1 | 0.1 |
| | 42/6 | CO/CL | 10.0 | 7.3 | NT | NT | NT | 1.0 | 98.8 | 0.2 |
| 40 | 1/NA | CO/CL | 10.0 | 7.3 | 26.3 | 42.5 | 31.2 | 0.4 | 99.5 | 0.1 |
| | 3/NA | CO/CL | 10.0 | 7.3 | 32.6 | 38.3 | 29.1 | 0.7 | 99.2 | 0.1 |
| | 7/1 | CO/CL | 10.0 | 7.3 | 33.9 | 39.6 | 26.8 | 1.3 | 98.5 | 0.2 |
| | 14/2 | CO/CL | 10.0 | 7.3 | NT | NT | NT | 3.2 | 96.6 | 0.2 |

CAC color, appearance, clarity; CO/CL: clear and colorless, NT: not tested, HMWF high molecular weight forms, LMWF: low molecular weight forms, ICIEF imaged capillary isoelectric focusing

TABLE 8

Stability of the IL-22 Fc Fusion Protein Pharmaceutical Composition in the Formulation of 10 mM sodium phosphate, 240 mM sucrose, and 0.02% polysorbate 20, pH 7.6 stored at −70, −20, 5, 25, 30, and 40° C. for up to 6 weeks (Screen 3)

| Temp. (° C.) | Time point (days/ weeks) | CAC | Strength (mg/mL) | pH | ICIEF | | | SE-HPLC | | |
|---|---|---|---|---|---|---|---|---|---|---|
| | | | | | % Acidic | % Main | % Basic | % HMWF | % Main | % LMWF |
| −70 | 0 | CO/CL | 10.0 | 7.6 | 28.6 | 41.3 | 30.2 | 0.4 | 99.7 | 0.0 |
| −20 | 7/1 | CO/CL | 10.0 | 7.6 | NT | NT | NT | 0.4 | 99.4 | 0.2 |
| | 14/2 | CO/CL | 10.0 | 7.6 | NT | NT | NT | 0.4 | 99.6 | 0.0 |
| | 28/4 | CO/CL | 10.0 | 7.6 | NT | NT | NT | 0.4 | 99.5 | 0.1 |
| 5 | 7/1 | CO/CL | 10.0 | 7.6 | NT | NT | NT | 0.4 | 99.4 | 0.2 |
| | 14/2 | CO/CL | 10.0 | 7.6 | NT | NT | NT | 0.4 | 99.6 | 0.0 |
| | 28/4 | CO/CL | 10.0 | 7.6 | 29.7 | 40.7 | 29.6 | 0.4 | 99.6 | 0.1 |
| 25 | 7/1 | CO/CL | 10.0 | 7.6 | NT | NT | NT | 0.4 | 99.5 | 0.2 |
| | 14/2 | CO/CL | 10.0 | 7.6 | NT | NT | NT | 0.4 | 99.6 | 0.0 |
| | 28/4 | CO/CL | 10.0 | 7.6 | NT | NT | NT | 0.5 | 99.4 | 0.1 |
| 30 | 7/1 | CO/CL | 10.0 | 7.6 | 30.2 | 40.7 | 29.1 | 0.4 | 99.5 | 0.2 |
| | 14/2 | CO/CL | 10.0 | 7.6 | 35.5 | 37.9 | 26.6 | 0.4 | 99.6 | 0.0 |
| | 28/4 | CO/CL | 10.0 | 7.6 | 41.0 | 35.9 | 23.2 | 0.7 | 99.2 | 0.1 |
| | 42/6 | CO/CL | 10.0 | 7.6 | NT | NT | NT | 0.9 | 98.9 | 0.2 |
| 40 | 1/NA | CO/CL | 10.0 | 7.6 | 30.1 | 39.9 | 30.0 | 0.5 | 99.5 | 0.1 |
| | 3/NA | CO/CL | 10.0 | 7.6 | 32.1 | 39.9 | 28.1 | 0.6 | 99.3 | 0.1 |
| | 7/1 | CO/CL | 10.0 | 7.6 | 36.0 | 39.1 | 24.9 | 1.2 | 98.7 | 0.2 |
| | 14/2 | CO/CL | 10.0 | 7.6 | NT | NT | NT | 2.9 | 96.9 | 0.3 |

CAC color, appearance, clarity; CO/CL: clear and colorless, NT: not tested, HMWF high molecular weight forms, LMWF: low molecular weight forms, ICIEF imaged capillary isoelectric focusing

TABLE 9

Stability of the IL-22 Fc Fusion Protein Pharmaceutical Composition in the Formulation of 20 mM Tris, 240 mM sucrose, and 0.02% polysorbate 20, pH 7.3 stored at −70, −20, 5, 25 and 30° C. for up to 6 weeks (Screen 3)

| Temp. (° C.) | Time point (days/ weeks) | CAC | Strength (mg/mL) | pH | ICIEF % Acidic | % Main | % Basic | SE-HPLC % HMWF | % Main | % LMWF |
|---|---|---|---|---|---|---|---|---|---|---|
| −70 | 0 | CO/CL | 10.0 | 7.3 | NT | NT | NT | 0.3 | 99.7 | 0.0 |
| −20 | 7/1 | CO/CL | 10.0 | 7.3 | NT | NT | NT | 0.4 | 99.4 | 0.2 |
|  | 14/2 | CO/CL | 10.0 | 7.3 | NT | NT | NT | 0.4 | 99.6 | 0.0 |
|  | 28/4 | CO/CL | 10.0 | 7.3 | NT | NT | NT | 0.4 | 99.5 | 0.1 |
| 5 | 7/1 | CO/CL | 10.0 | 7.3 | NT | NT | NT | 0.4 | 99.6 | 0.0 |
|  | 14/2 | CO/CL | 10.0 | 7.3 | NT | NT | NT | 0.4 | 99.6 | 0.0 |
|  | 28/4 | CO/CL | 10.0 | 7.3 | NT | NT | NT | 0.4 | 99.5 | 0.1 |
| 25 | 7/1 | CO/CL | 10.0 | 7.3 | NT | NT | NT | 0.4 | 99.4 | 0.2 |
|  | 14/2 | CO/CL | 10.0 | 7.3 | NT | NT | NT | 0.4 | 99.6 | 0.0 |
|  | 28/4 | CO/CL | 10.0 | 7.3 | NT | NT | NT | 0.5 | 99.4 | 0.1 |
| 30 | 7/1 | CO/CL | 10.0 | 7.3 | NT | NT | NT | 0.4 | 99.4 | 0.2 |
|  | 14/2 | CO/CL | 10.0 | 7.3 | NT | NT | NT | 0.4 | 99.6 | 0.0 |
|  | 28/4 | CO/CL | 10.0 | 7.3 | NT | NT | NT | 0.7 | 99.2 | 0.1 |
|  | 42/6 | CO/CL | 10.0 | 7.3 | NT | NT | NT | 1.0 | 98.8 | 0.2 |

CAC color, appearance, clarity; CO/CL: clear and colorless, NT: not tested, HMWF high molecular weight forms, LMWF: low molecular weight forms, ICIEF imaged capillary isoelectric focusing

TABLE 10

Stability of the IL-22 Fc Fusion Protein Pharmaceutical Composition Potency in the Formulation of 10 mM sodium phosphate, 240 mM sucrose, and 0.02% polysorbate 20, pH 7.0 stored at 30° C. up to 4 weeks and 40° C. for up to 1 weeks (Screen 3)

| Samples | Estimated % relative potency (n = 2) |
|---|---|
| control | 89 |
| T = 4 weeks, 30° C. | 79 |
| T = 1 week, 40° C. | 81 |

IL-22 Fc Fusion Protein Agitation Studies

To determine the effect of PS20 on protein stability, a protein agitation study was performed with the IL-22 Fc fusion protein. Results from agitation studies demonstrated no difference among samples with 0.01%, 0.02%, and 0.04% PS20 after 24 hours agitation as compared to controls without agitation by CAC, SE-HPLC, ICIEF, and turbidity (Table 11 and FIG. 7). A small increase in aggregates was observed in the agitated sample that contained no surfactant, with little increase in turbidity and no visual particulates observed. The study suggests that 0.01% of PS20 is sufficient to protect IL-22 Fc fusion protein during agitation. 0.02% (w/v) PS20 was selected in the final formulation to ensure manufacturability in the specification range of 0.01%-0.03% (w/v) PS20.

TABLE 11

Agitation stability of the IL-22 Fc Fusion Protein Pharmaceutical Composition in the Formulation of 10 mM sodium phosphate, 240 mM sucrose, 5 mM methionine and 0.02% polysorbate 20, pH 7.1

| Samples | CAC | Turbidity (350 nM) | SE-HPLC % HMWF | % Main | % LMWF |
|---|---|---|---|---|---|
| 0.02% PS20, no shaking (control) | CO/CL | NT | 0.1 | 99.4 | 0.2 |
| 0.0% PS20, 24 hrs shaking | CO/CL | 0.0445 | 0.9 | 99.0 | 0.2 |
| 0.01% PS20, 24 hrs shaking | CO/CL | 0.0399 | 0.5 | 99.3 | 0.2 |
| 0.02% PS20, 24 hrs shaking | CO/CL | 0.0448 | 0.6 | 99.3 | 0.2 |
| 0.04% PS20, 24 hrs shaking | CO/CL | 0.0450 | 0.5 | 99.3 | 0.2 |

CAC color, appearance, clarity; CO/CL: clear and colorless, NT: not tested, HMWF high molecular weight forms, LMWF: low molecular weight forms IL-22 Fc Fusion Protein Freeze-Thaw After three cycles of freezing at −20° C. and thawing at room temperature, there were no changes by CAC, pH, strength, and SE-HPLC (Table 12). Thus the IL-22 Fc fusion protein pharmaceutical composition is sufficiently tolerant to repeated freeze-thaw cycles during the manufacturing process.

TABLE 12

Stability of the IL-22 Fc Fusion Protein Pharmaceutical Composition in the Formulation of 10 mM sodium phosphate, 240 mM sucrose, and 0.02% polysorbate 20, 5 mM methionine, pH 7.0 after three freeze/thaw cycles

| | | | | SE-HPLC | | |
|---|---|---|---|---|---|---|
| Samples | CAC | Strength (mg/mL) | pH | % HMWF | % Main | % LMWF |
| T = 0, −20° C., pH 6.5 | CO/CL | 10.0 | 6.5 | 0.4 | 99.4 | 0.2 |
| T = 0, −20° C., pH 7.0 | CO/CL | 10.0 | 7.0 | 0.4 | 99.4 | 0.2 |
| T = 0, −20° C. pH 7.3 | CO/CL | 10.0 | 7.3 | 0.4 | 99.5 | 0.2 |
| T = 0, −20° C. pH 7.6 | CO/CL | 10.0 | 7.6 | 0.4 | 99.4 | 0.2 |
| T = 0, −20° C. Tris 7.3 | CO/CL | 10.0 | 7.3 | 0.4 | 99.4 | 0.2 |
| 3$^{rd}$ F/T, pH 6.5 | CO/CL | 10.0 | 6.5 | 0.4 | 99.4 | 0.2 |
| 3$^{rd}$ F/T, pH 7.0 | CO/CL | 10.0 | 7.0 | 0.4 | 99.4 | 0.2 |
| 3$^{rd}$ F/T, pH 7.3 | CO/CL | 10.0 | 7.3 | 0.4 | 99.5 | 0.1 |
| 3$^{rd}$ F/T, pH 7.6 | CO/CL | 10.0 | 7.6 | 0.4 | 99.5 | 0.1 |
| 3$^{rd}$ F/T, Tris pH 7.3 | CO/CL | 10.0 | 7.3 | 0.4 | 99.5 | 0.1 |

Figure 8:
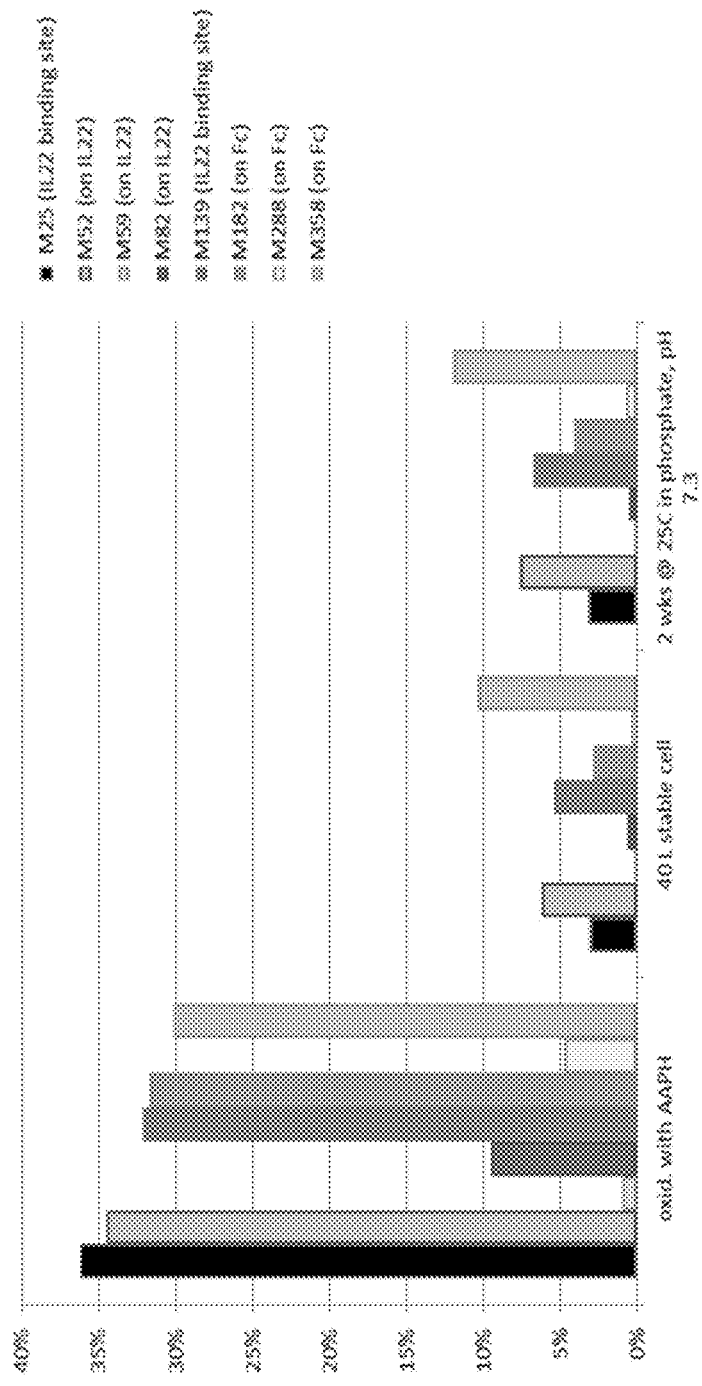
FIG. 8 is a graph showing the methionine oxidation of eight methionine-containing tryptic peptides of the IL-22 Fc fusion protein following treatment with 2,2'-azobis-2-methyl-propanimidamide, dihydrochloride (AAPH) and tryptic peptide mapping by liquid chromatography tandem mass spectrometry (LC-MS-MS). Methionine oxidation for each tryptic peptide is reported as a percentage from the ratio of oxidized tryptic peptide to that of total tryptic peptide (native+oxidized).

CAC color, appearance, clarity; CO/CL: clear and colorless; NT: not tested; HMWF high molecular weight forms; LMWF: low molecular weight forms, ICIEF imaged capillary isoelectric focusing AAPH Stress Studies Initial studies with AAPH treatment of the IL-22 Fc fusion protein analytical standard showed susceptibility of key methionines (M25 and M139) to oxidation (FIG. 8). Therefore, 5 mM methionine was added to the formulation to protect these methionine residues. Additionally, samples containing 3.5 mM and 3 mM methionine were stressed with AAPH and analyzed to determine if levels lower than the target level of 5 mM methionine would provide protection from methionine oxidation. Tryptic peptide map analysis by high-resolution liquid chromatography tandem mass spectrometry (LC-MS-MS) was used to assess oxidation of methionine. Tryptic peptide map data from the Reference Batch formulated with 3.5 mM and 3 mM AAPH-treated samples was compared to Reference Batch formulated with 5 mM methionine and either treated or not treated with AAPH. The data indicate that methionine oxidation does not increase significantly in the 3 mM or 3.5 mM methionine samples when compared to material formulated with 5 mM methionine (Table 13). Thus 3 mM methionine was set as the lower end of the acceptable concentration for the purpose of setting acceptance criteria.

TABLE 13

Tryptic Peptide Map LC-MS-MS Results of AAPH Stress Studies

| | (5 mM met; no AAPH) | 5 mM met; AAPH | 3 mM met; AAPH | 3.5 mM met; AAPH |
|---|---|---|---|---|
| TFMLAK (SEQ ID NO: 85) | 2.23% | 1.63% | 2.50% | 2.38% |
| LFHGVSMSER (SEQ ID NO: 86) | 7.00% | 5.60% | 7.59% | 7.18% |
| CYLMK (SEQ ID NO: 87) | 0.84% | 0.81% | 0.86% | 0.80% |
| FQPYMQEVVPFLAR (SEQ ID NO: 88) | 1.51% | 1.28% | 1.51% | 1.42% |
| AIGELDLLFMSLR (SEQ ID NO: 89) | 6.11% | 4.38% | 5.88% | 5.44% |
| DTLMISR (SEQ ID NO: 90) | 3.49% | 2.31% | 2.96% | 3.02% |
| EPQVYTLPPSQEEMTK (SEQ ID NO: 91) | 1.28% | 0.97% | 1.11% | 1.00% |
| WQEGNVFSCSVMHEALHNHYTQK (SEQ ID NO: 92) | 3.09% | 1.36% | 2.42% | 2.23% |

Conclusions

This study shows that IL-22 Fc fusion protein is suitable for use when formulated at 10 mg/mL for a pharmaceutical composition containing 10 mM sodium phosphate, 240 mM sucrose, 5 mM methionine, and 0.02% polysorbate 20, pH 7.1. To protect IL-22 Fc fusion protein from agitation stresses, polysorbate concentrations between 0.01 and 0.04% are suitable. 10 mg/mL IL-22 Fc fusion protein in this formulation was stable at −20° C. and 5° C. for 6 weeks and after 3 cycles for freezing at −20° C. and thawing at room temperature.

Example 2: Development of the Pharmaceutical Composition of the Invention

Description and Composition of the Pharmaceutical Composition of the Invention (IL-22 Fc Fusion Protein, Sterile Liquid, 10 mg/mL)

IL-22 Fc fusion protein is provided as a sterile slightly brownish yellow solution for intravenous infusion and contains no preservatives. Each single use, 2-mL vial contains 10 mg (nominal) of IL-22 Fc fusion protein at target pH 7.1. The pharmaceutical composition of the invention is formulated as 10 mg/mL IL-22 Fc fusion protein with the composition given in Table 14.

TABLE 14

Composition of IL-22 Fc Fusion Protein Pharmaceutical Composition

| Ingredients | Concentration | Function |
| --- | --- | --- |
| IL-22 Fc Fusion Protein | 10.0 mg/mL | Active ingredient |
| Sodium Phosphate Dibasic, Anydrous | 10 mM | Buffering agent |
| Sodium Phosphate Monobasic, Monohydrate | | Buffering agent |
| Methionine | 5 mM | Stabilizer |
| Sucrose | 240 mM | Tonicity agent |
| Polysorbate 20 | 0.02% (w/v) | Surfactant |
| Water for Injection | NA | Solvent |

IL-22 Fc Fusion Protein Pharmaceutical Composition

IL-22 Fc fusion protein is the only active ingredient in the pharmaceutical composition. No incompatibility exists between the excipients in the formulation and the active drug, as demonstrated by the IL-22 Fc fusion protein and pharmaceutical composition stability data.

Excipients

Table 15 contains a list of the excipients used in the pharmaceutical composition of the invention with corresponding functions and concentrations.

TABLE 15

Excipients

| Excipient | Function | Concentration |
| --- | --- | --- |
| Sodium Phosphate | Buffer to maintain solution pH at 7.1 | 10 mM |
| Sucrose | Tonicity agent | 240 mM |
| Methionine | Stabilizer | 5 mM |
| Polysorbate 20 | Surfactant to prevent losses due to surface adsorption, as well as to minimize the potential formation of soluble aggregates and/or insoluble proteinaceous particles | 0.02% (w/v) |

Pharmaceutical Formulation Development

A single-use pharmaceutical formulation designed as a solution for intravenous (IV) infusion of IL-22 Fc fusion protein was developed. The pharmaceutical composition of the invention is composed of 10 mg/mL IL-22 Fc fusion protein in 10 mM sodium phosphate, 5 mM methionine, 240 mM sucrose, 0.02% (w/v) polysorbate 20, pH 7.1.

To select the pharmaceutical formulation for IL-22 Fc fusion protein, formulation studies were performed which demonstrated that IL-22 Fc fusion protein has acceptable stability in a solution containing sodium phosphate, methionine, sucrose, and polysorbate 20 at pH 7.1. Based on the results of this study, the formulation for the pharmaceutical composition was defined as 10 mg/mL IL-22 Fc fusion protein in 10 mM sodium phosphate, 5 mM methionine, 240 mM sucrose, 0.02% (w/v) polysorbate 20, pH 7.1.

Overages

The IL-22 Fc fusion protein pharmaceutical formulation does not contain any overages.

Physiochemical and Biological Properties

All characterization testing was performed on the IL-22 Fc fusion protein. The composition remains stable at the recommended storage conditions of 2° C.-8° C. when protected from light. As a measure of precaution, an in-line filter (0.2 µm) is used for IV administration of the clinical material.

Monitoring of subvisible particles ≥2 µm and ≥5 µm in size will be conducted as extended characterization (in addition to ≥10 µm and ≥25 µm, which are part of the control strategy) using the light obscuration method through development. These evaluations will be conducted as a part of extended characterization performed with IL-22 Fc fusion protein pharmaceutical composition at the time of release and on stability.

Freeze/Thaw Stability Study Results

Freeze/thaw stability was monitored for IL-22 Fc fusion protein Reference Standard Batch after three cycles of freezing at −20° C. and thawing at room temperature. No changes in product quality were observed after three freeze/thaw cycles.

Microbiological Attributes

The IL-22 Fc fusion protein pharmaceutical composition liquid formulation does not contain any preservatives.

Compatibility

Intravenous Infusion

For IV administration, IL-22 Fc fusion protein pharmaceutical formulation (10 mg/mL) will be administered by infusion after dilution with isotonic sodium chloride solution (0.9% NaCl) and diluent, which is the formulation buffer without methionine (10 mM sodium phosphate, 240 mM sucrose, 0.02% [w/v] polysorbate 20, pH 7.1). The compatibility and stability of the active ingredient was tested under the following simulated preparation/administration conditions.

a) Dilution of IL-22 Fc fusion protein pharmaceutical formulation Clinical Batch 1 with diluent and diluted in saline bags in the range of 0.025-0.5 mg/mL to cover the dose range for IV administration in the clinical study.

b) Short-term exposure to infusion bags containing isotonic sodium chloride solution (bag product-contact surface material consisting of polyvinyl chloride [PVC] and polyolefin [PO]) for IV compatibility).

c) Use of IV infusion lines and infusion aids with product-contacting surfaces of polyvinyl chloride (PVC), polyethylene (PE), polycarbonate (PC), and polyetherurethane (PEU).

d) Use of 0.2 µm in-line filters for IV compatibility (filter membrane of polyethersulfone [PES].

For IV administration, saline bag samples were tested after 24 hours of storage at 2° C.-8° C. and 24 hours at 30° C. with exposure to diffused light followed by passing through the infusion line and in-line filter. At the lowest concentration in the saline bag, it was necessary to pre-dilute the IL-22 Fc fusion protein pharmaceutical composition with diluent before adding to the saline bag to ensure an adequate pH to maintain product stability.

The samples were tested using appropriate methods to assess product quality as follows: purity by size-exclusion high-performance liquid chromatography (SE-HPLC) and imaged capillary electrophoresis isoelectric focusing (cIEF)

(for samples ≥1 mg/mL), protein concentration (by ultraviolet), subvisible particles by light obscuration, color, clarity/opalescence, and pH. One sample was set up at 2 mg/mL in the saline bags and assayed by imaged cIEF to demonstrate that saline did not have a negative impact on product chemical stability.

Batch Formula (IL-22 Fc Fusion Protein, Sterile Liquid, 10 mg/mL)

The formulated IL-22 Fc fusion protein pharmaceutical composition solution remains unchanged with regard to concentration and composition compared to the IL-22 Fc fusion protein solution, i.e., no further compounding or dilution is performed during the pharmaceutical composition manufacturing process. The size of the bulk pharmaceutical composition is five (5) liters. The actual batch size is subject to change. Table 16 contains batch formulation information for the IL-22 Fc fusion protein pharmaceutical composition.

TABLE 16

Batch Formula for the IL-22 Fc Fusion Protein Pharmaceutical Composition

| Ingredients | Nominal Amount per Vial | Nominal Amount per Batch |
| --- | --- | --- |
| IL-22 Fc Fusion Protein | 10.0 mg | 50.0 g |
| Sodium Phosphate Dibasic, Anhydrous | 0.93 mg | 4.65 g |
| Sodium Phosphate, Monobasic, Monohydrate | 0.48 mg | 2.40 g |
| Methionine | 0.75 mg | 3.75 g |
| Sucrose | 82.08 mg | 410.40 g |
| Polysorbate 20 | 0.2 mg | 1.0 g |
| Water for Injection | q.s. to 1 mL | q.s. to 5 L | q.s. = quantum satis (as much as may suffice).

Example 3: Extended Stability Testing of IL-22 Fc Fusion Protein

Extended Stability Testing of IL-22 Fc Fusion Protein Clinical Batch 2 and Reference Standard Batch Procedures and Acceptance Criteria All samples were analyzed using the test procedures listed in Table 17. Representative stability is assessed at specified time intervals using the protocol provided in Table 18.

TABLE 17

Test Procedures to Assess IL-22 Fc Fusion Protein Stability

| Analytical Procedure | Acceptance Criteria for GMP Studies Performed at −20° C. |
| --- | --- |
| Color (Ph. Eur. Color Scale)[a] | Not more colored than BY5 |
| Clarity/Opalescence[b] | ≤Ref III |
| pH | 7.1 ± 0.3 |
| Purity by SE-HPLC | |
| Main Peak (area %) | ≥95.0 |
| Sum of HMW Forms (area %) | ≤5.0[c] |
| Sum of LMW Forms (area %) | Report |
| Purity by CE-SDS-NGS | |
| Main Peak (non-reduced) (% CPA) | ≥85.0 |
| Sum of Pre-Peaks (non-reduced) (% CPA) | ≤15.0[c] |
| Sum of Post-Peak (non-reduced) (% CPA) | Report |
| Purity by Imaged cIEF | |
| Main Peak (area %) | ≥42.9 |
| Acidic Region (area %) | ≤55.6[c] |
| Basic Region (area %) | ≤20.8[c] |
| Potency by Binding Assay (% relative potency)[d] | 40-130 |
| Content of Protein by UV Spec Scan (mg/mL) | 10.0 ± 1.0 |

Note:

Unless otherwise noted, the same test procedures are used in both representative and supportive stability studies.

CE-SDS-NGS = capillary electrophoresis sodium dodecyl sulfate non-gel sieving; cIEF = capillary isoelectric focusing; CPA = corrected peak area; HMW = high molecular weight; LMW = low molecular weight; SE-HPLC = size-exclusion high-performance liquid chromatography; UV Spec Scan = ultraviolet-visible spectrophotometric scan.

[a]A spectral method was employed to assess color in stability studies for the Reference Standard Batch as described in Example 1.

[b]Color, Appearance, and Clarity (CAC) assay was used to assess appearance and clarity in stability studies for the Reference Standard Batch.

[c]Quantitative acceptance criteria have been applied since 24-month time point for the stability programs. The time points before 24 months were tested with "Report".

[d]% Relative potency is reported as activity relative to the Reference Standard, which is assigned a relative potency of 100%.

TABLE 18

Stability Protocol for IL-22 Fc Fusion Protein Stability Studies

| Storage Temperature | Temperature Condition | Time Points (days/months) | | | | | | | | | | | |
| --- | --- | --- | --- | --- | --- | --- | --- | --- | --- | --- | --- | --- | --- |
| −20° C. | Intended storage condition | 0 | — | — | 91/3 | 183/6 | 274/9 | 365/12 | 548/18 | 730/24 | 913/30 | 1096/36 | 1461/48 | 1826/60[a] |
| 5° C. | Accelerated condition | 0 | 30/1 | 61/2 | 91/3 | 183/6 | — | — | — | — | — | — | — |

Note:

All analytical procedures listed in Table 17 are tested at each time point.

[a]Optional time point; 60 month time point will only be analyzed if 60-month shelf life is required in the further course of development.

Results

The results of the extended stability testing of IL-22 Fc fusion protein from Clinical Batch 2 and the Reference Standard Batch, conducted at −20° C. and 5° C. as described above, are presented in Table 19 and Table 20.

TABLE 19

Stability Data for IL-22 Fc Fusion Protein Clinical Batch 2

| Temp. (° C.) | Time (days/ months) | COC Clarity/ Opales- cence | Color | pH | Strength (mg/mL) | Imaged cIEF Acidic Region (area %) | Main Peak (area %) | Basic Region (area %) | SE-HPLC Sum of HMW Forms (area %) | Main Peak (area %) | Sum of LMW Forms (area %) |
|---|---|---|---|---|---|---|---|---|---|---|---|
| NA | T = 0/0 | ≤Ref I | ≤BY6 | 7.1 | 10.1 | 37.9 | 56.3 | 5.8 | 0.2 | 99.7 | 0.1 |
| −20° C. | 91/3 | ≤Ref I | ≤BY6 | 7.1 | 10.0 | 37.3 | 56.4 | 6.3 | 0.1 | 99.7 | 0.1 |
| −20° C. | 183/6 | ≤Ref I | ≤BY7 | 7.1 | 10.2 | 38.1 | 55.8 | 6.1 | 0.2 | 99.7 | 0.1 |
| −20° C. | 274/9 | ≤Ref I | ≤BY6 | 7.1 | 10.0 | 36.2 | 57.5 | 6.3 | 0.2 | 99.6 | 0.2 |
| −20° C. | 365/12 | ≤Ref I | ≤BY6 | 7.1 | 10.0 | 39.2 | 54.1 | 6.7 | 0.2 | 99.7 | 0.1 |
| −20° C. | 548/18 | ≤Ref I | ≤BY6 | 7.1 | 10.2 | 38.1 | 55.7 | 6.2 | 0.2 | 99.7 | 0.1 |
| −20° C. | 730/24 | ≤Ref I | ≤BY6 | 7.1 | 10.2 | 36.7 | 56.8 | 6.5 | 0.2 | 99.7 | 0.1 |
| −20° C. | 913/30 | ≤Ref I | ≤BY6 | 7.1 | 10.0 | 38.2 | 56.0 | 5.8 | 0.2 | 99.7 | 0.1 |
| −20° C. | 1096/36 | ≤Ref I | ≤BY6 | 7.0 | 10.0 | 38.7 | 54.7 | 6.6 | 0.1 | 99.8 | 0.1 |
| −20° C. | 1461/48 | ≤Ref I | ≤BY6 | 7.0 | 10.1 | 39.4 | 55.4 | 5.2 | 0.2 | 99.7 | 0.1 |
| 5° C. | 30/1 | ≤Ref I | ≤BY6 | 7.1 | 10.1 | 38.3 | 55.5 | 6.2 | 0.2 | 99.7 | 0.1 |
| 5° C. | 61/2 | ≤Ref I | ≤BY6 | 7.1 | 10.0 | 37.5 | 56.1 | 6.4 | 0.3 | 99.6 | 0.1 |
| 5° C. | 91/3 | ≤Ref I | ≤BY6 | 7.1 | 10.0 | 38.1 | 55.6 | 6.3 | 0.3 | 99.6 | 0.1 |
| 5° C. | 183/6 | ≤Ref I | ≤BY7 | 7.1 | 10.0 | 39.3 | 54.7 | 6.0 | 0.4 | 99.5 | 0.1 |

| Temperature (° C.) | Time (days/ months) | CE-SDS-NGS (non-reduced) Sum of Pre-Peaks (% CPA) | Main Peak (% CPA) | Sum of Post-Peaks (% CPA) | Potency by Binding Assay (% relative potency)[a] |
|---|---|---|---|---|---|
| NA | T = 0/0 | 2.9 | 96.9 | 0.2 | 71 |
| −20° C. | 91/3 | 2.9 | 97.0 | 0.1 | 72 |
| −20° C. | 183/6 | 2.9 | 97.0 | 0.1 | 73 |
| −20° C. | 274/9 | 2.9 | 97.0 | 0.1 | 68 |
| −20° C. | 365/12 | 3.0 | 97.0 | 0.1 | 69 |
| −20° C. | 548/18 | 2.9 | 97.0 | 0.1 | 70 |
| −20° C. | 730/24 | 3.0 | 97.0 | 0.1 | 70 |
| −20° C. | 913/30 | 2.9 | 97.0 | 0.1 | 70 |
| −20° C. | 1096/36 | 3.0 | 96.9 | 0.1 | 71 |
| −20° C. | 1461/48 | 3.0 | 96.9 | 0.1 | 72 |
| 5° C. | 30/1 | 2.9 | 96.9 | 0.2 | 73 |
| 5° C. | 61/2 | 2.9 | 96.9 | 0.2 | 75 |
| 5° C. | 91/3 | 2.9 | 96.9 | 0.2 | 73 |
| 5° C. | 183/6 | 3.0 | 96.8 | 0.2 | 71 |

CE-SDS-NGS = capillary electrophoresis sodium dodecyl sulfate non-gel sieving; cIEF = capillary isoelectric focusing; COC = color, opalescence, and clarity; CPA = corrected peak area; HMW = high molecular weight; NA = not applicable; SE-HPLC = size-exclusion high-performance liquid chromatography; LMW = low molecular weight; UV Spec Scan = ultraviolet-visible spectrophotometric scan.
[a]% Relative potency is reported as activity relative to the Reference Standard, which is assigned a relative potency of 100%.

TABLE 20

Stability Data for IL-22 Fc Fusion Protein Reference Standard Batch

| Temperature (° C.) | Time (days/ months) | Appearance and Clarity | Color | pH | Strength (mg/mL) | Imaged cIEF Acidic Region (area %) | Main Peak (area %) | Basic Region (area %) | SE-HPLC Sum of HMW Forms (area %) | Main Peak (area %) | Sum of LMW Forms (area %) |
|---|---|---|---|---|---|---|---|---|---|---|---|
| NA | T = 0/0 | CL, LIQ | ≤B7 | 7.1 | 10.3 | 42.4 | 52.5 | 5.1 | 0.5 | 99.4 | 0.1 |
| −20° C. | 30/1 | CL, LIQ | ≤B6 | 7.1 | 10.3 | 42.0 | 52.7 | 5.3 | 0.4 | 99.5 | 0.1 |
| −20° C. | 61/2 | CL, LIQ | ≤B7 | 7.1 | 10.4 | 41.0 | 53.2 | 5.8 | 0.4 | 99.5 | 0.2 |
| −20° C. | 91/3 | CL, LIQ | ≤B7 | 7.1 | 10.3 | 40.8 | 53.7 | 5.6 | 0.4 | 99.5 | 0.2 |
| −20° C. | 183/6 | CL, LIQ | ≤B6 | 7.1 | 10.7 | 40.8 | 53.8 | 5.5 | 0.4 | 99.5 | 0.1 |
| −20° C. | 365/12 | CL, LIQ | ≤B7 | 7.1 | 10.8 | 39.5 | 54.4 | 6.1 | 0.4 | 99.5 | 0.1 |
| −20° C. | 548/18 | CL, LIQ | ≤B7 | 7.1 | 10.6 | 41.7 | 53.0 | 5.3 | 0.4 | 99.5 | 0.2 |
| −20° C. | 730/24 | CL, LIQ | ≤B7 | 7.1 | 10.6 | 41.7 | 52.4 | 5.9 | 0.4 | 99.5 | 0.1 |

TABLE 20-continued

Stability Data for IL-22 Fc Fusion Protein Reference Standard Batch

| −20° C. | 913/30   | CL, LIQ | ≤B7 | 7.1 | 10.2 | 45.1 | 50.2 | 4.8 | 0.4 | 99.3 | 0.2 |
| −20° C. | 1096/36  | CL, LIQ | ≤B7 | 7.1 | 10.5 | 44.1 | 51.2 | 4.7 | 0.4 | 99.4 | 0.2 |
| −20° C. | 1461/48  | CL, LIQ | ≤B7 | 7.1 | 10.5 | 42.7 | 51.9 | 5.4 | 0.3 | 99.5 | 0.2 |
| −20° C. | 1825/60  | CL, LIQ | ≤B6 | 7.1 | 10.8 | 41.1 | 53.4 | 5.5 | 0.3 | 99.5 | 0.1 |
| 5° C.   | 30/1     | CL, LIQ | ≤B6 | 7.1 | 10.0 | 42.3 | 52.5 | 5.2 | 0.4 | 99.4 | 0.2 |
| 5° C.   | 61/2     | CL, LIQ | ≤B7 | 7.1 | 10.4 | 42.0 | 52.3 | 5.7 | 0.5 | 99.4 | 0.2 |
| 5° C.   | 91/3     | CL, LIQ | ≤B7 | 7.1 | 10.4 | 42.0 | 52.4 | 5.6 | 0.5 | 99.3 | 0.2 |
| 5° C.   | 183/6    | CL, LIQ | ≤B6 | 7.1 | 11.0 | 42.2 | 51.8 | 6.0 | 0.6 | 99.3 | 0.1 |

| | | CE-SDS-NGS (non-reduced) | | | Potency by |
| --- | --- | --- | --- | --- | --- |
| Temperature (° C.) | Time (days/months) | Sum of Pre-Peaks (% CPA) | Main Peak (% CPA) | Sum of Post-Peaks (% CPA) | Binding Assay (% relative potency)[a] |
| NA      | T = 0/0  | 3.0 | 96.6 | 0.4 | 108 |
| −20° C. | 30/1     | 2.9 | 96.8 | 0.3 | NR  |
| −20° C. | 61/2     | NR  | NR   | NR  | NR  |
| −20° C. | 91/3     | 3.0 | 96.7 | 0.3 | 104 |
| −20° C. | 183/6    | 3.2 | 96.3 | 0.4 | 112 |
| −20° C. | 365/12   | 3.2 | 96.6 | 0.3 | 91  |
| −20° C. | 548/18   | 3.2 | 96.4 | 0.4 | 101 |
| −20° C. | 730/24   | 2.8 | 96.9 | 0.3 | 97  |
| −20° C. | 913/30   | 3.4 | 96.4 | 0.3 | NR  |
| −20° C. | 1096/36  | 3.3 | 96.4 | 0.3 | 107 |
| −20° C. | 1461/48  | 3.1 | 96.7 | 0.2 | 93  |
| −20° C. | 1825/60  | 3.0 | 96.5 | 0.4 | 99  |
| 5° C.   | 30/1     | 3.0 | 96.7 | 0.3 | NR  |
| 5° C.   | 61/2     | NR  | NR   | NR  | NR  |
| 5° C.   | 91/3     | 3.0 | 96.6 | 0.4 | 105 |
| 5° C.   | 183/6    | 3.1 | 96.7 | 0.2 | 98  |

CE-SDS-NGS = capillary electrophoresis sodium dodecyl sulfate non-gel sieving; cIEF = capillary isoelectric focusing; CL = clear; CPA = corrected peak area; HMW = high molecular weight; LIQ = liquid; LMW = low molecular weight; NA = not applicable; NR = not required; SE-HPLC = size-exclusion high-performance liquid chromatography.
[a]% Relative potency is reported as activity relative to the Reference Standard, which is assigned a relative potency of 100%.

Shelf Life and Recommended Storage

The recommended storage condition for IL-22 Fc fusion protein is ≤−20° C. With storage at −20° C. for up to 48 months and 5° C. for up to 6 months, no significant changes in protein concentration, pH, color, clarity, potency, size-exclusion chromatography (SEC), imaged capillary isoelectric focusing (icIEF), and non-reduced (NR) capillary electrophoresis-sodium dodecyl sulfate (CE-SDS) were observed (Table 20). The stability testing results presented here demonstrate the IL-22 Fc fusion protein is stable over 48 months at −20° C. These data support a shelf life of 60 months or more at −20° C. Additionally, IL-22 Fc fusion protein may be stored up to one month at 5° C.

IL-22 Fc fusion protein was stored in a 50-cc bioprocess bag and freeze-thaw stability was monitored after three cycles of freezing at −20° C. and thawing at ambient temperature. The bioprocess bag was thawed at the 1, 2, and 3 month time points, such that the data at 3 months represents three freeze/thaw cycles. No significant changes in protein concentration, pH, color, clarity, potency, SEC, icIEF, and CE-SDS were observed after 3 cycles of freezing at −20° C. and thawing at ambient temperature. Therefore, IL-22 Fc fusion protein may be frozen at −20° C. and thawed for at least three cycles.

Extended Stability Testing of IL-22 Fc Fusion Protein Clinical Batch 1 and Reference Standard Batch The pharmaceutical composition of the IL-22 Fc fusion protein is a liquid formulation supplied in single-use 2 mL USP/Ph. Eur. Glass Type I vials containing 10 mg (nominal) of IL-22 Fc fusion protein. The pharmaceutical formulation of the invention is formulated as 10 mg of IL-22 Fc fusion protein in 10 mM sodium phosphate, 5 mM methionine, 240 mM sucrose, 0.02% (w/v) polysorbate 20, pH 7.1.

A pharmaceutical composition stability study was initiated with IL-22 Fc fusion protein Clinical Batch 1. Additionally, representative IL-22 Fc fusion protein pharmaceutical composition stability studies were initiated with Reference Standard Batch (Table 21). Stability was monitored at temperatures of 5° C. and 25° C. for both batches.

Long-term storage is tested at 5° C.±3° C., and accelerated stability studies were performed at 25° C.±2° C. (60% relative humidity [RH]±5% RH). In the following, the temperatures are indicated as 5° C. and 25° C., respectively.

Procedures and Acceptance Criteria

All samples were analyzed using the test procedures listed in Table 21. Representative stability was assessed at specified time intervals using the protocol provided in Table 22 and Table 23.

TABLE 21

Test Procedures to Assess IL-22 Fc Fusion Protein Pharmaceutical Formulation Stability

| Analytical Procedure | Acceptance Criteria for GMP Studies Performed at 5° C. |
| --- | --- |
| Color (Ph. Eur. Color Scale)[a] | Not more colored than BY5 |
| Clarity/Opalescence[b] | ≤Ref. III |
| Visible Particles | Practically free from particles |
| Subvisible Particles (light obscuration) | |
| Particles ≥10 μm per container | ≤6000 |
| Particles ≥25 μm per container | ≤600 |
| pH | 7.1 ± 0.3 |

TABLE 21-continued

Test Procedures to Assess IL-22 Fc Fusion Protein
Pharmaceutical Formulation Stability

| Analytical Procedure | Acceptance Criteria for GMP Studies Performed at 5° C. |
|---|---|
| Purity by SE-HPLC | |
| Main Peak (area %) | ≥95.0 |
| Sum of HMW Forms (area %) | ≤5.0[e] |
| Sum of LMW Forms (area %) | Report |
| Purity by CE-SDS-NGS | |
| Main Peak (non-reduced) (% CPA) | ≥85.0 |
| Sum of LMW Forms (Pre-Peaks) (non-reduced) (% CPA) | ≤15.0[e] |
| Sum of HMW Forms (Post-Peaks) (non-reduced) (% CPA) | Report |
| Purity by Imaged cIEF | |
| Main Peak (area %) | ≥40.8 |
| Acidic Region (area %) | ≤55.6[e] |
| Basic Region (area %) | ≤20.8[e] |
| Protein content by UV Spec Scan (mg/mL) | 10.0 ± 1.0 |
| Potency by Bioassay (% relative potency)[c] | 40-130 |
| Container closure integrity by Dye Leak Test[d] | No leakage detected |

Abbreviations: CE-SDS-NGS = capillary electrophoresis sodium dodecyl sulfate non-gel sieving; cIEF = capillary isoelectric focusing; CPA = corrected peak area; HMW = high molecular weight; LMW = low molecular weight; UV Spec Scan = ultraviolet-visible spectrophotometric scan.
[a]A spectral method was employed to assess color in stability studies for the Reference Standard Batch.
[b]CAC (color, appearance, and clarity) assay was used to assess appearance and clarity in stability studies for the Reference Standard Batch.
[c]% Relative potency is reported as activity relative to the reference standard, which is assigned a relative potency of 100%.
[d]Assays are not used in the stability studies for the Reference Standard Batch.
[e]Quantitative acceptance criteria have been applied since the 18-month time point for the stability programs. The time points before 18 months were tested with "Report."

TABLE 22

Stability Protocol for IL-22 Fc Fusion Protein Pharmaceutical
Formulation Stability Studies-Study Condition: 5° C.

| Analytical Procedure | Time Interval (days/months)[a] | | | | | | | | | | |
|---|---|---|---|---|---|---|---|---|---|---|---|
| | 0 | 30/1 | 91/3 | 183/6 | 274/9 | 365/12 | 548/18 | 730/24 | 913/30 | 1096/36 | 1278/42 |
| Color | X | X | X | X | X | X | X | X | X | X | X |
| Clarity/Opalescence | X | X | X | X | X | X | X | X | X | X | X |
| Visible Particles | X | NR | NR | X | NR | X | X | X | X | X | X |
| Subvisible Particles | X | NR | NR | X | NR | X | NR | X | NR | X | X |
| pH | X | X | X | X | X | X | X | X | X | X | X |
| Purity by SE-HPLC | X | X | X | X | X | X | X | X | X | X | X |
| Purity by CE-SDS-NGS | X | X | X | X | X | X | X | X | X | X | X |
| Purity by Imaged cIEF | X | X | X | X | X | X | X | X | X | X | X |
| Protein Content | X | X | X | X | X | X | X | X | X | X | X |
| Potency | X | X | X | X | X | X | X | X | X | X | X |
| Container Closure Integrity | NR | NR | NR | NR | NR | X | NR | X | NR | X | X |

Note:
Study to be conducted on vials stored in the inverted orientation.
Abbreviations: CE-SDS-NGS = capillary electrophoresis sodium dodecyl sulfate non-gel sieving; cIEF = capillary isoelectric focusing; NR = not required; SE-HPLC = size-exclusion high-performance liquid chromatography.
[a]Testing is performed as long as samples meet the specifications.

TABLE 23

Stability Protocol for IL-22 Fc Fusion Protein Pharmaceutical
Formulation Stability Studies-Study Condition: 25° C.

| Analytical Procedure | Time Interval (days/months)[a] | | | | |
|---|---|---|---|---|---|
| | 0 | 30/1 | 61/2 | 91/3 | 183/6 |
| Color | X | X | X | X | X |
| Clarity/Opalescence | X | X | X | X | X |
| pH | X | X | X | X | X |
| Purity by SE-HPLC | X | X | X | X | X |
| Purity by CE-SDS-NGS | X | X | X | X | X |
| Purity by Imaged cIEF | X | X | X | X | X |
| Protein Content | X | X | X | X | X |
| Potency | X | X | X | X | X |

Note:
Study to be conducted on vials stored in the inverted orientation.
Abbreviations: CE-SDS-NGS = capillary electrophoresis sodium dodecyl sulfate non-gel sieving; cIEF = capillary isoelectric focusing; SE-HPLC = size-exclusion high-performance liquid chromatography.
[a]Testing is performed as long as samples meet the specifications.

Results

The results of the extended stability testing of IL-22 Fc fusion protein from Clinical Batch 1 and the Reference Standard Batch, conducted at −20° C. and 5° C. as described above, are presented in Table 24 and Table 25.

Primary IL-22 Fc fusion protein pharmaceutical composition stability data showed similar trends to those observed in the supportive stability study. The stability data support an expiration date of 42 months (36 months real-time data plus 6 months provisional dating) at 5° C. for the IL-22 Fc fusion protein pharmaceutical composition.

The results of the supportive stability studies demonstrated a 0.7 decrease in percent main peak by SE-HPLC observed at 36 months with primarily an increase in dimer concentration. A decrease of 5 in percent main peak was observed by iCIEF with primarily an increase in acidic peaks. No change in IL-22 Fc fusion protein pharmaceutical composition was observed for up to 36 months of storage at 5° C. by the other methods. No change in the IL-22 Fc fusion protein pharmaceutical composition was observed for up to one month of storage at 25° C. Changes in IL-22 Fc fusion protein pharmaceutical composition were observed after storage at 25° C. for six months. Imaged cIEF demonstrated a decrease of 17.6 in percent main peak with primarily an increase of 18.3 in percent acidic peaks. A decrease of 1.3 was observed in percent main peak by SE-HPLC with primarily an increase of 1.2 in percent higher molecular weight species (HMWS). A decrease of 2.7 was observed in percent main peak by non-reduced CE-SDS with primarily an increase of 2.1 percent corrected peak area (% CPA) in sum of pre-peaks. A loss of 29% relative potency was observed after storage at 25° C. for 6 months while no change in potency was observed after storage at 25° C. for three months. No changes were observed in the remaining assays at 25° C. for six months.

TABLE 24

Stability Data for IL-22 Fc Fusion Protein Pharmaceutical Composition Clinical Batch 1

| Temperature (° C.) | Time (days/ months) | Color | Clarity/ Opales- cence | pH | Protein Concen- tration (mg/mL) | Imaged cIEF Acidic Region (area %) | Imaged cIEF Main Peak (area %) | Imaged cIEF Basic Region (area %) | SE-HPLC HMW Forms (area %) | SE-HPLC Main Peak (area %) |
|---|---|---|---|---|---|---|---|---|---|---|
| NA | T = 0/0 | ≤BY6 | ≤Ref I | 7.1 | 9.9 | 38.5 | 55.3 | 6.2 | 0.4 | 99.5 |
| 5° C. | 91/3 | ≤BY6 | ≤Ref I | NR | 9.9 | 38.7 | 55.1 | 6.2 | 0.5 | 99.4 |
| 5° C. | 183/6 | ≤BY6 | ≤Ref I | 7.1 | 10.0 | 39.4 | 54.7 | 5.9 | 0.5 | 99.3 |
| 5° C. | 274/9 | ≤BY7 | ≤Ref I | NR | 9.9 | 40.7 | 53.5 | 5.8 | 0.5 | 99.3 |
| 5° C. | 365/12 | ≤BY6 | ≤Ref I | 7.1 | 9.9 | 40.5 | 53.5 | 6.0 | 0.6 | 99.3 |
| 5° C. | 548/18 | ≤BY7 | ≤Ref I | 7.1 | 10.0 | 41.1 | 52.9 | 6.0 | 0.6 | 99.3 |
| 5° C. | 730/24 | ≤BY7 | ≤Ref I | 7.1 | 10.0 | 42.0 | 52.0 | 6.0 | 0.6 | 99.2 |
| 5° C. | 913/30 | ≤BY7 | ≤Ref I | 7.0 | 10.0 | 44.2 | 50.3 | 5.5 | 0.7 | 99.2 |
| 5° C. | 1096/36 | ≤BY7 | ≤Ref I | 7.0 | 10.0 | 42.5 | 51.2 | 6.3 | 0.6 | 99.3 |
| 5° C. | 1278/42 | ≤BY6 | ≤Ref I | 7.1 | 9.9 | 43.7 | 50.9 | 5.4 | 0.7 | 99.1 |
| 5° C. | 1461/48 | ≤BY7 | ≤Ref I | 7.0 | 10.0 | 47.9 | 47.3 | 4.8 | 0.8 | 99.1 |
| 25° C. | 30/1 | ≤BY6 | ≤Ref I | 7.1 | 9.9 | 42.1 | 52.0 | 5.9 | 0.5 | 99.3 |
| 25° C. | 61/2 | ≤BY7 | ≤Ref I | 7.1 | 9.9 | 45.3 | 49.0 | 5.7 | 0.6 | 99.3 |
| 25° C. | 91/3 | ≤BY7 | ≤Ref I | 7.1 | 9.9 | 50.1 | 44.8 | 5.1 | 0.8 | 99.0 |
| 25° C. | 183/6 | ≤BY6 | ≤Ref I | 7.1 | 9.9 | 58.2 | 37.7 | 4.1 | 1.3 | 98.3 |

| Temperature (° C.) | Time (days/ months) | CE-SDS-NGS (Non-Reduced) Sum of LMW Forms (Pre-Peaks) (% CPA) | CE-SDS-NGS (Non-Reduced) Main Peak (% CPA) | Potency (% relative potency) | Visible particles | Subvisible Particles (particles per container) 10 μm | Subvisible Particles (particles per container) 25 μm | Container Closure Integrity |
|---|---|---|---|---|---|---|---|---|
| NA | T = 0/0 | 3.0 | 96.7 | 73 | PFFP | 2 | 0 | NR |
| 5° C. | 91/3 | 3.0 | 96.7 | 73 | NR | NR | NR | NR |
| 5° C. | 183/6 | 3.0 | 96.7 | 64 | PFFP | 18 | 0 | NR |
| 5° C. | 274/9 | 3.1 | 96.5 | 63 | NR | NR | NR | NR |
| 5° C. | 365/12 | 3.2 | 96.4 | 67 | PFFP | 14 | 0 | NLD |
| 5° C. | 548/18 | 3.2 | 96.4 | 64 | PFFP | NR | NR | NR |
| 5° C. | 730/24 | 3.3 | 96.3 | 66 | PFFP | 51 | 1 | NLD |
| 5° C. | 913/30 | 3.2 | 96.3 | 65 | PFFP | NR | NR | NR |
| 5° C. | 1096/36 | 3.5 | 96.1 | 67 | PFFP | 63 | 1 | NLD |
| 5° C. | 1278/42 | 3.5 | 96.1 | 59 | PFFP | 7 | 0 | NLD |
| 5° C. | 1461/48 | 3.6 | 95.9 | 65 | PFFP | 7 | 0 | NLD |
| 25° C. | 30/1 | 3.4 | 96.3 | 68 | NR | NR | NR | NR |
| 25° C. | 61/2 | 3.7 | 96.0 | 60 | NR | NR | NR | NR |
| 25° C. | 91/3 | 4.0 | 95.6 | 57 | NR | NR | NR | NR |
| 25° C. | 183/6 | 5.1 | 94.2 | 47 | NR | NR | NR | NR |

Abbreviations: CE-SDS-NGS = capillary electrophoresis-sodium dodecyl sulfate-non-gel sieving; cIEF = capillary isoelectric focusing; HC = heavy chain; HMW = high-molecular-weight; LC = light chain; LMW = low-molecular-weight; NR = not reported; NLD = no leakage detected; PFFP = practically free from particles; SE-HPLC = size-exclusion high-performance liquid chromatography; UV = ultraviolet-visible spectrophotometry; % CPA = percentage corrected peak area.

TABLE 25

Stability Data for IL-22 Fc Fusion Protein Pharmaceutical Composition Reference Standard Batch

| Temperature (° C.) | Time (days/months) | Color | Appearance and Clarity | pH | Protein Content (mg/mL) | Imaged cIEF Acidic Region (area %) | Imaged cIEF Main Peak (area %) | Imaged cIEF Basic Region (area %) | SE-HPLC Sum of HMW Forms (area %) | SE-HPLC Main Peak (area %) | SE-HPLC Sum of LMW Forms (area %) |
|---|---|---|---|---|---|---|---|---|---|---|---|
| N/A | T = 0/0 | ≤B7 | CL, LIQ | 7.1 | 10.3 | 42.4 | 52.5 | 5.1 | 0.5 | 99.4 | 0.1 |
| 5 | 30/1 | ≤B6 | CL, LIQ | 7.1 | 10.3 | 42.5 | 52.1 | 5.4 | 0.5 | 99.3 | 0.2 |
| 5 | 61/2 | ≤B7 | CL, LIQ | 7.1 | 10.2 | 42.6 | 51.7 | 5.7 | 0.6 | 99.2 | 0.2 |
| 5 | 91/3 | ≤B7 | CL, LIQ | 7.1 | 10.5 | 41.7 | 52.7 | 5.6 | 0.6 | 99.3 | 0.2 |
| 5 | 183/6 | ≤B7 | CL, LIQ | 7.1 | 10.9 | 41.7 | 52.8 | 5.5 | 0.6 | 99.3 | 0.1 |
| 5 | 365/12 | ≤B7 | CL, LIQ | 7.1 | 10.6 | 43.0 | 51.3 | 5.7 | 0.7 | 99.1 | 0.2 |
| 5 | 548/18 | ≤B7 | CL, LIQ | 7.1 | 10.4 | 43.7 | 51.2 | 5.1 | 0.8 | 99.0 | 0.2 |
| 5 | 730/24 | ≤B7 | CL, LIQ | 7.1 | 10.4 | 44.2 | 50.1 | 5.8 | 0.9 | 98.9 | 0.3 |
| 5 | 913/30 | ≤B7 | CL, LIQ | 7.1 | 10.5 | 48.0 | 47.3 | 4.7 | 0.9 | 98.8 | 0.2 |
| 5 | 1096/36 | ≤B7 | CL, LIQ | 7.1 | 10.4 | 48.3 | 47.1 | 4.6 | 1.0 | 98.7 | 0.3 |
| 5 | 1278/42 | ≤B7 | CL, LIQ | 7.1 | 10.6 | 48.4 | 46.9 | 4.7 | 0.8 | 99.0 | 0.2 |
| 5 | 1460/48 | ≤B7 | CL, LIQ | 7.1 | 10.5 | 48.9 | 46.3 | 4.8 | 0.9 | 98.9 | 0.2 |
| 25 | 30/1 | ≤B6 | CL, LIQ | 7.1 | 10.0 | 45.1 | 49.6 | 5.3 | 0.7 | 99.1 | 0.2 |
| 25 | 61/2 | ≤B7 | CL, LIQ | 7.1 | 10.3 | 48.6 | 46.1 | 5.3 | 0.7 | 99.1 | 0.2 |
| 25 | 91/3 | ≤B7 | CL, LIQ | 7.1 | 10.1 | 52.0 | 43.1 | 4.9 | 0.9 | 98.9 | 0.2 |
| 25 | 183/6 | ≤B7 | CL, LIQ | 7.1 | 10.7 | 60.7 | 34.9 | 4.4 | 1.7 | 98.1 | 0.3 |

| Temperature (° C.) | Time (days/months) | CE-SDS-NGS (non-reduced) Sum of Pre-Peaks (% CPA) | CE-SDS-NGS (non-reduced) Main Peak (% CPA) | CE-SDS-NGS (non-reduced) Sum of Post-Peaks (% CPA) | Potency (% relative potency) | Visible Particles | Subvisible Particles (particles/mL) 10 μm | Subvisible Particles (particles/mL) 25 μm |
|---|---|---|---|---|---|---|---|---|
| NA | T = 0/0 | 3.0 | 96.6 | 0.4 | 101 | PFFP | 40 | 2 |
| 5 | 30/1 | 3.0 | 96.6 | 0.5 | NR | PFFP | 39 | 2 |
| 5 | 61/2 | NR | NR | NR | NR | PFFP | NR | NR |
| 5 | 91/3 | 3.1 | 96.5 | 0.4 | 104 | PFFP | 39 | 4 |
| 5 | 183/6 | 3.2 | 96.3 | 0.4 | 100 | PFFP | 50 | 2 |
| 5 | 180/12 | 3.4 | 96.2 | 0.5 | 86 | PFFP | 21 | 1 |
| 5 | 548/18 | 3.5 | 95.9 | 0.6 | 93 | PFFP | 6 | 1 |
| 5 | 730/24 | 3.0 | 96.3 | 0.7 | 83 | PFFP | 8 | 1 |
| 5 | 913/30 | 3.8 | 95.6 | 0.6 | NR | PFFP | 13 | 1 |
| 5 | 1096/36 | 4.6 | 94.8 | 0.6 | 99 | PFFP | 6 | 0 |
| 5 | 1278/42 | 3.7 | 95.7 | 0.6 | 87 | PFFP | 4 | 0 |
| 5 | 1460/48 | 3.8 | 95.5 | 0.8 | 91 | PFFP | 2 | 0 |
| 25 | 30/1 | 3.2 | 96.3 | 0.4 | NR | PFFP | 40 | 2 |
| 25 | 61/2 | NR | NR | NR | NR | PFFP | NR | NR |
| 25 | 91/3 | 3.9 | 95.3 | 0.8 | 95 | PFFP | 29 | 2 |
| 25 | 183/6 | 5.1 | 93.9 | 1.0 | 72 | PFFP | 76 | 21 |

Abbreviations: CE-SDS-NGS = capillary electrophoresis sodium dodecyl sulfate non-gel sieving; cIEF = capillary isoelectric focusing; CL = clear; CPA = corrected peak area; HMW = high molecular weight; LIQ = liquid; LMW = low molecular weight; NR = not required; PFFP = practically free from particles; SE-HPLC = size-exclusion high-performance liquid chromatography.

Comparative Stress Stability Testing of IL-22 Fc Fusion Protein Clinical Batch 3 and Reference Standard Batch Comparability between IL-22 Fc fusion protein Reference Standard Batch pharmaceutical composition and clinical pharmaceutical composition was established using IL-22 Fc fusion protein Reference Standard Batch and Clinical Batch 3 (Table 26). Material from both batches was manually filled into 2-mL glass vials to a fill volume of 1 mL. These materials were then assessed under stress conditions of 40° C.

TABLE 26

Comparative Stress Stability Data for IL-22 Fc Fusion Protein Pharmaceutical Composition Reference Standard Batch and Clinical Batch 3

| Temp. (40° C.) | Time (days) | Color | Appearance and Clarity | pH | Protein Content (mg/mL) | Imaged cIEF Acidic Region (area %) | Imaged cIEF Main Peak (area %) | Imaged cIEF Basic Region (area %) | SE-HPLC Sum of HMW Forms (area %) | SE-HPLC Main Peak (area %) | SE-HPLC Sum of LMW Forms (area %) |
|---|---|---|---|---|---|---|---|---|---|---|---|
| Reference Standard Batch | 0 | ≤B7 | CL, LIQ | 7.1 | 10.3 | 42.6 | 52.2 | 5.2 | 0.7 | 99.2 | 0.1 |
| | 5 | ≤B6 | CL, LIQ | 7.1 | 10.9 | 45.9 | 48.9 | 5.2 | 1.3 | 98.5 | 0.2 |
| | 10 | ≤B7 | CL, LIQ | 7.1 | 10.9 | 52.2 | 42.5 | 5.3 | 2.6 | 97.1 | 0.3 |
| | 14 | ≤B6 | CL, LIQ | 7.1 | 10.9 | 58.3 | 37.1 | 4.5 | 4.4 | 95.3 | 0.3 |

TABLE 26-continued

Comparative Stress Stability Data for IL-22 Fc Fusion Protein Pharmaceutical
Composition Reference Standard Batch and Clinical Batch 3

| Clinical Batch 3 | 0 | ≤B7 | CL, LIQ | 7.1 | 10.6 | 36.9 | 56.7 | 6.5 | 0.3 | 99.6 | 0.1 |
|---|---|---|---|---|---|---|---|---|---|---|---|
| | 5 | ≤B7 | CL, LIQ | 7.1 | 10.2 | 41.7 | 52.2 | 6.1 | 0.7 | 99.2 | 0.1 |
| | 10 | ≤B7 | CL, LIQ | 7.1 | 10.3 | 47.9 | 46.3 | 5.7 | 1.3 | 98.5 | 0.2 |
| | 14 | ≤B7 | CL, LIQ | 7.1 | 10.3 | 54.6 | 40.7 | 4.7 | 2.3 | 97.5 | 0.3 |

| Temperature (40° C.) | Time (days) | CE-SDS-NGS (non-reduced) ||| Potency (% relative potency) | Visible Particles |
|---|---|---|---|---|---|---|
| | | Sum of Pre-Peaks (% CPA) | Main Peak (% CPA) | Sum of Post-Peaks (% CPA) | | |
| Reference Standard Batch | 0 | 3.2 | 96.3 | 0.5 | 104 | PFFP |
| | 5 | 3.8 | 95.7 | 0.6 | 80 | PFFP |
| | 10 | 4.3 | 94.8 | 0.9 | 84 | PFFP |
| | 14 | 4.7 | 94.3 | 1.0 | 71 | PFFP |
| Clinical Batch 3 | 0 | 2.9 | 96.9 | 0.2 | 85 | PFFP |
| | 5 | 3.4 | 96.2 | 0.3 | 80 | PFFP |
| | 10 | 3.9 | 95.6 | 0.5 | 65 | PFFP |
| | 14 | 4.3 | 94.9 | 0.8 | 57 | PFFP |

Abbreviations: CE-SDS-NGS = capillary electrophoresis sodium dodecyl sulfate non-gel sieving; cIEF = capillary isoelectric focusing; CL = clear; CPA = corrected peak area; HMW = high molecular weight; LIQ = liquid; LMW = low molecular weight; NR = not required; PFFP = practically free from particles; SE-HPLC = size-exclusion high-performance liquid chromatography.

Results

The results of this study demonstrate the degradation rates of the two materials are comparable based on a decrease of 2-4 in percent main peak by size-exclusion high-performance liquid chromatography (SE-HPLC), a decrease of 15-16 in percent main peak by imaged capillary isoelectric focusing (cIEF) a decrease of 2 in percent main peak by capillary electrophoresis sodium dodecyl sulfate-non-gel sieving (CE-SDS-NGS), and a decrease of 28-33 in % relative potency after storage at 40° C. for two weeks. In addition, the chromatographic profiles are comparable, and no new peaks were observed in the clinical batch when compared to the development batch after storage at 40° C. for two weeks. IL-22 Fc fusion protein Reference Standard and clinical pharmaceutical composition batches have comparable stability based on the data presented. Therefore, the stability data from the Reference Standard Batch was used to assign shelf life for the clinical pharmaceutical composition.

Shelf Life and Recommended Storage

The recommended storage condition for the IL-22 Fc fusion protein pharmaceutical composition is 5° C.±3° C., protected from light. The shelf life will be extended based on available stability data. IL-22 Fc fusion protein pharmaceutical composition is stable over 36 months at 5° C.±3° C. Based on the available data the initial shelf life for IL-22 Fc fusion protein pharmaceutical composition is currently set at 42 months if stored at 5° C.±3° C., protected from light.

Results from Validation of the Analytical Procedures

Table 27 shows the results from validation of the analytical procedures.

TABLE 27

Validation of the Analytical Procedures

| Analytical Procedure | Validation Parameters and Results | |
|---|---|---|
| Color | Analytical procedure is performed as recommended in Ph. Eur./USP, no validation | |
| Clarity/Opalescence | Analytical procedure is performed as recommended in Ph. Eur., no validation | |
| pH | Analytical procedure is performed as recommended in Ph. Eur./USP, no validation | |
| Osmolality | Analytical procedure is performed as recommended in Ph. Eur./USP, no validation | |
| Content of Polysorbate 20 by HPLC-ELSD | Specificity is shown. | |
| | Accuracy: recovery: | 109%-119% |
| | Linearity: | R = 1.00 |
| | Repeatability: | RSD = 2% |
| | Range: | 0.1-0.3 mg/mL |
| Content of Methionine | Specificity is shown | |
| | Accuracy: recovery | 95%-105% |
| | Linearity | R = 1.00 |
| | Repeatability: | RSD ≤ 1% |
| | Range: | 2.5-7.5 mM |
| Quantitation of Sialic Acid by RP-HPLC | Specificity is shown | |
| | Accuracy: | 96.5%-104.6% |
| | Linearity: | R = 1.00 |
| | Repeatability | RSD ≤ 3.7% |
| | Intermediate Precision: | RSD = 4.8% |
| | Range | 5-50 µg/mL |

TABLE 27-continued

Validation of the Analytical Procedures

| Analytical Procedure | Validation Parameters and Results | |
|---|---|---|
| Identity of IL-22 Fc fusion protein by MALDI-TOF PMF | Specificity and robustness are shown | |
| Purity by SE-HPLC | Specificity is shown. Main Peak | |
| | Accuracy: | |
| | Protein Load: | 99.6%-106.5% |
| | Admixture: | 100% |
| | Linearity: | R = 1.00 |
| | Repeatability: | RSD ≤ 0.2% |
| | Sum of HMW Forms | |
| | Accuracy: | |
| | Protein Load: | 99.8%-114.4% |
| | Admixture: | 99-100% |
| | Linearity: | R = 1.00 |
| | Repeatability: | RSD ≤ 3.8% |
| | Range (protein concentration): | 50%-150% |
| Purity by Non-Reduced CE-SDS-NGS | Specificity is shown. Main Peak | |
| | Accuracy: recovery: | 100% |
| | Linearity: | R = 1.00 |
| | Repeatability: | |
| | Migration Time: | RSD = 0.1% |
| | % CPA: | RSD ≤ 0.04% |
| | Range (protein concentration): | 50%-150% |
| Purity by ICIEF | Specificity is shown. Main Peak | |
| | Accuracy: recovery: | 100.0%-101.8% |
| | Linearity: | R = 1.00 |
| | Repeatability: | RSD ≤ 1.8% |
| | Acidic Region | |
| | Accuracy: recovery: | 99.2%-100.1% |
| | Linearity: | R = 1.00 |
| | Repeatability: | RSD ≤ 0.6% |
| | Basic Region | |
| | Accuracy: recovery: | 94.2%-114.6% |
| | Linearity: | R = 1.00 |
| | Repeatability: | RSD ≤ 2.3% |
| | Range (protein concentration): | 50%-150% |
| Bioburden | Analytical procedure is performed as recommended in Ph. Eur./USP, with method suitability test criteria being satisfied. | |
| Bacterial Endotoxins | Analytical procedure is performed as recommended in Ph. Eur./USP with method suitability test criteria being satisfied. As supplemental testing, endotoxin recovery studies were performed on drug substance and drug product. No masking effect was observed. | |
| Potency by Binding Assay | Accuracy: | 101%-107% |
| | Repeatability: | RSD ≤ 2% |
| | Linearity: | R = 1.00 |
| | Range: | 10%-150% |
| Protein Concentration by UV | This method has been generically validated for multiproduct use and is suitable for testing IL-22 Fc fusion protein | |
| Host Cell Protein Content | Specificity is shown. | |
| | Accuracy: recovery: | 102%-127% |
| | Repeatability (RSD) | 4%-5% (intra-assay); 3%-5% (inter-assay) |
| | QL: | 3.82 ng/mL |
| | DL: | 1.26 ng/mL |
| | Range: | 5-320 ng/mL |

TABLE 27-continued

Validation of the Analytical Procedures

| Analytical Procedure | Validation Parameters and Results | |
|---|---|---|
| DNA Content | Specificity is shown. | |
| | Accuracy: recovery: | 98%-143% |
| | Linearity: | $R^2 > 0.98$ |
| | Repeatability (RSD): | <25% (intra-assay); <27% (inter-assay) |
| | QL: | 1 pg/mL |
| | DL: | ND |
| | Range: | 1-10,000 pg/mL |
| Protein A | Specificity is shown. | |
| | Accuracy: recovery: | 93%-115% |
| | Repeatability (RSD) | 1%-7% (intra-assay) |
| | QL: | 0.5 ng/mL |
| | DL: | ND |
| | Range: | 0.5-16 ng/mL |
| Rodent Parvovirus PCR | Specificity is shown. | |
| | DL: | |
| | MMV | 1 TCID$_{50}$/mL |
| Mycoplasma Detection Cultural Method and Indicator Cell/DNAF Method | Specificity is shown. | |
| | Cultural Method DL: | |
| | M. orale | 10 CFU/mL |
| | M. hyorhinis | 10 CFU/mL |
| | DNAF/Indicator Cell Method DL: | |
| | M. orale | 100 MPN/mL |
| | M. hyorhinis | 100 MPN/mL |
| Leptospira (testing of PHCCF) | Specificity is shown. | |
| | DL: | |
| | L. licerasiae | 7 cells/mL |
| General Viral Screening | Specificity is shown. | |
| | DL: | |
| | EMCV | 10 TCID$_{50}$/mL |
| | PI-2 | 20 TCID$_{50}$/mL |
| 324K Assay for Rodent Parvoviruses | Specificity is shown. | |
| | DL: | |
| | MMV | 1000 TCID$_{50}$/mL |

Abbreviations: CE-SDS-NGS = capillary electrophoresis sodium dodecyl sulfate-non-gel sieving; CFU = colony forming unit; CPA = corrected peak area; DL = detection limit; DNAF = DNA-binding fluorochrome; EMCV = encephalomyocarditis virus; HMW = high molecular weight; HPLC-ELSD = high-performance liquid chromatography evaporative light scattering detection; ICIEF = imaged capillary electrophoresis isoelectric focusing; MALDI-TOF PMF = matrix-assisted laser desorption/ionization time of flight peptide mass fingerprinting; MMV = murine minute virus; MPN = most probable number; ND = not detected; PCR = polymerase chain reaction; PHCCF = preharvest cell culture fluid; PI-2 = Parainfluenza virus type 2; QL = quantitation limit; R = correlation coefficient; RP-HPLC = reverse-phase high-performance liquid chromatography; RSD = relative standard deviation; SE-HPLC = size-exclusion high-performance liquid chromatography; TCID$_{50}$ = median tissue culture infective dose; UV = ultraviolet; Ph. Eur. = European Pharmacopoeia; USP = U.S. Pharmacopoeia.

OTHER EMBODIMENTS

Some embodiments of the technology described herein can be defined according to any of the following numbered embodiments:

1. A pharmaceutical composition comprising an interleukin (IL)-22 Fc fusion protein and a carrier, wherein the pharmaceutical composition has a shelf life of at least 36 months when stored at 5° C.±3° C. and protected from light, and wherein the IL-22 Fc fusion protein comprises an IL-22 polypeptide linked to an Fc region by a linker.
2. The pharmaceutical composition of embodiment 1, wherein the pharmaceutical composition has a shelf life of at least 42 months when stored at 5° C.±3° C. and protected from light.
3. The pharmaceutical composition of embodiment 1 or 2, wherein the concentration of the IL-22 Fc fusion protein is about 0.5 mg/mL to about 20 mg/mL.
4. The pharmaceutical composition of embodiment 3, wherein the concentration of the IL-22 Fc fusion protein is about 0.5 mg/mL to about 5 mg/mL.
5. The pharmaceutical composition of embodiment 4, wherein the concentration of the IL-22 Fc fusion protein is about 1 mg/mL.
6. The pharmaceutical composition of embodiment 3, wherein the concentration of the IL-22 Fc fusion protein is about 8 mg/mL to about 12 mg/mL.
7. The pharmaceutical composition of embodiment 6, wherein the concentration of the IL-22 Fc fusion protein is about 10 mg/mL.
8. The pharmaceutical composition of any one of embodiments 1-7, further comprising a stabilizer.
9. The pharmaceutical composition of embodiment 8, wherein the stabilizer is an amino acid, thiosorbitol, ascorbic acid, monothioglycerol, a cyclodextrin, Trolox (6-hydroxy-2,5,7,8-tetramethylchroman-2-carboxylic acid), pyridoxine, mannitol, a metal chelator, or a combination thereof.
10. The pharmaceutical composition of embodiment 9, wherein the stabilizer is an amino acid.
11. The pharmaceutical composition of embodiment 9 or 10, wherein the amino acid is methionine, cysteine, tryptophan, or a combination thereof.
12. The pharmaceutical composition of embodiment 11, wherein the amino acid is methionine.

13. The pharmaceutical composition of any one of embodiments 8-12, wherein the concentration of the stabilizer is about 1 mM to about 10 mM.
14. The pharmaceutical composition of embodiment 13, wherein the concentration of the stabilizer is about 2 mM to about 8 mM.
15. The pharmaceutical composition of embodiment 14, wherein the concentration of the stabilizer is about 5 mM.
16. The pharmaceutical composition of any one of embodiments 1-15, wherein the oxidation of methionine at position M25 or M139 of SEQ ID NO:4 is less than 10% as assessed by an AAPH stress test.
17. The pharmaceutical composition of embodiment 16, wherein the oxidation of methionine at position M25 of SEQ ID NO:4 is less than 5%, less than 3%, or less than 2%.
18. The pharmaceutical composition of embodiment 16 or 17, wherein the oxidation of methionine at position M139 of SEQ ID NO:4 is less than 7%, less than 6%, or less than 5%.
19. The pharmaceutical composition of any one of embodiments 1-18, further comprising a surfactant.
20. The pharmaceutical composition of embodiment 19, wherein the surfactant is a nonionic surfactant.
21. The pharmaceutical composition of embodiment 20, wherein the nonionic surfactant is a polysorbate, a poloxamer, a polyoxyethelene alkyl ether, an alkyl phenyl polyoxyethylene ether, or a combination thereof.
22. The pharmaceutical composition of embodiment 21, wherein the nonionic surfactant is a polysorbate.
23. The pharmaceutical composition of embodiment 22, wherein the polysorbate is polysorbate 20 or polysorbate 80.
24. The pharmaceutical composition of embodiment 23, wherein the polysorbate is polysorbate 20.
25. The pharmaceutical composition of embodiment 21, wherein the nonionic surfactant is a poloxamer.
26. The pharmaceutical composition of embodiment 25, wherein the nonionic surfactant is a poloxamer 188.
27. The pharmaceutical composition of any one of embodiments 19-26, wherein the concentration of the surfactant is about 0.001% (w/v) to about 0.1% (w/v).
28. The pharmaceutical composition of embodiment 27, wherein the concentration of the surfactant is about 0.01% (w/v) to about 0.05% (w/v).
29. The pharmaceutical composition of embodiment 27, wherein the concentration of the surfactant is about 0.01% (w/v) to about 0.07% (w/v).
30. The pharmaceutical composition of embodiment 28 or 29, wherein the concentration of the surfactant is about 0.02% (w/v).
31. The pharmaceutical composition of any one of embodiments 1-30, further comprising a buffering agent.
32. The pharmaceutical composition of embodiment 31, wherein the buffering agent is a phosphate, a succinate, an acetate, histidine, or a combination thereof.
33. The pharmaceutical composition of embodiment 32, wherein the buffering agent is a phosphate.
34. The pharmaceutical composition of embodiment 33, wherein the phosphate is sodium phosphate monobasic, sodium phosphate dibasic, sodium phosphate tribasic, potassium phosphate monobasic, potassium phosphate dibasic, potassium phosphate tribasic, or a mixture thereof.
35. The pharmaceutical composition of embodiment 34, wherein the phosphate is sodium phosphate monobasic.
36. The pharmaceutical composition of embodiment 34, wherein the phosphate is sodium phosphate dibasic.
37. The pharmaceutical composition of embodiment 34, wherein the phosphate is a mixture of sodium phosphate monobasic and sodium phosphate dibasic.
38. The pharmaceutical composition of any one of embodiments 31-37, wherein the concentration of the buffering agent is about 5 mM to about 20 mM.
39. The pharmaceutical composition of embodiment 38, wherein the concentration of the buffering agent is about 8 mM to about 12 mM.
40. The pharmaceutical composition of embodiment 39, wherein the concentration of the buffering agent is about 10 mM.
41. The pharmaceutical composition of any one of embodiments 1-40, further comprising a tonicity agent.
42. The pharmaceutical composition of embodiment 41, wherein the tonicity agent is a sugar, an amino acid, or a salt.
43. The pharmaceutical composition of embodiment 42, wherein the tonicity agent is a sugar.
44. The pharmaceutical composition of embodiment 43, wherein the sugar is sucrose, glucose, glycerol, or trehalose.
45. The pharmaceutical composition of embodiment 44, wherein the sugar is sucrose.
46. The pharmaceutical composition of embodiment 42, wherein the tonicity agent is a salt.
47. The pharmaceutical composition of embodiment 46, wherein the salt is sodium chloride or potassium chloride.
48. The pharmaceutical composition of any one of embodiments 41-47, wherein the concentration of the tonicity agent is about 100 mM to about 500 mM.
49. The pharmaceutical composition of embodiment 48, wherein the concentration of the tonicity agent is about 200 mM to about 300 mM.
50. The pharmaceutical composition of embodiment 49, wherein the concentration of the tonicity agent is about 240 mM.
51. The pharmaceutical composition of any one of embodiments 1-50, wherein the pharmaceutical composition has a pH of about 6.6 to about 8.
52. The pharmaceutical composition of embodiment 51, wherein the pharmaceutical composition has a pH of about 6.8 to about 7.4.
53. The pharmaceutical composition of embodiment 52, wherein the pharmaceutical composition has a pH of about 7.1.
54. A pharmaceutical composition comprising an IL-22 Fc fusion protein and a carrier, the IL-22 Fc fusion protein comprising an IL-22 polypeptide linked to an Fc region by a linker, wherein the pharmaceutical composition comprises about 1 mg/mL to about 10 mg/mL IL-22 Fc fusion protein, about 5 mM methionine, and about 0.02% (w/v) polysorbate 20, pH 7.1, final concentration.
55. The pharmaceutical composition of embodiment 54, further comprising about 10 mM sodium phosphate and about 240 mM sucrose.
56. The pharmaceutical composition of embodiment 54 or 55, wherein the pharmaceutical composition comprises about 1 mg/mL or about 10 mg/mL IL-22 Fc fusion protein.

57. The pharmaceutical composition of embodiment 55 or 56, wherein the sodium phosphate is a mixture of sodium phosphate monobasic and sodium phosphate dibasic.
58. The pharmaceutical composition of any one of embodiments 1-57, wherein the pharmaceutical composition is in a unit dosage form.
59. The pharmaceutical composition of embodiment 58, wherein the unit dosage form is a liquid formulation for infusion.
60. The pharmaceutical composition of embodiment 59, wherein the liquid formulation for infusion is supplied in a container with a nominal volume of less than 100 mL.
61. The pharmaceutical composition of embodiment 60, wherein the volume of the liquid formulation for infusion is between about 1 mL to about 2 mL.
62. The pharmaceutical composition of embodiment 61, wherein the volume of the liquid formulation for infusion is about 1 mL.
63. The pharmaceutical composition of any one of embodiments 60-62, wherein the number of particles ≥10 μm present in the container does not exceed 6000 particles.
64. The pharmaceutical composition of any one of embodiments 60-63, wherein the number of particles ≥25 μm present in the container does not exceed 600 particles.
65. The pharmaceutical composition of any one of embodiments 1-64, wherein the carrier is water.
66. The pharmaceutical composition of any one of embodiments 1-65, wherein the pharmaceutical composition is stable through one or more freeze-thaw cycles.
67. The pharmaceutical composition of embodiment 66, wherein the pharmaceutical composition is stable through three freeze-thaw cycles.
68. The pharmaceutical composition of any one of embodiments 1-67, wherein the pharmaceutical composition is stable for about 2 weeks or longer at about 25° C.
69. The pharmaceutical composition of embodiment 68, wherein the pharmaceutical composition is stable for about 4 weeks or longer at about 25° C.
70. The pharmaceutical composition of any one of embodiments 1-69, wherein the pharmaceutical composition is stable for about 48 months or longer at −20° C.
71. The pharmaceutical composition of any one of embodiments 1-70, wherein the pharmaceutical composition has a purity of about 85% or higher as assessed by size-exclusion high-performance liquid chromatography (SE-HPLC).
72. The pharmaceutical composition of embodiment 71, wherein the pharmaceutical composition has a purity of about 90% or higher as assessed by SE-HPLC.
73. The pharmaceutical composition of embodiment 72, wherein the pharmaceutical composition has a purity of about 95% or higher as assessed by SE-HPLC.
74. The pharmaceutical composition of any one of embodiments 71-73, wherein the pharmaceutical composition has a purity of about 95% or higher as assessed by SE-HPLC for about 36 months or longer at about 5° C.
75. The pharmaceutical composition of embodiment 74, wherein the pharmaceutical composition has a purity of about 95% or higher as assessed by SE-HPLC for about 42 months or longer at about 5° C.
76. The pharmaceutical composition of embodiment 75, wherein the pharmaceutical composition has a purity of about 95% or higher as assessed by SE-HPLC for about 42 months at about 5° C.
77. The pharmaceutical composition of any one of embodiments 1-76, wherein the pharmaceutical composition has a purity of about 75% or higher as assessed by non-reduced (NR) capillary electrophoresis sodium dodecyl sulfate non-gel sieving (CE-SDS-NGS).
78. The pharmaceutical composition of embodiment 77, wherein the pharmaceutical composition has a purity of about 80% or higher as assessed by NR CE-SDS-NGS.
79. The pharmaceutical composition of embodiment 78, wherein the pharmaceutical composition has a purity of about 85% or higher as assessed by NR CE-SDS-NGS.
80. The pharmaceutical composition of any one of embodiments 77-79, wherein the pharmaceutical composition has a purity of about 85% or higher as assessed by NR CE-SDS-NGS for about 36 months or longer at about 5° C.
81. The pharmaceutical composition of embodiment 80, wherein the pharmaceutical composition has a purity of about 85% or higher as assessed by NR CE-SDS-NGS for about 42 months or longer at about 5° C.
82. The pharmaceutical composition of embodiment 81, wherein the pharmaceutical composition has a purity of about 85% or higher as assessed by NR CE-SDS-NGS for about 42 months at about 5° C.
83. The pharmaceutical composition of any one of embodiments 1-82, wherein the pharmaceutical composition is formulated for intravenous, subcutaneous, intraperitoneal, or topical administration.
84. The pharmaceutical composition of embodiment 83, wherein the pharmaceutical composition is formulated for intravenous administration.
85. The pharmaceutical composition of embodiment 83, wherein the pharmaceutical composition is formulated for subcutaneous administration.
86. The pharmaceutical composition of any one of embodiments 1-85, wherein the pharmaceutical composition does not contain a preservative.
87. The pharmaceutical composition of any one of embodiments 1-86, wherein the pharmaceutical composition is formulated for administration by infusion after dilution with an isotonic sodium chloride solution and/or a diluent.
88. The pharmaceutical composition of embodiment 87, wherein the isotonic sodium chloride solution comprises about 0.1% to about 2% NaCl.
89. The pharmaceutical composition of embodiment 88, wherein the isotonic sodium chloride solution comprises about 0.5% to about 1.5% NaCl.
90. The pharmaceutical composition of embodiment 89, wherein the isotonic sodium chloride solution comprises about 0.9% (w/v) NaCl.
91. The pharmaceutical composition of any one of embodiments 87-90, wherein the diluent comprises a buffering agent, a tonicity agent, and a surfactant.
92. The pharmaceutical composition of any one of embodiments 87-91, wherein the diluent comprises about 10 mM sodium phosphate, about 240 mM sucrose, about 0.02% (w/v) polysorbate 20, pH 7.1, final concentration.

93. The pharmaceutical composition of any one of embodiments 1-92, wherein the IL-22 polypeptide is glycosylated.
94. The pharmaceutical composition of any one of embodiments 1-93, wherein the IL-22 polypeptide is N-glycosylated.
95. The pharmaceutical composition of any one of embodiments 1-94, wherein the Fc region is not glycosylated.
96. The pharmaceutical composition of embodiment 95, wherein the amino acid residue at position 297 as in the EU index of the Fc region is Gly.
97. The pharmaceutical composition of embodiment 95, wherein the amino acid residue at position 297 as in the EU index of the Fc region is Ala.
98. The pharmaceutical composition of any one of embodiments 95-97, wherein the amino acid residue at position 299 as in the EU index of the Fc region is Ala, Gly, or Val
99. The pharmaceutical composition of any one of embodiments 1-98, wherein the Fc region comprises the CH2 and CH3 domain of IgG1 or IgG4.
100. The pharmaceutical composition of embodiment 99, wherein the Fc region comprises the CH2 and CH3 domain of IgG4.
101. The pharmaceutical composition of any one of embodiments 1-100, wherein the IL-22 Fc fusion protein comprises an amino acid sequence having at least 95% sequence identity to the amino acid sequence of SEQ ID NO:8.
102. The pharmaceutical composition of embodiment 101, wherein the IL-22 Fc fusion protein comprises an amino acid sequence having at least 96% sequence identity to the amino acid sequence of SEQ ID NO:8.
103. The pharmaceutical composition of embodiment 102, wherein the IL-22 Fc fusion protein comprises an amino acid sequence having at least 97% sequence identity to the amino acid sequence of SEQ ID NO:8.
104. The pharmaceutical composition of embodiment 103, wherein the IL-22 Fc fusion protein comprises an amino acid sequence having at least 98% sequence identity to the amino acid sequence of SEQ ID NO:8.
105. The pharmaceutical composition of embodiment 104, wherein the IL-22 Fc fusion protein comprises an amino acid sequence having at least 99% sequence identity to the amino acid sequence of SEQ ID NO:8.
106. The pharmaceutical composition of any one of embodiments 1-105, wherein the IL-22 Fc fusion protein comprises the amino acid sequence of SEQ ID NO:8, SEQ ID NO:10, or SEQ ID NO:16.
107. The pharmaceutical composition of embodiment 106, wherein the IL-22 Fc fusion protein comprises the amino acid sequence of SEQ ID NO:8.
108. The pharmaceutical composition of embodiment 107, wherein the IL-22 Fc fusion protein consists of the amino acid sequence of SEQ ID NO:8.
109. The pharmaceutical composition of embodiment 106, wherein the IL-22 Fc fusion protein comprises the amino acid sequence of SEQ ID NO:10.
110. The pharmaceutical composition of embodiment 109, wherein the IL-22 Fc fusion protein consists of the amino acid sequence of SEQ ID NO:10.
111. The pharmaceutical composition of embodiment 106, wherein the IL-22 Fc fusion protein comprises the amino acid sequence of SEQ ID NO:16.
112. The pharmaceutical composition of embodiment 111, wherein the IL-22 Fc fusion protein consists of the amino acid sequence of SEQ ID NO:16.
113. The pharmaceutical composition of any one of embodiments 95-112, wherein the Fc region is not N-glycosylated.
114. The pharmaceutical composition of any one of embodiments 1-113, wherein the IL-22 Fc fusion protein is a dimeric IL-22 Fc fusion protein.
115. The pharmaceutical composition of any one of embodiments 1-113, wherein the IL-22 Fc fusion protein is a monomeric IL-22 Fc fusion protein.
116. The pharmaceutical composition of any one of embodiments 1-115, wherein the IL-22 polypeptide is a human IL-22 polypeptide.
117. The pharmaceutical composition of embodiment 116, wherein the IL-22 polypeptide comprises the amino acid sequence of SEQ ID NO:4.
118. The pharmaceutical composition of any one of embodiments 1-117, wherein the linker comprises the amino acid sequence RVESKYGPP (SEQ ID NO: 44).
119. The pharmaceutical composition of embodiment 118, wherein the linker consists of the amino acid sequence RVESKYGPP (SEQ ID NO: 44).
120. A pharmaceutical composition comprising an IL-22 Fc fusion protein and a carrier, the IL-22 Fc fusion protein comprising the amino acid sequence of SEQ ID NO:8, wherein the pharmaceutical composition comprises about 5 mM methionine, about 10 mM sodium phosphate, about 240 mM sucrose, and about 0.02% (w/v) polysorbate 20, pH 7.1, final concentration.
121. The pharmaceutical composition of any one of embodiments 1-120, wherein the IL-22 Fc fusion protein binds to IL-22 receptor.
122. The pharmaceutical composition of embodiment 121, wherein the IL-22 receptor is human IL-22 receptor.
123. The pharmaceutical composition of embodiment 121 or 122, wherein the IL-22 Fc fusion protein binds to IL-22RA1 and/or IL-10R2.
124. The IL-22 Fc fusion protein of embodiment 123, wherein the IL-22 Fc fusion protein binds to IL-22RA1.
125. The pharmaceutical composition of any one of embodiments 1-124, further comprising an additional therapeutic agent.
126. The pharmaceutical composition of any one of embodiments 1-125, further comprising a gelling agent.
127. The pharmaceutical composition of embodiment 126, wherein the gelling agent is a polysaccharide.
128. The pharmaceutical composition of embodiment 126 or 127, wherein the gelling agent is a cellulosic agent.
129. The pharmaceutical composition of any one of embodiments 126-128, wherein the gelling agent is methylcellulose, hydroxyethyl cellulose, carboxymethyl cellulose, hydroxypropyl cellulose, POE-POP block polymers, alginate, hyaluronic acid, polyacrylic acid, hydroxyethyl methylcellulose or hydroxypropyl methylcellulose.
130. The pharmaceutical composition of embodiment 129, wherein the gelling agent is hydroxypropyl methylcellulose.
131. The pharmaceutical composition of any one of embodiments 126-130, wherein the pharmaceutical formulation is for topical administration.

132. The pharmaceutical composition of any one of embodiments 1-131 for use as a medicament.
133. A method of treating inflammatory bowel disease (IBD) in a subject in need thereof, the method comprising administering to the subject the pharmaceutical composition of any one of embodiments 1-132.
134. The method of embodiment 133, wherein the IBD is ulcerative colitis or Crohn's disease.
135. The method of embodiment 134, wherein the IBD is ulcerative colitis.
136. The method of embodiment 135, wherein the ulcerative colitis is moderate to severe ulcerative colitis.
137. The method of embodiment 134, wherein the IBD is Crohn's disease.
138. A method of inhibiting microbial infection in the intestine, preserving goblet cells in the intestine during a microbial infection, enhancing epithelial cell integrity, epithelial cell proliferation, epithelial cell differentiation, epithelial cell migration or epithelial wound healing in the intestine, of a subject in need thereof, the method comprising administering to the subject the pharmaceutical composition of any one of embodiments 1-132.
139. The method of embodiment 138, wherein the epithelial cell is an intestinal epithelial cell.
140. A method of treating acute kidney injury or acute pancreatitis in a subject in need thereof, the method comprising administering to the subject the pharmaceutical composition of any one of embodiments 1-132.
141. A method of accelerating or improving wound healing in a subject in need thereof, the method comprising administering to the subject the pharmaceutical composition of any one of embodiments 1-132.
142. The method of embodiment 141, wherein the wound is a chronic wound or an infected wound.
143. The method of embodiment 141 or 142, wherein the subject is diabetic.
144. The method of embodiment 143, wherein the diabetic subject has type II diabetes.
145. The method of any one of embodiments 141-144, wherein the wound is a diabetic foot ulcer.
146. The method of any one of embodiments 141-145, wherein the IL-22 Fc fusion protein or the pharmaceutical composition is administered until there is complete wound closure.
147. A method for preventing or treating a cardiovascular condition in a subject in need thereof, which condition includes a pathology of atherosclerotic plaque formation, the method comprising administering to the subject the pharmaceutical composition of any one of embodiments 1-132.
148. The method of embodiment 147, wherein the cardiovascular disease is coronary artery disease, coronary microvascular disease, stroke, carotid artery disease, peripheral artery disease, or chronic kidney disease.
149. The method of embodiment 147 or 148, further comprising slowing down the progression of atherosclerotic plaque formation or preventing indicia of atherosclerosis.
150. The method of embodiment 149, wherein the indicia of atherosclerosis includes plaque accumulation or vascular inflammation.
151. A method for treating metabolic syndrome in a subject in need thereof, the method comprising administering to the subject the pharmaceutical composition of any one of embodiments 1-132.
152. The method of embodiment 151, further comprising reducing one or more risk factors associated with metabolic syndrome, including one or more of abdominal obesity, hyperglycemia, dyslipidemia, and hypertension.
153. The method of embodiment 151 or 152, further comprising reducing the level of bacterial lipopolysaccharide in the subject.
154. A method of treating acute endotoxemia, sepsis, or both, in a subject in need thereof, the method comprising administering the subject the pharmaceutical composition of any one of embodiments 1-132.
155. The method of any one of embodiments 151-154, wherein the subject is in need of a change in HDL/LDL lipid profile.
156. The method of any one of embodiments 133-155, wherein the composition comprises about 1 mg/mL to about 10 mg/mL IL-22 Fc fusion protein, about 10 mM sodium phosphate, about 240 mM sucrose, about 5 mM methionine, and about 0.02% (w/v) polysorbate 20, pH 7.1, final concentration.
157. The method of any one of embodiments 133-156, wherein the IL-22 Fc fusion protein comprises the amino acid sequence of SEQ ID NO:8, SEQ ID NO:10, or SEQ ID NO:16.
158. The method of embodiment 157, wherein the IL-22 Fc fusion protein comprises the amino acid sequence of SEQ ID NO:8.
159. The method of embodiment 157, wherein the IL-22 Fc fusion protein comprises the amino acid sequence of SEQ ID NO:16.
160. The method of any one of embodiments 133-159, wherein the pharmaceutical composition is administered intravenously, subcutaneously, intraperitoneally, or topically.
161. The method of embodiment 160, wherein the pharmaceutical composition is administered intravenously.
162. The method of embodiment 160, wherein the pharmaceutical composition is administered subcutaneously.
163. The method of any one of embodiments 133-162, wherein the subject is co-administered with at least one additional therapeutic agent.
164. The method of any one of embodiments 133-163, wherein the subject is a human.
165. The pharmaceutical composition of any one of embodiments 1-132 for use in a method of treating inflammatory bowel disease (IBD) in a subject in need thereof.
166. The pharmaceutical composition for use of embodiment 165, wherein the IBD is ulcerative colitis or Crohn's disease.
167. The pharmaceutical composition for use of embodiment 166, wherein the IBD is ulcerative colitis.
168. The pharmaceutical composition for use of embodiment 167, wherein the ulcerative colitis is moderate to severe ulcerative colitis.
169. The pharmaceutical composition for use of embodiment 166, wherein the IBD is Crohn's disease.
170. The pharmaceutical composition of any one of embodiments 1-132 for use in a method of inhibiting microbial infection in the intestine, preserving goblet cells in the intestine during a microbial infection, enhancing epithelial cell integrity, epithelial cell proliferation, epithelial cell differentiation, epithelial cell migration or epithelial wound healing in the intestine, of a subject in need thereof.

171. The pharmaceutical composition for use of embodiment 170, wherein the epithelial cell is an intestinal epithelial cell.
172. The pharmaceutical composition of any one of embodiments 1-132 for use in a method of treating acute kidney injury or acute pancreatitis in a subject in need thereof.
173. The pharmaceutical composition of any one of embodiments 1-132 for use in a method of accelerating or improving wound healing in a subject in need thereof.
174. The pharmaceutical composition for use of embodiment 173, wherein the wound is a chronic wound or an infected wound.
175. The pharmaceutical composition for use of embodiment 173 or 174, wherein the subject is diabetic.
176. The pharmaceutical composition for use of embodiment 175, wherein the diabetic subject has type II diabetes.
177. The pharmaceutical composition for use of any one of embodiments 173-176, wherein the wound is a diabetic foot ulcer.
178. The pharmaceutical composition for use of any one of embodiments 173-177, wherein the IL-22 Fc fusion protein or the pharmaceutical composition is administered until there is complete wound closure.
179. The pharmaceutical composition of any one of embodiments 1-132 for use in a method for preventing or treating a cardiovascular condition in a subject in need thereof, which condition includes a pathology of atherosclerotic plaque formation.
180. The pharmaceutical composition for use of embodiment 179, wherein the cardiovascular disease is coronary artery disease, coronary microvascular disease, stroke, carotid artery disease, peripheral artery disease, or chronic kidney disease.
181. The pharmaceutical composition for use of embodiment 179 or 180, further comprising slowing down the progression of atherosclerotic plaque formation or preventing indicia of atherosclerosis.
182. The pharmaceutical composition for use of embodiment 181, wherein the indicia of atherosclerosis includes plaque accumulation or vascular inflammation.
183. The pharmaceutical composition of any one of embodiments 1-132 for use in a method for treating metabolic syndrome in a subject in need thereof.
184. The pharmaceutical composition for use of embodiment 183, further comprising reducing one or more risk factors associated with metabolic syndrome, including one or more of abdominal obesity, hyperglycemia, dyslipidemia, and hypertension.
185. The pharmaceutical composition for use of embodiment 183 or 184, further comprising reducing the level of bacterial lipopolysaccharide in the subject.
186. The pharmaceutical composition of any one of embodiments 1-132 for use in a method of treating acute endotoxemia, sepsis, or both, in a subject in need thereof.
187. The pharmaceutical composition for use of any one of embodiments 183-186, wherein the subject is in need of a change in HDL/LDL lipid profile.
188. The pharmaceutical composition for use of any one of embodiments 165-187, wherein the composition comprises about 1 mg/mL to about 10 mg/mL IL-22 Fc fusion protein, about 10 mM sodium phosphate, about 240 mM sucrose, about 5 mM methionine, and about 0.02% (w/v) polysorbate 20, pH 7.1, final concentration.
189. The pharmaceutical composition for use of any one of embodiments 165-188, wherein the IL-22 Fc fusion protein comprises the amino acid sequence of SEQ ID NO:8, SEQ ID NO:10, or SEQ ID NO:16.
190. The pharmaceutical composition for use of embodiment 189, wherein the IL-22 Fc fusion protein comprises the amino acid sequence of SEQ ID NO:8.
191. The pharmaceutical composition for use of embodiment 189, wherein the IL-22 Fc fusion protein comprises the amino acid sequence of SEQ ID NO:16.
192. The pharmaceutical composition for use of any one of embodiments 165-191, wherein the pharmaceutical composition is administered intravenously, subcutaneously, intraperitoneally, or topically.
193. The pharmaceutical composition of embodiment 192, wherein the IL-22 Fc fusion protein or the pharmaceutical composition is administered intravenously.
194. The pharmaceutical composition of embodiment 193, wherein the IL-22 Fc fusion protein or the pharmaceutical composition is administered subcutaneously.
195. The pharmaceutical composition of any one of embodiments 165-194, wherein the subject is to be co-administered with at least one additional therapeutic agent.
196. The pharmaceutical composition of any one of embodiments 165-195, wherein the subject is a human.

The specification is considered to be sufficient to enable one skilled in the art to practice the invention. Although the foregoing invention has been described in some detail by way of illustration and example for purposes of clarity of understanding, the descriptions and examples should not be construed as limiting the scope of the invention. Indeed, various modifications of the invention in addition to those shown and described herein will become apparent to those skilled in the art from the foregoing description and fall within the scope of the appended claims.

What is claimed is:

1. A pharmaceutical composition comprising an IL-22 Fc fusion protein and a carrier, the IL-22 Fc fusion protein comprising an IL-22 polypeptide linked to an Fc region by a linker, wherein the IL-22 polypeptide comprises the amino acid sequence of SEQ ID NO: 4, wherein the pharmaceutical composition comprises about 1 mg/mL to about 10 mg/mL IL-22 Fc fusion protein, about 5 mM methionine, about 10 mM sodium phosphate, about 240 mM sucrose, and about 0.02% (w/v) polysorbate 20, and wherein the pharmaceutical composition has a pH of about 7.1.

2. The pharmaceutical composition of claim 1, wherein the sodium phosphate comprises a mixture of sodium phosphate dibasic and sodium phosphate monobasic.

3. The pharmaceutical composition of claim 1, wherein the IL-22 Fc fusion protein has one or more properties selected from the group consisting of:
  (i) the IL-22 polypeptide is glycosylated;
  (ii) the Fc region is not glycosylated;
  (iii) the amino acid residue at position 297 as in the EU index of the Fc region is Gly or Ala or the amino acid residue at position 299 as in the EU index of the Fc region is Ala, Gly, or Val;
  (iv) the Fc region comprises the CH2 and CH3 domain of IgG1 or IgG4;
  (v) the IL-22 Fc fusion protein comprises an amino acid sequence having at least 95% sequence identity to the amino acid sequence of SEQ ID NO:8; and
  (vi) the IL-22 Fc fusion protein comprises or consists of the amino acid sequence of SEQ ID NO:8, SEQ ID NO:10, or SEQ ID NO:16.

4. The pharmaceutical composition of claim 1, wherein the pharmaceutical composition comprises about 1 mg/mL IL-22 Fc fusion protein.

5. The pharmaceutical composition of claim 1, wherein the pharmaceutical composition comprises about 10 mg/mL IL-22 Fc fusion protein.

6. The pharmaceutical composition of claim 1, wherein the IL-22 Fc fusion protein comprises the amino acid sequence of SEQ ID NO:8.

7. The pharmaceutical composition of claim 1, wherein the pharmaceutical composition is in a unit dosage form.

8. The pharmaceutical composition of claim 1, wherein the carrier is water.

9. The pharmaceutical composition of claim 1, wherein the pharmaceutical composition is stable:
  (a) through one or more freeze-thaw cycles;
  (b) for about 2 weeks to about 52 weeks at about 25° C.; and/or
  (c) for about 48 months to about 100 months at −20° C.

10. The pharmaceutical composition of claim 1, wherein the pharmaceutical composition has a purity of about 85% to about 100% as assessed by size-exclusion high-performance liquid chromatography (SE-HPLC).

11. The pharmaceutical composition of claim 1, wherein the pharmaceutical composition has a purity of about 75% to about 100% as assessed by nonreduced (NR) capillary electrophoresis sodium dodecyl sulfate non-gel sieving (CE-SDS-NGS).

12. The pharmaceutical composition of claim 1, wherein the pharmaceutical composition is formulated for intravenous, subcutaneous, intraperitoneal, or topical administration.

13. The pharmaceutical composition of claim 1, wherein the pharmaceutical composition does not contain a preservative.

14. The pharmaceutical composition of claim 1, wherein the pharmaceutical composition is formulated for administration by infusion after dilution with an isotonic sodium chloride solution and/or a diluent.

15. The pharmaceutical composition of claim 1, wherein the pharmaceutical composition further comprises an additional therapeutic agent and/or a gelling agent.

16. A pharmaceutical composition comprising an IL-22 Fc fusion protein and a carrier, the IL-22 Fc fusion protein comprising the amino acid sequence of SEQ ID NO:8, wherein the pharmaceutical composition comprises about 10 mM sodium phosphate, about 240 mM sucrose, about 5 mM methionine, and about 0.02% (w/v) polysorbate 20, final concentration; and wherein the pharmaceutical composition has a pH of about 6.5 to about 8.

17. The pharmaceutical composition of claim 16, wherein the pharmaceutical composition has a pH of about 6.6 to about 7.5.

18. The pharmaceutical composition of claim 17, wherein the pharmaceutical composition has a pH of about 6.7 to about 7.4.

19. The pharmaceutical composition of claim 18, wherein the pharmaceutical composition has a pH of about 7 to about 7.1.

20. The pharmaceutical composition of claim 16, wherein the sodium phosphate comprises a mixture of sodium phosphate dibasic and sodium phosphate monobasic.

21. The pharmaceutical composition of claim 16, wherein the pharmaceutical composition comprises about 1 mg/mL to about 10 mg/mL IL-22 Fc fusion protein.

22. The pharmaceutical composition of claim 16, wherein the pharmaceutical composition is in a unit dosage form.

23. The pharmaceutical composition of claim 16, wherein the carrier is water.

24. The pharmaceutical composition of claim 16, wherein the pharmaceutical composition is stable:
   (a) through one or more freeze-thaw cycles;
   (b) for about 2 weeks to about 52 weeks at about 25° C.; and/or
   (c) for about 48 months to about 100 months at −20° C.

25. The pharmaceutical composition of claim 16, wherein the pharmaceutical composition has a purity of about 85% to about 100% as assessed by size-exclusion high-performance liquid chromatography (SE-HPLC).

26. The pharmaceutical composition of claim 16, wherein the pharmaceutical composition has a purity of about 75% to about 100% as assessed by nonreduced (NR) capillary electrophoresis sodium dodecyl sulfate non-gel sieving (CE-SDS-NGS).

27. The pharmaceutical composition of claim 16, wherein the pharmaceutical composition is formulated for intravenous, subcutaneous, intraperitoneal, or topical administration.

28. The pharmaceutical composition of claim 16, wherein the pharmaceutical composition does not contain a preservative.

29. The pharmaceutical composition of claim 16, wherein the pharmaceutical composition is formulated for administration by infusion after dilution with an isotonic sodium chloride solution and/or a diluent.

30. The pharmaceutical composition of claim 16, wherein the pharmaceutical composition further comprises an additional therapeutic agent and/or a gelling agent.

\* \* \* \* \*

SEQUENCE LISTING

```
<160> NUMBER OF SEQ ID NOS: 92

<210> SEQ ID NO 1
<211> LENGTH: 495
<212> TYPE: DNA
<213> ORGANISM: Homo sapiens
<220> FEATURE:
<223> OTHER INFORMATION: Human IL-22

<400> SEQUENCE: 1
```

-continued

| | |
|---|---|
| atgggatggt catgtatcat ccttttttcta gtagcaactg caactggagt acattcagcg | 60 |
| cccatcagct cccactgcag gcttgacaag tccaacttcc agcagcccta tatcaccaac | 120 |
| cgcaccttca tgctggctaa ggaggctagc ttggctgata acaacacaga cgttcgtctc | 180 |
| attggggaga aactgttcca cggagtcagt atgagtgagc gctgctatct gatgaagcag | 240 |
| gtgctgaact tcacccttga agaagtgctg ttccctcaat ctgataggtt ccagccttat | 300 |
| atgcaggagg tggtgccctt cctggccagg ctcagcaaca ggctaagcac atgtcatatt | 360 |
| gaaggtgatg acctgcatat ccagaggaat gtgcaaaagc tgaaggacac agtgaaaaag | 420 |
| cttggagaga gtggagagat caaagcaatt ggagaactgg atttgctgtt tatgtctctg | 480 |
| agaaatgcct gcatt | 495 |

<210> SEQ ID NO 2
<211> LENGTH: 165
<212> TYPE: PRT
<213> ORGANISM: Homo sapiens
<220> FEATURE:
<223> OTHER INFORMATION: Human IL-22

<400> SEQUENCE: 2

Met Gly Trp Ser Cys Ile Ile Leu Phe Leu Val Ala Thr Ala Thr Gly
1               5                   10                  15

Val His Ser Ala Pro Ile Ser Ser His Cys Arg Leu Asp Lys Ser Asn
            20                  25                  30

Phe Gln Gln Pro Tyr Ile Thr Asn Arg Thr Phe Met Leu Ala Lys Glu
        35                  40                  45

Ala Ser Leu Ala Asp Asn Asn Thr Asp Val Arg Leu Ile Gly Glu Lys
    50                  55                  60

Leu Phe His Gly Val Ser Met Ser Glu Arg Cys Tyr Leu Met Lys Gln
65                  70                  75                  80

Val Leu Asn Phe Thr Leu Glu Glu Val Leu Phe Pro Gln Ser Asp Arg
                85                  90                  95

Phe Gln Pro Tyr Met Gln Glu Val Val Pro Phe Leu Ala Arg Leu Ser
            100                 105                 110

Asn Arg Leu Ser Thr Cys His Ile Glu Gly Asp Asp Leu His Ile Gln
        115                 120                 125

Arg Asn Val Gln Lys Leu Lys Asp Thr Val Lys Lys Leu Gly Glu Ser
    130                 135                 140

Gly Glu Ile Lys Ala Ile Gly Glu Leu Asp Leu Leu Phe Met Ser Leu
145                 150                 155                 160

Arg Asn Ala Cys Ile
                165

<210> SEQ ID NO 3
<211> LENGTH: 438
<212> TYPE: DNA
<213> ORGANISM: Homo sapiens
<220> FEATURE:
<223> OTHER INFORMATION: IL-22 DNA (mature)

<400> SEQUENCE: 3

| | |
|---|---|
| gcgcccatca gctcccactg caggcttgac aagtccaact tccagcagcc ctatatcacc | 60 |
| aaccgcacct tcatgctggc taaggaggct agcttggctg ataacaacac agacgttcgt | 120 |
| ctcattgggg agaaactgtt ccacggagtc agtatgagtg agcgctgcta tctgatgaag | 180 |
| caggtgctga acttcaccct tgaagaagtg ctgttccctc aatctgatag gttccagcct | 240 |

```
tatatgcagg aggtggtgcc cttcctggcc aggctcagca acaggctaag cacatgtcat    300
attgaaggtg atgacctgca tatccagagg aatgtgcaaa agctgaagga cacagtgaaa    360
aagcttggag agagtggaga gatcaaagca attggagaac tggatttgct gtttatgtct    420
ctgagaaatg cctgcatt                                                  438
```

<210> SEQ ID NO 4
<211> LENGTH: 146
<212> TYPE: PRT
<213> ORGANISM: Homo sapiens
<220> FEATURE:
<223> OTHER INFORMATION: IL-22 (mature)

<400> SEQUENCE: 4

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile
145
```

<210> SEQ ID NO 5
<211> LENGTH: 57
<212> TYPE: DNA
<213> ORGANISM: Homo sapiens
<220> FEATURE:
<223> OTHER INFORMATION: IL-22 leader sequence

<400> SEQUENCE: 5

```
atgggatggt catgtatcat cctttttcta gtagcaactg caactggagt acattca       57
```

<210> SEQ ID NO 6
<211> LENGTH: 19
<212> TYPE: PRT
<213> ORGANISM: Homo sapiens
<220> FEATURE:
<223> OTHER INFORMATION: IL-22 leader sequence

<400> SEQUENCE: 6

```
Met Gly Trp Ser Cys Ile Ile Leu Phe Leu Val Ala Thr Ala Thr Gly
1               5                   10                  15

Val His Ser
```

<210> SEQ ID NO 7
<211> LENGTH: 1128
<212> TYPE: DNA

-continued

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG4 (minus C-terminal Lys)
      N297G

<400> SEQUENCE: 7

```
gcgcccatca gctcccactg caggcttgac aagtccaact tccagcagcc ctatatcacc    60
aaccgcacct tcatgctggc taaggaggct agcttggctg ataacaacac agacgttcgt   120
ctcattgggg agaaactgtt ccacggagtc agtatgagtg agcgctgcta tctgatgaag   180
caggtgctga acttcaccct tgaagaagtg ctgttccctc aatctgatag gttccagcct   240
tatatgcagg aggtggtgcc cttcctggcc aggctcagca caggctaag cacatgtcat   300
attgaaggtg atgacctgca tatccagagg aatgtgcaaa agctgaagga cacagtgaaa   360
aagcttggag agagtggaga gatcaaagca attggagaac tggatttgct gtttatgtct   420
ctgagaaatg cctgcattcg cgttgagtcc aaatatggtc ccccatgccc accatgccca   480
gcacctgagt tcctgggggg accatcagtc ttcctgttcc cccaaaaacc caaggacact   540
ctcatgatct cccggacccc tgaggtcacg tgcgtggtgg tggacgtgag ccaggaagac   600
cccgaggtcc agttcaactg gtacgtggat ggcgtggagg tgcataatgc caagacaaag   660
ccgcgggagg agcagttcgg aagcacgtac cgtgtggtca gcgtcctcac cgtcctgcac   720
caggactggc tgaacggcaa ggagtacaag tgcaaggtct ccaacaaagg cctcccgtcc   780
tccatcgaga aaaccatctc caaagccaaa gggcagcccc gagagccaca ggtgtacacc   840
ctgcccccat cccaggagga gatgaccaag aaccaggtca gcctgacctg cctggtcaaa   900
ggcttctacc ccagcgacat cgccgtggag tgggagagca atgggcagcc ggagaacaac   960
tacaagacca cgcctcccgt gctggactcc gacggctcct tcttcctcta cagcaggcta  1020
accgtggaca agagcaggtg gcaggagggg aatgtcttct catgctccgt gatgcatgag  1080
gctctgcaca accactacac acagaagagc ctctccctgt ctctgggt               1128
```

<210> SEQ ID NO 8
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG4 (minus C-terminal Lys)
      N297G

<400> SEQUENCE: 8

```
Ala Pro Ile Ser Ser His Cys Arg Leu Asp Lys Ser Asn Phe Gln Gln
1               5                  10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95
```

Ser Thr Cys His Ile Glu Gly Asp Asp Leu His Ile Gln Arg Asn Val
            100                 105                 110

Gln Lys Leu Lys Asp Thr Val Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile Arg Val Glu Ser Lys Tyr Gly Pro Pro Cys Pro Pro Cys Pro
145                 150                 155                 160

Ala Pro Glu Phe Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
        180                 185                 190

Val Val Asp Val Ser Gln Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Phe Gly Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Gly Leu Pro Ser Ser Ile Glu Lys Thr Ile Ser Lys Ala Lys Gly Gln
        260                 265                 270

Pro Arg Glu Pro Gln Val Tyr Thr Leu Pro Pro Ser Gln Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Arg Leu Thr Val Asp Lys Ser Arg Trp Gln Glu Gly Asn Val
        340                 345                 350

Phe Ser Cys Ser Val Met His Glu Ala Leu His Asn His Tyr Thr Gln
        355                 360                 365

Lys Ser Leu Ser Leu Ser Leu Gly
    370                 375

<210> SEQ ID NO 9
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG4 (minus C-terminal Lys)
      N297A

<400> SEQUENCE: 9
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag     180
caggtgctga acttcaccct tgaagaagtg ctgttccctc aatctgatag gttccagcct     240
tatatgcagg aggtggtgcc cttcctggcc aggctcagca acaggctaag cacatgtcat     300

-continued

```
attgaaggtg atgacctgca tatccagagg aatgtgcaaa agctgaagga cacagtgaaa   360
aagcttggag agagtggaga gatcaaagca attggagaac tggatttgct gtttatgtct   420
ctgagaaatg cctgcattcg cgttgagtcc aaatatggtc ccccatgccc accatgccca   480
gcacctgagt tcctgggggg accatcagtc ttcctgttcc ccccaaaacc caaggacact   540
ctcatgatct cccggacccc tgaggtcacg tgcgtggtgg tggacgtgag ccaggaagac   600
cccgaggtcc agttcaactg gtacgtggat ggcgtggagg tgcataatgc caagacaaag   660
ccgcgggagg agcagttcgc tagcacgtac cgtgtggtca gcgtcctcac cgtcctgcac   720
caggactggc tgaacggcaa ggagtacaag tgcaaggtct ccaacaaagg cctcccgtcc   780
tccatcgaga aaaccatctc caaagccaaa gggcagcccc gagagccaca ggtgtacacc   840
ctgcccccat cccaggagga tgaccaag aaccaggtca gcctgacctg cctggtcaaa    900
ggcttctacc ccagcgacat cgccgtggag tgggagagca tgggcagcc ggagaacaac    960 tacaagacca cgcctcccgt gctggactcc gacggctcct tcttcctcta cagcaggcta  1020
accgtggaca agagcaggtg gcaggagggg aatgtcttct catgctccgt gatgcatgag  1080
gctctgcaca accactacac acagaagagc ctctccctgt ctctgggt              1128
```

<210> SEQ ID NO 10
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG4 (minus C-terminal Lys)
      N297A

<400> SEQUENCE: 10

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Arg Val Glu Ser Lys Tyr Gly Pro Pro Cys Pro Pro Cys Pro
145                 150                 155                 160

Ala Pro Glu Phe Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser Gln Glu Asp Pro Glu Val Gln Phe Asn Trp Tyr
```

```
                195                 200                 205
Val Asp Gly Val Glu Val His Asn Ala Lys Thr Lys Pro Arg Glu Glu
210                 215                 220

Gln Phe Ala Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Gly Leu Pro Ser Ser Ile Glu Lys Thr Ile Ser Lys Ala Lys Gly Gln
            260                 265                 270

Pro Arg Glu Pro Gln Val Tyr Thr Leu Pro Pro Ser Gln Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Arg Leu Thr Val Asp Lys Ser Arg Trp Gln Glu Gly Asn Val
            340                 345                 350

Phe Ser Cys Ser Val Met His Glu Ala Leu His Asn His Tyr Thr Gln
        355                 360                 365

Lys Ser Leu Ser Leu Ser Leu Gly
    370                 375
```

<210> SEQ ID NO 11
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG1 (minus C-terminal Lys)
      N297G

<400> SEQUENCE: 11

```
gcgcccatca gctcccactg caggcttgac aagtccaact tccagcagcc ctatatcacc    60
aaccgcacct tcatgctggc taaggaggct agcttggctg ataacaacac agacgttcgt   120
ctcattgggg agaaactgtt ccacggagtc agtatgagtg agcgctgcta tctgatgaag   180
caggtgctga acttcaccct tgaagaagtg ctgttccctc aatctgatag gttccagcct   240
tatatgcagg aggtggtgcc cttcctggcc aggctcagca caggctaag cacatgtcat   300 attgaaggtg atgacctgca tatccagagg aatgtgcaaa agctgaagga cacagtgaaa   360
aagcttggag agagtggaga gatcaaagca attggagaac tggatttgct gtttatgtct   420
ctgagaaatg cctgcattga gcccaaatct agtgacaaaa ctcacacatg cccaccgtgc   480
ccagcacctg aactcctggg gggaccgtca gtcttcctct ccccccaaa acccaaggac   540 accctcatga tctcccggac ccctgaggtc acatgcgtgg tggtggacgt gagccacgaa   600
gaccctgagg tcaagttcaa ctggtacgtg gacggcgtgg aggtgcataa tgccaagaca   660
aagccgcggg aggagcagta cggaagcacg taccgtgtgg tcagcgtcct caccgtcctg   720
caccaggact ggctgaatgg caaggagtac aagtgcaagg tctccaacaa agccctccca   780
gcccccatcg agaaaaccat ctccaaagcc aaagggcagc ccgagaacc acaggtgtac   840 accctgcccc catcccggga agagatgacc aagaaccagg tcagcctgac ctgcctggtc   900
```

```
aaaggcttct atcccagcga catcgccgtg gagtgggaga gcaatgggca gccggagaac    960
aactacaaga ccacgcctcc cgtgctggac tccgacggct ccttcttcct ctacagcaag   1020
ctcaccgtgg acaagagcag gtggcagcag gggaacgtct tctcatgctc cgtgatgcat   1080
gaggctctgc acaaccacta cacgcagaag agcctctccc tgtctccggg t            1131
```

```
<210> SEQ ID NO 12
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG1 (minus C-terminal Lys)
      N297G

<400> SEQUENCE: 12

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Glu Pro Lys Ser Ser Asp Lys Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
    210                 215                 220

Glu Gln Tyr Gly Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
            260                 265                 270

Gln Pro Arg Glu Pro Gln Val Tyr Thr Leu Pro Pro Ser Arg Glu Glu
        275                 280                 285

Met Thr Lys Asn Gln Val Ser Leu Thr Cys Leu Val Lys Gly Phe Tyr
    290                 295                 300
```

```
Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
            325                 330                 335

Leu Tyr Ser Lys Leu Thr Val Asp Lys Ser Arg Trp Gln Gln Gly Asn
        340                 345                 350

Val Phe Ser Cys Ser Val Met His Glu Ala Leu His Asn His Tyr Thr
    355                 360                 365

Gln Lys Ser Leu Ser Leu Ser Pro Gly
370                 375

<210> SEQ ID NO 13
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG1 (minus C-terminal Lys)
      N297A

<400> SEQUENCE: 13
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag    180
caggtgctga acttcaccct tgaagaagtg ctgttccctc aatctgatag gttccagcct    240
tatatgcagg aggtggtgcc cttcctggcc aggctcagca acaggctaag cacatgtcat    300
attgaaggtg atgacctgca tatccagagg aatgtgcaaa agctgaagga cacagtgaaa    360
aagcttggag agagtggaga gatcaaagca attggagaac tggatttgct gtttatgtct    420
ctgagaaatg cctgcattga gcccaaatct agtgacaaaa ctcacacatg cccaccgtgc    480
ccagcacctg aactcctggg gggaccgtca gtcttcctct tccccccaaa acccaaggac    540
accctcatga tctcccggac ccctgaggtc acatgcgtgg tggtggacgt gagccacgaa    600
gaccctgagg tcaagttcaa ctggtacgtg gacggcgtgg aggtgcataa tgccaagaca    660
aagccgcggg aggagcagta cgctagcacg taccgtgtgg tcagcgtcct caccgtcctg    720
caccaggact ggctgaatgg caaggagtac aagtgcaagg tctccaacaa agccctccca    780
gcccccatcg agaaaaccat ctccaaagcc aagggcagc ccgagaacc acaggtgtac       840 accctgcccc catcccggga agagatgacc aagaaccagg tcagcctgac ctgcctggtc    900
aaaggcttct atcccagcga catcgccgtg gagtgggaga gcaatgggca gccggagaac    960
aactacaaga ccacgcctcc cgtgctggac tccgacggct ccttcttcct ctacagcaag   1020
ctcaccgtgg acaagagcag gtggcagcag gggaacgtct tctcatgctc cgtgatgcat   1080
gaggctctgc acaaccacta cacgcagaag agcctctccc tgtctccggg t            1131

<210> SEQ ID NO 14
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG1 (minus C-terminal Lys)
      N297A
```

```
<400> SEQUENCE: 14

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile Glu Pro Lys Ser Ser Asp Lys Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
210                 215                 220

Glu Gln Tyr Ala Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
            260                 265                 270

Gln Pro Arg Glu Pro Gln Val Tyr Thr Leu Pro Pro Ser Arg Glu Glu
        275                 280                 285

Met Thr Lys Asn Gln Val Ser Leu Thr Cys Leu Val Lys Gly Phe Tyr
290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
            340                 345                 350

Val Phe Ser Cys Ser Val Met His Glu Ala Leu His Asn His Tyr Thr
        355                 360                 365

Gln Lys Ser Leu Ser Leu Ser Pro Gly
    370                 375

<210> SEQ ID NO 15
<211> LENGTH: 1131
<212> TYPE: DNA
<213> ORGANISM: Artificial Sequence
```

<220> FEATURE:
<223> OTHER INFORMATION: Description of Artificial Sequence: Synthetic
polynucleotide
<220> FEATURE:
<223> OTHER INFORMATION: IL-22 Fc fusion IgG4 (full) N297G

<400> SEQUENCE: 15

```
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag     180
caggtgctga acttcaccct tgaagaagtg ctgttccctc aatctgatag gttccagcct     240
tatatgcagg aggtggtgcc cttcctggcc aggctcagca caggctaag cacatgtcat      300
attgaaggtg atgacctgca tatccagagg aatgtgcaaa agctgaagga cacagtgaaa     360
aagcttggag agagtggaga gatcaaagca attggagaac tggatttgct gtttatgtct     420
ctgagaaatg cctgcattcg cgttgagtcc aaatatggtc ccccatgccc accatgccca     480
gcacctgagt tcctgggggg accatcagtc ttcctgttcc ccccaaaacc caaggacact     540
ctcatgatct cccggacccc tgaggtcacg tgcgtggtgg tggacgtgag ccaggaagac     600
cccgaggtcc agttcaactg gtacgtggat ggcgtggagg tgcataatgc caagacaaag     660
ccgcgggagg agcagttcgg aagcacgtac cgtgtggtca gcgtcctcac cgtcctgcac     720
caggactggc tgaacggcaa ggagtacaag tgcaaggtct ccaacaaagg cctcccgtcc     780
tccatcgaga aaaccatctc caaagccaaa gggcagcccc gagagccaca ggtgtacacc     840
ctgcccccat cccaggagga gatgaccaag aaccaggtca gcctgacctg cctggtcaaa     900
ggcttctacc ccagcgacat cgccgtggag tgggagagca atgggcagcc ggagaacaac     960
tacaagacca cgcctcccgt gctggactcc gacggctcct tcttcctcta cagcaggcta    1020
accgtggaca agagcaggtg gcaggagggg aatgtcttct catgctccgt gatgcatgag    1080
gctctgcaca accactacac acagaagagc ctctccctgt ctctgggtaa a             1131
```

<210> SEQ ID NO 16
<211> LENGTH: 377
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: IL-22 Fc fusion IgG4 (full) N297G

<400> SEQUENCE: 16

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110
```

Gln Lys Leu Lys Asp Thr Val Lys Leu Gly Glu Ser Gly Glu Ile
            115                 120                 125

Lys Ala Ile Gly Glu Leu Asp Leu Leu Phe Met Ser Leu Arg Asn Ala
    130                 135                 140

Cys Ile Arg Val Glu Ser Lys Tyr Gly Pro Pro Cys Pro Pro Cys Pro
145                 150                 155                 160

Ala Pro Glu Phe Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser Gln Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Phe Gly Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Gly Leu Pro Ser Ser Ile Glu Lys Thr Ile Ser Lys Ala Lys Gly Gln
            260                 265                 270

Pro Arg Glu Pro Gln Val Tyr Thr Leu Pro Pro Ser Gln Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Arg Leu Thr Val Asp Lys Ser Arg Trp Gln Glu Gly Asn Val
            340                 345                 350

Phe Ser Cys Ser Val Met His Glu Ala Leu His Asn His Tyr Thr Gln
        355                 360                 365

Lys Ser Leu Ser Leu Ser Leu Gly Lys
    370                 375

<210> SEQ ID NO 17
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG4 (full) N297A

<400> SEQUENCE: 17
gcgcccatca gctcccactg caggcttgac aagtccaact tccagcagcc ctatatcacc    60
aaccgcacct tcatgctggc taaggaggct agcttggctg ataacaacac agacgttcgt   120
ctcattgggg agaaactgtt ccacggagtc agtatgagtg agcgctgcta tctgatgaag   180
caggtgctga acttcaccct tgaagaagtg ctgttccctc aatctgatag gttccagcct   240
tatatgcagg aggtggtgcc cttcctggcc aggctcagca acaggctaag cacatgtcat   300
attgaaggtg atgacctgca tatccagagg aatgtgcaaa agctgaagga cacagtgaaa   360
aagcttggag agagtggaga gatcaaagca attggagaac tggatttgct gtttatgtct   420

```
ctgagaaatg cctgcattcg cgttgagtcc aaatatggtc ccccatgccc accatgccca    480
gcacctgagt tcctgggggg accatcagtc ttcctgttcc ccccaaaacc caaggacact    540
ctcatgatct cccggacccc tgaggtcacg tgcgtggtgg tggacgtgag ccaggaagac    600
cccgaggtcc agttcaactg gtacgtggat ggcgtggagg tgcataatgc caagacaaag    660
ccgcgggagg agcagttcgc tagcacgtac cgtgtggtca gcgtcctcac cgtcctgcac    720
caggactggc tgaacggcaa ggagtacaag tgcaaggtct ccaacaaagg cctcccgtcc    780
tccatcgaga aaaccatctc caaagccaaa gggcagcccc gagagccaca ggtgtacacc    840
ctgcccccat cccaggagga gatgaccaag aaccaggtca gcctgacctg cctggtcaaa    900
ggcttctacc ccagcgacat cgccgtggag tgggagagca atgggcagcc ggagaacaac    960
tacaagacca cgcctcccgt gctggactcc gacggctcct tcttcctcta cagcaggcta   1020
accgtggaca agagcaggtg gcaggagggg aatgtcttct catgctccgt gatgcatgag   1080
gctctgcaca accactacac acagaagagc ctctccctgt ctctgggtaa a            1131

<210> SEQ ID NO 18
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG4 (full) N297A

<400> SEQUENCE: 18

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Arg Val Glu Ser Lys Tyr Gly Pro Pro Cys Pro Pro Cys Pro
145                 150                 155                 160

Ala Pro Glu Phe Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser Gln Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220
```

Gln Phe Ala Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Gly Leu Pro Ser Ser Ile Glu Lys Thr Ile Ser Lys Ala Lys Gly Gln
            260                 265                 270

Pro Arg Glu Pro Gln Val Tyr Thr Leu Pro Pro Ser Gln Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Arg Leu Thr Val Asp Lys Ser Arg Trp Gln Glu Gly Asn Val
                340                 345                 350

Phe Ser Cys Ser Val Met His Glu Ala Leu His Asn His Tyr Thr Gln
            355                 360                 365

Lys Ser Leu Ser Leu Ser Leu Gly Lys
    370                 375

<210> SEQ ID NO 19
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG1 (full) N297G

<400> SEQUENCE: 19
gcgcccatca gctcccactg caggcttgac aagtccaact tccagcagcc ctatatcacc        60
aaccgcacct tcatgctggc taaggaggct agcttggctg ataacaacac agacgttcgt       120
ctcattgggg agaaactgtt ccacggagtc agtatgagtg agcgctgcta tctgatgaag       180
caggtgctga acttcaccct tgaagaagtg ctgttccctc aatctgatag gttccagcct       240
tatatgcagg aggtggtgcc cttcctggcc aggctcagca acaggctaag cacatgtcat       300
attgaaggtg atgacctgca tatccagagg aatgtgcaaa agctgaagga cacagtgaaa       360
aagcttggag agagtggaga gatcaaagca attggagaac tggatttgct gtttatgtct       420
ctgagaaatg cctgcattga gcccaaatct agtgacaaaa ctcacacatg cccaccgtgc       480
ccagcacctg aactcctggg gggaccgtca gtcttcctct tccccccaaa acccaaggac       540
accctcatga tctcccggac ccctgaggtc acatgcgtgg tggtggacgt gagccacgaa       600
gaccctgagg tcaagttcaa ctggtacgtg gacggcgtgg aggtgcataa tgccaagaca       660
aagccgcggg aggagcagta cggaagcacg taccgtgtgg tcagcgtcct caccgtcctg       720
caccaggact ggctgaatgg caaggagtac aagtgcaagg tctccaacaa agccctccca       780
gcccccatcg agaaaaccat ctccaaagcc aaagggcagc cccgagaacc acaggtgtac       840
accctgcccc catcccggga agagatgacc aagaaccagg tcagcctgac ctgcctggtc       900
aaaggcttct atcccagcga catcgccgtg gagtgggaga gcaatgggca gccggagaac       960
aactacaaga ccacgcctcc cgtgctggac tccgacggct ccttcttcct ctacagcaag      1020
ctcaccgtgg acaagagcag gtggcagcag gggaacgtct tctcatgctc cgtgatgcat      1080
gaggctctgc acaaccacta cacgcagaag agcctctccc tgtctccggg taaa      1134

<210> SEQ ID NO 20
<211> LENGTH: 378
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: IL-22 Fc fusion IgG1 (full) N297G

<400> SEQUENCE: 20

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Glu Pro Lys Ser Ser Asp Lys Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
    210                 215                 220

Glu Gln Tyr Gly Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
            260                 265                 270

Gln Pro Arg Glu Pro Gln Val Tyr Thr Leu Pro Pro Ser Arg Glu Glu
        275                 280                 285

Met Thr Lys Asn Gln Val Ser Leu Thr Cys Leu Val Lys Gly Phe Tyr
    290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
```

```
                    340                 345                 350
Val Phe Ser Cys Ser Val Met His Glu Ala Leu His Asn His Tyr Thr
                355                 360                 365

Gln Lys Ser Leu Ser Leu Ser Pro Gly Lys
        370                 375
```

<210> SEQ ID NO 21
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG1 (full) N297A

<400> SEQUENCE: 21

```
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag     180
caggtgctga acttcaccct tgaagaagtg ctgttccctc aatctgatag gttccagcct     240
tatatgcagg aggtggtgcc cttcctggcc aggctcagca caggctaag cacatgtcat      300
attgaaggtg atgacctgca tatccagagg aatgtgcaaa agctgaagga cacagtgaaa     360
aagcttggag agagtggaga gatcaaagca attggagaac tggatttgct gtttatgtct     420
ctgagaaatg cctgcattga gcccaaatct agtgacaaaa ctcacacatg cccaccgtgc     480
ccagcacctg aactcctggg gggaccgtca gtcttcctct tccccccaaa acccaaggac     540
accctcatga tctcccggac ccctgaggtc acatgcgtgg tggtggacgt gagccacgaa     600
gaccctgagg tcaagttcaa ctggtacgtg gacggcgtgg aggtgcataa tgccaagaca     660
aagccgcggg aggagcagta cgctagcacg taccgtgtgg tcagcgtcct caccgtcctg     720
caccaggact ggctgaatgg caaggagtac aagtgcaagg tctccaacaa agccctccca     780
gcccccatcg agaaaaccat ctccaaagcc aaagggcagc cccgagaacc acaggtgtac     840
accctgcccc catcccggga gagatgacc aagaaccagg tcagcctgac ctgcctggtc      900
aaaggcttct atcccagcga catcgccgtg gagtgggaga gcaatgggca gccggagaac     960
aactacaaga ccacgcctcc cgtgctggac tccgacggct ccttcttcct ctacagcaag    1020
ctcaccgtgg acaagagcag gtggcagcag gggaacgtct tctcatgctc cgtgatgcat    1080
gaggctctgc acaaccacta cacgcagaag agcctctccc tgtctccggg taaa          1134
```

<210> SEQ ID NO 22
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG1 (full) N297A

<400> SEQUENCE: 22

```
Ala Pro Ile Ser Ser His Cys Arg Leu Asp Lys Ser Asn Phe Gln Gln
  1               5                  10                  15

Pro Tyr Ile Thr Asn Arg Thr Phe Met Leu Ala Lys Glu Ala Ser Leu
                 20                  25                  30

Ala Asp Asn Asn Thr Asp Val Arg Leu Ile Gly Glu Lys Leu Phe His
```

```
                35                  40                  45
Gly Val Ser Met Ser Glu Arg Cys Tyr Leu Met Lys Gln Val Leu Asn
 50                  55                  60

Phe Thr Leu Glu Glu Val Leu Phe Pro Gln Ser Asp Arg Phe Gln Pro
 65                  70                  75                  80

Tyr Met Gln Glu Val Val Pro Phe Leu Ala Arg Leu Ser Asn Arg Leu
                 85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile Glu Pro Lys Ser Ser Lys Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
210                 215                 220

Glu Gln Tyr Ala Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
            260                 265                 270

Gln Pro Arg Glu Pro Gln Val Tyr Thr Leu Pro Pro Ser Arg Glu Glu
        275                 280                 285

Met Thr Lys Asn Gln Val Ser Leu Thr Cys Leu Val Lys Gly Phe Tyr
290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
            340                 345                 350

Val Phe Ser Cys Ser Val Met His Glu Ala Leu His Asn His Tyr Thr
        355                 360                 365

Gln Lys Ser Leu Ser Leu Ser Pro Gly Lys
    370                 375

<210> SEQ ID NO 23
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG4 (wt N297, minus Lys)

<400> SEQUENCE: 23
gcgcccatca gctcccactg caggcttgac aagtccaact tccagcagcc ctatatcacc        60
```

```
aaccgcacct tcatgctggc taaggaggct agcttggctg ataacaacac agacgttcgt    120
ctcattgggg agaaactgtt ccacggagtc agtatgagtg agcgctgcta tctgatgaag    180
caggtgctga acttcaccct tgaagaagtg ctgttccctc aatctgatag gttccagcct    240
tatatgcagg aggtggtgcc cttcctggcc aggctcagca acaggctaag cacatgtcat    300
attgaaggtg atgacctgca tatccagagg aatgtgcaaa agctgaagga cacagtgaaa    360
aagcttggag agagtggaga gatcaaagca attggagaac tggatttgct gtttatgtct    420
ctgagaaatg cctgcattcg cgttgagtcc aaatatggtc ccccatgccc accatgccca    480
gcacctgagt tcctgggggg accatcagtc ttcctgttcc ccccaaaacc caaggacact    540
ctcatgatct cccggacccc tgaggtcacg tgcgtggtgg tggacgtgag ccaggaagac    600
cccgaggtcc agttcaactg gtacgtggat ggcgtggagg tgcataatgc caagacaaag    660
ccgcgggagg agcagttcaa cagcacgtac cgtgtggtca gcgtcctcac cgtcctgcac    720
caggactggc tgaacggcaa ggagtacaag tgcaaggtct ccaacaaagg cctcccgtcc    780
tccatcgaga aaaccatctc caaagccaaa gggcagcccc gagagccaca ggtgtacacc    840
ctgcccccat cccaggagga gatgaccaag aaccaggtca gcctgacctg cctggtcaaa    900
ggcttctacc ccagcgacat cgccgtggag tgggagagca atgggcagcc ggagaacaac    960
tacaagacca cgcctcccgt gctggactcc gacggctcct tcttcctcta cagcaggcta   1020
accgtggaca agagcaggtg gcaggagggg aatgtcttct catgctccgt gatgcatgag   1080
gctctgcaca accactacac acagaagagc ctctccctgt ctctgggt                1128
```

<210> SEQ ID NO 24  
<211> LENGTH: 376  
<212> TYPE: PRT  
<213> ORGANISM: Artificial Sequence  
<220> FEATURE:  
<223> OTHER INFORMATION: Description of Artificial Sequence: Synthetic polypeptide  
<220> FEATURE:  
<223> OTHER INFORMATION: IL-22 Fc fusion IgG4 (wt N297, minus Lys)

<400> SEQUENCE: 24

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Arg Val Glu Ser Lys Tyr Gly Pro Pro Cys Pro Pro Cys Pro
145                 150                 155                 160
```

```
Ala Pro Glu Phe Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser Gln Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Phe Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Gly Leu Pro Ser Ser Ile Glu Lys Thr Ile Ser Lys Ala Lys Gly Gln
            260                 265                 270

Pro Arg Glu Pro Gln Val Tyr Thr Leu Pro Pro Ser Gln Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Arg Leu Thr Val Asp Lys Ser Arg Trp Gln Glu Gly Asn Val
            340                 345                 350

Phe Ser Cys Ser Val Met His Glu Ala Leu His Asn His Tyr Thr Gln
        355                 360                 365

Lys Ser Leu Ser Leu Ser Leu Gly
    370                 375

<210> SEQ ID NO 25
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG1 (wt N297, minus Lys)

<400> SEQUENCE: 25
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag     180
caggtgctga acttcaccct tgaagaagtg ctgttccctc aatctgatag gttccagcct     240
tatatgcagg aggtggtgcc cttcctggcc aggctcagca caggctaag cacatgtcat     300 attgaaggtg atgacctgca tatccagagg aatgtgcaaa agctgaagga cagtgaaa      360 aagcttggag agagtggaga gatcaaagca attggagaac tggatttgct gtttatgtct     420
ctgagaaatg cctgcattga gcccaaatct agtgacaaaa ctcacacatg cccaccgtgc     480
ccagcacctg aactcctggg gggaccgtca gtcttcctct tccccccaaa acccaaggac     540
accctcatga tctcccggac ccctgaggtc acatgcgtgg tggtggacgt gagccacgaa     600
gaccctgagg tcaagttcaa ctggtacgtg gacggcgtgg aggtgcataa tgccaagaca     660
aagccgcggg aggagcagta caacagcacg taccgtgtgg tcagcgtcct caccgtcctg     720
```

```
caccaggact ggctgaatgg caaggagtac aagtgcaagg tctccaacaa agccctccca    780
gcccccatcg agaaaccat ctccaaagcc aagggcagc cccgagaacc acaggtgtac       840
accctgcccc catcccggga agagatgacc aagaaccagg tcagcctgac ctgcctggtc    900
aaaggcttct atcccagcga catcgccgtg gagtgggaga gcaatgggca gccggagaac    960
aactacaaga ccacgcctcc cgtgctggac tccgacggct ccttcttcct ctacagcaag   1020
ctcaccgtgg acaagagcag gtggcagcag gggaacgtct tctcatgctc cgtgatgcat   1080
gaggctctgc acaaccacta cacgcagaag agcctctccc tgtctccggg t            1131
```

```
<210> SEQ ID NO 26
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG1 (wt N297, minus Lys)

<400> SEQUENCE: 26
```

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Glu Pro Lys Ser Ser Asp Lys Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
    210                 215                 220

Glu Gln Tyr Asn Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
            260                 265                 270
```

Gln Pro Arg Glu Pro Gln Val Tyr Thr Leu Pro Pro Ser Arg Glu Glu
            275                 280                 285

Met Thr Lys Asn Gln Val Ser Leu Thr Cys Leu Val Lys Gly Phe Tyr
        290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
            340                 345                 350

Val Phe Ser Cys Ser Val Met His Glu Ala Leu His Asn His Tyr Thr
        355                 360                 365

Gln Lys Ser Leu Ser Leu Ser Pro Gly
    370                 375

<210> SEQ ID NO 27
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG4 (N297 wt)

<400> SEQUENCE: 27
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag     180
caggtgctga acttcaccct tgaagaagtg ctgttccctc aatctgatag gttccagcct     240
tatatgcagg aggtggtgcc cttcctggcc aggctcagca caggctaag cacatgtcat     300 attgaaggtg atgacctgca tatccagagg aatgtgcaaa agctgaagga cacagtgaaa     360
aagcttggag agagtggaga gatcaaagca attggagaac tggatttgct gtttatgtct     420
ctgagaaatg cctgcattcg cgttgagtcc aaatatggtc ccccatgccc accatgccca     480
gcacctgagt tcctgggggg accatcagtc ttcctgttcc ccccaaaacc caaggacact     540
ctcatgatct cccggacccc tgaggtcacg tgcgtggtgg tggacgtgag ccaggaagac     600
cccgaggtcc agttcaactg gtacgtggat ggcgtggagg tgcataatgc caagacaaag     660
ccgcgggagg agcagttcaa cagcacgtac cgtgtggtca gcgtcctcac cgtcctgcac     720
caggactggc tgaacggcaa ggagtacaag tgcaaggtct ccaacaaagg cctcccgtcc     780
tccatcgaga aaaccatctc caaagccaaa gggcagcccc gagagccaca ggtgtacacc     840
ctgcccccat cccaggagga tgaccaag aaccaggtca gcctgacctg cctggtcaaa      900
ggcttctacc ccagcgacat cgccgtggag tgggagagca atgggcagcc ggagaacaac     960
tacaagacca cgcctcccgt gctggactcc gacggctcct tcttcctcta cagcaggcta    1020
accgtggaca agagcaggtg gcaggagggg aatgtcttct catgctccgt gatgcatgag    1080
gctctgcaca accactacac acagaagagc ctctccctgt ctctgggtaa a            1131

<210> SEQ ID NO 28
<211> LENGTH: 377
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: IL-22 Fc fusion IgG4 (N297 wt)

<400> SEQUENCE: 28

| Ala | Pro | Ile | Ser | Ser | His | Cys | Arg | Leu | Asp | Lys | Ser | Asn | Phe | Gln | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Pro | Tyr | Ile | Thr | Asn | Arg | Thr | Phe | Met | Leu | Ala | Lys | Glu | Ala | Ser | Leu |
|     |     |     | 20  |     |     |     |     | 25  |     |     |     |     | 30  |     |     |

| Ala | Asp | Asn | Asn | Thr | Asp | Val | Arg | Leu | Ile | Gly | Glu | Lys | Leu | Phe | His |
|     |     |     | 35  |     |     |     |     | 40  |     |     |     |     | 45  |     |     |

| Gly | Val | Ser | Met | Ser | Glu | Arg | Cys | Tyr | Leu | Met | Lys | Gln | Val | Leu | Asn |
|     |     | 50  |     |     |     |     | 55  |     |     |     |     | 60  |     |     |     |

| Phe | Thr | Leu | Glu | Glu | Val | Leu | Phe | Pro | Gln | Ser | Asp | Arg | Phe | Gln | Pro |
| 65  |     |     |     |     | 70  |     |     |     |     | 75  |     |     |     |     | 80  |

| Tyr | Met | Gln | Glu | Val | Val | Pro | Phe | Leu | Ala | Arg | Leu | Ser | Asn | Arg | Leu |
|     |     |     |     | 85  |     |     |     |     | 90  |     |     |     |     | 95  |     |

| Ser | Thr | Cys | His | Ile | Glu | Gly | Asp | Asp | Leu | His | Ile | Gln | Arg | Asn | Val |
|     |     |     | 100 |     |     |     |     | 105 |     |     |     |     | 110 |     |     |

| Gln | Lys | Leu | Lys | Asp | Thr | Val | Lys | Lys | Leu | Gly | Glu | Ser | Gly | Glu | Ile |
|     |     |     | 115 |     |     |     |     | 120 |     |     |     |     | 125 |     |     |

| Lys | Ala | Ile | Gly | Glu | Leu | Asp | Leu | Leu | Phe | Met | Ser | Leu | Arg | Asn | Ala |
| 130 |     |     |     |     | 135 |     |     |     |     | 140 |     |     |     |     |     |

| Cys | Ile | Arg | Val | Glu | Ser | Lys | Tyr | Gly | Pro | Pro | Cys | Pro | Pro | Cys | Pro |
| 145 |     |     |     |     | 150 |     |     |     |     | 155 |     |     |     |     | 160 |

| Ala | Pro | Glu | Phe | Leu | Gly | Gly | Pro | Ser | Val | Phe | Leu | Phe | Pro | Pro | Lys |
|     |     |     |     | 165 |     |     |     |     | 170 |     |     |     |     | 175 |     |

| Pro | Lys | Asp | Thr | Leu | Met | Ile | Ser | Arg | Thr | Pro | Glu | Val | Thr | Cys | Val |
|     |     |     | 180 |     |     |     |     | 185 |     |     |     |     | 190 |     |     |

| Val | Val | Asp | Val | Ser | Gln | Glu | Asp | Pro | Glu | Val | Gln | Phe | Asn | Trp | Tyr |
|     |     | 195 |     |     |     |     | 200 |     |     |     |     | 205 |     |     |     |

| Val | Asp | Gly | Val | Glu | Val | His | Asn | Ala | Lys | Thr | Lys | Pro | Arg | Glu | Glu |
|     | 210 |     |     |     |     | 215 |     |     |     |     | 220 |     |     |     |     |

| Gln | Phe | Asn | Ser | Thr | Tyr | Arg | Val | Val | Ser | Val | Leu | Thr | Val | Leu | His |
| 225 |     |     |     |     | 230 |     |     |     |     | 235 |     |     |     |     | 240 |

| Gln | Asp | Trp | Leu | Asn | Gly | Lys | Glu | Tyr | Lys | Cys | Lys | Val | Ser | Asn | Lys |
|     |     |     |     | 245 |     |     |     |     | 250 |     |     |     |     | 255 |     |

| Gly | Leu | Pro | Ser | Ser | Ile | Glu | Lys | Thr | Ile | Ser | Lys | Ala | Lys | Gly | Gln |
|     |     |     | 260 |     |     |     |     | 265 |     |     |     |     | 270 |     |     |

| Pro | Arg | Glu | Pro | Gln | Val | Tyr | Thr | Leu | Pro | Pro | Ser | Gln | Glu | Glu | Met |
|     |     | 275 |     |     |     |     | 280 |     |     |     |     | 285 |     |     |     |

| Thr | Lys | Asn | Gln | Val | Ser | Leu | Thr | Cys | Leu | Val | Lys | Gly | Phe | Tyr | Pro |
|     | 290 |     |     |     |     | 295 |     |     |     |     | 300 |     |     |     |     |

| Ser | Asp | Ile | Ala | Val | Glu | Trp | Glu | Ser | Asn | Gly | Gln | Pro | Glu | Asn | Asn |
| 305 |     |     |     |     | 310 |     |     |     |     | 315 |     |     |     |     | 320 |

| Tyr | Lys | Thr | Thr | Pro | Pro | Val | Leu | Asp | Ser | Asp | Gly | Ser | Phe | Phe | Leu |
|     |     |     |     | 325 |     |     |     |     | 330 |     |     |     |     | 335 |     |

| Tyr | Ser | Arg | Leu | Thr | Val | Asp | Lys | Ser | Arg | Trp | Gln | Glu | Gly | Asn | Val |
|     |     |     | 340 |     |     |     |     | 345 |     |     |     |     | 350 |     |     |

| Phe | Ser | Cys | Ser | Val | Met | His | Glu | Ala | Leu | His | Asn | His | Tyr | Thr | Gln |
|     |     | 355 |     |     |     |     | 360 |     |     |     |     | 365 |     |     |     |

| Lys | Ser | Leu | Ser | Leu | Ser | Leu | Gly | Lys |
|     | 370 |     |     |     |     | 375 |     |     |

<210> SEQ ID NO 29
<211> LENGTH: 1134
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: IL-22 Fc fusion IgG1 (N297 wt)

<400> SEQUENCE: 29

```
gcgcccatca gctcccactg caggcttgac aagtccaact tccagcagcc ctatatcacc    60
aaccgcacct tcatgctggc taaggaggct agcttggctg ataacaacac agacgttcgt   120
ctcattgggg agaaactgtt ccacggagtc agtatgagtg agcgctgcta tctgatgaag   180
caggtgctga acttcaccct tgaagaagtg ctgttccctc aatctgatag gttccagcct   240
tatatgcagg aggtggtgcc cttcctggcc aggctcagca caggctaag cacatgtcat   300
attgaaggtg atgacctgca tatccagagg aatgtgcaaa agctgaagga cagtgaaaa   360
aagcttggag agagtggaga gatcaaagca attggagaac tggatttgct gtttatgtct   420
ctgagaaatg cctgcattga gcccaaatct agtgacaaaa ctcacacatg cccaccgtgc   480
ccagcacctg aactcctggg gggaccgtca gtcttcctct tccccccaaa acccaaggac   540
accctcatga tctcccggac ccctgaggtc acatgcgtgg tggtggacgt gagccacgaa   600
gaccctgagg tcaagttcaa ctggtacgtg gacggcgtgg aggtgcataa tgccaagaca   660
aagccgcggg aggagcagta caacagcacg taccgtgtgg tcagcgtcct caccgtcctg   720
caccaggact ggctgaatgg caaggagtac aagtgcaagg tctccaacaa agccctccca   780
gcccccatcg agaaaaccat ctccaaagcc aaagggcagc cccgagaacc acaggtgtac   840
accctgcccc catcccggga agagatgacc aagaaccagg tcagcctgac ctgcctggtc   900
aaaggcttct atcccagcga catcgccgtg gagtgggaga gcaatgggca gccggagaac   960
aactacaaga ccacgcctcc cgtgctggac tccgacggct ccttcttcct ctacagcaag  1020
ctcaccgtgg acaagagcag gtggcagcag gggaacgtct tctcatgctc cgtgatgcat  1080
gaggctctgc acaaccacta cacgcagaag agcctctccc tgtctccggg taaa         1134
```

<210> SEQ ID NO 30
<211> LENGTH: 378
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: IL-22 Fc fusion IgG1 (N297 wt)

<400> SEQUENCE: 30

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
```

-continued

```
                85                  90                  95
Ser Thr Cys His Ile Glu Gly Asp Asp Leu His Ile Gln Arg Asn Val
            100                 105                 110
Gln Lys Leu Lys Asp Thr Val Lys Leu Gly Glu Ser Gly Glu Ile
            115                 120                 125
Lys Ala Ile Gly Glu Leu Asp Leu Leu Phe Met Ser Leu Arg Asn Ala
            130                 135                 140
Cys Ile Glu Pro Lys Ser Ser Asp Lys Thr His Thr Cys Pro Pro Cys
145                 150                 155                 160
Pro Ala Pro Glu Leu Leu Gly Gly Pro Ser Val Phe Leu Phe Pro Pro
                165                 170                 175
Lys Pro Lys Asp Thr Leu Met Ile Ser Arg Thr Pro Glu Val Thr Cys
                180                 185                 190
Val Val Val Asp Val Ser His Glu Asp Pro Glu Val Lys Phe Asn Trp
            195                 200                 205
Tyr Val Asp Gly Val Glu Val His Asn Ala Lys Thr Lys Pro Arg Glu
            210                 215                 220
Glu Gln Tyr Asn Ser Thr Tyr Arg Val Val Ser Val Leu Thr Val Leu
225                 230                 235                 240
His Gln Asp Trp Leu Asn Gly Lys Glu Tyr Lys Cys Lys Val Ser Asn
                245                 250                 255
Lys Ala Leu Pro Ala Pro Ile Glu Lys Thr Ile Ser Lys Ala Lys Gly
                260                 265                 270
Gln Pro Arg Glu Pro Gln Val Tyr Thr Leu Pro Pro Ser Arg Glu Glu
            275                 280                 285
Met Thr Lys Asn Gln Val Ser Leu Thr Cys Leu Val Lys Gly Phe Tyr
            290                 295                 300
Pro Ser Asp Ile Ala Val Glu Trp Glu Ser Asn Gly Gln Pro Glu Asn
305                 310                 315                 320
Asn Tyr Lys Thr Thr Pro Pro Val Leu Asp Ser Asp Gly Ser Phe Phe
                325                 330                 335
Leu Tyr Ser Lys Leu Thr Val Asp Lys Ser Arg Trp Gln Gln Gly Asn
                340                 345                 350
Val Phe Ser Cys Ser Val Met His Glu Ala Leu His Asn His Tyr Thr
            355                 360                 365
Gln Lys Ser Leu Ser Leu Ser Pro Gly Lys
            370                 375

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      hinge peptide

<400> SEQUENCE: 31

Cys Pro Pro Cys Pro
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide
```

```
<400> SEQUENCE: 32

Asp Lys Thr His Thr
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 33

Glu Pro Lys Ser Cys Asp Lys Thr His Thr
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 34

Val Glu Pro Lys Ser Cys Asp Lys Thr His Thr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 35

Lys Val Glu Pro Lys Ser Cys Asp Lys Thr His Thr
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 36

Lys Lys Val Glu Pro Lys Ser Cys Asp Lys Thr His Thr
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 37

Asp Lys Lys Val Glu Pro Lys Ser Cys Asp Lys Thr His Thr
1               5                   10

<210> SEQ ID NO 38
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      linker peptide

<400> SEQUENCE: 38

Val Asp Lys Lys Val Glu Pro Lys Ser Cys Asp Lys Thr His Thr
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 39

Lys Val Asp Lys Lys Val Glu Pro Lys Ser Cys Asp Lys Thr His Thr
1               5                   10                  15

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 40

Glu Pro Lys Ser Ser Asp Lys Thr His Thr
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 41

Gly Gly Gly Asp Lys Thr His Thr
1               5

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      linker (IgG3) peptide

<400> SEQUENCE: 42

Glu Leu Lys Thr Pro Leu Gly Asp Thr Thr His Thr
1               5                   10

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 43

Ser Lys Tyr Gly Pro Pro
1               5
```

```
<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 44

Arg Val Glu Ser Lys Tyr Gly Pro Pro
1               5

<210> SEQ ID NO 45
<211> LENGTH: 3
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 45

Gly Gly Ser
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 46

Gly Gly Gly Ser
1

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 47

Gly Gly Gly Gly Ser
1               5

<210> SEQ ID NO 48
<211> LENGTH: 146
<212> TYPE: PRT
<213> ORGANISM: Pan troglodytes

<400> SEQUENCE: 48

Ala Pro Ile Ser Ser His Cys Arg Leu Asp Lys Ser Ser Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80
```

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Asn Gly Glu Ile
        115                 120                 125

Lys Ala Ile Gly Glu Leu Asp Leu Leu Phe Met Ser Leu Arg Asn Ala
130                 135                 140

Cys Ile
145

<210> SEQ ID NO 49
<211> LENGTH: 146
<212> TYPE: PRT
<213> ORGANISM: Pongo abelii

<400> SEQUENCE: 49

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile
145

<210> SEQ ID NO 50
<211> LENGTH: 146
<212> TYPE: PRT
<213> ORGANISM: Mus musculus

<400> SEQUENCE: 50

Leu Pro Val Asn Thr Arg Cys Lys Leu Glu Val Ser Asn Phe Gln Gln
1               5                   10                  15

Pro Tyr Ile Val Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
        35                  40                  45

Gly Val Ser Ala Lys Asp Gln Cys Tyr Leu Met Lys Gln Val Leu Asn
    50                  55                  60

Phe Thr Leu Glu Asp Val Leu Leu Pro Gln Ser Asp Arg Phe Gln Pro
65                  70                  75                  80

Tyr Met Gln Glu Val Val Pro Phe Leu Thr Lys Leu Ser Asn Gln Leu
                85                  90                  95

Ser Ser Cys His Ile Ser Gly Asp Asp Gln Asn Ile Gln Lys Asn Val
            100                 105                 110

Arg Arg Leu Lys Glu Thr Val Lys Leu Gly Ser Gly Glu Ile
        115                 120                 125

Lys Ala Ile Gly Glu Leu Asp Leu Leu Phe Met Ser Leu Arg Asn Ala
    130                 135                 140

Cys Val
145

<210> SEQ ID NO 51
<211> LENGTH: 146
<212> TYPE: PRT
<213> ORGANISM: Canis familiaris

<400> SEQUENCE: 51

Leu Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Asn Met Gly Glu Arg Cys Tyr Leu Met Lys Glu Val Leu Asn
50                  55                  60

Phe Thr Leu Glu Glu Val Leu Leu Pro Gln Ser Asp Arg Phe Gln Pro
65                  70                  75                  80

Tyr Met Gln Glu Val Val Pro Phe Leu Ala Arg Leu Ser Asn Lys Leu
                85                  90                  95

Ser Gln Cys His Ile Glu Asn Asp Asp Gln His Ile Gln Arg Asn Val
            100                 105                 110

Gln Lys Leu Lys Asp Thr Val Gln Lys Leu Gly Glu Asn Gly Glu Ile
        115                 120                 125

Lys Ala Ile Gly Glu Leu Asp Leu Leu Phe Met Ala Leu Arg Asn Ala
    130                 135                 140

Cys Val
145

<210> SEQ ID NO 52
<211> LENGTH: 94
<212> TYPE: DNA
<213> ORGANISM: Artificial Sequence
<220> FEATURE:
<223> OTHER INFORMATION: Description of Artificial Sequence: Synthetic
      IL-22 Fc fusion protein IgG1 forward primer

<400> SEQUENCE: 52
ttgaattcca ccatgggatg gtcatgtatc atcctttttc tagtagcaac tgcaactgga      60
gtacattcag cgcccatcag ctcccactgc aggc                                  94

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence: Synthetic
      IL-22 Fc fusion IgG1 reverse primer

<400> SEQUENCE: 53
aggtcgactc atttacccgg agacagggag agg                                   33

<210> SEQ ID NO 54
<211> LENGTH: 94
<212> TYPE: DNA
<213> ORGANISM: Artificial Sequence
<220> FEATURE:
<223> OTHER INFORMATION: Description of Artificial Sequence: Synthetic
    IL-22 Fc fusion IgG4 forward primer

<400> SEQUENCE: 54
ttgaattcca ccatgggatg gtcatgtatc atccttttc tagtagcaac tgcaactgga    60
gtacattcag cgcccatcag ctcccactgc aggc    94

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
    IL-22 Fc fusion IgG4 reverse primer

<400> SEQUENCE: 55
aggtcgactt atttacccag agacagggag agg    33

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
    IgG1 N297G forward primer

<400> SEQUENCE: 56
gcgggaggag cagtacggaa gcacgtaccg tgtgg    35

<210> SEQ ID NO 57
<211> LENGTH: 35
<212> TYPE: DNA
<213> ORGANISM: Artificial Sequence
<220> FEATURE:
<223> OTHER INFORMATION: Description of Artificial Sequence: Synthetic
    IgG1 N297G reverse primer

<400> SEQUENCE: 57
ccacacggta cgtgcttccg tactgctcct cccgc    35

<210> SEQ ID NO 58
<211> LENGTH: 51
<212> TYPE: DNA
<213> ORGANISM: Artificial Sequence
<220> FEATURE:
<223> OTHER INFORMATION: Description of Artificial Sequence: Synthetic
    IgG4 N297G forward primer

<400> SEQUENCE: 58
acaaagccgc gggaggagca gttcggaagc acgtaccgtg tggtcagcgt c    51

<210> SEQ ID NO 59
<211> LENGTH: 51
<212> TYPE: DNA
<213> ORGANISM: Artificial Sequence
<220> FEATURE:
<223> OTHER INFORMATION: Description of Artificial Sequence: Synthetic
    IgG4 N297G reverse primer

<400> SEQUENCE: 59
gacgctgacc acacggtacg tgcttccgaa ctgctcctcc cgcggctttg t    51

<210> SEQ ID NO 60
<211> LENGTH: 411
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: IL-22 Fc fusion IgG2a

<400> SEQUENCE: 60

```
Met Ala Val Leu Gln Lys Ser Met Ser Phe Ser Leu Met Gly Thr Leu
1               5                   10                  15

Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
    130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val Ala Arg Gly Pro Thr Ile Lys Pro Cys Pro Pro Cys Lys
            180                 185                 190

Cys Pro Ala Pro Asn Leu Leu Gly Gly Pro Ser Val Phe Ile Phe Pro
        195                 200                 205

Pro Lys Ile Lys Asp Val Leu Met Ile Ser Leu Ser Pro Ile Val Thr
    210                 215                 220

Cys Val Val Val Asp Val Ser Glu Asp Asp Pro Asp Val Gln Ile Ser
225                 230                 235                 240

Trp Phe Val Asn Asn Val Glu Val His Thr Ala Gln Thr Gln Thr His
                245                 250                 255

Arg Glu Asp Tyr Asn Ser Thr Leu Arg Val Val Ser Ala Leu Pro Ile
            260                 265                 270

Gln His Gln Asp Trp Met Ser Gly Lys Glu Phe Lys Cys Lys Val Asn
        275                 280                 285

Asn Lys Asp Leu Pro Ala Pro Ile Glu Arg Thr Ile Ser Lys Pro Lys
    290                 295                 300

Gly Ser Val Arg Ala Pro Gln Val Tyr Val Leu Pro Pro Pro Glu Glu
305                 310                 315                 320

Glu Met Thr Lys Lys Gln Val Thr Leu Thr Cys Met Val Thr Asp Phe
                325                 330                 335

Met Pro Glu Asp Ile Tyr Val Glu Trp Thr Asn Asn Gly Lys Thr Glu
            340                 345                 350
```

```
Leu Asn Tyr Lys Asn Thr Glu Pro Val Leu Asp Ser Asp Gly Ser Tyr
        355                 360                 365

Phe Met Tyr Ser Lys Leu Arg Val Glu Lys Lys Asn Trp Val Glu Arg
370                 375                 380

Asn Ser Tyr Ser Cys Ser Val Val His Glu Gly Leu His Asn His His
385                 390                 395                 400

Thr Thr Lys Ser Phe Ser Arg Thr Pro Gly Lys
            405                 410

<210> SEQ ID NO 61
<211> LENGTH: 372
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 IgG1 fusion knob (T366W) minus Lys

<400> SEQUENCE: 61

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Glu Glu Met Thr Lys Asn Gln
        275                 280                 285
```

-continued

```
Val Ser Leu Trp Cys Leu Val Lys Gly Phe Tyr Pro Ser Asp Ile Ala
    290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
            325                 330                 335

Thr Val Asp Lys Ser Arg Trp Gln Gln Gly Asn Val Phe Ser Cys Ser
        340                 345                 350

Val Met His Glu Ala Leu His Asn His Tyr Thr Gln Lys Ser Leu Ser
    355                 360                 365

Leu Ser Pro Gly
    370

<210> SEQ ID NO 62
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Monomeric Fc hole

<400> SEQUENCE: 62

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 63
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 63

Gly Gly Gly Ser Thr His Thr
1               5

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 64

Asp Lys Lys Val Glu Pro Lys Ser Ser Asp Lys Thr His Thr
1               5                   10

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 65

Lys Val Asp Lys Lys Val Glu Pro Lys Ser Ser Asp Lys Thr His Thr
1               5                   10                  15

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 66

Lys Lys Val Glu Pro Lys Ser Ser Asp Lys Thr His Thr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 67

Val Glu Pro Lys Ser Ser Asp Lys Thr His Thr
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 68
```

```
Lys Val Glu Pro Lys Ser Ser Asp Lys Thr His Thr
1               5                   10
```

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 69

```
Val Asp Lys Lys Val Glu Pro Lys Ser Ser Asp Lys Thr His Thr
1               5                   10                  15
```

<210> SEQ ID NO 70
<211> LENGTH: 1152
<212> TYPE: DNA
<213> ORGANISM: Homo sapiens
<220> FEATURE:
<221> NAME/KEY: CDS
<222> LOCATION: (58)..(597)

<400> SEQUENCE: 70

```
cttcagaaca ggttctcctt ccccagtcac cagttgctcg agttagaatt gtctgca           57 atg gcc gcc ctg cag aaa tct gtg agc tct ttc ctt atg ggg acc ctg         105
Met Ala Ala Leu Gln Lys Ser Val Ser Ser Phe Leu Met Gly Thr Leu
1               5                   10                  15 gcc acc agc tgc ctc ctt ctc ttg gcc ctc ttg gta cag gga gga gca         153
Ala Thr Ser Cys Leu Leu Leu Ala Leu Leu Val Gln Gly Gly Ala
                20                  25                  30 gct gcg ccc atc agc tcc cac tgc agg ctt gac aag tcc aac ttc cag         201
Ala Ala Pro Ile Ser Ser His Cys Arg Leu Asp Lys Ser Asn Phe Gln
            35                  40                  45 cag ccc tat atc acc aac cgc acc ttc atg ctg gct aag gag gct agc         249
Gln Pro Tyr Ile Thr Asn Arg Thr Phe Met Leu Ala Lys Glu Ala Ser
        50                  55                  60 ttg gct gat aac aac aca gac gtt cgt ctc att ggg gag aaa ctg ttc         297
Leu Ala Asp Asn Asn Thr Asp Val Arg Leu Ile Gly Glu Lys Leu Phe
65                  70                  75                  80 cac gga gtc agt atg agt gag cgc tgc tat ctg atg aag cag gtg ctg         345
His Gly Val Ser Met Ser Glu Arg Cys Tyr Leu Met Lys Gln Val Leu
                85                  90                  95 aac ttc acc ctt gaa gaa gtg ctg ttc cct caa tct gat agg ttc cag         393
Asn Phe Thr Leu Glu Glu Val Leu Phe Pro Gln Ser Asp Arg Phe Gln
            100                 105                 110 cct tat atg cag gag gtg gtg ccc ttc ctg gcc agg ctc agc aac agg         441
Pro Tyr Met Gln Glu Val Val Pro Phe Leu Ala Arg Leu Ser Asn Arg
        115                 120                 125 cta agc aca tgt cat att gaa ggt gat gac ctg cat atc cag agg aat         489
Leu Ser Thr Cys His Ile Glu Gly Asp Asp Leu His Ile Gln Arg Asn
    130                 135                 140 gtg caa aag ctg aag gac aca gtg aaa aag ctt gga gag agt gga gag         537
Val Gln Lys Leu Lys Asp Thr Val Lys Lys Leu Gly Glu Ser Gly Glu
145                 150                 155                 160 atc aaa gca att gga gaa ctg gat ttg ctg ttt atg tct ctg aga aat         585
Ile Lys Ala Ile Gly Glu Leu Asp Leu Leu Phe Met Ser Leu Arg Asn
                165                 170                 175 gcc tgc att tga ccagagcaaa gctgaaaaat gaataactaa ccccctttcc             637
Ala Cys Ile ctgctagaaa taacaattag atgccccaaa gcgatttttt ttaaccaaaa ggaagatggg       697
```

| | |
|---|---|
| aagccaaact ccatcatgat gggtggattc caaatgaacc cctgcgttag ttacaaagga | 757 |
| aaccaatgcc actttgttt ataagaccag aaggtagact ttctaagcat agatattat | 817 |
| tgataacatt tcattgtaac tggtgttcta tacacagaaa acaatttatt ttttaaataa | 877 |
| ttgtcttttt ccataaaaaa gattactttc cattcctta ggggaaaaaa cccctaaata | 937 |
| gcttcatgtt tccataatca gtactttata tttataaatg tatttattat tattataaga | 997 |
| ctgcattta tttatatcat tttattaata tggatttatt tatagaaaca tcattcgata | 1057 |
| ttgctacttg agtgtaaggc taatattgat atttatgaca ataattatag agctataaca | 1117 |
| tgtttatttg acctcaataa acacttggat atccc | 1152 |

<210> SEQ ID NO 71
<211> LENGTH: 179
<212> TYPE: PRT
<213> ORGANISM: Homo sapiens

<400> SEQUENCE: 71

Met Ala Ala Leu Gln Lys Ser Val Ser Ser Phe Leu Met Gly Thr Leu
1               5                   10                  15

Ala Thr Ser Cys Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile

<210> SEQ ID NO 72
<211> LENGTH: 1236
<212> TYPE: DNA
<213> ORGANISM: Artificial Sequence
<220> FEATURE:
<223> OTHER INFORMATION: Synthetic polypeptide

<400> SEQUENCE: 72

| | |
|---|---|
| atggctgtcc tgcagaaatc tatgagtttt tcccttatgg ggactttggc cgccagctgc | 60 |
| ctgcttctca ttgccctgtg ggcccaggag gcaaatgcgc tgcccgtcaa cacccggtgc | 120 |
| aagcttgagg tgtccaactt ccagcagcca tacatcgtca accgcacctt tatgctggcc | 180 |
| aaggaggcca gccttgcaga taacaacaca gatgtccggc tcatcgggga gaaactgttc | 240 |
| cgaggagtca gtgctaagga tcagtgctac ctgatgaagc aggtgctcaa cttcaccctg | 300 |

-continued

```
gaagacgttc tgctccccca gtcagacagg ttccagccct acatgcagga ggtggtgcct    360
ttcctgacca aactcagcaa tcagctcagc tcctgtcaca tcagcggtga cgaccagaac    420
atccagaaga atgtcagaag gctgaaggag acagtgaaaa agcttggaga gagtggagag    480
atcaaggcga ttggggaact ggacctgctg tttatgtctc tgagaaatgc ttgcgtcgct    540
cgaggaccca caatcaagcc ctgtcctcca tgcaaatgcc cagcacctaa cctcttgggt    600
ggaccatccg tcttcatctt ccctccaaag atcaaggatg tactcatgat ctccctgagc    660
cccatagtca catgtgtggt ggtggatgtg agcgaggatg acccagatgt ccagatcagc    720
tggtttgtga acaacgtgga agtacacaca gctcagacac aaacccatag agaggattac    780
aacagtactc tacgcgtggt cagtgccctc cccatccagc accaggactg gatgagtggc    840
aaggagttca atgcaaggt caacaacaaa gacctcccag cgcccatcga gagaaccatc    900
tcaaaaccca agggtcagt aagagctcca caggtatatg tcttgcctcc accagaagaa    960
gagatgacta agaaacaggt cactctgacc tgcatggtca cagacttcat gcctgaagac    1020
atttacgtgg agtggaccaa caacgggaaa acagagctaa actacaagaa cactgaacca    1080
gtcctggact ctgatggttc ttacttcatg tacagcaagc tgagagtgga aaagaagaac    1140
tgggtggaaa gaaatagcta ctcctgttca gtggtccacg agggtctgca caatcaccac    1200
acgactaaga gcttctcccg gactccgggt aaatga                              1236
```

<210> SEQ ID NO 73
<211> LENGTH: 411
<212> TYPE: PRT
<213> ORGANISM: Artificial Sequence
<220> FEATURE:
<223> OTHER INFORMATION: Synthetic polypeptide

<400> SEQUENCE: 73

```
Met Ala Val Leu Gln Lys Ser Met Ser Phe Ser Leu Met Gly Thr Leu
1               5                   10                  15

Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
    130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val Ala Arg Gly Pro Thr Ile Lys Pro Cys Pro Pro Cys Lys
            180                 185                 190

Cys Pro Ala Pro Asn Leu Leu Gly Gly Pro Ser Val Phe Ile Phe Pro
```

```
            195                 200                 205
Pro Lys Ile Lys Asp Val Leu Met Ile Ser Leu Ser Pro Ile Val Thr
    210                 215                 220
Cys Val Val Asp Val Ser Glu Asp Pro Asp Val Gln Ile Ser
225                 230                 235                 240
Trp Phe Val Asn Asn Val Glu Val His Thr Ala Gln Thr Gln Thr His
                245                 250                 255
Arg Glu Asp Tyr Asn Ser Thr Leu Arg Val Val Ser Ala Leu Pro Ile
            260                 265                 270
Gln His Gln Asp Trp Met Ser Gly Lys Glu Phe Lys Cys Lys Val Asn
        275                 280                 285
Asn Lys Asp Leu Pro Ala Pro Ile Glu Arg Thr Ile Ser Lys Pro Lys
    290                 295                 300
Gly Ser Val Arg Ala Pro Gln Val Tyr Val Leu Pro Pro Pro Glu Glu
305                 310                 315                 320
Glu Met Thr Lys Lys Gln Val Thr Leu Thr Cys Met Val Thr Asp Phe
                325                 330                 335
Met Pro Glu Asp Ile Tyr Val Glu Trp Thr Asn Asn Gly Lys Thr Glu
            340                 345                 350
Leu Asn Tyr Lys Asn Thr Glu Pro Val Leu Asp Ser Asp Gly Ser Tyr
        355                 360                 365
Phe Met Tyr Ser Lys Leu Arg Val Glu Lys Lys Asn Trp Val Glu Arg
    370                 375                 380
Asn Ser Tyr Ser Cys Ser Val Val His Glu Gly Leu His Asn His His
385                 390                 395                 400
Thr Thr Lys Ser Phe Ser Arg Thr Pro Gly Lys
                405                 410

<210> SEQ ID NO 74
<211> LENGTH: 20
<212> TYPE: DNA
<213> ORGANISM: Artificial Sequence
<220> FEATURE:
<223> OTHER INFORMATION: Synthetic primer

<400> SEQUENCE: 74
aggtccattc agatgctggt                                             20

<210> SEQ ID NO 75
<211> LENGTH: 20
<212> TYPE: DNA
<213> ORGANISM: Artificial Sequence
<220> FEATURE:
<223> OTHER INFORMATION: Synthetic primer

<400> SEQUENCE: 75
taggtgtggt tgacgtggag                                             20

<210> SEQ ID NO 76
<211> LENGTH: 20
<212> TYPE: DNA
<213> ORGANISM: Artificial Sequence
<220> FEATURE:
<223> OTHER INFORMATION: Synthetic primer

<400> SEQUENCE: 76
ccaccccaca ctcacaccgg                                             20

<210> SEQ ID NO 77
```

```
<211> LENGTH: 177
<212> TYPE: PRT
<213> ORGANISM: Homo sapiens

<400> SEQUENCE: 77

Met Lys Leu Gln Cys Val Ser Leu Trp Leu Leu Gly Thr Ile Leu Ile
1               5                   10                  15

Leu Cys Ser Val Asp Asn His Gly Leu Arg Arg Cys Leu Ile Ser Thr
                20                  25                  30

Asp Met His His Ile Glu Glu Ser Phe Gln Glu Ile Lys Arg Ala Ile
                35                  40                  45

Gln Ala Lys Asp Thr Phe Pro Asn Val Thr Ile Leu Ser Thr Leu Glu
50                  55                  60

Thr Leu Gln Ile Ile Lys Pro Leu Asp Val Cys Cys Val Thr Lys Asn
65                  70                  75                  80

Leu Leu Ala Phe Tyr Val Asp Arg Val Phe Lys Asp His Gln Glu Pro
                85                  90                  95

Asn Pro Lys Ile Leu Arg Lys Ile Ser Ser Ile Ala Asn Ser Phe Leu
                100                 105                 110

Tyr Met Gln Lys Thr Leu Arg Gln Cys Gln Glu Gln Arg Gln Cys His
                115                 120                 125

Cys Arg Gln Glu Ala Thr Asn Ala Thr Arg Val Ile His Asp Asn Tyr
130                 135                 140

Asp Gln Leu Glu Val His Ala Ala Ala Ile Lys Ser Leu Gly Glu Leu
145                 150                 155                 160

Asp Val Phe Leu Ala Trp Ile Asn Lys Asn His Glu Val Met Ser Ser
                165                 170                 175

Ala

<210> SEQ ID NO 78
<211> LENGTH: 176
<212> TYPE: PRT
<213> ORGANISM: Homo sapiens

<400> SEQUENCE: 78

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
                20                  25                  30

Cys Val Ile Ala Thr Asn Leu Gln Glu Ile Arg Asn Gly Phe Ser Glu
                35                  40                  45

Ile Arg Gly Ser Val Gln Ala Lys Asp Gly Asn Ile Asp Ile Arg Ile
50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
                100                 105                 110

Ala Asn Ser Phe Leu Thr Ile Lys Lys Asp Leu Arg Leu Cys His Ala
                115                 120                 125

His Met Thr Cys His Cys Gly Glu Glu Ala Met Lys Lys Tyr Ser Gln
130                 135                 140

Ile Leu Ser His Phe Glu Lys Leu Glu Pro Gln Ala Ala Val Val Lys
145                 150                 155                 160
```

```
Ala Leu Gly Glu Leu Asp Ile Leu Leu Gln Trp Met Glu Glu Thr Glu
                165                 170                 175
```

```
<210> SEQ ID NO 79
<211> LENGTH: 207
<212> TYPE: PRT
<213> ORGANISM: Homo sapiens

<400> SEQUENCE: 79
```

```
Met Asn Phe Gln Gln Arg Leu Gln Ser Leu Trp Thr Leu Ala Ser Arg
1               5                   10                  15

Pro Phe Cys Pro Pro Leu Leu Ala Thr Ala Ser Gln Met Gln Met Val
                20                  25                  30

Val Leu Pro Cys Leu Gly Phe Thr Leu Leu Leu Trp Ser Gln Val Ser
            35                  40                  45

Gly Ala Gln Gly Gln Glu Phe His Phe Gly Pro Cys Gln Val Lys Gly
    50                  55                  60

Val Val Pro Gln Lys Leu Trp Glu Ala Phe Trp Ala Val Lys Asp Thr
65                  70                  75                  80

Met Gln Ala Gln Asp Asn Ile Thr Ser Ala Arg Leu Leu Gln Gln Glu
                85                  90                  95

Val Leu Gln Asn Val Ser Asp Ala Glu Ser Cys Tyr Leu Val His Thr
                100                 105                 110

Leu Leu Glu Phe Tyr Leu Lys Thr Val Phe Lys Asn Tyr His Asn Arg
            115                 120                 125

Thr Val Glu Val Arg Thr Leu Lys Ser Phe Ser Thr Leu Ala Asn Asn
    130                 135                 140

Phe Val Leu Ile Val Ser Gln Leu Gln Pro Ser Gln Glu Asn Glu Met
145                 150                 155                 160

Phe Ser Ile Arg Asp Ser Ala His Arg Arg Phe Leu Leu Phe Arg Arg
                165                 170                 175

Ala Phe Lys Gln Leu Asp Val Glu Ala Ala Leu Thr Lys Ala Leu Gly
                180                 185                 190

Glu Val Asp Ile Leu Leu Thr Trp Met Gln Lys Phe Tyr Lys Leu
            195                 200                 205
```

```
<210> SEQ ID NO 80
<211> LENGTH: 171
<212> TYPE: PRT
<213> ORGANISM: Homo sapiens

<400> SEQUENCE: 80
```

```
Met Leu Val Asn Phe Ile Leu Arg Cys Gly Leu Leu Leu Val Thr Leu
1               5                   10                  15

Ser Leu Ala Ile Ala Lys His Lys Gln Ser Ser Phe Thr Lys Ser Cys
                20                  25                  30

Tyr Pro Arg Gly Thr Leu Ser Gln Ala Val Asp Ala Leu Tyr Ile Lys
            35                  40                  45

Ala Ala Trp Leu Lys Ala Thr Ile Pro Glu Asp Arg Ile Lys Asn Ile
    50                  55                  60

Arg Leu Leu Lys Lys Lys Thr Lys Lys Gln Phe Met Lys Asn Cys Gln
65                  70                  75                  80

Phe Gln Glu Gln Leu Leu Ser Phe Phe Met Glu Asp Val Phe Gly Gln
                85                  90                  95

Leu Gln Leu Gln Gly Cys Lys Lys Ile Arg Phe Val Gly Asp Phe His
            100                 105                 110
```

```
Ser Leu Arg Gln Lys Leu Ser His Cys Ile Ser Cys Ala Ser Ser Ala
        115                 120                 125

Arg Glu Met Lys Ser Ile Thr Arg Met Lys Arg Ile Phe Tyr Arg Ile
130                 135                 140

Gly Asn Lys Gly Ile Tyr Lys Ala Ile Ser Glu Leu Asp Ile Leu Leu
145                 150                 155                 160

Ser Trp Ile Lys Lys Leu Leu Glu Ser Ser Gln
                165                 170

<210> SEQ ID NO 81
<211> LENGTH: 574
<212> TYPE: PRT
<213> ORGANISM: Homo sapiens

<400> SEQUENCE: 81

Met Arg Thr Leu Leu Thr Ile Leu Thr Val Gly Ser Leu Ala Ala His
1               5                   10                  15

Ala Pro Glu Asp Pro Ser Asp Leu Leu Gln His Val Lys Phe Gln Ser
            20                  25                  30

Ser Asn Phe Glu Asn Ile Leu Thr Trp Asp Ser Gly Pro Glu Gly Thr
        35                  40                  45

Pro Asp Thr Val Tyr Ser Ile Glu Tyr Lys Thr Tyr Gly Glu Arg Asp
    50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His Val Leu Ile Pro Val Phe Asp
        275                 280                 285

Leu Ser Gly Pro Ser Ser Leu Ala Gln Pro Val Gln Tyr Ser Gln Ile
    290                 295                 300

Arg Val Ser Gly Pro Arg Glu Pro Ala Gly Ala Pro Gln Arg His Ser
305                 310                 315                 320
```

```
Leu Ser Glu Ile Thr Tyr Leu Gly Gln Pro Asp Ile Ser Ile Leu Gln
            325                 330                 335

Pro Ser Asn Val Pro Pro Gln Ile Leu Ser Pro Leu Ser Tyr Ala
        340                 345                 350

Pro Asn Ala Ala Pro Glu Val Gly Pro Pro Ser Tyr Ala Pro Gln Val
            355                 360                 365

Thr Pro Glu Ala Gln Phe Pro Phe Tyr Ala Pro Gln Ala Ile Ser Lys
    370                 375                 380

Val Gln Pro Ser Ser Tyr Ala Pro Gln Ala Thr Pro Asp Ser Trp Pro
385                 390                 395                 400

Pro Ser Tyr Gly Val Cys Met Glu Gly Ser Gly Lys Asp Ser Pro Thr
                405                 410                 415

Gly Thr Leu Ser Ser Pro Lys His Leu Arg Pro Lys Gly Gln Leu Gln
            420                 425                 430

Lys Glu Pro Pro Ala Gly Ser Cys Met Leu Gly Gly Leu Ser Leu Gln
        435                 440                 445

Glu Val Thr Ser Leu Ala Met Glu Glu Ser Gln Glu Ala Lys Ser Leu
    450                 455                 460

His Gln Pro Leu Gly Ile Cys Thr Asp Arg Thr Ser Asp Pro Asn Val
465                 470                 475                 480

Leu His Ser Gly Glu Glu Gly Thr Pro Gln Tyr Leu Lys Gly Gln Leu
                485                 490                 495

Pro Leu Leu Ser Ser Val Gln Ile Glu Gly His Pro Met Ser Leu Pro
            500                 505                 510

Leu Gln Pro Pro Ser Arg Pro Cys Ser Pro Ser Asp Gln Gly Pro Ser
        515                 520                 525

Pro Trp Gly Leu Leu Glu Ser Leu Val Cys Pro Lys Asp Glu Ala Lys
    530                 535                 540

Ser Pro Ala Pro Glu Thr Ser Asp Leu Glu Gln Pro Thr Glu Leu Asp
545                 550                 555                 560

Ser Leu Phe Arg Gly Leu Ala Leu Thr Val Gln Trp Glu Ser
                565                 570

<210> SEQ ID NO 82
<211> LENGTH: 559
<212> TYPE: PRT
<213> ORGANISM: Homo sapiens

<400> SEQUENCE: 82

His Ala Pro Glu Asp Pro Ser Asp Leu Leu Gln His Val Lys Phe Gln
1               5                   10                  15

Ser Ser Asn Phe Glu Asn Ile Leu Thr Trp Asp Ser Gly Pro Glu Gly
            20                  25                  30

Thr Pro Asp Thr Val Tyr Ser Ile Glu Tyr Lys Thr Tyr Gly Glu Arg
        35                  40                  45

Asp Trp Val Ala Lys Lys Gly Cys Gln Arg Ile Thr Arg Lys Ser Cys
    50                  55                  60

Asn Leu Thr Val Glu Thr Gly Asn Leu Thr Glu Leu Tyr Tyr Ala Arg
65                  70                  75                  80

Val Thr Ala Val Ser Ala Gly Gly Arg Ser Ala Thr Lys Met Thr Asp
                85                  90                  95

Arg Phe Ser Ser Leu Gln His Thr Thr Leu Lys Pro Pro Asp Val Thr
            100                 105                 110

Cys Ile Ser Lys Val Arg Ser Ile Gln Met Ile Val His Pro Thr Pro
```

```
            115                 120                 125
Thr Pro Ile Arg Ala Gly Asp Gly His Arg Leu Thr Leu Glu Asp Ile
            130                 135                 140

Phe His Asp Leu Phe Tyr His Leu Glu Leu Gln Val Asn Arg Thr Tyr
145                 150                 155                 160

Gln Met His Leu Gly Gly Lys Gln Arg Glu Tyr Glu Phe Phe Gly Leu
                165                 170                 175

Thr Pro Asp Thr Glu Phe Leu Gly Thr Ile Met Ile Cys Val Pro Thr
                180                 185                 190

Trp Ala Lys Glu Ser Ala Pro Tyr Met Cys Arg Val Lys Thr Leu Pro
                195                 200                 205

Asp Arg Thr Trp Thr Tyr Ser Phe Ser Gly Ala Phe Leu Phe Ser Met
            210                 215                 220

Gly Phe Leu Val Ala Val Leu Cys Tyr Leu Ser Tyr Arg Tyr Val Thr
225                 230                 235                 240

Lys Pro Pro Ala Pro Pro Asn Ser Leu Asn Val Gln Arg Val Leu Thr
                245                 250                 255

Phe Gln Pro Leu Arg Phe Ile Gln Glu His Val Leu Ile Pro Val Phe
                260                 265                 270

Asp Leu Ser Gly Pro Ser Ser Leu Ala Gln Pro Val Gln Tyr Ser Gln
                275                 280                 285

Ile Arg Val Ser Gly Pro Arg Glu Pro Ala Gly Ala Pro Gln Arg His
            290                 295                 300

Ser Leu Ser Glu Ile Thr Tyr Leu Gly Gln Pro Asp Ile Ser Ile Leu
305                 310                 315                 320

Gln Pro Ser Asn Val Pro Pro Gln Ile Leu Ser Pro Leu Ser Tyr
                325                 330                 335

Ala Pro Asn Ala Ala Pro Glu Val Gly Pro Pro Ser Tyr Ala Pro Gln
                340                 345                 350

Val Thr Pro Glu Ala Gln Phe Pro Phe Tyr Ala Pro Gln Ala Ile Ser
                355                 360                 365

Lys Val Gln Pro Ser Ser Tyr Ala Pro Gln Ala Thr Pro Asp Ser Trp
            370                 375                 380

Pro Pro Ser Tyr Gly Val Cys Met Glu Gly Ser Gly Lys Asp Ser Pro
385                 390                 395                 400

Thr Gly Thr Leu Ser Ser Pro Lys His Leu Arg Pro Lys Gly Gln Leu
                405                 410                 415

Gln Lys Glu Pro Pro Ala Gly Ser Cys Met Leu Gly Gly Leu Ser Leu
            420                 425                 430

Gln Glu Val Thr Ser Leu Ala Met Glu Glu Ser Gln Glu Ala Lys Ser
            435                 440                 445

Leu His Gln Pro Leu Gly Ile Cys Thr Asp Arg Thr Ser Asp Pro Asn
            450                 455                 460

Val Leu His Ser Gly Glu Glu Gly Thr Pro Gln Tyr Leu Lys Gly Gln
465                 470                 475                 480

Leu Pro Leu Leu Ser Ser Val Gln Ile Glu Gly His Pro Met Ser Leu
                485                 490                 495

Pro Leu Gln Pro Pro Ser Arg Pro Cys Ser Pro Ser Asp Gln Gly Pro
                500                 505                 510

Ser Pro Trp Gly Leu Leu Glu Ser Leu Val Cys Pro Lys Asp Glu Ala
            515                 520                 525

Lys Ser Pro Ala Pro Glu Thr Ser Asp Leu Glu Gln Pro Thr Glu Leu
            530                 535                 540
```

-continued

Asp Ser Leu Phe Arg Gly Leu Ala Leu Thr Val Gln Trp Glu Ser
545                 550                 555

<210> SEQ ID NO 83
<211> LENGTH: 325
<212> TYPE: PRT
<213> ORGANISM: Homo sapiens

<400> SEQUENCE: 83

Met Ala Trp Ser Leu Gly Ser Trp Leu Gly Gly Cys Leu Leu Val Ser
1               5                   10                  15

Ala Leu Gly Met Val Pro Pro Glu Asn Val Arg Met Asn Ser Val
            20                  25                  30

Asn Phe Lys Asn Ile Leu Gln Trp Glu Ser Pro Ala Phe Ala Lys Gly
                35                  40                  45

Asn Leu Thr Phe Thr Ala Gln Tyr Leu Ser Tyr Arg Ile Phe Gln Asp
    50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Asp Thr Ile
            100                 105                 110

Ile Gly Pro Pro Gly Met Gln Val Glu Val Leu Ala Asp Ser Leu His
        115                 120                 125

Met Arg Phe Leu Ala Pro Lys Ile Glu Asn Glu Tyr Glu Thr Trp Thr
    130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Arg Asn Lys Ala Gly Glu Trp Ser Glu Pro Val
        195                 200                 205

Cys Glu Gln Thr Thr His Asp Glu Thr Val Pro Ser Trp Met Val Ala
    210                 215                 220

Val Ile Leu Met Ala Ser Val Phe Met Val Cys Leu Ala Leu Leu Gly
225                 230                 235                 240

Cys Phe Ala Leu Leu Trp Cys Val Tyr Lys Lys Thr Lys Tyr Ala Phe
                245                 250                 255

Ser Pro Arg Asn Ser Leu Pro Gln His Leu Lys Glu Phe Leu Gly His
            260                 265                 270

Pro His His Asn Thr Leu Leu Phe Phe Ser Phe Pro Leu Ser Asp Glu
        275                 280                 285

Asn Asp Val Phe Asp Lys Leu Ser Val Ile Ala Glu Asp Ser Glu Ser
    290                 295                 300

Gly Lys Gln Asn Pro Gly Asp Ser Cys Ser Leu Gly Thr Pro Pro Gly
305                 310                 315                 320

Gln Gly Pro Gln Ser
                325

<210> SEQ ID NO 84
<211> LENGTH: 306
<212> TYPE: PRT

-continued

<213> ORGANISM: Homo sapiens

<400> SEQUENCE: 84

Met Val Pro Pro Pro Glu Asn Val Arg Met Asn Ser Val Asn Phe Lys
1               5                   10                  15

Asn Ile Leu Gln Trp Glu Ser Pro Ala Phe Ala Lys Gly Asn Leu Thr
            20                  25                  30

Phe Thr Ala Gln Tyr Leu Ser Tyr Arg Ile Phe Gln Asp Lys Cys Met
        35                  40                  45

Asn Thr Thr Leu Thr Glu Cys Asp Phe Ser Ser Leu Ser Lys Tyr Gly
    50                  55                  60

Asp His Thr Leu Arg Val Arg Ala Glu Phe Ala Asp Glu His Ser Asp
65                  70                  75                  80

Trp Val Asn Ile Thr Phe Cys Pro Val Asp Asp Thr Ile Ile Gly Pro
                85                  90                  95

Pro Gly Met Gln Val Glu Val Leu Ala Asp Ser Leu His Met Arg Phe
            100                 105                 110

Leu Ala Pro Lys Ile Glu Asn Glu Tyr Glu Thr Trp Thr Met Lys Asn
        115                 120                 125

Val Tyr Asn Ser Trp Thr Tyr Asn Val Gln Tyr Trp Lys Asn Gly Thr
    130                 135                 140

Asp Glu Lys Phe Gln Ile Thr Pro Gln Tyr Asp Phe Glu Val Leu Arg
145                 150                 155                 160

Asn Leu Glu Pro Trp Thr Thr Tyr Cys Val Gln Val Arg Gly Phe Leu
                165                 170                 175

Pro Asp Arg Asn Lys Ala Gly Glu Trp Ser Glu Pro Val Cys Glu Gln
            180                 185                 190

Thr Thr His Asp Glu Thr Val Pro Ser Trp Met Val Ala Val Ile Leu
        195                 200                 205

Met Ala Ser Val Phe Met Val Cys Leu Ala Leu Leu Gly Cys Phe Ala
    210                 215                 220

Leu Leu Trp Cys Val Tyr Lys Lys Thr Lys Tyr Ala Phe Ser Pro Arg
225                 230                 235                 240

Asn Ser Leu Pro Gln His Leu Lys Glu Phe Leu Gly His Pro His His
                245                 250                 255

Asn Thr Leu Leu Phe Phe Ser Phe Pro Leu Ser Asp Glu Asn Asp Val
            260                 265                 270

Phe Asp Lys Leu Ser Val Ile Ala Glu Asp Ser Glu Ser Gly Lys Gln
        275                 280                 285

Asn Pro Gly Asp Ser Cys Ser Leu Gly Thr Pro Pro Gly Gln Gly Pro
    290                 295                 300

Gln Ser
305

<210> SEQ ID NO 85
<211> LENGTH: 6
<212> TYPE: PRT
<213> ORGANISM: Artificial Sequence
<220> FEATURE:
<223> OTHER INFORMATION: Synthetic Construct

<400> SEQUENCE: 85

Thr Phe Met Leu Ala Lys
1               5

<210> SEQ ID NO 86

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 86

Leu Phe His Gly Val Ser Met Ser Glu Arg
1               5                   10

<210> SEQ ID NO 87
<211> LENGTH: 5
<212> TYPE: PRT
<213> ORGANISM: Artificial Sequence
<220> FEATURE:
<223> OTHER INFORMATION: Synthetic Construct

<400> SEQUENCE: 87

Cys Tyr Leu Met Lys
1               5

<210> SEQ ID NO 88
<211> LENGTH: 14
<212> TYPE: PRT
<213> ORGANISM: Artificial Sequence
<220> FEATURE:
<223> OTHER INFORMATION: Synthetic Construct

<400> SEQUENCE: 88

Phe Gln Pro Tyr Met Gln Glu Val Val Pro Phe Leu Ala Arg
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetic Construct

<400> SEQUENCE: 89

Ala Ile Gly Glu Leu Asp Leu Leu Phe Met Ser Leu Arg
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Synthetic Construct

<400> SEQUENCE: 90

Asp Thr Leu Met Ile Ser Arg
1               5

<210> SEQ ID NO 91
<211> LENGTH: 16
<212> TYPE: PRT
<213> ORGANISM: Artificial Sequence
<220> FEATURE:
<223> OTHER INFORMATION: Synthetic Construct

<400> SEQUENCE: 91

Glu Pro Gln Val Tyr Thr Leu Pro Pro Ser Gln Glu Glu Met Thr Lys
1               5                   10                  15

<210> SEQ ID NO 92
<211> LENGTH: 23
```

```
<212> TYPE: PRT
<213> ORGANISM: Artificial Sequence
<220> FEATURE:
<223> OTHER INFORMATION: Synthetic Construct

<400> SEQUENCE: 92

Trp Gln Glu Gly Asn Val Phe Ser Cys Ser Val Met His Glu Ala Leu
1               5                   10                  15

His Asn His Tyr Thr Gln Lys
            20
```